(12) United States Patent
Shapiro

(10) Patent No.: US 9,567,341 B2
(45) Date of Patent: Feb. 14, 2017

(54) PYRROLOPYRIMIDINE DERIVATIVES AS NR2B NMDA RECEPTOR ANTAGONISTS

(71) Applicant: Rugen Holdings (Cayman) Limited, Grand Cayman (KY)

(72) Inventor: Gideon Shapiro, Gainesville, FL (US)

(73) Assignee: Rugen Holdings (Cayman) Limited, Grand Cayman (KY)

( * ) Notice: Subject to any disclaimer, the term of this patent is extended or adjusted under 35 U.S.C. 154(b) by 0 days.

(21) Appl. No.: 14/855,010

(22) Filed: Sep. 15, 2015

(65) Prior Publication Data
US 2016/0075713 A1 Mar. 17, 2016

Related U.S. Application Data

(60) Provisional application No. 62/050,692, filed on Sep. 15, 2014.

(51) Int. Cl.
C07D 487/04 (2006.01)
A61K 31/519 (2006.01)

(52) U.S. Cl.
CPC ........... *C07D 487/04* (2013.01); *A61K 31/519* (2013.01)

(58) Field of Classification Search
CPC .......................... C07D 487/04; A61K 31/519
USPC .......................... 544/280; 514/255.05, 265.1
See application file for complete search history.

(56) References Cited

U.S. PATENT DOCUMENTS 7,592,360 B2   9/2009   Liverton et al.

FOREIGN PATENT DOCUMENTS

| WO | WO-2004/108705 A1 | 12/2004 |
|---|---|---|
| WO | WO-2006/113471 A2 | 10/2006 |
| WO | WO-2010/015637 A1 | 2/2010 |
| WO | WO-2014/120800 A1 | 8/2014 |
| WO | WO-2015/187845 | 12/2015 |
| WO | WO-2016/044323 | 3/2016 |

OTHER PUBLICATIONS

Damasio, Alzheimer's Disease and Related Dementias, Cecil Textbook of Medicine, 20th Edition, vol. 2, pp. 1992-1996 (1996).*
Jordan, Nature Reviews: Drug Discovery, vol. 2, Issue 3, pp. 205-213 (2003).*
Addy, C. et al., Single-dose administration of MK-0657, an NR2B-selective NMDA antagonist, does not result in clinically meaningful improvement in motor function in patients with moderate Parkinson's disease, J Clin Pharmacol, 49(7):856-864 (2009).
Bandyopadhyay, S. and Hablitz, J., NR2B antagonists restrict spatiotemporal spread of activity in a rat model of cortical dysplasia, Epilepsy Research, 72:127-139 (2006).
Barton, M. et al., Pharmacological characterization of the 6 Hz psychomotor seizure model of partial epilepsy, Epilepsy Res, 47(3):217-227 (2001).
Bausch, S. et al., Inverse relationship between seizure expression and extrasynaptic NMDAR function following chronic NMDAR inhibition, Epilepsia, 51(Suppl 3):102-105 (2010).
Beinat, C. et al., Current Medicinal Chemistry, 17:4166-4190 (2010).
Berge, S. et al., Pharmaceutical salts, J Pharm Sci, 66(1):1-19 (1977).
Borza, I. and Domány, G., NR2B selective NMDA antagonists: the evolution of the ifenprodil-type pharmacophore, Curr Top Med Chem, 6(7):687-695 (2006).
Brown, D. et al., 2,6-Disubstituted pyrazines and related analogs as NR2B site antagonists of the NMDA receptor with anti-depressant activity, Bioorg Med Chem Lett, 21(11):3399-3403 (2011).
Brown, W. et al., Comparative assay of an antiepileptic drugs by psychomotor seizure test and minimal electroshock threshold test, J Pharmacol Exp Ther, 107(3):273-283 (1953).
Castel-Branco, M. et al., The maximal electroshock seizure (MES) model in the preclinical assessment of potential new antiepileptic drugs, Methods Find Exp Clin Pharmacol, 31(2):101-106 (2009).
Chenard, B. et al., (1S,2S)-1-(4-hydroxyphenyl)-2-(4-hydroxy-4-phenylpiperidino)-1-propanol: a potent new neuroprotectant which blocks N-methyl-D-aspartate responses, J Med Chem, 38(16):3138-3145 (1995).
Chermat and Simon, Fiche Technique, Journal of Pharmacology, 6:494-496 (1975).
Cull-Candy, S. et al., NMDA receptor diversity in the cerebellum: identification of subunits contributing to functional receptors, Neuropharmacology, 37(10-11):1369-1380 (1998).

(Continued)

*Primary Examiner* — Deepak Rao
(74) *Attorney, Agent, or Firm* — Choate, Hall & Stewart LLP; Brenda Herschbach Jarrell; Kristen C. Buteau

(57) ABSTRACT

Disclosed are chemical entities of formula I:

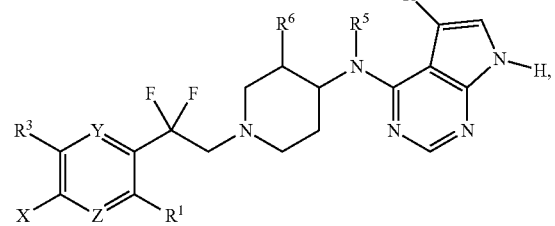

wherein X, Y, Z, $R^1$, $R^3$, $R^4$, $R^5$ and $R^6$ are defined herein, as NR2B subtype selective receptor antagonists. Also disclosed are pharmaceutical compositions comprising a chemical entity of formula I, and methods of treating various diseases and disorders associated with NR2B antagonism, e.g., diseases and disorders of the CNS, such as depression, by administering a chemical entity of formula I.

17 Claims, 9 Drawing Sheets

(56) References Cited

OTHER PUBLICATIONS

Curran, H. and Morgan, C., Cognitive, dissociative and psychotogenic effects of ketamine in recreational users on the night of drug use and 3 days later, Addiction, 95(4):575-590 (2000).

Dalby, N. and Nielsen, E., Comparison of the preclinical anticonvulsant profiles of tiagabine, lamotrigine, gabapentin and vigabatrin, Epilepsy Res, 28(1):63-72 (1997).

Esneault, E. et al., Evaluation of pro-convulsant risk in the rat: spontaneous and provoked convulsions, J Pharmacol Toxicol Methods, 72:59-66 (2015).

Fischer, G. et al., Ro 25-6981, a highly potent and selective blocker of N-methyl-D-aspartate receptors containing the NR2B subunit, Characterization in vitro, J Pharmacol Exp Ther, 283(3):1285-1292 (1997).

Fisher, R. et al., Epileptic seizures and epilepsy: definitions proposed by the International League Against Epilepsy (ILAE) and the International Bureau for Epilepsy (IBE), Epilepsia, 46(4):470-472 (2005).

Giannini, A. James et al., Phencyclidine and the Dissociativese, Psychiatric Medicine, 3:197-217 (1985).

Haas, D. and Harper, D., Ketamine: a review of its pharmacologic properties and use in ambulatory anesthesia, Anesth Prog, 39(3):61-68 (1992).

Hancox, J. and James, A., Refining insights into high-affinity drug binding to the human ether-à-go-go-related gene potassium channel, Mol Pharmacol, 73(6):1592-1595 (2008).

Hansen, K. et al., Pharmacological characterization of ligands at recombinant NMDA receptor subtypes by electrophysiological recordings and intracellular calcium measurements, Comb Chem High Throughput Screen, 11(4):304-315 (2008).

Hardy, J. et al., Randomized, double-blind, placebo-controlled study to assess the efficacy and toxicity of subcutaneous ketamine in the management of cancer pain, J Clin Oncol, 30(29):3611-3617 (2012).

Ibrahim, L. et al., Randomized, placebo-controlled, crossover pilot trial of the oral selective NR2B antagonist MK-0657 in patients with treatment-resistant major depressive disorder, J Clin Psychopharmacol, 32(4):551-557 (2012).

International Search Report for PCT/US2015/034009, 3 pages (Sep. 30, 2015).

International Search Report for PCT/US2015/050267, 4 pages (Dec. 9, 2015).

Katalinic, N. et al., Ketamine as a new treatment for depression: a review of its efficacy and adverse effects, Aust N Z J Psychiatry, 47(8):710-727 (2013).

Kawai, M. et al., Discovery of novel and orally active NR2B-selective N-methyl-D-aspartate (NMDA) antagonists, pyridinol derivatives with reduced HERG binding affinity, Bioorg Med Chem Lett, 17(20):5533-5536 (2007).

Layton, M. et al., Recent advances in the development of NR2B subtype-selective NMDA receptor antagonists, Curr Top Med Chem, 6(7):697-709 (2006).

Lemke, J. et al., GRIN2B Mutations in West Syndrome and Intellectual Disability with Focal Epilepsy, Ann Neurol, 75:147-154 (2014).

Liverton, N. et al., Identification and characterization of 4-methylbenzyl 4-[(pyrimidin-2-ylamino)methyl]piperidine-1-carboxylate, an orally bioavailable, brain penetrant NR2B selective N-methyl-D-aspartate receptor antagonist, J Med Chem, 50(4):807-819 (2007).

Lucki, I. et al., Sensitivity to the effects of pharmacologically selective antidepressants in different strains of mice, Psychopharmacology (Berl), 155(3):315-322 (2001).

Mares, Pavel, Age and activation determines the anticonvulsant effect of ifenprodil in rats, Naunyn-Schmiedeberg's Arch Pharmacol, 387:753-761 (2014).

Mathews, D. and Zarate, C., Current status of ketamine and related compounds for depression, J Clin Psychiatry, 74(5):516-517 (2013).

Menniti, F. et al., CP-101,606: An NR2B- Selective NMDA Receptor Antagonist, CNS Drug Reviews, 4(4):307-322 (1998).

Mony, L. et al., Allosteric modulators of NR2B-containing NMDA receptors: molecular mechanisms and therapeutic potential, Br J Pharmacol, 157(8):1301-1317 (2009).

Murrough, J. et al., Antidepressant efficacy of ketamine in treatment-resistant major depression: a two-site randomized controlled trial, Am J Psychiatry, 170(10):1134-1142 (2013).

Neligan, et al., The epidemiology of the epilepsies, Handb Clin Neurol, 107:113-133 (2012).

Nielsen, D. et al., Antidepressant-like activity of corticotropin-releasing factor type-1 receptor antagonists in mice, European Journal of Pharmacology, 499:135-146 (2004).

Noppers, I. et al., Drug-induced liver injury following a repeated course of ketamine treatment for chronic pain in CRPS type 1 patients: a report of 3 cases, Pain, 152(9):2173-2178 (2011).

Paoletti, P. et al., NMDA receptor subunit diversity: impact on receptor properties, synaptic plasticity and disease, Nat Rev Neurosci, 14(6):383-400 (2013).

Porsolt, R. et al., Behavioral despair in mice: a primary screening test for antidepressants, Arch Int Pharmacodyn Ther, 229(2):327-336 (1977).

Preskorn, S. et al., An innovative design to establish proof of concept of the antidepressant effects of the NR2B subunit selective N-methyl-D-aspartate antagonist, CP-101,606, in patients with treatment-refractory major depressive disorder, J Clin Psychopharmacol, 28(6):631-637 (2008).

Reynolds, I. and Miller, R., Ifenprodil is a novel type of N-methyl-D-aspartate receptor antagonist: interaction with polyamines, Mol Pharmacol, 36(5):758-765 (1989).

Ruppa, K. et al., NMDA Antagonists of GluN2B Subtype and Modulators of GluN2A, GluN2C, and GluN2D Subtypes—Recent Results and Developments, Annual Reports in Medicinal Chemistry, 47:89-103 (2012).

Sanacora, G. et al., Targeting the glutamatergic system to develop novel, improved therapeutics for mood disorders, Nat Rev Drug Discov, 7(5):426-437 (2008).

Steece-Collier, K. et al., Antiparkinsonian actions of CP-101,606, an antagonist of NR2B subunit-containing N-methyl-d-aspartate receptors, Exp Neurol, 163(1):239-243 (2000).

Swinyard, E. et al., Comparative assays of antiepileptic drugs in mice and rats, J Pharmacol Exp Ther, 106(3):319-330 (1952).

Szczurowska, E. and Mares, P., Different action of a specific NR2B/NMDA antagonist Ro 25-6981 on cortical evoked potentials and epileptic afterdischarges in immature rats, Brain Research Bulletin, 111:1-8 (2015).

Traynelis, S. et al., Glutamate receptor ion channels: structure, regulation, and function, Pharmacol Rev, 62(3):405-496 (2010).

Written Opinion for PCT/US2015/034009, 6 pages (Sep. 30, 2015).
Written Opinion for PCT/US2015/050267, 5 pages (Dec. 9, 2015).

Zarate, C. et al., A randomized trial of an N-methyl-D-aspartate antagonist in treatment-resistant major depression, Arch Gen Psychiatry, 63(8):856-864 (2006).

Zarate, C. et al., Replication of ketamine's antidepressant efficacy in bipolar depression: a randomized controlled add-on trial, Biol Psychiatry, 71(11):939-946 (2012).

* cited by examiner

PYRROLOPYRIMIDINE DERIVATIVES AS NR2B NMDA RECEPTOR ANTAGONISTS

BACKGROUND

Non-selective NMDA receptor antagonists, originally developed in stroke and head trauma, have more recently shown clinical efficacy in treating depression. The non-selective NMDA receptor antagonist, ketamine, has been shown to have rapid onset and efficacy in depression resistant to standard monoamine reuptake inhibitor therapy (Mathews and Zarate, 2013, *J. Clin. Psychiatry* 74:516-158). However, non-selective NMDA receptor antagonists such as ketamine have a range of undesirable pharmacological activities which limit application in humans. In particular dissociative or psychogenic side effects are particularly prominent for non-selective NMDA receptor antagonists. More recently, NR2B subtype selective NMDA receptor antagonists have demonstrated potential in a wide range of clinical indications. In particular, NR2B antagonists have also demonstrated antidepressant activity in early stage clinical trials (Ibrahim et al., 2012, *J. Clin. Psychopharmacol.* 32, 551-557; Preskorn et al., 2008, *J. Clin. Psychopharmacol.* 28, 631-637). Furthermore, selective NR2B antagonists have advantages over unselective NMDA receptor antagonists such as ketamine due to greatly diminished dissociative side effects. However, NR2B antagonists described to date have generally exhibited drawbacks with regard to other drug properties which have limited potential use in human drug therapy.

SUMMARY

For broad scope of application and safe human use in a range of clinical indications including depression, improved NR2B subtype selective antagonists are needed. The present invention, among other things, addresses the need for NR2B receptor antagonists that are improved in one or more aspects exemplified by pharmacokinetic performance, oral activity, cardiovascular safety, and in vitro and in vivo therapeutic safety index measures.

In some embodiments, the present invention encompasses the insight that chemical entities of formula I:

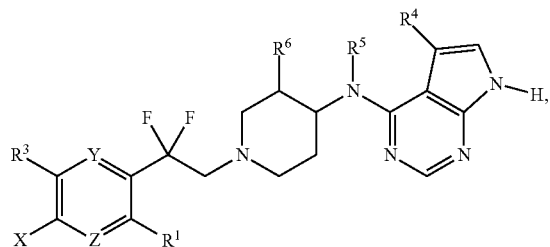

wherein X, Y, Z, $R^1$, $R^3$, $R^4$, $R^5$ and $R^6$ are defined herein, are NR2B subtype selective receptor antagonists. Chemical entities of formula I, and pharmaceutically acceptable compositions thereof, are useful for treating a variety of diseases and disorders associated with NR2B receptor antagonism. Such diseases and disorders include those described herein.

DETAILED DESCRIPTION OF CERTAIN EMBODIMENTS

General Description of Chemical Entities

Figure 1:
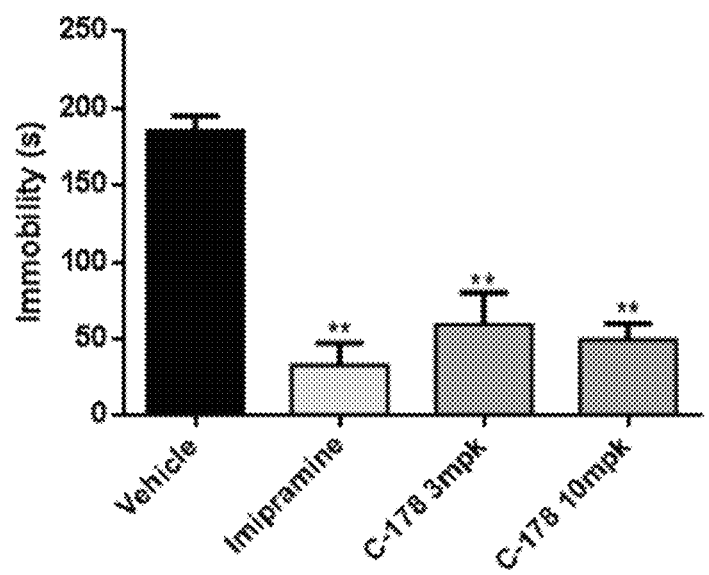
FIG. 1 shows the results of compound C-178 in the forced swim test as described in Example 2.4.1.

In some embodiments, the present invention provides chemical entities of formula I:

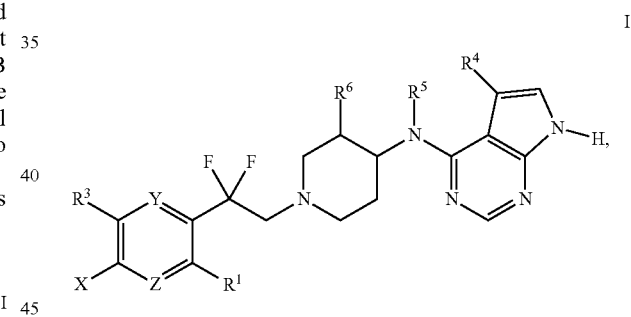

wherein:
Y and Z are independently N or $C(R^2)$;
X is —H; halo; $C_1$-$C_6$ alkyl optionally substituted with 1 to 6 fluoro; $C_3$-$C_6$ cycloalkyl; $C_1$-$C_4$ alkoxy optionally substituted with 1 to 6 fluoro; —CN; —$NO_2$; —$N(R^7)(R^8)$; —$SR^7$; —$S(O)_2R^9$; or —$C(O)OR^7$;
$R^1$ is —H; halo; $C_1$-$C_4$ alkyl optionally substituted with 1 to 3 fluoro; $C_3$-$C_6$ cycloalkyl; $C_1$-$C_4$ alkoxy optionally substituted with 1 to 3 fluoro; —CN; —$NO_2$; —$N(R^7)(R^8)$; —$C(O)OR^7$; or —$C(O)N(R^7)(R^8)$;
$R^2$ is —H; halo; $C_1$-$C_4$ alkyl optionally substituted with 1 to 3 fluoro; cyclopropyl; or $C_1$-$C_4$ alkoxy optionally substituted with 1 to 3 fluoro;
$R^3$ is —H, —F, —Cl, —$CH_3$, —$CF_3$ or —$OCH_3$;
$R^4$ is —H; —F; —Cl; $C_1$-$C_3$ alkyl optionally substituted with 1 to 3 fluoro; or cyclopropyl;
$R^5$ is —H or —$CH_3$;
$R^6$ is —H, —F or —$CH_3$;
each instance of $R^7$ independently is $C_1$-$C_4$ alkyl;
each instance of $R^8$ independently is —H or $C_1$-$C_4$ alkyl; and
$R^9$ is $C_1$-$C_4$ alkyl optionally substituted with 1 to 3 fluoro.

Unless otherwise specified or clear from context, the term "chemical entity" refers to a compound having the indicated structure, whether in its "free" form (e.g., "free compound" or "free base" or "free acid" form, as applicable), or in a salt form, particularly a pharmaceutically acceptable salt form, and furthermore whether in solid state form or otherwise. Thus, in some embodiments the term "chemical entity" refers to a compound having the indicated structure, or a pharmaceutically acceptable salt thereof. In some embodiments, a solid state form is an amorphous (i.e., non-crystalline) form; in some embodiments, a solid state form is a crystalline form. In some embodiments, a crystalline form (e.g., a polymorph, pseudohydrate, or hydrate). Similarly, the term encompasses the compound whether provided in solid form or otherwise. Unless otherwise specified, all statements made herein regarding "compounds" apply to the associated chemical entities, as defined.

CHEMICAL ENTITIES AND DEFINITIONS

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

Chemical entities of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, *Organic Chemistry,* University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations,* VCH Publishers, Inc., New York, 1989; and Carruthers, *Some Modern Methods of Organic Synthesis,* 3rd Edition, Cambridge University Press, Cambridge, 1987.

The term "alkyl", as by itself or as part of another substituent, means a substituted or unsubstituted, linear or branched, univalent hydrocarbon chain that is completely saturated or that contains one or more units of unsaturation. Unless otherwise specified, alkyl groups contain 1 to 7 carbon atoms ("$C_1$-$C_7$ alkyl"). In some embodiments, alkyl groups contain 1 to 6 carbon atoms ("$C_1$-$C_6$ alkyl"). In some embodiments, alkyl groups contain 1 to 5 carbon atoms ("$C_1$-$C_5$ alkyl"). In some embodiments, alkyl groups contain 1 to 4 carbon atoms ("$C_1$-$C_4$ alkyl"). In some embodiments, alkyl groups contain 3 to 7 carbon atoms ("$C_3$-$C_7$ alkyl"). Examples of saturated alkyl groups include methyl, ethyl, n-propyl, i-propyl, n-butyl, t-butyl, i-butyl, s-butyl, homologs and isomers of, for example, n-pentyl, n-hexyl, n-heptyl, n-octyl, and the like. An unsaturated alkyl group is one having one or more carbon-carbon double bonds or carbon-carbon triple bonds. Examples of unsaturated alkyl groups include allyl, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the like. The term "lower alkyl" refers to alkyl groups having 1 to 4 (if saturated) or 2 to 4 (if unsaturated) carbon atoms. Exemplary lower alkyl groups include methyl, ethyl, n-propyl, i-propyl, n-butyl, s-butyl, i-butyl, t-butyl and the like. The term "alkenyl" refers to alkyl groups having at least two carbon atoms and at least one carbon-carbon double bond. The term "alkynyl" refers to alkyl groups having at least two carbon atoms and at least one carbon-carbon triple bond.

The term "cycloalkyl", by itself or as part of another substituent, refers to a monocyclic univalent hydrocarbon that is completely saturated or that contains one or more units of unsaturation, but which is not aromatic, that has a single point of attachment to the rest of the molecule. In some embodiments, cycloalkyl groups contain 3 to 8 ring carbon atoms ("$C_3$-$C_8$ cycloalkyl"). Examples of cycloalkyl include cyclopropyl, cyclobutyl, cyclopentyl, cyclohexyl, 1-cyclohexenyl, 3-cyclohexenyl, cycloheptyl, and the like.

The term "alkoxy", by itself or as part of another substituent, refers to the group —O-alkyl.

The term "halogen" or "halo", by itself or as part of another substituent, refers to fluorine, chlorine, bromine or iodine.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66:1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement hydrogen, carbon, nitrogen, oxygen, chlorine or fluorine with $^2$H, $^3$H, $^{11}$C, $^{13}$C, $^{14}$C, $^{13}$N, $^{15}$N, $^{17}$O, $^{18}$O, $^{36}$Cl or $^{18}$F, respectively, are within the scope of this invention. Such compounds are useful, for example, as analytical tools, as probes in biological assays, or as therapeutic agents in accordance with the present invention. Additionally, incorporation of heavier isotopes such as deuterium ($^2$H) can afford certain therapeutic advantages resulting from greater metabolic stability, for example, increase in vivo half-life, or reduced dosage requirements.

Exemplary Embodiments of Chemical Entities

In some embodiments, the present invention provides chemical entities of formula I:

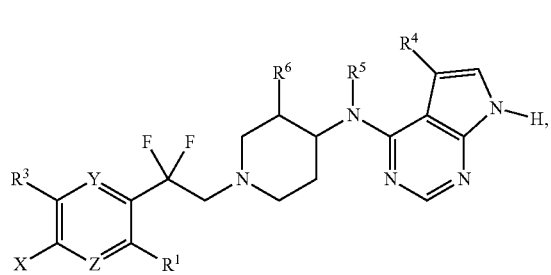

(I)

wherein:
Y and Z are independently N or C(R$^2$);
X is —H; halo; C$_1$-C$_6$ alkyl optionally substituted with 1 to 6 fluoro; C$_3$-C$_6$ cycloalkyl; C$_1$-C$_4$ alkoxy optionally substituted with 1 to 6 fluoro; —CN; —NO$_2$; —N(R$^7$)(R$^8$); —SR$^7$; —S(O)$_2$R$^9$; or —C(O)OR$^7$;
R$^1$ is —H; halo; C$_1$-C$_4$ alkyl optionally substituted with 1 to 3 fluoro; C$_3$-C$_6$ cycloalkyl; C$_1$-C$_4$ alkoxy optionally substituted with 1 to 3 fluoro; —CN; —NO$_2$; —N(R$^7$)(R$^8$); —C(O)OR$^7$; or —C(O)N(R$^7$)(R$^8$);
R$^2$ is —H; halo; C$_1$-C$_4$ alkyl optionally substituted with 1 to 3 fluoro; cyclopropyl; or C$_1$-C$_4$ alkoxy optionally substituted with 1 to 3 fluoro;
R$^3$ is —H, —F, —Cl, —CH$_3$, —CF$_3$ or —OCH$_3$;
R$^4$ is —H; —F; —Cl; C$_1$-C$_3$ alkyl optionally substituted with 1 to 3 fluoro; or cyclopropyl;
R$^5$ is —H or —CH$_3$;
R$^6$ is —H, —F or —CH$_3$;
each instance of R$^7$ independently is C$_1$-C$_4$ alkyl;
each instance of R$^8$ independently is —H or C$_1$-C$_4$ alkyl; and
R$^9$ is C$_1$-C$_4$ alkyl optionally substituted with 1 to 3 fluoro.
In some such embodiments, at least one of Y and Z is N.
In some embodiments, Y and Z are independently N or C(R$^2$);

X is —H; halo; C$_1$-C$_4$ alkyl optionally substituted with 1 to 6 fluoro; cyclopropyl; C$_1$-C$_2$ alkoxy optionally substituted with 1 to 3 fluoro; —CN; —NO$_2$; —N(R$^7$)(R$^8$); —SR$^7$; or —S(O)$_2$R$^9$;
R$^1$ is —H; halo; C$_1$-C$_4$ alkyl optionally substituted with 1 to 3 fluoro; cyclopropyl; C$_1$-C$_2$ alkoxy optionally substituted with 1 to 3 fluoro; —CN; —NO$_2$; —N(R$^7$)(R$^8$); —C(O)OR$^7$; or —C(O)N(R$^7$)(R$^8$);
R$^2$ is —H; halo; C$_1$-C$_4$ alkyl optionally substituted with 1 to 3 fluoro; cyclopropyl; or C$_1$-C$_2$ alkoxy optionally substituted with 1 to 3 fluoro;
R$^3$ is —H, —F, —Cl, —CH$_3$, —CF$_3$ or —OCH$_3$;
R$^4$ is —H; —F; —Cl; C$_1$-C$_3$ alkyl optionally substituted with 1 to 3 fluoro; or cyclopropyl;
R$^5$ is —H or —CH$_3$;
R$^6$ is —H, —F or —CH$_3$;
each instance of R$^7$ independently is C$_1$-C$_2$ alkyl;
each instance of R$^8$ independently is —H or C$_1$-C$_2$ alkyl; and
R$^9$ is C$_1$-C$_2$ alkyl optionally substituted with 1 to 3 fluoro.
In some such embodiments, at least one of Y and Z is N.
In some embodiments, Y and Z are independently N or C(R$^2$);
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —NH(CH$_3$), —N(CH$_3$)$_2$, —N(CH$_3$)(CH$_2$CH$_3$), —SCH$_3$, —SCH$_2$CH$_3$, —SO$_2$CH$_3$, —SO$_2$CH$_2$CH$_3$ or —SO$_2$CF$_3$;
R$^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or —C(O)N(CH$_3$)(CH$_2$CH$_3$);
R$^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$;
R$^3$ is —H, —F, —Cl, —CH$_3$, —CF$_3$ or —OCH$_3$;
R$^4$ is —H, —F, —Cl, —CH$_3$ or cyclopropyl;
R$^5$ is —H or —CH$_3$; and
R$^6$ is —H, —F or —CH$_3$.
In some such embodiments, at least one of Y and Z is N.
In some embodiments, Y and Z are independently N or C(R$^2$);
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
R$^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);
R$^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$;
R$^3$ is —H, —F, —Cl, —CH$_3$, —CF$_3$ or —OCH$_3$;
R$^4$ is —H, —F, —Cl, —CH$_3$ or cyclopropyl;
R$^5$ is —H or —CH$_3$; and
R$^6$ is —H, —F or —CH$_3$.
In some such embodiments, at least one of Y and Z is N.
In some embodiments, Y and Z are independently N or C(R$^2$);
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$;
R$^1$ is —H, —F, —Cl, —CH$_3$ or —CF$_3$;
R$^2$ is —H, —F, —Cl, —CH$_3$ or —CF$_3$;

$R^3$ is —H, —F, —Cl, —CH$_3$ or —CF$_3$;
$R^4$ is —H, —Cl or —CH$_3$;
$R^5$ is —H or —CH$_3$; and
$R^6$ is —H, —F or —CH$_3$.

In some such embodiments, at least one of Y and Z is N.

In some embodiments, X is —H; halo; C$_1$-C$_4$ alkyl optionally substituted with 1 to 6 fluoro; cyclopropyl; C$_1$-C$_2$ alkoxy optionally substituted with 1 to 3 fluoro; —CN; —NO$_2$; —N(R$^7$)(R$^8$); —SR$^7$; or —S(O)$_2$R$^9$. In some embodiments, X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —NH(CH$_3$), —N(CH$_3$)$_2$, —N(CH$_3$)(CH$_2$CH$_3$), —SCH$_3$, —SCH$_2$CH$_3$, —SO$_2$CH$_3$, —SO$_2$CH$_2$CH$_3$ or —SO$_2$CF$_3$. In some embodiments, X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$. In some embodiments, X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$.

In some embodiments, X is —H.

In some embodiments, X is halo. In some embodiments, X is —F or —Cl.

In some embodiments, X is C$_1$-C$_6$ alkyl optionally substituted with 1 to 6 fluoro. In some embodiments, X is C$_1$-C$_4$ alkyl optionally substituted with 1 to 6 fluoro. In some embodiments, X is —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$ or —CH(CF$_3$)$_2$. In some embodiments, X is —CH$_3$, —CH$_2$CH$_3$, —CH(CH$_3$)$_2$, —CF$_3$, —CHF$_2$ or —CH$_2$F.

In some embodiments, X is C$_3$-C$_6$ cycloalkyl. In some embodiments X is cyclopropyl.

In some embodiments, X is C$_1$-C$_4$ alkoxy optionally substituted with 1 to 6 fluoro. In some embodiments, X is C$_1$-C$_2$ alkoxy optionally substituted with 1 to 3 fluoro. In some embodiments, X is —OCH$_3$, —OCF$_3$, —OCHF$_2$ or —OCFH$_2$. In some embodiments, X is —OCH$_3$, —OCF$_3$ or —OCHF$_2$, In some embodiments, X is —CN.

In some embodiments, X is —NO$_2$.

In some embodiments, X is —N(R$^7$)(R$^8$). In some embodiments, X is —NH(CH$_3$), —N(CH$_3$)$_2$ or —N(CH$_3$)(CH$_2$CH$_3$). In some embodiments, X is —N(CH$_3$)$_2$.

In some embodiments, X is —SR$^7$. In some embodiments, X is —SCH$_3$ or —SCH$_2$CH$_3$. In some embodiments, X is —SCH$_3$.

In some embodiments, X is —S(O)$_2$R$^9$. In some embodiments, X is —SO$_2$CH$_3$, —SO$_2$CH$_2$CH$_3$ or —SO$_2$CF$_3$. In some embodiments, X is —SO$_2$CH$_3$ or —SO$_2$CF$_3$.

In some embodiments, $R^1$ is —H; halo; C$_1$-C$_4$ alkyl optionally substituted with 1 to 3 fluoro; cyclopropyl; C$_1$-C$_2$ alkoxy optionally substituted with 1 to 3 fluoro; —CN; —NO$_2$; —N(R$^7$)(R$^8$); —C(O)OR$^7$; or —C(O)N(R$^7$)(R$^8$). In some embodiments, $R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or —C(O)N(CH$_3$)(CH$_2$CH$_3$). In some embodiments, $R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$). In some embodiments, $R^1$ is —H, —F, —Cl, —CH$_3$ or —CF$_3$.

In some embodiments, $R^1$ is —H.

In some embodiments, $R^1$ is halo. In some embodiments, $R^1$ is —F or —Cl.

In some embodiments, $R^1$ is C$_1$-C$_4$ alkyl optionally substituted with 1 to 3 fluoro. In some embodiments, $R^1$ is —CH$_3$, —CH$_2$CH$_3$, —CH(CH$_3$)$_2$ or —CF$_3$. In some embodiments, $R^1$ is —CH$_3$ or —CF$_3$.

In some embodiments, $R^1$ is C$_3$-C$_6$ cycloalkyl. In some embodiments, $R^1$ is cyclopropyl.

In some embodiments, $R^1$ is C$_1$-C$_4$ alkoxy optionally substituted with 1 to 3 fluoro. In some embodiments, $R^1$ is C$_1$-C$_2$ alkoxy optionally substituted with 1 to 3 fluoro. In some embodiments, $R^1$ is —OCH$_3$, —OCF$_3$, —OCHF$_2$ or —OCFH$_2$.

In some embodiments, $R^1$ is —CN.

In some embodiments, $R^1$ is —NO$_2$.

In some embodiments, $R^1$ is —N(R$^7$)(R$^8$).

In some embodiments, $R^1$ is —C(O)OR$^7$. In some embodiments, $R^1$ is —CO$_2$CH$_3$ or —CO$_2$CH$_2$CH$_3$.

In some embodiments, $R^1$ is —C(O)N(R$^7$)(R$^8$). In some embodiments, $R^1$ is —C(O)N(CH$_3$)$_2$, —C(O)NH(CH$_3$) or —C(O)N(CH$_3$)(CH$_2$CH$_3$). In some embodiments, $R^1$ is —C(O)N(CH$_3$)$_2$ or —C(O)NH(CH$_3$).

In some embodiments, $R^2$ is —H; halo; C$_1$-C$_4$ alkyl optionally substituted with 1 to 3 fluoro; cyclopropyl; C$_1$-C$_2$ alkoxy optionally substituted with 1 to 3 fluoro. In some embodiments, $R^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$. In some embodiments, $R^2$ is —H, —F, —Cl, —CH$_3$ or —CF$_3$.

In some embodiments, $R^2$ is —H.

In some embodiments, $R^2$ is halo. In some embodiments, $R^2$ is —F or —Cl.

In some embodiments, $R^2$ is C$_1$-C$_4$ alkyl optionally substituted with 1 to 3 fluoro. In some embodiments, $R^2$ is —CH$_3$, —CH$_2$CH$_3$, —CH(CH$_3$)$_2$ or —CF$_3$. In some embodiments, $R^2$ is —CH$_3$ or —CF$_3$.

In some embodiments, $R^2$ is cyclopropyl.

In some embodiments, $R^2$ is C$_1$-C$_4$ alkoxy optionally substituted with 1 to 3 fluoro. In some embodiments, $R^2$ is C$_1$-C$_2$ alkoxy optionally substituted with 1 to 3 fluoro. In some embodiments, $R^2$ is —OCH$_3$, —OCF$_3$, —OCHF$_2$ or —OCFH$_2$.

In some embodiments, $R^3$ is —H, —F, —Cl, —CH$_3$, —CF$_3$ or —OCH$_3$. In some embodiments, $R^3$ is —H, —F, —Cl, —CH$_3$ or —CF$_3$.

In some embodiments, $R^3$ is —H.

In some embodiments, $R^3$ is —F or —Cl.

In some embodiments, $R^3$ is —CH$_3$ or —CF$_3$.

In some embodiments, $R^3$ is —OCH$_3$.

In some embodiments, $R^4$ is —H; —F; —Cl; C$_1$-C$_3$ alkyl optionally substituted with 1 to 3 fluoro; or cyclopropyl. In some embodiments, $R^4$ is —H, —F, —Cl, —CH$_3$ or cyclopropyl. In some embodiments, $R^4$ is —H, —Cl or —CH$_3$.

In some embodiments, $R^4$ is —H.

In some embodiments, $R^4$ is —F or —Cl.

In some embodiments, $R^4$ is C$_1$-C$_3$ alkyl optionally substituted with 1 to 3 fluoro. In some embodiments, $R^4$ is —CH$_3$.

In some embodiments, $R^4$ is cyclopropyl.

In some embodiments, $R^5$ is —H or —CH$_3$.

In some embodiments, $R^5$ is —H.

In some embodiments, $R^5$ is —CH$_3$.

In some embodiments, $R^6$ is —H, —F or —CH$_3$.

In some embodiments, $R^6$ is —H.

In some embodiments, $R^6$ is —F.

In some embodiments, $R^6$ is —CH$_3$.

In some embodiments, a chemical entity of formula (I) is a chemical entity of formula (Ia):

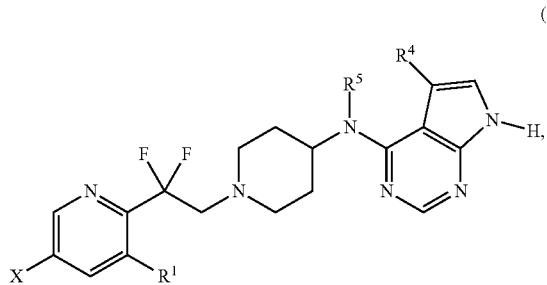

wherein each of $R^1$, X, $R^4$ and $R^5$ is as described in embodiments of formula (I), supra, or described in embodiments herein, both singly and in combination.

In some embodiments of formula (Ia):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);
$R^4$ is —H, —F, —Cl, —CH$_3$ or cyclopropyl; and
$R^5$ is —H or —CH$_3$.

In some embodiments of formula (Ia):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$;
$R^1$ is —H, —F, —Cl, —CH$_3$ or —CF$_3$;
$R^4$ is —H, —Cl or —CH$_3$; and
$R^5$ is —H or —CH$_3$.

In some embodiments of formula (Ia):
X is —Cl, —CH$_3$ or —CF$_3$;
$R^1$ is —H or —F;
$R^4$ is —Cl or —CH$_3$; and
$R^5$ is —H.

In some embodiments of formula (Ia):
X is —Cl, —CH$_3$ or —CF$_3$;
$R^1$ is —H;
$R^4$ is —H; and
$R^5$ is —CH$_3$.

In some embodiments, a chemical entity of formula (I) is a chemical entity of formula (II):

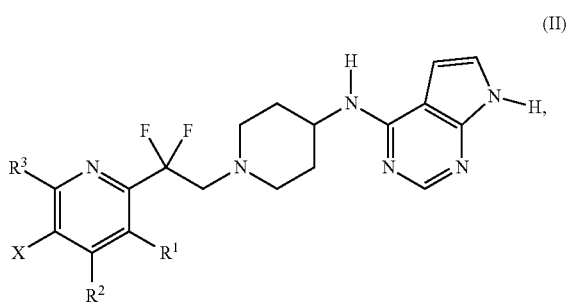

wherein each of $R^1$, $R^2$, X and $R^3$ is as described in embodiments of formula (I), supra, or described in embodiments herein, both singly and in combination.

In some embodiments of formula (II):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);
$R^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and
$R^3$ is —H, —F, —Cl, —CH$_3$, —CF$_3$ or —OCH$_3$.

In some embodiments of formula (II):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$;
$R^1$ is —H, —F, —Cl, —CH$_3$ or —CF$_3$;
$R^2$ is —H, —F, —Cl, —CH3 or —CF$_3$; and
$R^3$ is —H, —F, —Cl, —CH$_3$ or —CF$_3$ In some embodiments of formula (II):
X is —F, —Cl, —CH$_3$ or —CF$_3$;
$R^1$ is —H;
$R^2$ is —H, —F, —Cl or —CH$_3$; and
$R^3$ is —H, —F, —Cl, or —CH$_3$. In some embodiments, a chemical entity of formula (I) is a chemical entity of formula (IIa):

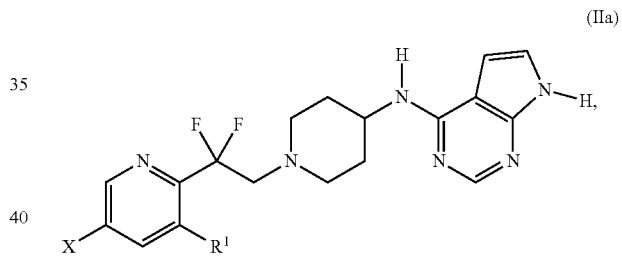

wherein each of $R^1$ and X is as described in embodiments of formula (I), supra, or described in embodiments herein, both singly and in combination.

In some embodiments of formula (IIa):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$).

In some embodiments of formula (IIa):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and
$R^1$ is —H, —F, —Cl, —CH$_3$ or —CF$_3$.

In some embodiments of formula (IIa):
X is —H, —F, —Cl, —CH$_3$, —CH$_2$CH$_3$, —CF$_3$, —CHF$_2$, —CH$_2$F, cyclopropyl, —OCH$_3$, —OCF$_3$, —OCHF$_2$, —CN or —SCH$_3$; and
$R^1$ is —H, —F, —Cl, or —CH$_3$.

In some embodiments, a chemical entity of formula (I) is a chemical entity of formula (III):

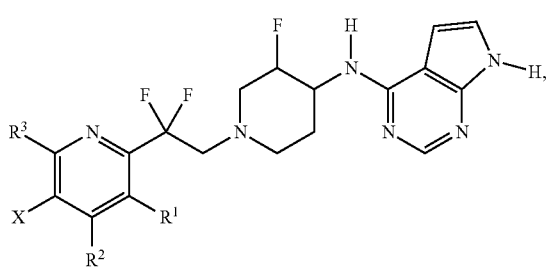

(III)

wherein each of $R^1$, $R^2$, X and $R^3$ is as described in embodiments of formula (I), supra, or described in embodiments herein, both singly and in combination.

In some embodiments of formula (III):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);
$R^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and
$R^3$ is —H, —F, —Cl, —CH$_3$, —CF$_3$ or —OCH$_3$.

In some embodiments of formula (III):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$;
$R^1$ is —H, —F, —Cl, —CH$_3$ or —CF$_3$;
$R^2$ is —H, —F, —Cl, —CH$_3$ or —CF$_3$; and
$R^3$ is —H, —F, —Cl, —CH$_3$ or —CF$_3$. In some embodiments, a chemical entity of formula (I) is a chemical entity of formula (IIIa):

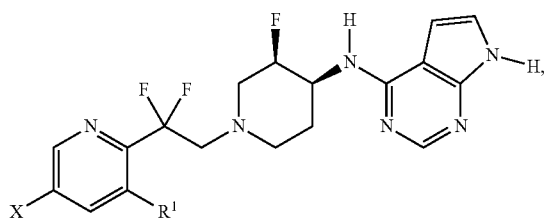

(IIIa)

wherein each of $R^1$ and X is as described in embodiments for formula (I), supra, or described in embodiments herein, both singly and in combination.

In some embodiments of formula (IIIa):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$).

In some embodiments of formula (IIIa):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and
$R^1$ is —H, —F, —Cl, —CH$_3$ or —CF$_3$. In some embodiments of formula (IIIa):
X is —F, —Cl, —CH$_3$, —CH$_2$CH$_3$, —CF$_3$, —CHF$_2$, —CH$_2$F, cyclopropyl, —OCF$_3$, —OCHF$_2$; and
$R^1$ is —H or —F.

In some embodiments, a chemical entity of formula (I) is a chemical entity of formula (IIIb):

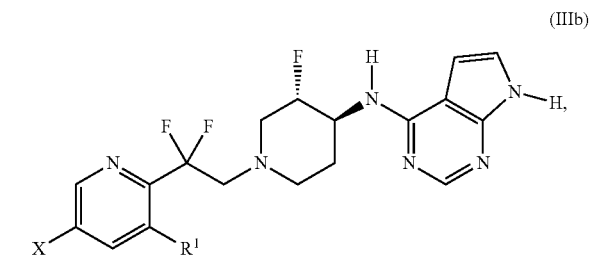

(IIIb)

wherein each of $R^1$ and X is as described in embodiments for formula (I), supra, or described in embodiments herein, both singly and in combination.

In some embodiments of formula (IIIb),
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$).

In some embodiments of formula (IIIb):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and
$R^1$ is —H, —F, —Cl, —CH$_3$ or —CF$_3$.

In some embodiments of formula (IIIb):
X is —F, —Cl, —CH$_3$, —CH$_2$CH$_3$, —CF$_3$, —CHF$_2$, —CH$_2$F, cyclopropyl, —OCF$_3$, —OCHF$_2$; and
$R^1$ is —H or —F.

In some embodiments, a chemical entity of formula (I) is a chemical entity of formula (IV):

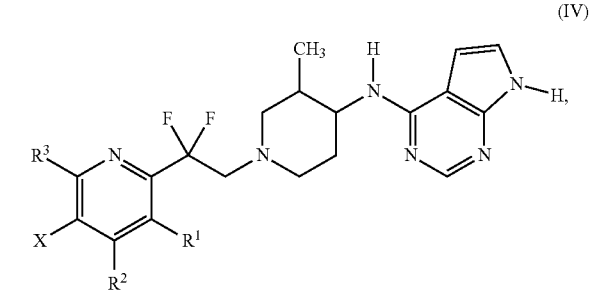

(IV)

wherein each of $R^1$, $R^2$, X and $R^3$ is as described in embodiments of formula (I), supra, or described in embodiments herein, both singly and in combination.

In some embodiments of formula (IV):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;

R$^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);

R$^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and R$^3$ is —H, —F, —Cl, —CH$_3$, —CF$_3$ or —OCH$_3$.

In some embodiments of formula (IV):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$;

R$^1$ is —H, —F, —Cl, —CH$_3$ or —CF$_3$;

R$^2$ is —H, —F, —Cl, —CH3 or —CF$_3$; and

R$^3$ is —H, —F, —Cl, —CH$_3$ or —CF$_3$.

In some embodiments, a chemical entity of formula (I) is a chemical entity of formula (IVa):

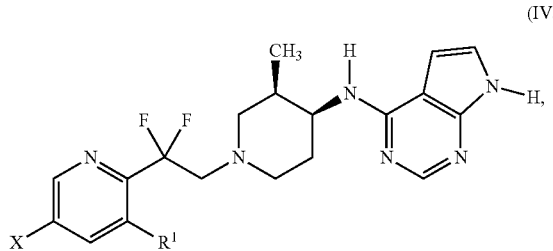

(IVa)

wherein each of R$^1$ and X is as described in embodiments for formula (I), supra, or described in embodiments herein, both singly and in combination.

In some embodiments of formula (IVa):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and R$^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$).

In some embodiments of formula (IVa):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and R$^1$ is —H, —F, —Cl, —CH$_3$ or —CF$_3$.

In some embodiments of formula (IVa):
X is —F, —Cl, —CH$_3$, —CH$_2$CH$_3$, —CF$_3$, —CHF$_2$, —CH$_2$F, cyclopropyl, —OCF$_3$, —OCHF$_2$; and R$^1$ is —H or —F.

In some embodiments, a chemical entity of formula (I) is a chemical entity of formula (IVb):

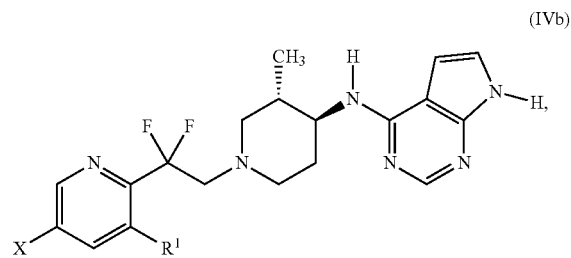

(IVb)

wherein each of R$^1$ and X is as described in embodiments for formula (I), supra, or described in embodiments herein, both singly and in combination.

In some embodiments of formula (IVb):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and R$^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$).

In some embodiments of formula (IVb):
X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and R$^1$ is —H, —F, —Cl, —CH$_3$ or —CF$_3$.

In some embodiments of formula (IVb):
X is —F, —Cl, —CH$_3$, —CH$_2$CH$_3$, —CF$_3$, —CHF$_2$, —CH$_2$F, cyclopropyl, —OCF$_3$, —OCHF$_2$; and R$^1$ is —H or —F.

In some embodiments, a chemical entity of formula (I) is a chemical entity of formula (V):

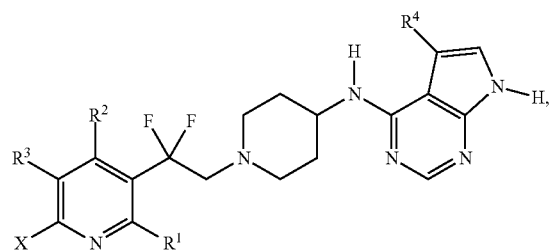

(V)

wherein each of R$^1$, R$^2$, X, R$^3$ and R$^4$ is as described in embodiments of formula (I), supra, or described in embodiments herein, both singly and in combination.

In some embodiments of formula (V):
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;

R$^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);

R$^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$;

R³ is —H, —F, —Cl, —CH₃, —CF₃ or —OCH₃; and
R⁴ is —H, —F, —Cl, —CH₃ or cyclopropyl. In some embodiments of formula (V):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃;
R¹ is —H, —F, —Cl, —CH₃ or —CF₃;
R² is —H, —F, —Cl, —CH₃ or —CF₃;
R³ is —H, —F, —Cl, —CH₃ or —CF₃; and
R⁴ is —H, —Cl or —CH₃.

In some embodiments of formula (V):
X is —H, —CH₃ or —CF₃;
R¹ is —H, —F or —CF₃;
R² is —H;
R³ is —H or —CF₃; and
R⁴ is —Cl or —CH₃.

In some embodiments, a chemical entity of formula (I) is a chemical entity of formula (Va):

(Va)

wherein each of R² and X is as described in embodiments of formula (I), supra, or described in embodiments herein, both singly and in combination.

In some embodiments of formula (Va):
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃; and
R² is —H, —F, —Cl, —CH₃, —CH₂CH₃, —CH(CH₃)₂, —CF₃, cyclopropyl, —OCH₃, —OCF₃, —OCHF₂ or —OCFH₂.

In some embodiments of formula (Va):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃; and
R² is —H, —F, —Cl, —CH₃ or —CF₃.

In some embodiments of formula (Va):
X is —H, —F, —Cl, —CH₃, —CH₂CH₃, —CF₃, cyclopropyl, —OCH₃, —OCF₃ or —SCH₃; and
R² is —H, —F or —CF₃.

In some embodiments, a chemical entity of formula (I) is a chemical entity of formula (VI):

(VI)

wherein each of R¹, R², X and R³ is as described in embodiments of formula (I), supra, or described in embodiments herein, both singly and in combination.

In some embodiments of formula (VI):
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃;
R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);
R² is —H, —F, —Cl, —CH₃, —CH₂CH₃, —CH(CH₃)₂, —CF₃, cyclopropyl, —OCH₃, —OCF₃, —OCHF₂ or —OCFH₂; and
R³ is —H, —F, —Cl, —CH₃, —CF₃ or —OCH₃.

In some embodiments of formula (VI):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃;
R¹ is —H, —F, —Cl, —CH₃ or —CF₃;
R² is —H, —F, —Cl, —CH3 or —CF₃; and
R³ is —H, —F, —Cl, —CH₃ or —CF₃.

In some embodiments, a chemical entity of formula (I) is a chemical entity of formula (VIa):

(VIa)

wherein each of R² and X is as described in embodiments for formula (I), supra, or described in embodiments herein, both singly and in combination.

In some embodiments of formula (VIa):
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃; and
R² is —H, —F, —Cl, —CH₃, —CH₂CH₃, —CH(CH₃)₂, —CF₃, cyclopropyl, —OCH₃, —OCF₃, —OCHF₂ or —OCFH₂.

In some embodiments of formula (VIa):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃; and
R² is —H, —F, —Cl, —CH₃ or —CF₃.

In some embodiments of formula (VIa):
X is —CH₃, —CH₂CH₃, —CF₃, cyclopropyl, —OCH₃, —OCF₃ or —SCH₃; and
R² is —H. In some embodiments, a chemical entity of formula (I) is a chemical entity of formula (VIb):

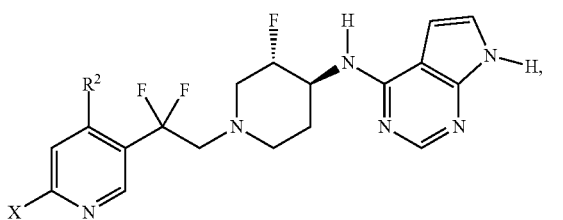

(VIb)

wherein each of R² and X is as described in embodiments for formula (I), supra, or described in embodiments herein, both singly and in combination.

In some embodiments of formula (VIb):
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃; and
R² is —H, —F, —Cl, —CH₃, —CH₂CH₃, —CH(CH₃)₂, —CF₃, cyclopropyl, —OCH₃, —OCF₃, —OCHF₂ or —OCFH₂.

In some embodiments of formula (VIb):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃; and
R² is —H, —F, —Cl, —CH₃ or —CF₃.

In some embodiments of formula (VIb):
X is —CH₃, —CH₂CH₃, —CF₃, cyclopropyl, —OCH₃, —OCF₃ or —SCH₃; and
R² is —H.

In some embodiments, a chemical entity of formula (I) is a chemical entity of formula (VII):

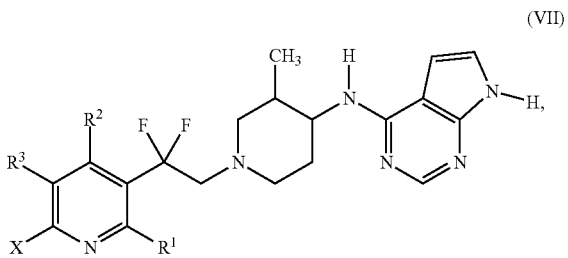

(VII)

wherein each of R¹, R², X and R³ is as described in embodiments of formula (I), supra, or described in embodiments herein, both singly and in combination.

In some embodiments of formula (VII):
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃;
R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);
R² is —H, —F, —Cl, —CH₃, —CH₂CH₃, —CH(CH₃)₂, —CF₃, cyclopropyl, —OCH₃, —OCF₃, —OCHF₂ or —OCFH₂; and
R³ is —H, —F, —Cl, —CH₃, —CF₃ or —OCH₃.

In some embodiments of formula (VII):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃;
R¹ is —H, —F, —Cl, —CH₃ or —CF₃;
R² is —H, —F, —Cl, —CH3 or —CF₃; and
R³ is —H, —F, —Cl, —CH₃ or —CF₃.

In some embodiments, a chemical entity of formula (I) is a chemical entity of formula (VIIa):

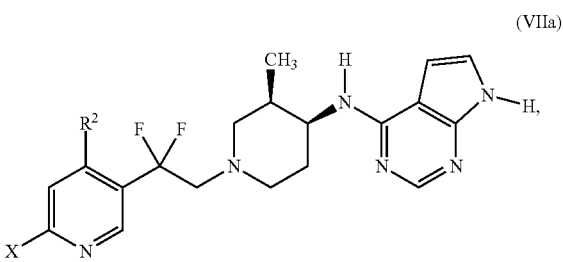

(VIIa)

wherein each of R² and X is as described in embodiments for formula (I), supra, or described in embodiments herein, both singly and in combination.

In some embodiments of formula (VIIa):
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃; and
R² is —H, —F, —Cl, —CH₃, —CH₂CH₃, —CH(CH₃)₂, —CF₃, cyclopropyl, —OCH₃, —OCF₃, —OCHF₂ or —OCFH₂.

In some embodiments of formula (VIIa):
X is —H, —F, —Cl, —CH₃, —CH₂CH₃, —CH(CH₃)₂, —CF₃, —CHF₂, —CH₂F, cyclopropyl, —OCH₃, —OCF₃, —OCHF₂, —CN or —SCH₃; and
R² is —H, —F, —Cl, —CH₃ or —CF₃.

In some embodiments of formula (VIIa):
X is —CH₃, —CH₂CH₃, —CF₃, cyclopropyl, —OCH₃, —OCF₃ or —SCH₃; and
R² is —H.

In some embodiments, a chemical entity of formula (I) is a chemical entity of formula (VIIb):

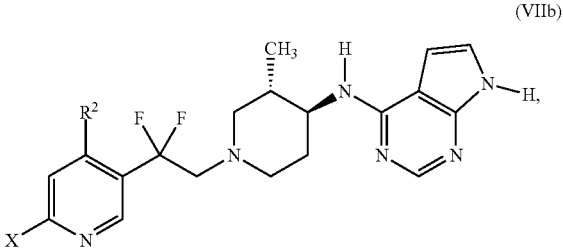

(VIIb)

wherein each of R² and X is as described in embodiments for formula (I), supra, or described in embodiments herein, both singly and in combination.

In some embodiments of formula (VIIb),
X is —H, —F, —Cl, —CH₃, —CH₂CH₃, —CH(CH₃)₂, —CF₃, —CHF₂, —CH₂F, —CF₂CF₃, —CH₂CF₂CF₃, —CH(CF₃)₂, cyclopropyl, —OCH₃, —OCF₃, —OCHF₂, —OCFH₂, —CN, —NO₂, —N(CH₃)₂, —SCH₃, —SO₂CH₃ or —SO₂CF₃; and $R^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$.

In some embodiments of formula (VIIb):

X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and $R^2$ is —H, —F, —Cl, —CH$_3$ or —CF$_3$.

In some embodiments of formula (VIIb):

X is —CH$_3$, —CH$_2$CH$_3$, —CF$_3$, cyclopropyl, —OCH$_3$, —OCF$_3$ or —SCH$_3$; and $R^2$ is —H.

In some embodiments, a chemical entity of formula (I) is a chemical entity of formula (VIII):

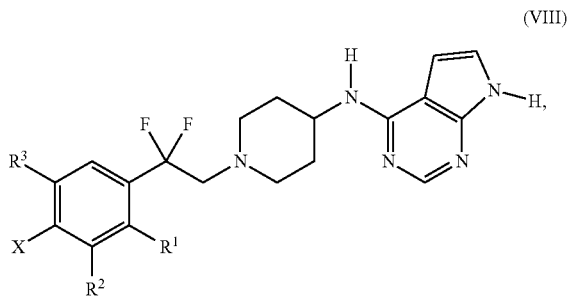

(VIII)

wherein each of $R^1$, $R^2$, X and $R^3$ is as described in embodiments of formula (I), supra, or described in embodiments herein, both singly and in combination.

In some embodiments of formula (VIII):

X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;

$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);

$R^2$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and $R^3$ is —H, —F, —Cl, —CH$_3$, —CF$_3$ or —OCH$_3$.

In some embodiments of formula (VIII):

X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$;

$R^1$ is —H, —F, —Cl, —CH$_3$ or —CF$_3$;

$R^2$ is —H, —F, —Cl, —CH$_3$ or —CF$_3$; and $R^3$ is —H, —F, —Cl, —CH$_3$ or —CF$_3$.

In some embodiments of formula (VIII):

X is —F, —Cl, —CH$_3$ or —CF$_3$;

$R^1$ is —H;

$R^2$ is —H, —F, —Cl or —CH$_3$; and $R^3$ is —H, —F, —Cl or —CH$_3$.

In some embodiments, a chemical entity of formula (I) is a chemical entity of formula (VIIIa):

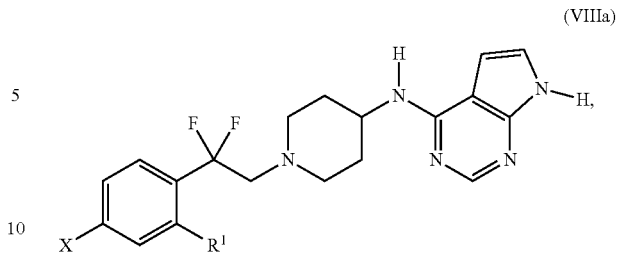

(VIIIa)

wherein each of $R^1$ and X is as described in embodiments of formula (I), supra, or described in embodiments herein, both singly and in combination.

In some embodiments of formula (VIIIa):

X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and $R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$).

In some embodiments of formula (VIIIa):

X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and $R^1$ is —H, —F, —Cl, —CH$_3$ or —CF$_3$.

In some embodiments of formula (VIIIa):

X is —H, —F, —Cl, —CH$_3$, —CH$_2$CH$_3$, —CF$_3$, —CHF$_2$, —CH$_2$F, cyclopropyl, —OCH$_3$, —OCF$_3$, —OCHF$_2$, —CN or —SCH$_3$; and $R^1$ is —H, —F, —Cl or —CH$_3$.

In some embodiments, a chemical entity of formula (I) is a chemical entity of formula (IX):

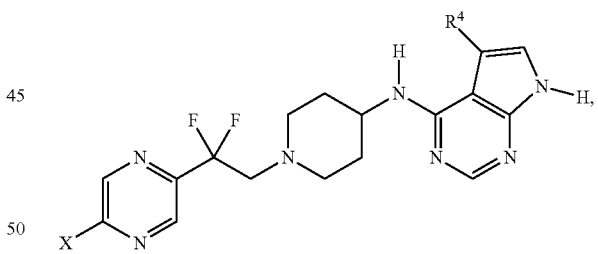

(IX)

wherein each of X and $R^4$ is as described in embodiments of formula (I), supra, or described in embodiments herein, both singly and in combination.

In some embodiments of formula (IX):

X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$; and $R^4$ is —H, —F, —Cl, —CH$_3$ or cyclopropyl.

In some embodiments of formula (IX):

X is —H, —F, —Cl, —CH$_3$, —CH$_2$CH$_3$, —CH(CH$_3$)$_2$, —CF$_3$, —CHF$_2$, —CH$_2$F, cyclopropyl, —OCH$_3$, —OCF$_3$, —OCHF$_2$, —CN or —SCH$_3$; and $R^4$ is —H, —Cl or —CH$_3$.

In some embodiments of formula (IX):
X is —F, —Cl, —CH₃, —CH₂CH₃, —CH(CH₃)₂, —CF₃, —CHF₂, cyclopropyl, —OCF₃ or —OCHF₂; and
R⁴ is —H or —CH₃.

Exemplary chemical entities of formula I are shown in Tables 1.C to 11.C, below.

TABLE 1.C

| compound | X | R¹ |
|---|---|---|
| C-1 | H | H |
| C-2 | F | H |
| C-3 | Cl | H |
| C-4 | CH₃ | H |
| C-5 | CF₃ | H |
| C-6 | CF₂H | H |
| C-7 | CH₂F | H |
| C-8 | CH₂CH₃ | H |
| C-9 | cyclopropyl | H |
| C-10 | CH₃O | H |
| C-11 | CF₃O | H |
| C-12 | CHF₂O | H |
| C-13 | SCH₃ | H |
| C-14 | CN | H |
| C-15 | F | F |
| C-16 | Cl | F |
| C-17 | CH₃ | F |
| C-18 | CF₃ | F |
| C-19 | CF₂H | F |
| C-20 | CH₂F | F |
| C-21 | CH₂CH₃ | F |
| C-22 | cyclopropyl | F |
| C-23 | F | Cl |
| C-24 | Cl | Cl |
| C-25 | CH₃ | Cl |
| C-26 | CF₃ | Cl |
| C-27 | cyclopropyl | Cl |
| C-28 | F | CH₃ |
| C-29 | Cl | CH₃ |
| C-30 | CH₃ | CH₃ |
| C-31 | CF₃ | CH₃ |
| C-32 | cyclopropyl | CH₃ |

TABLE 2.C

| compound | X | R¹ | R⁴ | R⁵ |
|---|---|---|---|---|
| C-33 | CF₃ | H | CH₃ | H |
| C-34 | Cl | H | CH₃ | H |
| C-35 | CH₃ | H | CH₃ | H |
| C-36 | CF₃ | H | Cl | H |
| C-37 | Cl | H | Cl | H |
| C-38 | CH₃ | H | Cl | H |
| C-39 | CF₃ | F | CH₃ | H |
| C-40 | Cl | F | CH₃ | H |
| C-41 | CH₃ | F | CH₃ | H |
| C-42 | CF₃ | F | Cl | H |
| C-43 | Cl | F | Cl | H |
| C-44 | CH₃ | F | Cl | H |
| C-45 | CF₃ | H | H | CH₃ |
| C-46 | Cl | H | H | CH₃ |
| C-47 | CH₃ | H | H | CH₃ |

TABLE 3.C

| compound | X | R² | R³ |
|---|---|---|---|
| C-48 | F | F | H |
| C-49 | Cl | F | H |
| C-50 | CH₃ | F | H |
| C-51 | CF₃ | F | H |
| C-52 | F | CH₃ | H |
| C-53 | Cl | CH₃ | H |
| C-54 | CH₃ | CH₃ | H |
| C-55 | CF₃ | CH₃ | H |
| C-56 | F | Cl | H |
| C-57 | Cl | Cl | H |
| C-58 | CH₃ | Cl | H |
| C-59 | CF₃ | Cl | F |
| C-60 | F | H | F |
| C-61 | Cl | H | F |
| C-62 | CH₃ | H | F |
| C-63 | CF₃ | H | Cl |
| C-64 | F | H | Cl |
| C-65 | Cl | H | Cl |
| C-66 | CH₃ | H | Cl |
| C-67 | CF₃ | H | CH₃ |
| C-68 | F | H | CH₃ |
| C-69 | Cl | H | CH₃ |
| C-70 | CH₃ | H | CH₃ |

TABLE 4.C

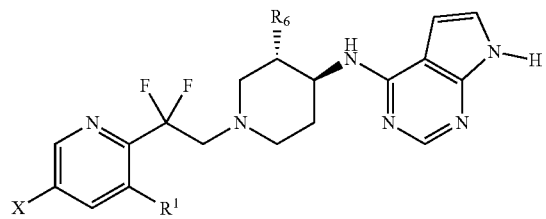

| compound | X | R¹ | R⁶ |
|---|---|---|---|
| C-71 | F | H | CH₃ |
| C-72 | Cl | H | CH₃ |
| C-73 | CH₃ | H | CH₃ |
| C-74 | CF₃ | H | CH₃ |
| C-75 | CF₂H | H | CH₃ |
| C-76 | CH₂F | H | CH₃ |
| C-77 | OCF₃ | H | CH₃ |
| C-78 | OCF₂H | H | CH₃ |
| C-79 | CH₂CH₃ | H | CH₃ |
| C-80 | cyclopropyl | H | CH₃ |
| C-81 | F | H | F |
| C-82 | Cl | H | F |
| C-83 | CH₃ | H | F |
| C-84 | CF₃ | H | F |
| C-85 | CF₂H | H | F |
| C-86 | CH₂F | H | F |
| C-87 | OCF₃ | H | F |
| C-88 | OCF₂H | H | F |
| C-89 | CH₂CH₃ | H | F |
| C-90 | cyclopropyl | H | F |
| C-91 | F | F | CH₃ |
| C-92 | Cl | F | CH₃ |
| C-93 | CH₃ | F | CH₃ |
| C-94 | CF₃ | F | CH₃ |
| C-95 | F | F | F |
| C-96 | Cl | F | F |
| C-97 | CH₃ | F | F |
| C-98 | CF₃ | F | F |

TABLE 5.C

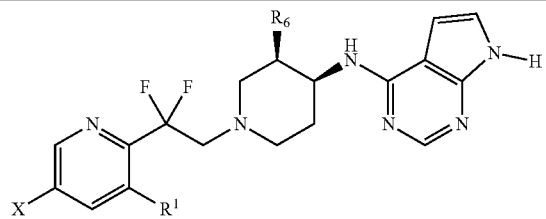

| compound | X | R¹ | R⁶ |
|---|---|---|---|
| C-99 | F | H | CH₃ |
| C-100 | Cl | H | CH₃ |
| C-101 | CH₃ | H | CH₃ |
| C-102 | CF₃ | H | CH₃ |
| C-103 | CF₂H | H | CH₃ |
| C-104 | CH₂F | H | CH₃ |
| C-105 | OCF₃ | H | CH₃ |
| C-106 | OCF₂H | H | CH₃ |
| C-107 | CH₂CH₃ | H | CH₃ |
| C-108 | cyclopropyl | H | CH₃ |
| C-109 | F | H | F |
| C-110 | Cl | H | F |
| C-111 | CH₃ | H | F |
| C-112 | CF₃ | H | F |
| C-113 | CF₂H | H | F |
| C-114 | CH₂F | H | F |
| C-115 | OCF₃ | H | F |
| C-116 | OCF₂H | H | F |
| C-117 | CH₂CH₃ | H | F |
| C-118 | cyclopropyl | H | F |

TABLE 5.C-continued

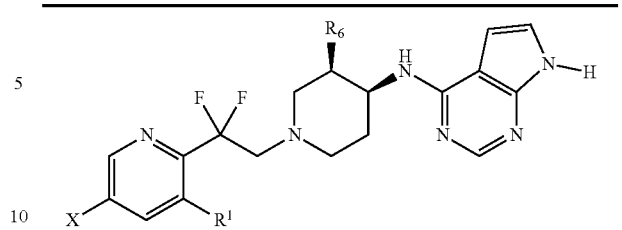

| compound | X | R¹ | R⁶ |
|---|---|---|---|
| C-119 | F | F | CH₃ |
| C-120 | Cl | F | CH₃ |
| C-121 | CH₃ | F | CH₃ |
| C-122 | CF₃ | F | CH₃ |
| C-123 | F | F | F |
| C-124 | Cl | F | F |
| C-125 | CH₃ | F | F |
| C-126 | CF₃ | F | F |

TABLE 6.C

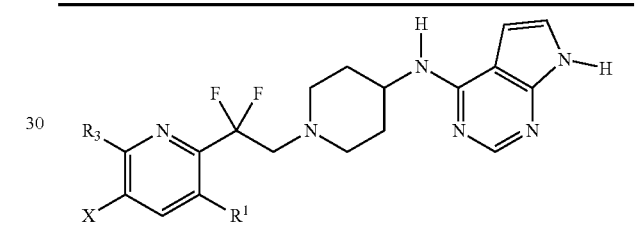

| compound | X | R¹ | R² | R³ |
|---|---|---|---|---|
| C-127 | CF₃ | H | H | H |
| C-128 | CH₃ | H | H | H |
| C-129 | F | H | H | H |
| C-130 | Cl | H | H | H |
| C-131 | OCH₃ | H | H | H |
| C-132 | OCF₃ | H | H | H |
| C-133 | SCH₃ | H | H | H |
| C-134 | CH₂CH₃ | H | H | H |
| C-135 | cyclopropyl | H | H | H |
| C-136 | CF₃ | F | H | H |
| C-137 | CF₃ | H | F | H |
| C-138 | CF₃ | H | H | F |
| C-139 | H | CF₃ | H | H |
| C-140 | H | H | CF₃ | H |
| C-141 | H | H | H | CF₃ |

TABLE 7.C

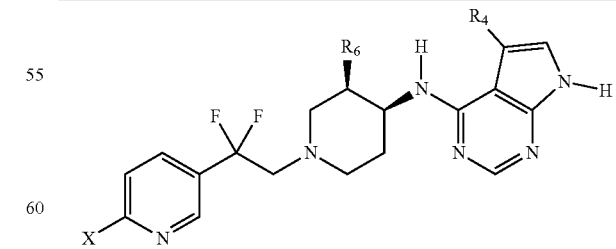

| compound | X | R⁴ | R⁶ |
|---|---|---|---|
| C-142 | CF₃ | CH₃ | H |
| C-143 | CH₃ | CH₃ | H |
| C-144 | CF₃ | H | F |

TABLE 7.C-continued

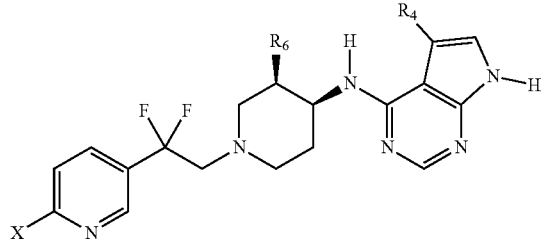

| compound | X | R⁴ | R⁶ |
|---|---|---|---|
| C-145 | CH₃ | H | F |
| C-146 | CH₂CH₃ | H | F |
| C-147 | SCH₃ | H | F |
| C-148 | cyclopropyl | H | F |
| C-149 | OCF₃ | H | F |
| C-150 | OCH₃ | H | F |
| C-151 | CF₃ | H | CH₃ |
| C-152 | CH₃ | H | CH₃ |
| C-153 | CH₂CH₃ | H | CH₃ |
| C-154 | SCH₃ | H | CH₃ |
| C-155 | cyclopropyl | H | CH₃ |
| C-156 | OCF₃ | H | CH₃ |
| C-157 | OCH₃ | H | CH₃ |

TABLE 8.C

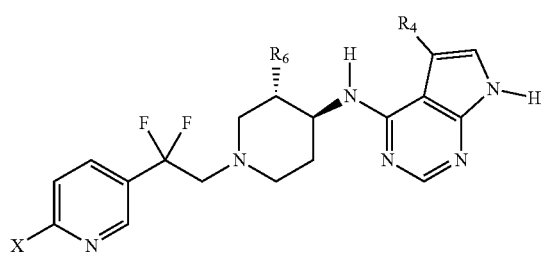

| compound | X | R⁴ | R⁶ |
|---|---|---|---|
| C-158 | CF₃ | Cl | H |
| C-159 | CH₃ | Cl | H |
| C-160 | CF₃ | H | F |
| C-161 | CH₃ | H | F |
| C-162 | CH₂CH₃ | H | F |
| C-163 | SCH₃ | H | F |
| C-164 | cyclopropyl | H | F |
| C-165 | OCF₃ | H | F |
| C-166 | OCH₃ | H | F |
| C-167 | CF₃ | H | CH₃ |
| C-168 | CH₃ | H | CH₃ |
| C-169 | CH₂CH₃ | H | CH₃ |
| C-170 | SCH₃ | H | CH₃ |
| C-171 | cyclopropyl | H | CH₃ |
| C-172 | OCF₃ | H | CH₃ |
| C-173 | OCH₃ | H | CH₃ |

TABLE 9.C

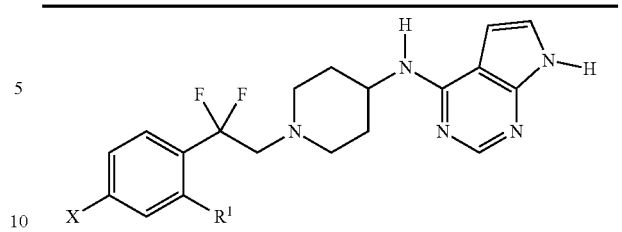

| compound | X | R¹ |
|---|---|---|
| C-174 | H | H |
| C-175 | F | H |
| C-176 | Cl | H |
| C-177 | CH₃ | H |
| C-178 | CF₃ | H |
| C-179 | CF₂H | H |
| C-180 | CH₂F | H |
| C-181 | CH₂CH₃ | H |
| C-182 | cyclopropyl | H |
| C-183 | CH₃O | H |
| C-184 | CF₃O | H |
| C-185 | CHF₂O | H |
| C-186 | SCH₃ | H |
| C-187 | CN | H |
| C-188 | F | F |
| C-189 | Cl | F |
| C-190 | CH₃ | F |
| C-191 | CF₃ | F |
| C-192 | CF₂H | F |
| C-193 | CH₂F | F |
| C-194 | CH₂CH₃ | F |
| C-195 | cyclopropyl | F |
| C-196 | F | Cl |
| C-197 | Cl | Cl |
| C-198 | CH₃ | Cl |
| C-199 | CF₃ | Cl |
| C-200 | cyclopropyl | Cl |
| C-201 | F | CH₃ |
| C-202 | Cl | CH₃ |
| C-203 | CH₃ | CH₃ |
| C-204 | CF₃ | CH₃ |
| C-205 | cyclopropyl | CH₃ |

TABLE 10.C

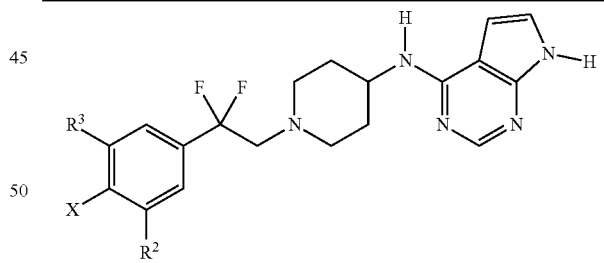

| compound | X | R² | R³ |
|---|---|---|---|
| C-206 | F | F | H |
| C-207 | Cl | F | H |
| C-208 | CH₃ | F | H |
| C-209 | CF₃ | F | H |
| C-210 | F | CH₃ | H |
| C-211 | Cl | CH₃ | H |
| C-212 | CH₃ | CH₃ | H |
| C-213 | CF₃ | CH₃ | H |
| C-214 | F | Cl | H |
| C-215 | Cl | Cl | H |
| C-216 | CH₃ | Cl | H |
| C-217 | CF₃ | Cl | F |
| C-218 | F | H | F |
| C-219 | Cl | H | F |

TABLE 10.C-continued

| compound | X | R² | R³ |
|---|---|---|---|
| C-220 | CH₃ | H | F |
| C-221 | CF₃ | H | Cl |
| C-222 | F | H | Cl |
| C-223 | Cl | H | Cl |
| C-224 | CH₃ | H | Cl |
| C-225 | CF₃ | H | CH₃ |
| C-226 | F | H | CH₃ |
| C-227 | Cl | H | CH₃ |
| C-228 | CH₃ | H | CH₃ |

TABLE 11.C

| compound | X | R⁴ |
|---|---|---|
| C-229 | CF₃ | H |
| C-230 | CH₃ | H |
| C-231 | Cl | H |
| C-232 | F | H |
| C-233 | CF₂H | H |
| C-234 | OCF₃ | H |
| C-235 | OCF₂H | H |
| C-236 | CH₂CH₃ | H |
| C-237 | cyclopropyl | H |
| C-238 | isopropyl | H |
| C-239 | CF₃ | CH₃ |
| C-240 | CH₃ | CH₃ |
| C-241 | CH₂CH₃ | CH₃ |
| C-242 | cyclopropyl | CH₃ |
| C-243 | isopropyl | CH₃ |
| C-244 | OCF₃ | CH₃ |

Pharmacology

Glutamate (GLU) is a fundamental excitatory neurotransmitter in the mammalian brain and central nervous system (CNS). The effects of this endogenous neurotransmitter are mediated through binding to and activation of GLU to glutamate receptors (GLURs), which are broadly classified into metabotropic G-protein coupled (mGluRs) and ligand gated ion channels or ionotropic GluRs. The ionotropic GLURs are pharmacologically classified into three main types based on the actions of selective receptor agonists: NMDA (N-methyl D-aspartate selective), KA (kainic acid selective) and AMPA (α-amino-3-hydroxy-5-methyl-4-isoxazolepropionic acid) receptors whose structure and pharmacological function has been recently reviewed in detail (S. F. Traynelis et al. *Pharmacology Reviews*, 2010, 62, 405-496). Electrophysiology studies have demonstrated NMDARs to be cation ion channels that are subject to voltage-dependent channel block by endogenous $Mg^{2+}$. Activation of NMDARs by glutamate in the presence of glycine as a co-agonist results in opening of the receptor ion channel. This in turn allows for the flow of $Na^+$ and $Ca^{2+}$ into the cell generating excitatory postsynaptic potentials (EPSPs) and $Ca^{2+}$ activated second messenger signaling pathways in neurons. By virtue of their permeability to $Ca^{2+}$, activation of NMDA receptors regulates long-term changes in neuronal communication such as learning and memory and synaptic plasticity.

Since the original pharmacological characterization with selective ligands, molecular biology and cloning studies have enabled detailed characterization of NMDARs at the molecular level (Paoletti et al., 2013, *Nat. Rev. Neurosci.* 14:383-400). Thus, NMDARs are heterotetramers comprised of two NR1 subunits and two NR2 subunits. NR1 subunits contain the binding site for the glycine co-agonist while NR2 subunits contain the binding site for glutamate. The existence of multiple splice variants for NR1 and four isoforms of NR2 (NR2A, NR2B, NR2C and NR2D) from different genes results in a diverse molecular array and of NMDARs. The pharmacological and electrophysiological properties of NMDARs vary depending on the particular NR1 isoform and NR2 subtype composition. Furthermore, the NR2 subtype isoforms are differentially expressed across cell types and brain regions. Thus, compounds that interact selectivity with NR2 subunits can exert specific pharmacological effects in particular brain regions and have potential to treat CNS diseases with a high degree of specificity and selectivity (e.g. vz side effects). For example the low expression of the NR2B subtype in the cerebellum relative to other brain structures (Cull-Candy et al., 1998, *Neuropharmacol.* 37:1369-1380) indicated lower motor side effects for this subtype.

NMDA receptor antagonism has been extensively investigated for its potential to treat a variety of CNS diseases including stroke, epilepsy, pain, depression Parkinson's Disease and Alzheimer's disease (Paoletti et al., Nat. Rev. Neurosci 14:383-400; Sancora, 2008, *Nature Rev. Drug Disc.*, 7, 426-437). The NMDA receptor offers a number of pharmacological entry points for developing receptor inhibitors. Direct blockers of the NMDAR ion channel pore represent one family of antagonist compounds for which efficacy could be demonstrated in diverse in vitro and in vivo CNS disease models including, epilepsy, pain and neurodegeneration/stroke. However, compounds from this class, as exemplified by phencyclidine (PCP), MK-801, and ketamine, are generally categorized as unselective across the diversity of NMDA receptor subtypes.

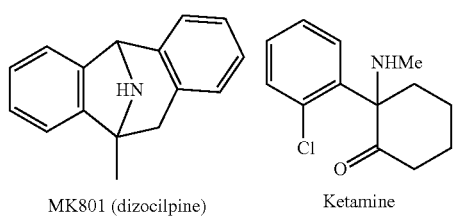

MK801 (dizocilpine)    Ketamine

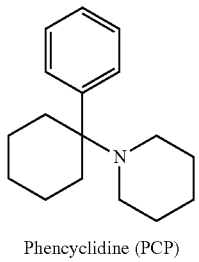

Phencyclidine (PCP)

In humans unselective, high-affinity NMDAR antagonists have generally been associated with serious clinical side effects including hallucinations, dysphoria and lack of coordination. Nevertheless, ketamine, an intravenous drug originally approved for use in anesthesia (Haas et. al, 1992, *Anesthesia Prog.*, 39, 61-68) has more recently demonstrated clinical efficacy as an antidepressant therapy (Katalinic et al. 2013, *Aust. N. Z. J. Psychiatry*, 47, 710-727). The antidepressant action of acute ketamine therapy has an essentially immediate onset compared to approximately six weeks required for standard serotonin reuptake inhibitor (SSRI) drug therapy. Thus, intravenous administration of the drug has shown rapid onset and prolonged efficacy that can be maintained with continued intermittent administrations (Zarate et al., 2006, *Arch. Gen. Psychiatry* 63, 856-864). Finally, ketamine has been shown to be effective in cases of depression resistant to standard drug therapies (Murrough et al., 2013, *American J. Psychiatry*, 170, 1134-1142) including bipolar depression (Zarate et al. 2012, *Biol. Psychiatry*, 71, 939-946). However, as an intravenous drug with serious side effects (Gianni et. al 1985, *Psychiatric Medicine*, 3, 197-217; Curran et al 2000, *Addiction*, 95, 575-590) and potential chronic toxicity (Hardy et al., 2012, *J. Clin. Oncol.* 30:3611-3617; Noppers et al., 2011, *Pain* 152:2173-2178) ketamine therapy is of limited utility and restricted to acute or intermittent administration. To have broader scope of application and utility as a therapy for depression and other CNS diseases, orally active selective NMDA antagonists with reduced side effects are needed that can be administered chronically.

Ifenprodil, a vasodilator $\alpha_1$-adrenergic antagonist drug, was determined to have a novel allosteric modulator mechanism of action at the NR2B NMDA receptor subtype (Reynolds et al. 1989, *Mol. Pharmacol.*, 36, 758-765). This new mechanism held promise for a new class of NMDA antagonist drugs having therapeutic efficacy without the limiting side effects of subtype unselective ion channel blockers. Following this discovery, NR2B selective antagonist analogs of ifenprodil (Borza et al., 2006, *Current Topics in Medicinal Chemistry*, 6, 687-695; Layton et al. *Current Topics in Medicinal Chemistry*, 6, 697-709) optimized against the undesirable $\alpha_1$-adrenergic activity included Ro-25,6981 (Fischer et al. 1997, *J. Pharmacol. Exp. Ther.*, 283, 1285-1292) and CP-101,606 otherwise known as traxoprodil (Chenard et al. 1995, *Journal of Medicinal Chemistry*, 38, 3138-3145; Menniti et al. 1998, *CNS Drug Reviews.*, 4, 307-322). In a clinical study, CP-101,606 evidenced antidepressant activity in humans after intravenous administration with a favorable dissociative side effect profile relative to unselective NMDA antagonists (Preskorn et al. 2008, *Journal of Clinical Psychopharmacology*, 28, 631-637). However, CP-101,606 has suboptimal pharmacokinetic properties and requires limiting intravenous administration. For CP-101,606 a slow intravenous infusion protocol was required for optimal results in the aforementioned antidepressant clinical study (Preskorn et al. 2008, *Journal of Clinical Psychopharmacology*, 28, 631-637).

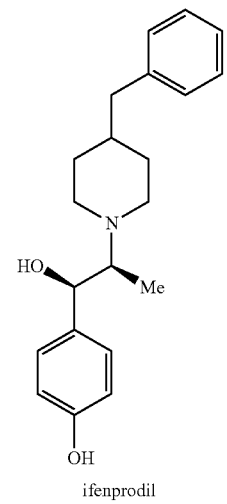

ifenprodil

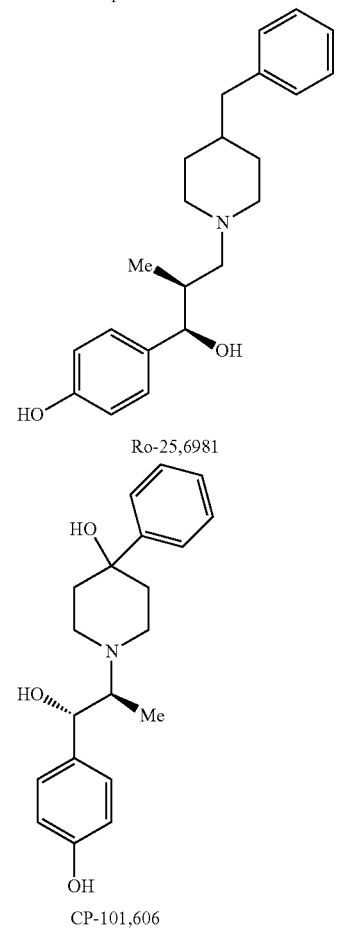

Ro-25,6981

CP-101,606

Other NR2B antagonists which have been described as reviewed by B. Ruppa et al. (K. B. Ruppa et al., *Annual Reports in Medicinal Chemistry* 2012, 47:89-103) include MK0657 (J. A. McCauley et al., 3rd *Anglo-Swedish Medicinal Chemistry Symposium*, Åre, Sweden, Mar. 11-14, 2007; L. Mony et al., *British J. of Pharmacology* 2009, 157:1301-1317; see also Intl. Appl. Publ. No. WO 2004/108705; U.S.

Pat. No. 7,592,360) and compounds of formula LX (Intl. Appl. Publ. No. WO 2006/113471), below, including the specific analog LX-1 depicted below.

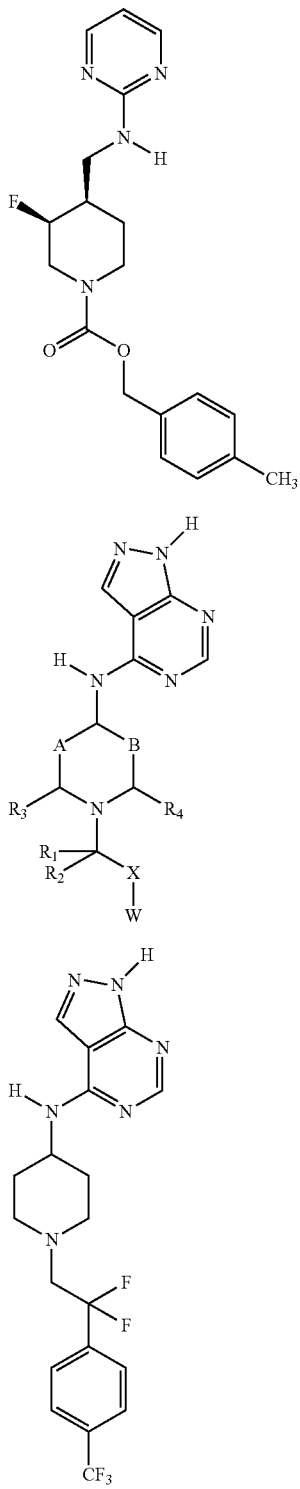

The difficulties presented by NR2B antagonists having basic amine moieties with regard to overcoming hERG and CYP2D6 safety liabilities while maintaining NR2B in vitro and in vivo potency are well established as noted by Kawai et al. (M. Kawai et al., *Bioorganic and Medicinal Chem. Lett.* 2007, v17:5533-5536) and Brown et al. (Brown et al., *Bioorganic and Medicinal Chem. Lett.* 2011, v21:3399-3403). Compound inhibition of hERG channels and associated QT prolongation in the electrocardiograph (ECG) represents a well recognized serious human cardiovascular safety risk (Hancox et al., *Molecular Pharmacology* 2008, 73:1592-1595). QT prolongation can lead to torsades de pointes (TdP) cardiac arrhythmia which can degenerate into ventricular tachycardia and sudden death.

Compound inhibition of human metabolic cytochrome P-450 enzymes including CYP2D6 represents a risk with regard to human drug safety due to drug-drug interactions (*Drug Metabolism Handbook: Concepts and Applications*, ed. Ala F. Nassar copyright 2009 Wiley & Sons, Hoboken, N.J.). Thus, the clearance of drugs that are substrates of CYP2D6 can be reduced by compounds that inhibit CYP2D6. The result can be toxic or side effect overload due to accumulation of the given CYP2D6 drug substrate. CNS drugs including antidepressant drugs feature prominently among the established CYP2D6 substrates. Therefore, CYP2D6 inhibition is highly undesirable for an NR2B antagonist drug especially given the common application of comedications or polypharmacy in CNS indications including depression. Examples of CY2D6 substrates include antidepressants from the SSRI class such as fluoxetine, paroxetine, and fluvoxamine, duloxetine, an antidepressants from the SSNI class, numerous antipsychotics including haloperidol, risperidone and aripiperazole, numerous beta-blocker antihypertensives including metaprolol, propranolol, timolol and alprenolol and the Alzheimer's disease anticholinesterase inhibitor drug donepezil (Flockhart D A (2007). "Drug Interactions: Cytochrome P450 Drug Interaction Table", Indiana University School of Medicine, accessed at <<http://medicine.iupui.edu/clinpharm/ddis/>> on May 28, 2014).

MK0657 and closely related analogs (Liverton et al., *J. Med. Chem.* 2007, v50:807-819) represent an improved generation of NR2B antagonists with respect to human oral bioavailability. However, drug-related systolic as well as diastolic blood pressure elevation cardiovascular side effect for MK0657 after oral dosing have been described in a published clinical efficacy trial study in patients with Parkinson's Disease (Addy et al., *J. Clin. Pharm.* 2009, v49: 856-864). Similar blood pressure effects were reported to have also been observed after single doses of MK0657 in safety studies with healthy elderly subjects. Compound LX-1 demonstrates oral bioavailability in animals and lacks a phenolic group which can compromise oral bioavailability in humans. However, as noted herein, compound LX-1, which has a basic piperidine nitrogen atom, exhibits human hERG channel inhibition with an $IC_{50}$<10 μM (~4.5 μM), and exhibits human CYP2D6 metabolic enzyme inhibition activity ($IC_{50}$~1.0 μM).

For broad scope of application and safe human use, improved NR2B selective antagonists are needed, as noted in a recent review (K. B. Ruppa et al., *Annual Reports in Medicinal Chemistry* 2012, 47:89-103). There is a need for NR2B antagonist compounds which are improved in one or more aspects exemplified by pharmacokinetic, absorption, metabolism, excretion (ADME, e.g., oral activity), improved efficacy, off-target activity, improved therapeutic safety index relative and compatibility with chronic oral therapy.

Provided chemical entities are antagonists of the NR2B receptor and have technical advantages with regard to one or more pharmaceutical drug properties, such as oral bioavailability, pharmacokinetic parameters, ADME properties (e.g., CYP inhibition), cardiac ion channel (e.g., hERG) activity and other non-NMDA off-target side effect mediating receptors. In some embodiments, the present invention encompasses the discovery that a provided chemical entity can exhibit low human CYP2D6 inhibition and/or low hERG inhibition while exhibiting potent human NR2B receptor inhibition antagonism, and as such is favorable for application in humans.

In some embodiments, a provided chemical entity has NR2B functional NMDA receptor selectivity versus NR2A ("NR2B selectivity", determined as the ratio NR2A $IC_{50}$/NR2B $IC_{50}$, in which the $IC_{50}$ values are measured according to the procedure of Example 2.1) ≥300. In some embodiments, a provided chemical entity has NR2B selectivity ≥250. In some embodiments, a provided chemical entity has NR2B selectivity ≥200. In some embodiments, a provided chemical entity has NR2B selectivity ≥150. In some embodiments, a provided chemical entity has NR2B selectivity ≥100. In some embodiments, a provided chemical entity has NR2B selectivity ≥50.

In some embodiments, a provided chemical entity has hERG activity (determined as hERG $IC_{50}$ measured according to the procedure of Example 2.2) ≥5 μM. In some embodiments, a provided chemical entity has hERG $IC_{50}$≥10 μM. In some embodiments, a provided chemical entity has hERG $IC_{50}$≥15 μM. In some embodiments, a provided chemical entity has hERG $IC_{50}$≥20 μM. In some embodiments, a provided chemical entity has hERG $IC_{50}$≥25 μM.

In some embodiments, a provided chemical entity has NR2B functional antagonist activity (determined as NR2B $IC_{50}$ measured according to the procedure of Example 2.1) ≤100 nM and hERG activity (determined as hERG $IC_{50}$ measured according to the procedure of Example 2.2) ≥5 μM. In some embodiments, a provided chemical entity has NR2B $IC_{50}$≤100 nM and hERG $IC_{50}$≥10 μM. In some embodiments, a provided chemical entity has NR2B $IC_{50}$≤100 nM and hERG $IC_{50}$≥15 μM. In some embodiments, a provided chemical entity has NR2B $IC_{50}$≤100 nM and hERG $IC_{50}$≥20 μM. In some embodiments, a provided chemical entity has NR2B $IC_{50}$≤100 nM and hERG $IC_{50}$≥25 μM. In some embodiments, a provided chemical entity has NR2B $IC_{50}$≤50 nM and hERG $IC_{50}$≥5 μM. In some embodiments, a provided chemical entity has NR2B $IC_{50}$≤50 nM and hERG $IC_{50}$≥10 μM.

In some embodiments, a provided chemical entity has NR2B functional antagonist activity (determined as NR2B $IC_{50}$ measured according to the procedure of Example 2.1) ≤100 nM and CYP2D6 inhibition (measured as CYP2D6 $IC_{50}$ determined according to the procedure of Example 2.3) ≥2 μM. In some embodiments, a provided chemical entity has NR2B $IC_{50}$≤100 nM and CYP2D6 $IC_{50}$≥3 μM. In some embodiments, a provided chemical entity has NR2B $IC_{50}$≤100 nM and CYP2D6 $IC_{50}$≥4 μM. In some embodiments, a provided chemical entity has NR2B $IC_{50}$≤100 nM and CYP2D6 $IC_{50}$≥5 μM. In some embodiments, a provided chemical entity has NR2B $IC_{50}$≤100 nM and CYP2D6 $IC_{50}$ of about 5-10 μM. In some embodiments, a provided chemical entity has NR2B $IC_{50}$≤100 nM and CYP2D6 $IC_{50}$≥10 μM. In some embodiments, a provided chemical entity has NR2B $IC_{50}$≤50 nM and CYP2D6 $IC_{50}$≥2 μM. In some embodiments, a provided chemical entity has NR2B $IC_{50}$≤50 nM and CYP2D6 $IC_{50}$≥3 μM. In some embodiments, a provided chemical entity has NR2B $IC_{50}$≤50 nM and CYP2D6 $IC_{50}$≥4 μM. In some embodiments, a provided chemical entity has NR2B $IC_{50}$≤50 nM and CYP2D6 $IC_{50}$≥5 04. In some embodiments, a provided chemical entity has NR2B $IC_{50}$≤50 nM and CYP2D6 $IC_{50}$ of about 5-10 μM. In some embodiments, a provided chemical entity has NR2B $IC_{50}$≤50 nM and CYP2D6 $IC_{50}$≥10 μM.

Uses, Formulation and Administration, and Pharmaceutically Acceptable Compositions In some embodiments, the invention provides a composition comprising a chemical entity of the invention or a pharmaceutically acceptable derivative thereof and a pharmaceutically acceptable carrier, adjuvant, or vehicle. The amount of chemical entity in compositions of this invention is such that is effective to measurably inhibit NR2B, in a biological sample or in a patient. In some embodiments, the amount of chemical entity in compositions of this invention is such that is effective to measurably inhibit NR2B, in a biological sample or in a patient. In some embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the chemical entity with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic ester, salt of an ester or other derivative of a chemical entity of this invention (e.g., a prodrug) that, upon administration to a recipient, is capable of providing, either directly or indirectly, a chemical entity of this invention or an inhibitorily active metabolite or residue thereof.

As used herein, the term "inhibitorily active metabolite or residue thereof" means that a metabolite or residue thereof is also an inhibitor of NR2B.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Chemical Entities and Pharmaceutically Acceptable Compositions

Human therapeutic applications of NR2B receptor antagonists have been summarized in reviews by Traynelis et al. (S. F. Traynelis et al., *Pharmacology Reviews*, 2010, 62:405-496), Beinat et al. (C. Beinat et al., *Current Medicinal Chemistry*, 2010, 17:4166-4190) and Mony et al. (L. Mony et al., *British J. of Pharmacology*, 2009, 157:1301-1317). Antagonism of NR2B can be useful in the treatment of diseases and disorders including depression, pain, Parkinson's disease, Huntington's disease, Alzheimer's disease, cerebral ischaemia, traumatic brain injury, seizure disorders (e.g., epilepsy) and migraine. (S. B. Bausch et al., *Epilepsia*, 2010, 51:102-105; P. Mares, *Naunyn-Schmiedeberg's Arch Pharmacol*, 2014, 387:753-761; E. Szczurowska et al., *Brain Research Bulletin*, 2015, 111:1-8).

The activity of a chemical entity utilized in this invention as an antagonist of NR2B or a treatment for a disease or disorder of the central nervous system (CNS) may be assayed in vitro or in vivo. An in vivo assessment of the efficacy of the compounds of the invention may be made using an animal model of a disease or disorder of the CNS, e.g., a rodent or primate model. Cell-based assays may be performed using, e.g., a cell line isolated from a tissue that expresses NR2B, or a cell line that recombinantly expresses NR2B. Additionally, biochemical or mechanism-based assays, e.g., measuring cAMP or cGMP levels, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with chemical entities of the invention. Alternate in vitro assays quantify the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an antagonist of NR2B are set forth in the Examples below. The aforementioned assays are exemplary and not intended to limit the scope of the invention. A person skilled in the art can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The chemical entities and compositions, according to the method of the present invention, may be administered using any amount and any route of administration effective for treating or lessening the severity of a CNS disease or disorder.

In some embodiments, the chemical entities and compositions, according to the method of the present invention, may be administered using any amount and any route of administration effective for treating or lessening the severity of a disease or disorder associated with NR2B.

In some embodiments, the chemical entities and compositions, according to the method of the present invention, may be administered using any amount and any route of administration effective for treating or lessening the severity of a CNS disease or disorder.

In some embodiments, the disease or disorder is depression with or without concomitant anxiety disorder, e.g., single episode and recurrent depressive disorder, dysthymic disorder, major depressive disorder, psychotic depression, premenstrual dysphoric disorder, postpartum depression, seasonal affective disorder (SAD), mood disorder, treatment-resistant depression (TRD, i.e., major depressive disorder that has not responded to other drug therapies), depression caused by a chronic medical condition such as cancer or chronic pain, chemotherapy, chronic stress, and post traumatic stress disorders.

In some embodiments, the disease or disorder is an acute affective disorder, e.g., selected from bipolar disorders including bipolar I and bipolar II manic disorders.

In some embodiments, the present invention provides a method of treating substance abuse disorders, wherein treatment results in decreased tolerance and/or dependence to opioid treatment of pain, and/or by treating withdrawal syndrome of e.g., alcohol, opioids, heroin, and cocaine. As used herein, the term "substance abuse disorders" includes substance dependence or abuse with or without physiological dependence. The substances associated with these disorders include: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In some embodiments, a substance abuse disorder includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation. Other substance abuse disorders include substance-induced anxiety disorder with onset during withdrawal; substance-induced mood disorder with onset during withdrawal; and substance-induced sleep disorder with onset during withdrawal.

In some embodiments, the disease or disorder is pain, e.g., selected from pain states arising from a variety of sources including neuropathic pain (such as post herpetic neuralgia, nerve injury/damage, the "dynias", e.g., vulvodynia, phantom limb pain, root avulsions, painful diabetic neuropathy, compressive mononeuropathy, ischemic neuropathy, painful traumatic mononeuropathy, or painful polyneuropathy), central pain syndromes (potentially caused by virtually any lesion at any level of the nervous system), and postsurgical pain syndromes (e.g., postmastectomy syndrome, postthoracotomy syndrome, stump pain), bone and joint pain (osteoarthritis, rheumatoid arthritis, ankylosing spondylitis), repetitive motion pain, carpal tunnel syndrome, dental pain, cancer pain, myofascial pain (muscular injury, fibromyalgia), perioperative pain (general surgery, gynecological), chronic pain, dysmenorrhea, as well as pain associated with angina, and inflammatory pain of varied origins (e.g. osteoarthritis, rheumatoid arthritis, rheumatic disease, tenosynovitis and gout), headache, migraine and cluster headache. In some embodiments, the disease or disorder is associated with intractable pain, such as migraine, fibromyalgia, and trigeminal neuralgia.

In some embodiments, the disease or disorder is selected from sleep disorders and their sequelae including insomnia, narcolepsy and idiopathic hypersomnia.

In some embodiments, the disease or disorder is selected from CNS disorders characterized by neuronal hyperexcitablity, such as epilepsy, convulsions, seizures, partial seizure disorders, generalized seizure disorders such as absence seizures, atonic, myoclonic, tonic, tonic-clonic or "grand-mal" seizures, status epilepticus, cortical spreading depression, migraine headaches, cerebral palsy, Ohtahara Syndrome, Fragile X Syndrome, pediatric or genetic seizures such as West syndrome, Lennox-Gastaut syndrome and Angleman syndrome, tuberosclerosis, intracranial hypertension, central nervous system edema, neuronal toxicity, such as toxicity induced by alcohol exposure, pathophysiological effects of head trauma, stroke, ischemia, hypoxia and other conditions resulting from or producing ionic imbalances in the central nervous system, or synchronized discharges of neuronal populations.

In some embodiments, the disease or disorder is characterized by the occurrence of a seizure. Seizures are a result of uncontrolled discharges of electrical activity in the brain. A seizure typically manifests as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool. There are both convulsive and non-convulsive seizures. Convulsive seizures can be generalized seizures or partial seizures. There are six main types of generalized seizures: tonic-clonic, tonic, clonic, myoclonic, absence, and atonic seizures. A non-convulsive seizure, for example an absence seizure, presents as a decreased level of consciousness and usually lasts about 10 seconds.

In some embodiments, the disease or disorder is epilepsy. Epilepsy is a disorder of the brain characterized by an enduring predisposition to generate epileptic seizures and by the neurobiologic, cognitive, psychological, and social consequences of this condition. (R. S. Fisher et al., *Epilepsia*, 2005, 46(4):470-472). Epilepsy can be the occurrence of at least one epileptic seizure. An epileptic seizure is a transient occurrence of signs and/or symptoms due to abnormal excessive or synchronous neuronal activity in the brain. Epilepsy affects people of all ages; however, epilepsy most often occurs in childhood and older adulthood (Institute of Medicine 2012). The exact cause of epilepsy is uncertain. Some known causes of epilepsy include head trauma, stroke, tumors, infection, or abnormalities of the brain.

Epilepsy is categorized as idiopathic (genetic cause) or symptomatic (cause unknown), and is further grouped into either generalized, affecting both hemispheres of the brain, or partial epilepsy, which affects one hemisphere of the brain. Examples of idiopathic generalized epilepsy include childhood absence epilepsy, juvenile myoclonic epilepsy and epilepsy with grand mal seizures. Examples of idiopathic partial epilepsy include benign focal epilepsy of childhood. Symptomatic generalized epilepsy includes West syndrome, Lennox-Gastaut syndrome and others. Symptomatic partial epilepsy includes temporal lobe epilepsy, frontal lobe epilepsy and others.

In some embodiments, the seizure disorder is a pediatric seizure disorder. The ability to categorize a case of a seizure disorder, e.g. epilepsy, into a specific syndrome occurs more often with children since the onset of seizures is commonly early. Less serious examples are benign rolandic epilepsy, childhood absence epilepsy and juvenile myoclonic epilepsy (A. Neligan et al., *Handbook of clinical neurology* 2012, 107:113-33). Other examples of pediatric seizures include febrile seizures, infantile spasms and neonatal seizures.

In some embodiments, the seizure disorder is frontal lobe epilepsy, juvenile myoclonic epilepsy, myoclonic epilepsy, absence epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease or photosensitive epilepsy, or a combination of one or more of these.

For most cases of epilepsy, the disease is chronic and requires chronic medications for treatment. Antiepileptic drugs (AEDs) generally suppress neural activity by a variety of mechanisms, including altering the activity of cell membrane ion channels and the propensity of action potentials or bursts of action potentials to be generated. These desired therapeutic effects are often accompanied by the undesired side effect of sedation. Other medications have significant non-neurological side effects, such as gingival hyperplasia, a cosmetically undesirable overgrowth of the gums, and/or a thickening of the skull, as occurs with phenytoin. While chronic usage of AEDs has proven to be effective for a majority of patients suffering from epilepsy, the persistent side effects can cause a significant impairment to a patient's quality of life. Furthermore, in spite of the currently available arsenal of old and new AEDs, almost one-third of epileptic patients are non-responsive (e.g. refractory) to all pharmacological regimens. (M. M. Castel-Branco et al., *Methods Find Exp Clin Pharmacol*, 2009, 31(2):101-106). Subsequently, there is a substantial need to develop new and more effective AEDs.

In some embodiments, the seizure disorder is refractory to treatment. Severe syndromes with diffuse brain dysfunction, also referred to as epileptic encephalopathies, are refractory to current treatment. Epileptic encephalopathies constitute a group of disorders in which the epileptic activity itself is considered to contribute to severe cognitive impairment or decline above and beyond what might be expected from the underlying pathology alone. In further embodiments, the refractory seizure disorder is a disorder associated with neuronal migration, such as human microgyria. (S. Bandyopadhyay et al., *Epilepsy Research*, 2006, 72:127-139). Another important disturbance in a subgroup of patients surgically treated for intractable seizures is focal dysplasia of the cerebral cortex. Anticonvulsant drug therapy is often ineffective in patients with such cortical malformations. In some embodiments, the seizure disorder involves cortical hyperexcitability in focal cortical dysplasia (malformations). (S. Bandyopadhyay et al., *Epilepsy Research*, 2006, 72:127-139).

In some embodiments, the seizure or epilepsy disorder is caused by a genetic abnormality. Genetics is believed to play an important role in epilepsies by a number of mechanisms. Simple and complex modes of inheritance have been identified for some of them. Recent exome and genome sequencing studies have begun to reveal a number of de novo gene mutations that are responsible for some epileptic encephalopathies, including CHD2 and SYNGAP1 and DMN1, GABBR2, FASN and RYR3. Patients with the epileptic encephalopathie, West syndrome, present distinct clinical electrophysiological features usually manifesting between 3 and 12 months as clusters of infantile spasms (IS) and a characteristic electroencephalogram (EEG) pattern called hypsarrhythmia. West syndrome has been associated with mutations in ARX, CDKL5, STXBP1, and ST3GAL3 as well as various copy number variations (CNVs). R. Lemke et al., *Ann Neurol*, 2014, 75L174-157). Mutations in GRIN2A and GRIN2B encoding the NR2A and NR2B of the NMDA receptor are associated with several neurodevelopmental disorders. Mutations in GRIN2A have recently been detected in idiopathic focal epilepsy with rolandic spikes and related epileptic encephalopathies, that is, in Landau-Kleffner syndrome, epilepsy with continuous spike-and-waves during slow sleep syndrome, and nonsyndromic epilepsy associated with intellectual disability. By contrast, GRIN2B has not been described as an epilepsy gene to date but has repeatedly been considered as a putative candidate gene for seizures, and mutations were detected in patients with ID and schizophrenia. (J. R. Lemke et al., *Ann Neurol*, 2014, 75L174-157).

In some embodiments, the disease or disorder is a movement disorder. Movement disorders include Parkinson's disease, dyskinesias (including the side effects accompanying normal doses of L-Dopa), tardive dyskinesia, drug-induced parkinsonism, postencephalitic parkinsonism, progressive supranuclear palsy, multiple system atrophy, corticobasal degeneration, parkinsonian-ALS dementia complex, basal ganglia calcification, akinesia, akinetic-rigid syndrome, bradykinesia, dystonia, medication-induced parkinsonian, Gilles de la Tourette syndrome, Huntingon's disease, tremor, chorea, myoclonus, tick disorder and dystonia.

In some embodiments, the movement disorder is one or more of akinesias and akinetic-rigid syndromes, dyskinesias and medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor). Examples of "akinetic-rigid syndromes" include Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification. Examples of dyskinesias include tremor (including rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia).

In some embodiments, the disease or disorder is Huntington's disease.

In some embodiments, the disease or disorder is cognitive dysfunction associated with disorders including schizophrenia, Alzheimer's disease, fronto-temporal dementia, Pick's disease, Lewy body disease, and other senile dementias (e.g., vascular dementia).

In some embodiments, the present invention provides a method of treating a disorder described herein, comprising administering a chemical entity of the invention in conjunction with one or more pharmaceutical agents. Suitable pharmaceutical agents that may be used in combination with the chemical entities of the present invention include selective serotonin reuptake inhibitors (SSRIs), e.g., in the treatment of depression; dopamine replacement therapy regimens and dopamine agonists, e.g., in the treatment of Parkinson's disease; typical antipsychotics; atypical antipsychotics; anticonvulsants; stimulants; Alzheimer's disease therapies; anti-migraine agents; and anxiolytic agents.

Suitable SSRIs include citalopram, dapoxetine, escitalopram, fluoxetine, fluvoxamine, indalpine, paroxetine, sertraline, vilazodone and zimelidine.

Suitable dopamine replacement therapy regimens include replacement of L-DOPA with a DOPA decarboxylase inhibitor such as carbidopa.

Suitable dopamine receptor agonists include aplindore, apomorphine, bromocriptine, cabergoline, ciladopa, dihydroergocryptine, lisuride, pardoprunox, pergolide, piribedil, pramipexole, ropinirole and rotigotine.

Suitable typical antipsychotics include chlorpromazine, thioridazine, mesoridazine, levomepromazine, loxapine, molindone, perphenazine, thiothixene, trifluoperazine, haloperidol, fluphenazine, droperidol, zuclopenthixol, flupentixol and prochlorperazine.

Suitable atypical antipsychotics include amisulpride, aripiprazole, asenapine, blonanserin, clotiapine, clozapine, iloperidone, llurasidone, mosapramine, olanzapine, paliperidone, perospirone, quetiapine, remoxipride, risperidone, sertindole, sulpiride, ziprasidone, zotepine, bifeprunox, pimavanserin and vabicaserin.

Suitable anticonvulsants include phenytoin, carbamazepine, barbiturates, phenobarbital, phenobarbital, mephobarbital, trimethadione, mephenytoin, paramethadione, phenthenylate, phenacemide, metharbital, benzchlorpropamide, phensuximide, priraidone, methsuximide, ethotoin, aminoglutethinide, diazepam, clonazepam, clorazepate, fosphenytoin, ethosuximide, valproate, felbamate, gabapentin, lamotrigine, topiramate, vigrabatrin, tiagabine, ziamide, clobazam, thiopental, midazolam, propofol, levetiracetam, oxcarbazepine, CCPene, and GYKI 52466.

Suitable stimulants include Adderall (amphetamine, dextroamphetamine mixed salts), methylphenidate, dextroamphetamine, dexmethylphenidate and lisdexamfetamine.

Suitable Alzheimer's disease therapies include acetylcholinesterase inhibitors such as rivastigmine, donepezil, galanthamine and huperazine; alpha-7 nicotinic agonists such as encenicline; and drugs that reduce $A\beta 42$ such as BACE inhibitors, gamma secretase modulators and beta amyloid peptide antibodies.

Suitable anti-migraine drugs include ergotamine and 5-HT1D agonist triptans such as sumitriptan.

Suitable anxiolytic drugs include benzodiazepine receptor modulators such as diazepam, alprazolam, lorazepam and clonazepam.

Other suitable agents for use in conjunction with a chemical entity of the invention include memantine and modafinil.

The exact amount required will vary from subject to subject, depending on the species, age, and general condition of the subject, the severity of the infection, the particular agent, its mode of administration, and the like. The chemical entities of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the chemical entities and compositions of the present invention will be decided by the attending physician within the scope of sound medical judgment. The specific effective dose level for any particular patient or organism will depend upon a variety of factors including the disorder being treated and the severity of the disorder; the activity of the specific chemical entity employed; the specific composition employed; the age, body weight, general health, sex and diet of the patient; the time of administration, route of administration, and rate of excretion of the specific chemical entity employed; the duration of the treatment; drugs used in combination or coincidental with the specific chemical entity employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the chemical entities of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a chemical entity of the present invention, it is often desirable to slow the absorption of the chemical entity from subcutaneous or intramuscular injection. This may be accomplished by the use of a liquid suspension of crystalline or amorphous material with poor water solubility. The rate of absorption of the chemical entity then depends upon its rate of dissolution that, in turn, may depend upon crystal size and crystalline form. Alternatively, delayed absorption of a parenterally administered chemical entity form is accomplished by dissolving or suspending the chemical entity in an oil vehicle. Injectable depot forms are made by forming microencapsule matrices of the chemical entity in biodegradable polymers such as polylactide-polyglycolide. Depending upon the ratio of chemical entity to polymer and the nature of the particular polymer employed, the rate of chemical entity release can be controlled. Examples of other biodegradable polymers include poly(orthoesters) and poly(anhydrides). Depot injectable formulations are also prepared by entrapping the chemical entity in liposomes or microemulsions that are compatible with body tissues.

Compositions for rectal or vaginal administration are preferably suppositories which can be prepared by mixing the chemical entities of this invention with suitable non-irritating excipients or carriers such as cocoa butter, polyethylene glycol or a suppository wax which are solid at ambient temperature but liquid at body temperature and therefore melt in the rectum or vaginal cavity and release the active chemical entity.

Solid dosage forms for oral administration include capsules, tablets, pills, powders, and granules. In such solid dosage forms, the active chemical entity is mixed with at least one inert, pharmaceutically acceptable carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active chemical entities can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active chemical entity may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a chemical entity of the invention include ointments, pastes, creams, lotions, gels, powders, solutions, sprays, inhalants or patches. The active chemical entity is admixed under sterile conditions with a pharmaceutically acceptable carrier and any needed preservatives or buffers as may be required. Ophthalmic formulation, ear drops, and eye drops are also contemplated as being within the scope of the invention. Additionally, the present invention contemplates the use of transdermal patches, which have the added advantage of providing controlled delivery of a chemical entity to the body. Such dosage forms can be made by dissolving or dispensing the chemical entity in the proper medium. Absorption enhancers can also be used to increase the flux of the chemical entity across the skin. The rate can be controlled by either providing a rate controlling membrane or by dispersing the chemical entity in a polymer matrix or gel.

As used herein, the term "combination," "combined," and related terms refers to the simultaneous or sequential administration of therapeutic agents in accordance with this invention. For example, a chemical entity of the present invention may be administered with another therapeutic agent simultaneously or sequentially in separate unit dosage forms or together in a single unit dosage form. Accordingly, the present invention provides a single unit dosage form comprising a chemical entity of formula I, an additional therapeutic agent, and a pharmaceutically acceptable carrier, adjuvant, or vehicle.

The amount of both, a provided chemical entity and additional therapeutic agent (in those compositions which comprise an additional therapeutic agent as described above), that may be combined with the carrier materials to produce a single dosage form will vary depending upon the host treated and the particular mode of administration. Preferably, compositions of this invention should be formulated so that a dosage of between 0.01-100 mg/kg body weight/day of a provided chemical entity can be administered.

In those compositions which comprise an additional therapeutic agent, that additional therapeutic agent and the chemical entity of this invention may act synergistically. Therefore, the amount of additional therapeutic agent in such compositions will be less than that required in a monotherapy utilizing only that therapeutic agent. In such compositions a dosage of between 0.01-100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one chemical entity of formula I and a pharmaceutically acceptable carrier, adjuvant or vehicle.

In some embodiments, the present invention provides the use of a chemical entity of formula I in the manufacture of a medicament for the treatment of a CNS disease or disorder.

General Synthetic Methods

Chemical entities of formula I can be synthesized according to Scheme 1 or Scheme 2 and/or using methods known in the art.

Scheme 1

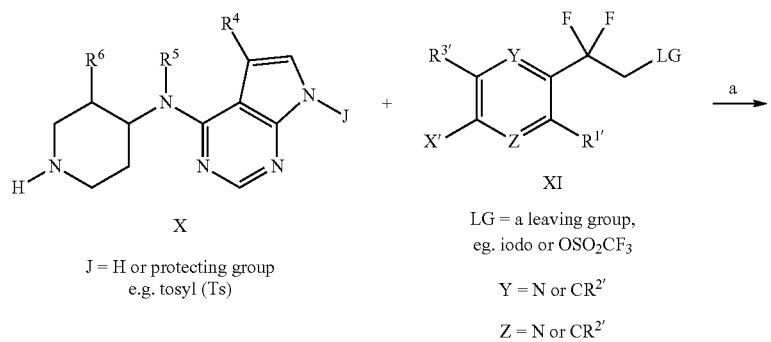

X
J = H or protecting group
e.g. tosyl (Ts)

XI
LG = a leaving group,
eg. iodo or OSO$_2$CF$_3$

Y = N or CR$^{2'}$

Z = N or CR$^{2'}$

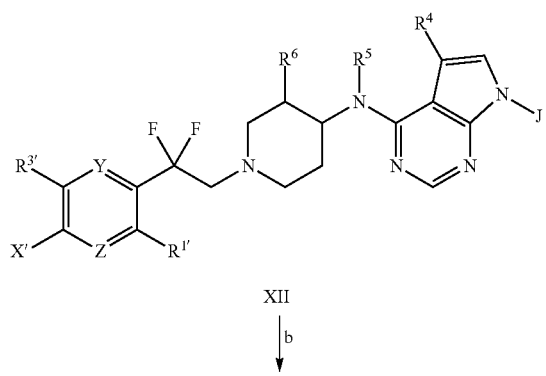

XII b

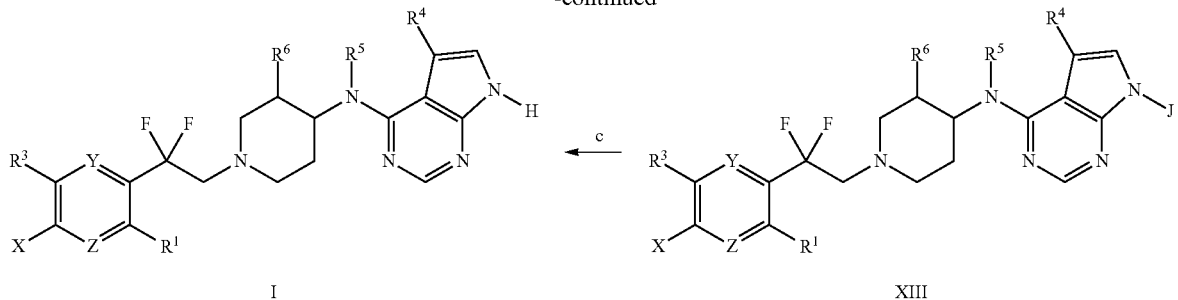

a. base (e.g. diisopropylethylamine), organic solvent (e.g. dichloromethane), heat
b. optional functional group conversion(s)
c. removal of J when it is a protecting group (e.g. 50% NaOH/THF heat for J = tosyl)

In the method depicted in Scheme 1, in a first step, compounds of formula XII may be prepared by piperidine nitrogen alkylation of intermediates of general formula X, wherein J is hydrogen or a suitable protecting group (e.g. tosyl=Ts) and $R^4$, $R^5$ and $R^6$ are as defined above, with intermediates of general formula XI wherein X', $R^{1'}$, $R^{2'}$ and $R^{3'}$ are as defined above for X, $R^1$, $R^2$ and $R^3$, or are independently suitably masked equivalents thereof. The leaving group (LG) in alkylating intermediates of general formula XI represents an anionic leaving group such as halogen (chlorine, bromine or iodine) or a sulfonate group such as mesylate, tosylate, triflate ($OSO_2CF_3$) or nonaflate ($OSO_2CF_2CF_2CF_3$). The alkylation reaction can be conducted in suitable protic (e.g. isopropanol, n-butanol) or aprotic (e.g. $CH_2Cl_2$, DMF, DMSO, $CH_3CN$) solvents at temperatures from ambient to 160° C., preferably between 50° C. and 130° C. in the presence of a suitable base (e.g. triethylamine, diisopropylethylamine). In the case where intermediates of formula X have J=H and X', $R^{1'}$, $R^{2'}$ and $R^{3'}$ in the intermediates of formula XI are as defined above for X, $R^1$, $R^2$ and $R^3$, the alkylation products of formula XII are compounds of formula I. Alternatively in an optional step or steps, compounds of formula XII containing one or more X', $R^{1'}$, $R^{2'}$ or $R^{3'}$ substituents as suitably masked groups can be converted using methods known in the art to yield compounds of formula XIII wherein X, $R^1$, $R^2$ and $R^3$ are as defined above (e.g. for a compound of formula XII in which X'=$NO_2$, a hydrogenation step yields a compound of formula XIII in which X=$NH_2$). Intermediates of formula XIII in which J is a protecting group can be converted to compounds of formula I using methods known in the art (e.g. 50% NaOH/THF heat for J=tosyl).

An alternate method to synthesizing compounds of formula I is depicted in Scheme 2.

Scheme 2

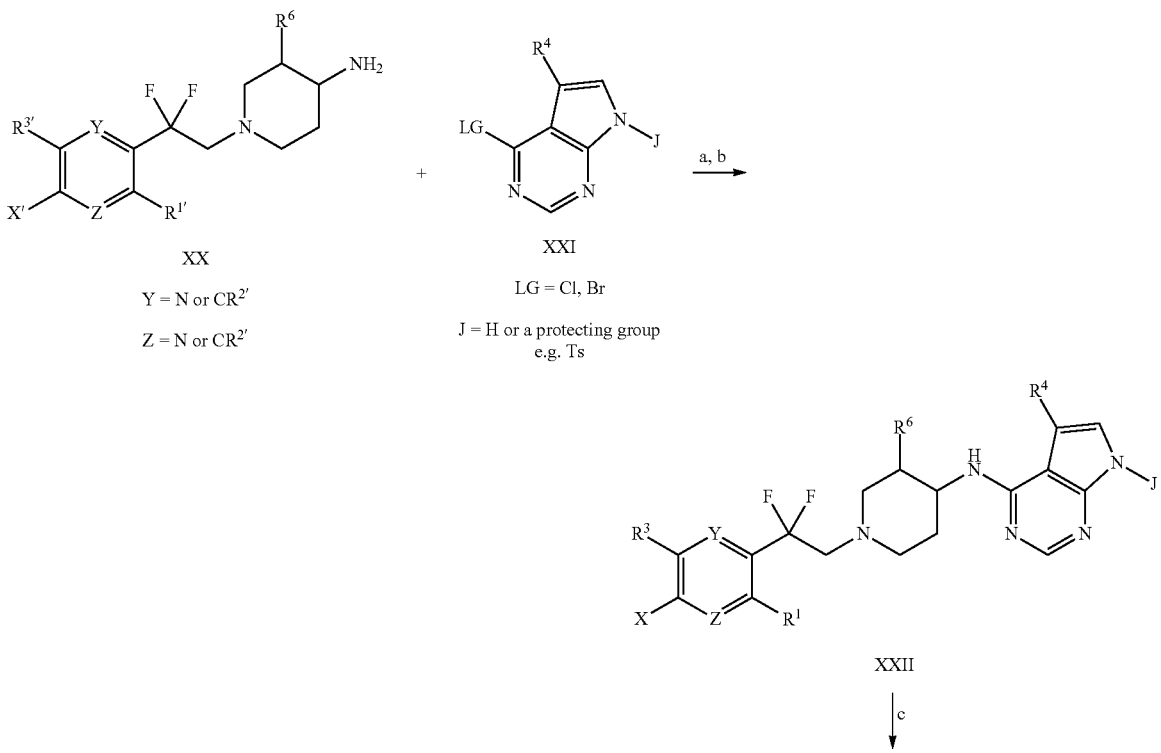

-continued

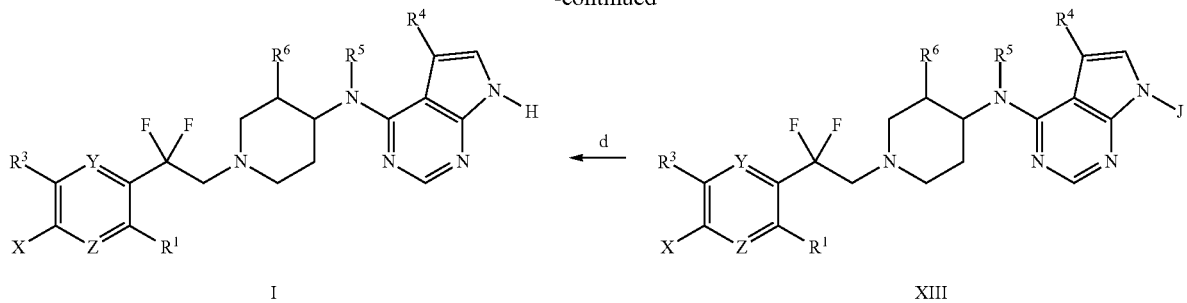

I                          XIII a. base or Buchwald reaction mediated amine coupling reaction conditions
b. optional steps e.g. functional group conversions and removal of J protecting group
c. base, $R^5LG$
d. removal of J protecting group In a first step, base or Buchwald reaction mediated coupling of intermediates of formula XX, wherein X', $R^{1'}$, $R^{2'}$ and $R^{3'}$ in the intermediates of formula XI are as defined above for X, $R^1$, $R^2$ and $R^3$, or are independently suitably masked equivalents thereof, with pyrazolopyrimidine intermediates of formula XXI wherein J is hydrogen or a suitable protecting group, $R^4$ is as defined above and LG is suitable leaving group, yields compounds of formula XXII. In certain cases base mediated coupling is suitable and can be conducted in an organic solvent (e.g. NMP, DMF, DMSO, $CH_3CN$) at temperatures from 50° C. to 180° C., preferably between 70° C. and 120° C. in the presence of a suitable tertiary amine base (e.g. triethylamine, diisopropylethylamine). In certain cases Buchwald conditions using a palladium catalyst can be used for the coupling reaction. To prepare intermediates of formula XIII in which $R^5$ is methyl, compounds of formula XXII can be treated with a suitable base (e.g. NaH) in a suitable aprotic organic solvent (e.g. DMF) followed by the addition of a methylating reagent (e.g. methyliodide or dimethylsulfate) at a suitable temperature. Intermediates of formula XIII in which J is a protecting group can be converted to compounds of formula I using methods known in the art (e.g. 50% NaOH/THF heat for J=tosyl).

Intermediates of general formula XI wherein X', $R^{1'}$, $R^{2'}$ and $R^{3'}$ are as defined above for X, $R^1$, $R^2$ and $R^3$, or are independently suitably masked equivalents thereof, can be synthesized according to Scheme 3 and/or using methods known in the art.

Scheme 3

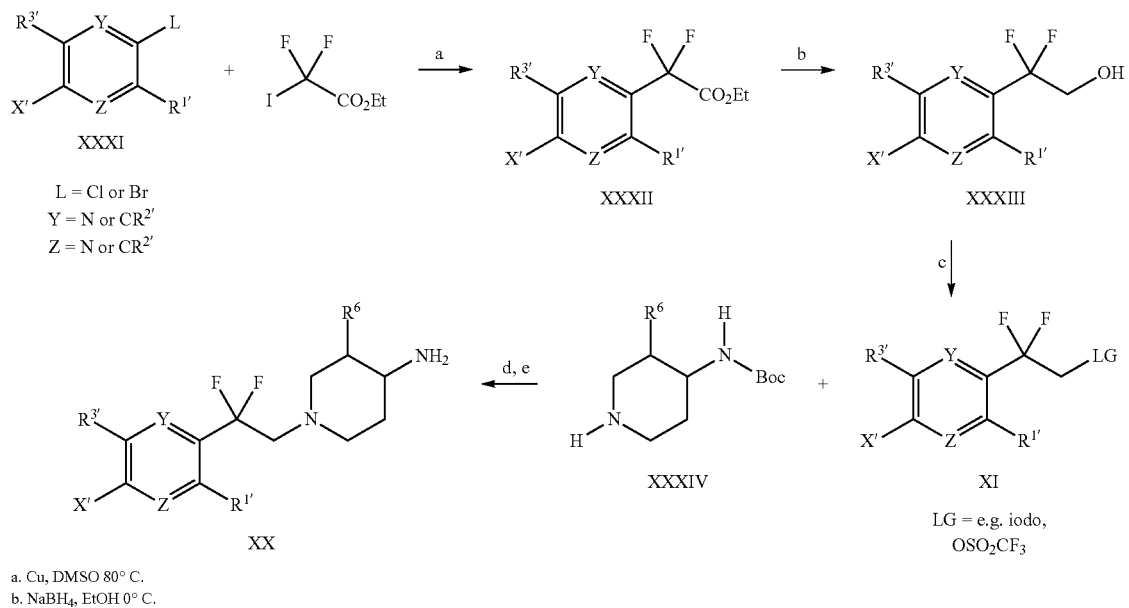

a. Cu, DMSO 80° C.
b. $NaBH_4$, EtOH 0° C.
c. $Tf_2O$, $Et_2O$, DIPEA 0° C.

Starting material compounds of formula XXXI can be purchased, or synthesized using methods known in the art e.g. by Sandmeyer reaction. Copper mediated coupling of compounds of formula XXXI with ethyl 2,2-difluoro-2-iodoacetate at elevated temperature in dry DMSO yields intermediates of general formula XXXII. Subsequent ester group reduction under appropriate conditions e.g. using sodium borohydride in ethanol yields corresponding alcohols of general formula XXXIII The alcohol group in compounds of general formula XXXIII can be converted to a suitable leaving group e.g. iodide or trifluoromethanesulfonate using methods known in the art. For example treatment with triflic anhydride in ether solvent with N,N-diisopropylethyl amine at 0° C. can be used to prepare trifluoromethanesulfonates of formula XI ($Y=OSO_2CF_3$). Alkylation of 4-Boc amino piperidines of formula XXXIV with intermediates of formula XI yields compounds of formula XX. The alkylation reaction can be conducted in suitable aprotic (e.g. $CH_2Cl_2$, DMF, DMSO, $CH_3CN$) solvents at temperatures from −10° C. to 100° C. (preferably from 0° C. to 80° C.) in the presence of a suitable base (e.g. triethylamine, diisopropylethylamine).

Intermediates of general formula X can be synthesized according to Scheme 4 and/or using methods known in the art.

Scheme 5

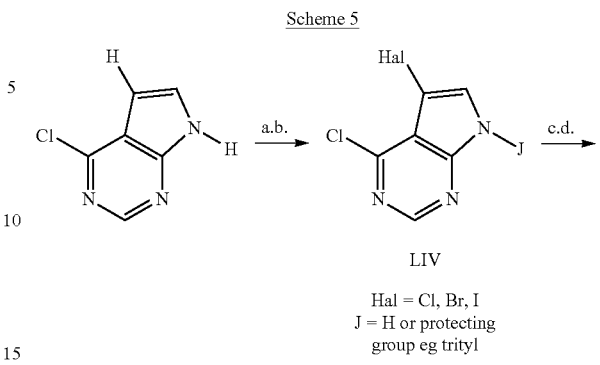

Hal = Cl, Br, I
J = H or protecting group eg trityl

Scheme 4

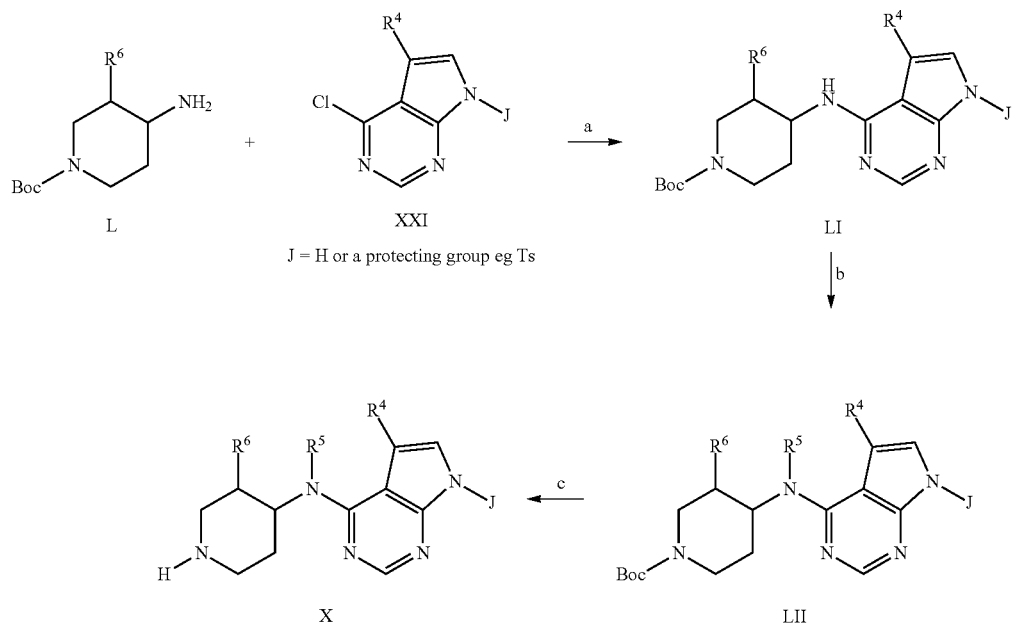

a. base or Buchwald reaction mediated amine coupling reaction conditions
b. optional introduction of $R^5$ group using alkylation conditions e.g. base, $R^5I$
c. Boc removal e.g. with 2N HCl/MeOH In a first step, starting 4-amino-N-t-butoxycarbonyl protected piperidines of formula L can be coupled with intermediates of formula XXI under base or Buchwald reaction conditions to give intermediates of general formula LI. In an optional second step when J is a protecting group (e.g. Ts), an $R^5$ group can be introduced by alkylation reaction to give intermediates of general formula LII in which $R^5$ is methyl. In the final step the Boc protecting group can be removed by under standard acidic conditions or alternative methods known in the art to give intermediates of general formula X.

Intermediates of general formula XXI can be synthesized according to Scheme 5 and/or using methods known in the art.

-continued

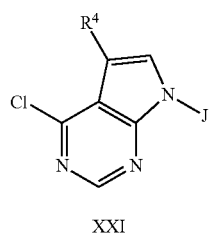

XXI a. NCS, NBS or NIS, ether
b. optional protection e.g. with base/trityl chloride
c. optional BuLi exchange and alkylation reaction or Suzuki coupling reaction
d. optional function group conversion of $R^4$ or J group deprotection In a first step 4-chloro-7H-pyrrolo[2,3-d]pyrimidine can be halogenated using an N-halosuccinimide to give corresponding intermediates with $R^4$ as chloro, bromo or iodo.

These intermediates may be then protected e.g. with J=trityl. To prepare analogs where $R^4$ can be introduced by nucleophilic displacement (e.g. when $R^4$ is methyl), bromo intermediates can be metallated with BuLi followed by treatment with a suitable alkylating agent, e.g. methyliodide or fluorinating agent, e.g. Selectfluor® (1-chloromethyl-4-fluoro-1,4-diazoniabicyclo[2.2.2]octane bis(tetrafluoroborate)). To prepare analogs where $R^4$ can be introduced by palladium mediated coupling reactions e.g. Suzuki reaction (e.g. when $R^4$ is cyclopropyl), bromo or iodo intermediates can be subject to coupling with a suitable intermediate, e.g. an alkylboronic acid. For example, intermediates of formula XXI wherein $R^4$ is cyclopropyl and J is a trityl protecting group can be prepared according to Intl. Patent Appl. Publ. No. WO 2010/015637.

EXAMPLES

As depicted in the Examples below, in certain exemplary embodiments, chemical entities are prepared according to the following procedures. It will be appreciated that, although the general methods depict the synthesis of certain chemical entities of the present invention, the following methods, and other methods known to persons skilled in the art, can be applied to all chemical entities and subclasses and species of each of these chemical entities, as described herein.

Temperatures are given in degrees centigrade. If not mentioned otherwise, all evaporations are performed under reduced pressure, preferably between 15 mm Hg and 100 mm Hg. The structures of intermediates and final products are confirmed by standard analytical methods, for example, mass spectrometry and NMR spectroscopy.

ABBREVIATIONS aq aqueous
Boc t-butoxycarbonyl
Cbz benzyloxycarbonyl
DAST diethylamino sulfur trifluoride
DCM dichloromethane
DCE 1,2-dichloroethane
DIPEA N,N-diisopropylethylamine
DMF N,N-dimethylformamide
DMSO dimethyl sulfoxide
$Et_2O$ diethyl ether ("ether")
EtOAc ethyl acetate
EtOH ethanol
eq equivalents
h hours
HPLC high performance liquid chromatography
LC liquid chromatography
Me methyl
MS mass spectrometry
MS (ESI) mass spectrometry electrospray ionization
NMP N-methyl-2-pyrrolidone
NMR nuclear magnetic resonance
PEG polyethylene glycol
rt room temperature
Tf triflate
$Tf_2O$ triflic anhydride
TFAA trifluoroacetic anhydride
THF tetrahydrofuran
TLC thin layer chromatography
Ts p-toluenesulfonyl Example 1

Chemical Entities

Example 1.A

Intermediates

Example 1.A.1

Intermediate 1: N-(piperidin-4-yl)-7-tosyl-7H-pyrrolo[2,3-d]-pyrimidin-4-amine

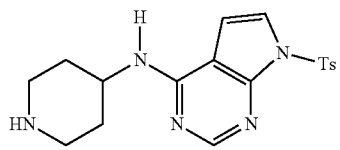 [SMILES: Cc1ccc(S(=O)(=O)n2ccc3c(NC4CCNCC4)ncnc32)cc1]

Step 1.
4-chloro-7-tosyl-7H-pyrrolo[2,3-d]pyrimidine

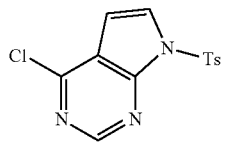 [SMILES: Cc1ccc(S(=O)(=O)n2ccc3c(Cl)ncnc32)cc1]

A mixture of 4-chloro-7H-pyrrolo[2,3-d]pyrimidine (10.0 g, 65 mmol), TsCl (13.7 g, 72 mmol) and NaOH (40 mL, 2N) in acetone (100 mL) was stirred at room temperature overnight. The resulting solid was collected by filtration and washed with acetone and then with water to give the title compound as a white solid (16 g, 80%). $^1$H NMR (400 MHz, $CDCl_3$) δ 8.77 (s, 1H), 8.09 (d, J=8.0 Hz, 2H), 7.77 (d, J=4.0 Hz, 1H), 7.33 (d, J=8.0 Hz, 2H), 6.70 (d, J=4.0 Hz, 2H), 2.40 (s, 3H).

Step 2. tert-butyl 4-(7-tosyl-7H-pyrrolo[2,3-d]pyrimidin-4-ylamino)piperidine-1-carboxylate

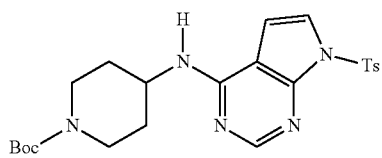 [SMILES: Cc1ccc(S(=O)(=O)n2ccc3c(NC4CCN(C(=O)OC(C)(C)C)CC4)ncnc32)cc1]

A mixture of 4-chloro-7-tosyl-7H-pyrrolo[2,3-d]pyrimidine (10.0 g, 32 mmol), tert-butyl 4-aminopiperidine-1-carboxylate (6.4 g, 32 mmol) and DIPEA (10 mL) in NMP (100 mL) was heated under reflux overnight. The mixture was filtered. The solid was then washed with ethyl acetate and dried under vacuum to afford the title product as a white solid (10 g, 67%). $^1$H NMR (400 MHz, DMSO-d6) δ 8.23 (s, 1H), 7.95 (d, J=8.0 Hz, 2H), 7.65 (d, J=8.0 Hz, 1H), 7.54 (d, J=4.0 Hz, 1H), 7.42 (d, J=8.0 Hz, 2H), 6.88 (d, J=4.0 Hz, 1H), 4.16-4.23 (m, 1H), 3.92-3.95 (m, 2H), 2.70-2.82 (m, 2H), 2.35 (s, 3H), 1.84-1.88 (m, 2H), 1.40 (s, 9H), 1.32-1.36 (m, 2H).

Step 3. N-(piperidin-4-yl)-7-tosyl-7H-pyrrolo[2,3-d]pyrimidin-4-amine

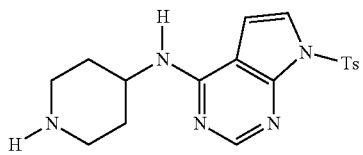 [SMILES: Cc1ccc(S(=O)(=O)n2ccc3c(NC4CCNCC4)ncnc32)cc1]

To a mixture of tert-butyl 4-(7-tosyl-7H-pyrrolo[2,3-d]pyrimidin-4-ylamino)-piperidine-1-carboxylate (10.0 g, 21 mmol) in MeOH (100 mL) was added HCl/MeOH (50 mL, 2N, 100 mmol). The resulting solution was stirred at room temperature overnight and then evaporated to dryness. The residue was then dissolved in DCM and washed with sat. NaHCO$_3$, water, brine, dried and filtered. The filtrate was concentrated to afford the title product as a white solid (7.4 g, 95%). MS (ESI) calcd for $C_{18}H_{21}N_3O_2S$: 371.1. found: 372.3 [M+H]. $^1$HNMR (400 MHz, CDCl$_3$) δ 8.45 (s, 1H), 8.08 (d, J=8.0 Hz, 2H), 7.48 (d, J=4.0 Hz, 1H), 7.31 (d, J=8.0 Hz, 2H), 6.43 (d, J=4.0 Hz, 1H), 4.87-4.92 (m, 1H), 4.16-4.23 (m, 1H), 3.12-3.15 (m, 2H), 2.76-2.82 (m, 2H), 2.40 (s, 3H), 2.07-2.12 (m, 2H), 1.40-1.44 (m, 2H).

Example 1.1

N-(1-(2,2-difluoro-2-(pyridin-2-yl)ethyl)piperidin-4-yl)-7H-pyrrolo[2,3-d]-pyrimidin-4-amine (C-1)

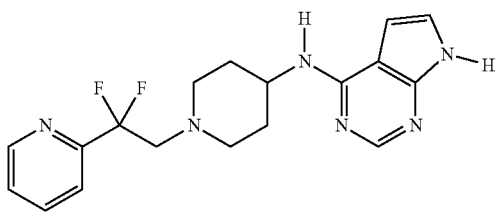 [SMILES: FC(F)(CN1CCC(Nc2ncnc3[nH]ccc23)CC1)c1ccccn1]

Step 1. Ethyl 2,2-difluoro-2-(pyridin-2-yl)acetate

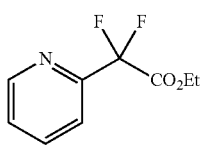 [SMILES: CCOC(=O)C(F)(F)c1ccccn1]

To a stirred solution of 2-bromopyridine (1.0 g, 6.3 mmol) and ethyl 2-bromo-2,2-difluoroacetate (1.2 mL, 1.5 mmol) in DMSO (10 mL) was added copper powder (800 mg, 13 mmol). The mixture was heated to 90° C., and stirred overnight. The mixture was poured into water, and stirred for additional 1 h at room temperature. The final suspension was filtered through a pad of celite, and the filter mass was washed with EtOAc. The combined organic phases were washed with water and brine, dried over Na$_2$SO$_4$ and concentrated in vacuo to afford the crude product as a yellow oil (1.1 g, 86%) which was directly used for reduction in the next step.

Step 2. 2,2-difluoro-2-(pyridin-2-yl)ethanol

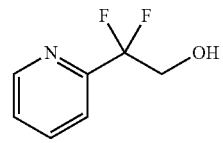 [SMILES: OCC(F)(F)c1ccccn1]

To a stirred solution of ethyl 2,2-difluoro-2-(pyridin-2-yl)acetate (1.1 g, 59 mmol) in ethanol (25 mL) was added the NaBH$_4$ (330 mg, 8.7 mmol) at room temperature. After stirring for 30 min, the mixture was quenched with aqueous 1M HCl under ice-water bath cooling. The mixture was basified with aqueous 1M NaOH, and extracted with EtOAc. The combined EtOAc phases were washed with brine, dried over Na$_2$SO$_4$ and concentrated in vacuo. The crude product was purified by column chromatography over silica gel (hexane/EtOAc=2/1) to afford the title compound as a white solid (520 mg, 60%). $^1$H NMR (400 MHz, CDCl$_3$) δ 8.61 (d, J=4.7 Hz, 1H), 7.88 (td, J=7.8, 1.7 Hz, 1H), 7.73 (d, J=7.8 Hz, 1H), 7.43 (dd, J=7.2 and 4.7 Hz, 1H), 4.26 (dt, J=7.0 and 12.4 Hz, 2H), 3.50 (t, J=7.0 Hz, 1H).

Step 3. 2,2-difluoro-2-(pyridin-2-yl)ethyltrifluoromethanesulfonate

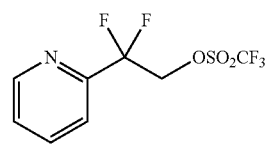

To a stirred solution of 2,2-difluoro-2-(pyridin-2-yl)ethanol (220 mg, 1.25 mmol) and DIPEA (0.35 mL, 1.88 mmol) in ether (10 mL) was added Tf$_2$O (0.25 mL, 1.50 mmol) dropwise at 0° C. under N$_2$ atmosphere. The pink suspension thus obtained was stirred for 2 hours at room temperature. The suspension was filtered through a pad of celite. The filtrate was concentrated in vacuo, and purified by column chromatography over silica gel (hexane/EtOAc=10/1) to afford the title compound as a colorless oil (320 mg, 87%). $^1$H NMR (400 MHz, CDCl$_3$) δ 8.67 (d, J=4.3 Hz, 1H), 7.89 (td, J=7.8 and 1.6 Hz, 1H), 7.75 (d, J=7.8 Hz, 1H), 7.47 (dd, J=7.8 and 4.3 Hz, 1H), 5.12 (t, J=12.0 Hz, 2H).

Step 4. tert-butyl 1-(2,2-difluoro-2-(pyridin-2-yl)ethyl)piperidin-4-ylcarbamate

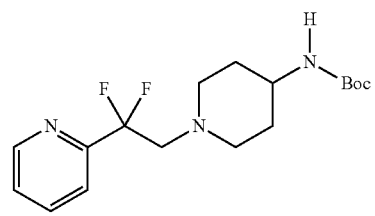 [SMILES: CC(C)(C)OC(=O)NC1CCN(CC(F)(F)c2ccccn2)CC1]

A mixture of 2,2-difluoro-2-(pyridin-2-yl)ethyl trifluoromethanesulfonate (365 mg, 1.25 mmol) and tert-butyl piperidin-4-ylmethylcarbamate (274 mg, 1.37 mmol) and DIPEA (0.6 ml, 3.8 mmol) in DCM (5 mL) was heated to 40° C. After stirring overnight at 40° C., the mixture was concentrated to dryness. The concentrate was purified by column chromatography over silica gel (hexane/ethyl acetate=10/1) to afford the title compound as a white solid (340 mg, 80%). MS (ESI) calcd for $C_{17}H_{25}F_2N_3O_2$: 341.2. found: 342.2 [M+H].

Step 5. 1-(2,2-difluoro-2-(pyridin-2-yl)ethyl)piperidin-4-amine

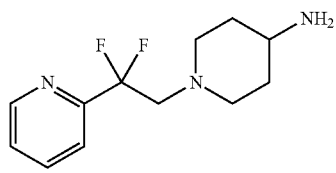 [SMILES: NC1CCN(CC(F)(F)c2ccccn2)CC1]

To the solution of tert-butyl 1-(2,2-difluoro-2-(pyridin-2-yl)ethyl)piperidin-4-ylcarbamate (340 mg, 0.99 mmol) in DCM (4 mL) was added TFA (3 mL) under ice-water bath cooling. After stirring for 30 min at rt, the starting material was consumed, and the mixture was concentrated. The concentrate was basified with 1 N NaOH, and extracted with ethyl acetate. The organic phase was washed with brine, dried $Na_2SO_4$, and concentrated to afford the title compound as an off-white powder (230 mg, 100%) which was used in the next step without further purification. MS (ESI) calcd for $C_{12}H_{17}F_2N_3$: 309.1. found: 310.3 [M+H].

Step 6. N-(1-(2,2-difluoro-2-(pyridin-2-yl)ethyl) piperidin-4-yl)-7H-pyrrolo[2,3-d]-pyrimidin-4-amine

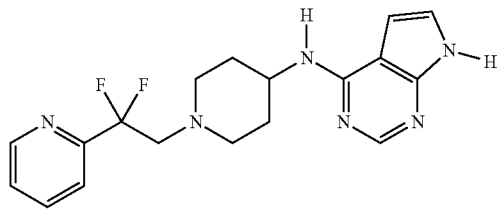 [SMILES: FC(F)(CN1CCC(Nc2ncnc3[nH]ccc23)CC1)c1ccccn1]

A mixture of 1-(2,2-difluoro-2-(pyridin-2-yl)ethyl)piperidin-4-amine (230 mg, 0.95 mmol), 4-chloro-7H-pyrrolo[2,3-d]pyrimidine (160 mg, 1.05 mmol) and DIPEA (0.33 mL, 1.91 mmol) in butyl alcohol (4 mL) was heated to 130° C. After stirring overnight at 130° C., the orange solution was concentrated. The concentrate was purified by column chromatography over silica gel (hexane/ethyl acetate=1:1) to afford the title compound as a gray powder (140 mg, 41%). MS (ESI) calcd for $C_{18}H_{20}F_2N_6$: 358.2. found: 359.2 [M+H]. $^1$H NMR (400 MHz, $CD_3OD$) δ 8.65 (d, J=4.4 Hz, 1H), 8.07 (s, 1H), 7.98 (dt, J=8.0 and 1.6 Hz, 1H), 7.76 (d, J=8.0 Hz, 1H), 7.52-7.55 (m, 1H), 7.05 (d, J=3.6 Hz, 1H), 6.58 (d, J=3.6 Hz, 1H), 4.05-3.95 (m, 1H), 3.26 (t, J=14.4 Hz, 2H), 2.94 (d, J=12.0 Hz, 2H), 2.45-2.52 (m, 2H), 1.96-1.87 (m, 2H), 1.50-1.60 (m, 2H).

Example 1.1a (HCl Salt)

N-(1-(2,2-difluoro-2-(pyridin-2-yl)ethyl)piperidin-4-yl)-7H-pyrrolo-[2,3-d]pyrimidin-4-amine hydrochloride (C-1.HCl)

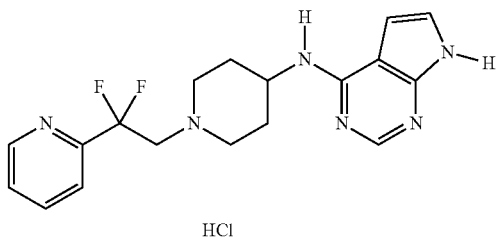 [SMILES: FC(F)(CN1CCC(Nc2ncnc3[nH]ccc23)CC1)c1ccccn1 ; Cl]

To a solution of N-(1-(2,2-difluoro-2-(pyridin-2-yl)ethyl) piperidin-4-yl)-7H-pyrrolo[2,3-d]pyrimidin-4-amine (96 mg, 0.27 mmol) in MeOH (3.0 mL) was added HCl/MeOH (2.0M, 0.14 mL) at rt. After stirring for 15 min, the mixture was concentrated to afford the title compound as an off-white powder (96 mg, 98%). MS (ESI) calcd for $C_{18}H_{21}ClF_2N_6$: 358.2. found: 359.3 [M+H]. $^1$H NMR (400 MHz, $CD_3OD$) δ 8.73 (d, J=4.4 Hz, 1H), 8.32 (s, 1H), 8.07 (dt, J=8.0 and 1.6 Hz, 1H), 7.86 (d, J=8.0 Hz, 1H), 7.65-7.57 (m, 1H), 7.36 (d, J=3.6 Hz, 1H), 6.96 (d, J=3.6 Hz, 1H), 4.28 (brs, 1H), 4.01-4.10 (m, 2H), 3.60-3.70 (m, 2H), 3.32-3.21 (m, 2H), 2.26-2.32 (m, 2H), 2.17-1.98 (m, 2H).

Example 1.2

N-(1-(2,2-difluoro-2-(5-fluoropyridin-2-yl)ethyl) piperidin-4-yl)-7H-pyrrolo[2,3-d]-pyrimidin-4-amine (C-2)

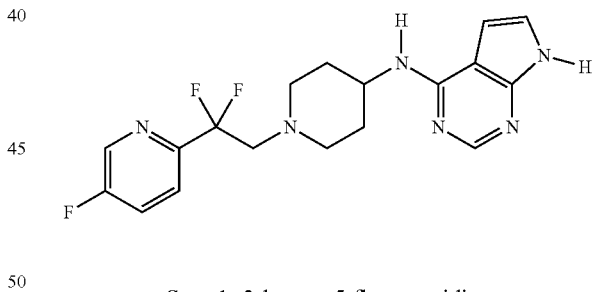

Step 1. 2-bromo-5-fluoropyridine

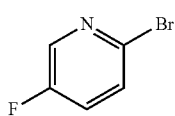

To a 3-neck flask equipped with a dropping funnel and thermometer, 48% HBr (26.7 mL) was added. 5-Fluoropyridin-2-amine (6.0 g, 0.05 mol) was added dropwise at 0° C. $Br_2$ (8.0 mL, 0.16 mol) was then added at 0° C. dropwise over 20 min. The reaction mixture was cooled to −10° C. and a solution of $NaNO_2$ (9.3 g, 0.14 mol) in water (30 mL) was added over 1.5 hours. The resulting mixture was stirred for an additional 30 minutes. A solution of NaOH (20 g, 0.50 mol) in water (30 mL) was added over 30 minutes. The reaction mixture was warmed to 5° C. and then extracted with ether (3×100 mL). The combined organic phases were washed with brine, dried over sodium sulfate, filtered, and concentrated. The concentrate was purified by column chromatography over silica gel (hexane/EtOAc=100:1) to afford the title compound as a colorless liquid (3.37 g, 36%). $^1$H NMR (400 MHz, CDCl$_3$) δ 8.27 (d, J=3.0 Hz, 1H), 7.48 (dd, J=8.7, 4.0 Hz, 1H), 7.35-7.28 (m, 1H).

Step 2. ethyl 2,2-difluoro-2-(5-fluoropyridin-2-yl)acetate

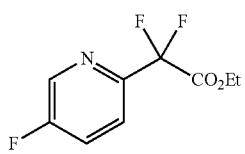

To the solution of 2-bromo-5-fluoropyridine (3.0 g, 17 mmol) and ethyl 2-bromo-2,2-difluoroacetate (3.46 g, 17 mmol) in DMSO (45 mL) was added Cu powder (2.17 g, 34 mmol). The mixture was heated to 50° C. overnight. After stirring overnight, the reaction mixture was poured into a solution of dibasic potassium hydrogen phosphate, trihydrate (38 g, 170 mmol) in water (380 mL) with vigorous stirring. The suspension was filtered and the solid was rinsed with EtOAc. The filtrate was added to brine and extracted with EtOAc (50 mL×2). The combined organic phases were washed with brine, dried over sodium sulfate, filtered, and concentrated. The concentrate was purified by column chromatography over silica gel (hexane/EtOAc=50:1) to afford the title compound as a colorless liquid (2.83 g, 76%). $^1$H NMR (400 MHz, CDCl$_3$) δ 8.50 (d, J=2.7 Hz, 1H), 7.78 (dd, J=8.7, 4.2 Hz, 1H), 7.57 (td, J=8.3, 2.8 Hz, 1H), 4.41-4.35 (q, 2H), 1.34 (m, 3H).

Step 3. 2,2-difluoro-2-(5-fluoropyridin-2-yl)ethanol

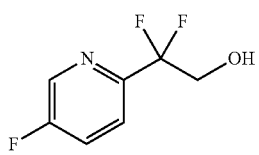

To a solution of ethyl 2,2-difluoro-2-(5-fluoropyridin-2-yl)acetate (1.0 g, 4.6 mmol) in ethanol (23 mL) was added NaBH$_4$ (250 mg, 6.6 mmol) slowly at r.t. The mixture was stirred for 30 min at r.t. After 30 min, the reaction mixture was quenched with 1N HCl under ice-water bath cooling. The mixture was concentrated and extracted with EtOAc. The organic layer was washed with water and brine, dried and concentrated to afford the title compound as a white solid (805 mg, 99%). $^1$H NMR (400 MHz, CDCl$_3$) δ 8.48 (s, 1H), 7.77 (dd, J=8.6, 4.2 Hz, 1H), 7.58 (m, 1H), 4.24 (m, 2H), 3.00 (d, J=6.5 Hz, 1H).

Step 4. 2,2-difluoro-2-(5-fluoropyridin-2-yl)ethyltrifluoromethanesulfonate

To a stirred solution of 2,2-difluoro-2-(5-fluoropyridin-2-yl)ethanol (805 mg, 4.54 mmol) and DIPEA (2.38 mL, 13.6 mmol) in dried ether (45 mL) was added Tf$_2$O (1.52 mL, 9.08 mmol) slowly at 0° C. The reaction mixture was warmed to rt. After stirring for 1 h at r.t., the orange suspension was filtered through celite, and the solid was washed with ether. The filtrate was concentrated to afford the title compound as a pale yellow oil (1.2 g, 85%) which was used in the next step without further purification.

Step 5. tert-butyl 1-(2,2-difluoro-2-(5-fluoropyridin-2-yl)ethyl)piperidin-4-ylcarbamate

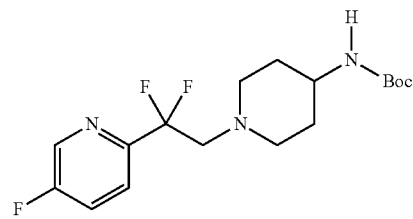 [SMILES: CC(C)(C)OC(=O)NC1CCN(CC(F)(F)c2ccc(F)cn2)CC1]

A mixture of 2,2-difluoro-2-(5-fluoropyridin-2-yl)ethyltrifluoromethanesulfonate (1.2 g, 3.9 mmol), tert-butyl piperidin-4-ylcarbamate (1.56 g, 7.8 mmol) and DIPEA (2.1 mL, 12 mmol) in DCM (20 mL) was heated to 40° C. After stirring overnight at 40° C., the mixture was concentrated and extracted with EtOAc. The organic layer was washed with water and brine, dried and concentrated. The concentrate was purified by column chromatography over silica gel (hexane/EtOAc=10:1) to afford the title compound as a white solid (844 mg, 61%). MS (ESI) calcd for C$_{17}$H$_{24}$F$_3$N$_3$O$_2$: 359.2. found: 360.3 [M+H]. $^1$H NMR (400 MHz, CDCl$_3$) δ 8.49 (d, J=2.7 Hz, 1H), 7.67 (dd, J=8.7, 4.3 Hz, 1H), 7.49 (dt, J=8.4, 2.8 Hz, 1H), 4.35 (s, 1H), 3.39 (s, 1H), 3.19 (t, J=14 Hz, 2H), 2.75-2.82 (m, 2H), 2.32-2.41 (m, 2H), 1.75-1.85 (m, 2H), 1.43 (s, 9H), 1.24-1.32 (m, 2H).

Step 6. 1-(2,2-difluoro-2-(5-fluoropyridin-2-yl)ethyl)piperidin-4-amine

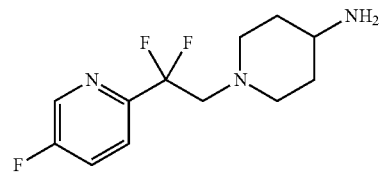 [SMILES: NC1CCN(CC(F)(F)c2ccc(F)cn2)CC1]

To the solution of tert-butyl 1-(2,2-difluoro-2-(5-fluoropyridin-2-yl)ethyl)piperidin-4-ylcarbamate (844 mg, 2.35 mmol) in DCM (12 mL) was added TFA (6 mL) under ice-water bath cooling. After stirring for 30 min at r.t., the mixture was concentrated. The concentrate was basified with 1N NaOH, and extracted with EtOAc. The organic phase was washed with brine, dried Na$_2$SO$_4$, and concentrated to afford the title compound as a yellow solid (634 mg, 100%). MS (ESI) calcd for C$_{12}$H$_{16}$F$_3$N$_3$: 259.1. found: 260.3 [M+H]. $^1$H NMR (400 MHz, CDCl$_3$) δ 8.49 (d, J=2.7 Hz, 1H), 7.67 (dd, J=8.7, 4.3 Hz, 1H), 7.49 (dt, J=8.4, 2.8 Hz, 1H), 3.18 (t, J=14 hz, 2H), 2.85-2.77 (m, 2H), 2.67-2.57 (m, 1H), 2.28-2.32 (m, 2H), 1.74-1.64 (m, 2H), 1.20-1.30 (m, 2H).

Step 7. N-(1-(2,2-difluoro-2-(5-fluoropyridin-2-yl)ethyl)piperidin-4-yl)-7H-pyrrolo[2,3-d]-pyrimidin-4-amine

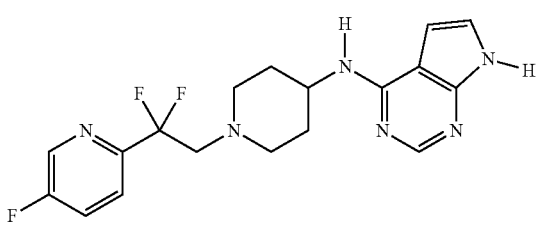 [SMILES: Fc1ccc(C(F)(F)CN2CCC(Nc3ncnc4[nH]ccc34)CC2)nc1]

A mixture of 1-(2,2-difluoro-2-(5-fluoropyridin-2-yl)ethyl)piperidin-4-amine (609 mg, 2.35 mmol), 4-chloro-7H-pyrrolo[2,3-d]pyrimidine (301 mg, 1.96 mmol) and DIPEA (0.7 mL, 3.92 mmol) in n-butyl alcohol (12 mL) was heated to 130° C. After stirring overnight at 130° C., the reaction solution was concentrated and extracted with EtOAc. The organic layers were washed with water and brine, dried and concentrated. The concentrate was purified by column chromatography over silica gel (hexane/EtOAc=1/3) to afford the title compound as a white solid (282 mg, 38%). MS (ESI) calcd for C$_{18}$H$_{19}$F$_3$N$_6$: 376.2. found: 377.3 [M+H]. $^1$H NMR (400 MHz, CD$_3$OD) δ 8.57 (d, J=2.7 Hz, 1H), 8.07 (s, 1H), 7.82 (dd, J=8.7, 4.4 Hz, 1H), 7.76 (dt, J=8.5, 2.7 Hz, 1H), 7.05 (d, J=3.5 Hz, 1H), 6.58 (d, J=3.5 Hz, 1H), 4.06-3.95 (m, 1H), 3.27 (t, J=14 Hz, 2H), 2.92-2.96 (m, 2H), 2.45-2.52 (m, 2H), 1.88-1.94 (m, 2H), 1.50-1.60 (m, 2H).

Example 1.2a (HCl Salt)

N-(1-(2,2-difluoro-2-(5-fluoropyridin-2-yl)ethyl)piperidin-4-yl)-7H-pyrrolo-[2,3-d]pyrimidin-4-amine hydrochloride (C-2.HCl)

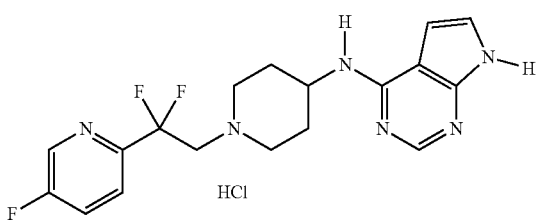 [SMILES: Fc1ccc(C(F)(F)CN2CCC(Nc3ncnc4[nH]ccc34)CC2)nc1 ; Cl]

To the solution of N-(1-(2,2-difluoro-2-(5-fluoropyridin-2-yl)ethyl)piperidin-4-yl)-7H-pyrrolo[2,3-d]pyrimidin-4-amine (120 mg, 0.32 mmol) in MeOH (2 mL) was added HCl/MeOH (2M, 0.16 mL, 0.32 mmol) at rt. After stirring for 10 min, the mixture was concentrated to afford the title compound as a pale yellow solid (129 mg, 98%). MS (ESI) calcd for C$_{18}$H$_{19}$F$_3$N$_6$: 376.2. found: 377.3 [M+H]. $^1$H NMR (400 MHz, CD$_3$OD) δ 8.61 (d, J=2.5 Hz, 1H), 8.27 (s, 1H), 7.89 (dd, J=8.7 and 4.4 Hz, 1H), 7.83 (dt, J=8.5 and 2.7 Hz, 1H), 7.34 (d, J=3.5 Hz, 1H), 6.91 (d, J=3.5 Hz, 1H), 4.10 (brs, 1H), 3.76 (brs, 2H), 3.38 (m, 2H), 2.98 (brs, 2H), 2.16 (m, 2H), 1.90 (m, 2H).

Example 1.3

N-(1-(2-(5-chloropyridin-2-yl)-2,2-difluoroethyl)piperidin-4-yl)-7H-pyrrolo-[2,3-d]pyrimidin-4-amine (C-3)

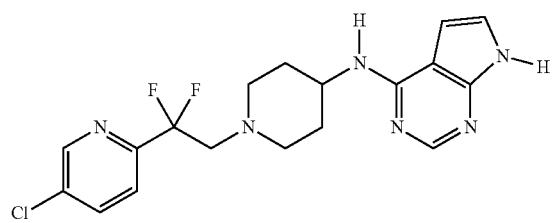

Step 1. ethyl 2-(5-chloropyridin-2-yl)-2,2-difluoroacetate

To a solution of 5-chloro-2-iodopyridine (2.50 g, 10.4 mmol) and ethyl 2-bromo-2,2-difluoroacetate (2.11 g, 10.4 mmol) in DMSO (26 mL) was added Cu powder (1.33 g, 20.8 mmol). The mixture was heated to 50° C. overnight. The reaction mixture was poured into a solution of dibasic potassium hydrogen phosphate, trihydrate (24 g, 104 mmol) in water (240 mL) with vigorous stirring. The suspension was filtered and the solid was rinsed with EtOAc. The filtrate was diluted with brine and extracted with EtOAc (20 mL×2). The combined organic phases were washed with brine, dried over sodium sulfate, filtered, and concentrated. The concentrate was purified by column chromatography over silica gel (hexane/EtOAc=100:1) to afford the title compound as a colorless oil (885 mg, 36%). MS (ESI) calcd for C$_9$H$_8$ClF$_2$NO$_2$: 235.0. found: 236.2 [M+H]. $^1$H NMR (400 MHz, CDCl$_3$) δ 8.61 (d, J=2.0 Hz, 1H), 7.85 (dd, J=8.4 and 2.0 Hz, 1H), 7.71 (d, J=8.4 Hz, 1H), 4.37 (q, J=7.2 Hz, 2H), 1.34 (t, J=7.2 Hz, 3H).

Step 2. 2-(5-chloropyridin-2-yl)-2,2-difluoroethanol

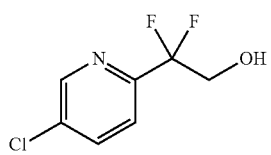 [SMILES: OCC(F)(F)c1ccc(Cl)cn1]

To s solution of ethyl 2-(5-chloropyridin-2-yl)-2,2-difluoroacetate (780 mg, 3.3 mmol) in ethanol (16.5 mL) was added NaBH$_4$ (180 mg, 4.76 mmol) slowly at r.t. The mixture was stirred for 30 min at r.t. The reaction mixture was quenched with 1N HCl under ice-water bath cooling. The mixture was concentrated and extracted with EtOAc. The organic layer was washed with water and brine, dried and concentrated to afford the title compound as a white solid (538 mg, 84%). $^1$H NMR (400 MHz, CDCl$_3$) δ 8.58 (s, 1H), 7.85 (d, J=8.4 Hz, 1H), 7.69 (d, J=8.4 Hz, 1H), 4.23 (t, J=12.4 Hz, 2H).

Step 3. 2-(5-chloropyridin-2-yl)-2,2-difluoroethyl trifluoromethanesulfonate

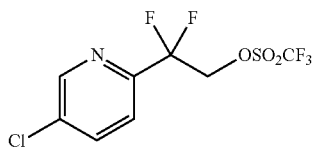

To the solution of 2-(5-chloropyridin-2-yl)-2,2-difluoroethanol (538 mg, 2.78 mmol) and DIPEA (1.5 mL, 5.56 mmol) in ether (28 mL) was added Tf$_2$O (0.94 mL, 5.56 mmol) slowly at 0° C. After stirring for 1 h at rt, the reaction mixture was filtered through celite, and the filter mass was washed with ether. The combined organic phases were concentrated to afford the crude title compound as a pale yellow solid (905 mg, 100%).

Step 4. tert-butyl 1-(2-(5-chloropyridin-2-yl)-2,2-difluoroethyl)piperidin-4-ylcarbamate

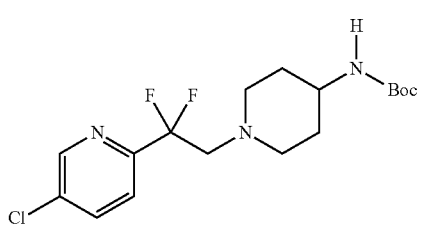 [SMILES: CC(C)(C)OC(=O)NC1CCN(CC(F)(F)c2ccc(Cl)cn2)CC1]

The mixture of 2-(5-chloropyridin-2-yl)-2,2-difluoroethyl trifluoromethanesulfonate (905 mg, 2.77 mmol), tert-butyl piperidin-4-ylcarbamate (1.11 g, 5.56 mmol) and DIPEA (1.46 mL, 8.34 mmol) in DCM (15 mL) was heated to 40° C. After stirring overnight at 40° C., the mixture was concentrated and extracted with EtOAc. The organic phases were washed with water and brine, dried and concentrated. The concentrate was purified by column chromatography over silica gel (hexane/EtOAc=10:1) to afford the title compound as a white solid (922 mg, 89%). MS (ESI) calcd for C$_{17}$H$_{24}$ClF$_2$N$_3$O$_2$: 375.2. found: 376.2 [M+H]. $^1$H NMR (400 MHz, CDCl$_3$) δ 8.59 (d, J=2.4 Hz, 1H), 7.77 (dd, J=8.4 and 2.4 Hz, 1H), 7.60 (d, J=8.4 Hz, 1H), 4.35 (s, 1H), 3.38 (s, 1H), 3.18 (t, J=14.3 Hz, 2H), 2.84-2.76 (m, 2H), 2.37 (m, 2H), 1.80 (m, 2H), 1.43 (s, 9H), 1.27 (m, 3H).

Step 5. 1-(2-(5-chloropyridin-2-yl)-2,2-difluoroethyl)piperidin-4-amine

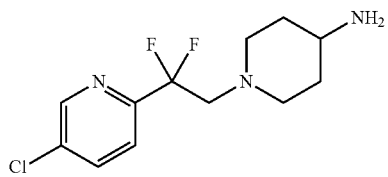 [SMILES: NC1CCN(CC(F)(F)c2ccc(Cl)cn2)CC1]

To the solution of tert-butyl 1-(2-(5-chloropyridin-2-yl)-2,2-difluoroethyl)piperidin-4-ylcarbamate (919 mg, 2.45 mmol) in DCM (14 mL) was added TFA (7 mL) under ice-water bath cooling. After stirring for 30 min at r.t., the mixture was concentrated. The concentrate was basified with 1N NaOH, and extracted with EtOAc. The organic phase was washed with brine, dried over Na$_2$SO$_4$, and concentrated to afford the title compound as a white solid (674 mg, 100%). MS (ESI) calcd for C$_{12}$H$_{16}$ClF$_2$N$_3$: 275.1. found: 276.2 [M+H]. $^1$H NMR (400 MHz, CDCl$_3$) δ 8.59 (d, J=2.4 Hz, 1H), 7.77 (dd, J=8.4 and 2.4 Hz, 1H), 7.59 (d, J=8.4 Hz, 1H), 3.80 (s, 4H), 3.18 (t, J=14.1 Hz, 2H), 2.85 (m, 2H), 2.81-2.74 (m, 1H), 2.33 (m, 2H), 1.75 (m, 2H), 1.37 (m, 2H).

Step 6. N-(1-(2-(5-chloropyridin-2-yl)-2,2-difluoroethyl)piperidin-4-yl)-7H-pyrrolo-[2,3-d]pyrimidin-4-amine

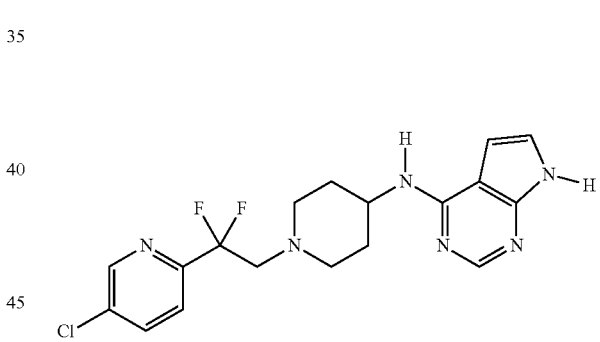

A mixture of 1-(2-(5-chloropyridin-2-yl)-2,2-difluoroethyl)piperidin-4-amine (674 mg, 2.45 mmol), 4-chloro-7H-pyrrolo[2,3-d]pyrimidine (314 mg, 2.04 mmol) and DIPEA (0.72 mL, 4.08 mmol) in n-butyl alcohol (10 mL) was heated to 130° C. After stirring overnight at 130° C., the reaction solution was concentrated and extracted with EtOAc. The combined organic layers were washed with water and brine, dried and concentrated. The concentrate was purified by column chromatography over silica gel (hexane/EtOAc=1/3) to afford the title compound as a white solid (306 mg, 38%). MS (ESI) calcd for C$_{18}$H$_{19}$ClF$_2$N$_6$: 392.1. found: 393.2 [M+H]. $^1$H NMR (400 MHz, CD$_3$OD) δ 8.66 (d, J=2.4 Hz, 1H), 8.07 (s, 1H), 8.01 (dd, J=8.4 and 2.4 Hz, 1H), 7.75 (d, J=8.4 Hz, 1H), 7.05 (d, J=3.5 Hz, 1H), 6.58 (d, J=3.5 Hz, 1H), 4.05-3.95 (m, 1H), 3.27 (t, J=14.3 Hz, 2H), 2.95 (m, 2H), 2.49 (m, 2H), 1.92 (m, 2H), 1.54 (m, 2H).

Example 1.3a (HCl Salt)

N-(1-(2-(5-chloropyridin-2-yl)-2,2-difluoroethyl)piperidin-4-yl)-7H-pyrrolo[2,3-d]pyrimidin-4-amine hydrochloride (C-3.HCl)

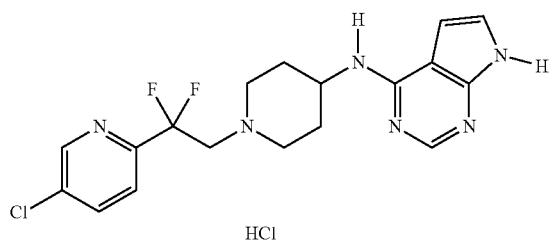 [SMILES: FC(F)(CN1CCC(Nc2ncnc3[nH]ccc23)CC1)c1ccc(Cl)cn1 ; Cl]

HCl

To the solution of N-(1-(2-(5-chloropyridin-2-yl)-2,2-difluoroethyl)piperidin-4-yl)-7H-pyrrolo[2,3-d]-pyrimidin-4-amine (283 mg, 0.72 mmol) in MeOH (3.6 mL) was added HCl/MeOH (2M, 0.36 mL, 0.72 mmol) at rt. After stirring for 10 min, the mixture was concentrated to afford the title compound as a white solid (305 mg, 98%). MS (ESI) calcd for $C_{18}H_{19}ClF_2N_6$: 392.1. found: 393.2 [M+H]. $^1$H NMR (400 MHz, CD$_3$OD) δ 8.70 (d, J=2.4 Hz, 1H), 8.24 (s, 1H), 8.06 (dd, J=8.5, 2.4 Hz, 1H), 7.80 (d, J=8.5 Hz, 1H), 7.32 (d, J=3.5 Hz, 1H), 6.89 (d, J=3.5 Hz, 1H), 4.01 (s, 1H), 3.57 (m, 2H), 3.25 (m, 2H), 2.81 (s, 2H), 2.08 (m, 2H), 1.80 (m, 2H).

Example 1.4

N-(1-(2,2-difluoro-2-(5-methylpyridin-2-yl)ethyl)piperidin-4-yl)-7H-pyrrolo[2,3-d]pyrimidin-4-amine (C-4)

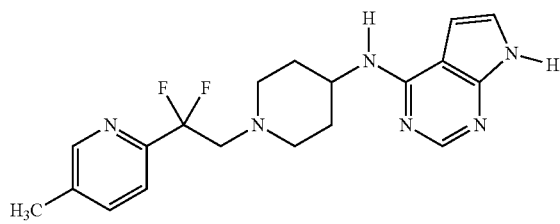

Step 1: ethyl 2,2-difluoro-2-(5-methylpyridin-2-yl)acetate

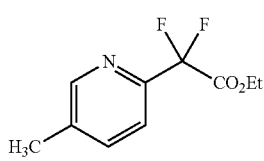

To a solution of ethyl 2-bromo-5-methylpyridine (4.0 g, 24 mmol) and ethyl 2-bromo-2,2-difluoroacetate (4.8 g, 24 mmol) in DMSO (80 mL) was added Cu powder (3.0 g, 47 mmol). The mixture was heated at 50° C. overnight. The reaction mixture was filtered through celite. The filtrate was extracted with ethyl acetate. The combined ethyl acetate layers were dried over sodium sulfate, filtered, and concentrated. The concentrate was purified by column chromatography over silica gel (hexane/ethyl acetate=100:1) to afford the title compound as a colorless oil (3.7 g, 74%) $^1$H NMR (400 MHz, CDCl$_3$) δ 8.47 (s, 1H), 7.69-7.57 (m, 2H), 4.37 (q, J=7.1 Hz, 2H), 2.40 (s, 3H), 1.33 (t, J=7.1 Hz, 3H).

Step 2: 2,2-difluoro-2-(5-methylpyridin-2-yl)ethanol

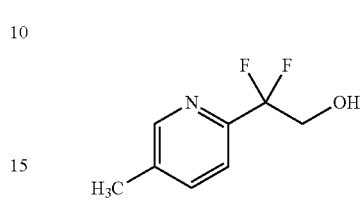

To a solution of ethyl 2,2-difluoro-2-(5-methylpyridin-2-yl)acetate (2.0 g, 9.3 mmol) in ethanol (45 mL) was added NaBH$_4$ (500 mg, 13.4 mmol) slowly. The mixture was stirred for 30 min at rt. After 30 min, the reaction mixture was quenched with 1N HCl under ice-water bath cooling, concentrated and extracted with ethyl acetate. The ethyl acetate layer was washed with water and brine, then dried and concentrated to afford the title compound as a white solid (1.6 g, 100%). $^1$H NMR (400 MHz, CDCl$_3$) δ 8.44 (s, 1H), 7.71 (d, J=8 Hz, 1H), 7.64 (d, J=8.0 Hz, 1H), 4.22 (t, J=12.4 Hz, 2H), 3.03 (brs, 1H), 2.41 (s, 3H).

Step 3: 2,2-difluoro-2-(5-methylpyridin-2-yl)ethyl trifluoromethanesulfonate

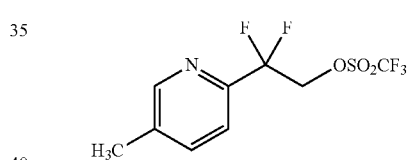

To a solution of 2,2-difluoro-2-(5-methylpyridin-2-yl)ethanol (800 mg, 4.6 mmol) and DIPEA (2.8 ml, 13.8 mmol) in anhydrous ether (40 ml) was added Tf$_2$O (1.5 ml, 9.2 mmol) at 0° C. After stirring for 1 hr at rt, the white suspension was filtered through celite, and the filtered mass was washed with ether. The combined filtrates were concentrated and purified by column chromatography over silica gel (hexane) to afford the title compound as a colorless oil (1.0 g, 70%). $^1$H NMR (400 MHz, CDCl$_3$) δ 8.47 (s, 1H), 7.65 (m, 2H), 5.10 (t, J=12.0 Hz, 2H), 2.42 (s, 3H).

Step 4: tert-buty 11-(2,2-difluoro-2-(5-methylpyridin-2-yl)ethyl)piperidin-4-yl-carbamate

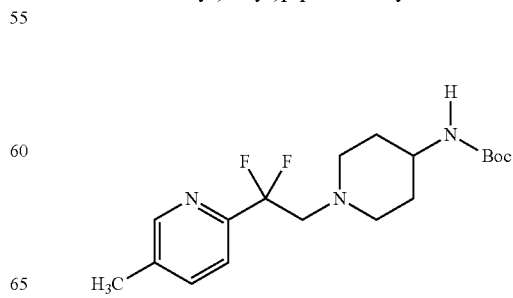

A mixture of 2,2-difluoro-2-(5-methylpyridin-2-yl)ethyl trifluoromethanesulfonate (1.0 g, 3.3 mmol), tert-butyl piperidin-4-ylmethylcarbamate (1.3 g, 6.6 mmol) and DIPEA (2.0 ml, 9.9 mmol) in DCM (16 ml) was heated to 40° C. with stirring. After stirring overnight at 40° C., the mixture was concentrated to dryness. The concentrate was purified by column chromatography over silica gel (hexane/ethyl acetate=10/1) to afford the title compound as a yellow solid (1.0 g, 83%). MS (ESI) calcd for $C_{18}H_{27}F_2N_3O_2$: 355.2. found: 356.2 [M+H]. $^1$H NMR (400 MHz, CDCl$_3$) δ 8.46 (s, 1H), 7.60-7.50 (m, 2H), 3.72-3.61 (m, 1H), 3.40 (brs, 1H), 3.19 (t, J=14.7 Hz, 2H), 2.85-2.80 (m, 2H), 2.38 (s, 3H), 2.32-3.40 (m, 2H), 1.82-1.78 (m, 2H), 1.43 (s, 9H), 1.25-1.30 (m, 2H).

Step 5: 1-(2,2-difluoro-2-(5-methylpyridin-2-yl)ethyl)piperidin-4-amine

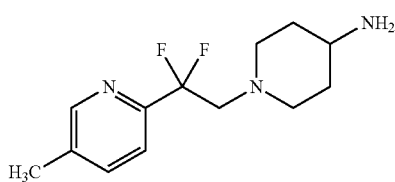

To a solution of tert-butyl 1-(2,2-difluoro-2-(5-methylpyridin-2-yl)ethyl) piperidin-4-ylcarbamate (1.0 g, 2.8 mmol) in DCM (15 ml) was added TFA (12.5 ml) at 0° C. After stirring for 30 min at rt., the mixture was concentrated. The concentrate was basified with 1 N NaOH and extracted with ethyl acetate. The organic phase was washed with brine, dried over Na$_2$SO$_4$, and concentrated to afford the title compound as an off-white powder (400 mg, 60%). MS (ESI) calcd for $C_{13}H_{19}F_2N_3$: 255.2. found: 256.2 [M+H]. $^1$H NMR (400 MHz, CDCl$_3$) δ 8.47 (s, 1H), 7.59-7.52 (m, 2H), 3.18 (t, J=14.6 Hz, 2H), 2.85-2.82 (m, 2H), 2.64-2.54 (m, 1H), 2.38 (s, 3H), 2.35-2.28 (m, 2H), 1.69-1.66 (m, 2H), 1.32-1.26 (m, 2H).

Step 6: N-(1-(2,2-difluoro-2-(5-methylpyridin-2-yl)ethyl)piperidin-4-yl)-7H-pyrrolo[2,3-d]pyrimidin-4-amine

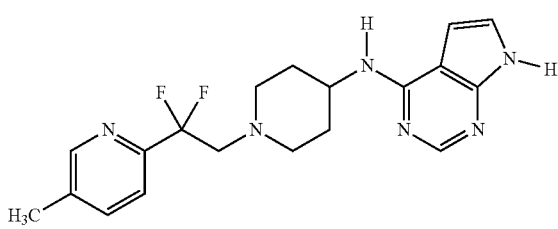 [SMILES: FC(F)(F)c1ccc(C(F)(F)CN2CCC(Nc3ncnc4[nH]ccc34)CC2)nc1]

A mixture of 1-(2,2-difluoro-2-(5-methylpyridin-2-yl)ethyl) piperidin-4-amine (400 mg, 1.60 mmol), 4-chloro-7H-pyrrolo[2,3-d]pyrimidine (200 mg, 1.30 mmol) and DIPEA (0.5 mL, 2.6 mmol) in butyl alcohol (8 mL) was heated to 130° C. After stirring overnight at 130° C., the orange solution was concentrated. The concentrate was purified by column chromatography over silica gel (hexane/ethyl acetate=1:3) to afford the title compound as a white solid (130 mg, 24%). MS (ESI) calcd for $C_{19}H_{22}F_2N_6$: 372.2. found: 373.3 [M+H]. $^1$H NMR (400 MHz, CDCl$_3$) δ 10.44 (s, 1H), 8.48 (s, 1H), 8.31 (s, 1H), 7.62-7.55 (m, 2H), 7.07 (d, J=3.5 Hz, 1H), 6.34 (d, J=3.5 Hz, 1H), 4.12 (m, 1H), 3.26 (t, J=14.6 Hz, 2H), 2.95-2.92 (m, 2H), 2.56-2.50 (m, 2H), 2.39 (s, 3H), 2.00-2.01 (m, 2H), 1.57-1.48 (m, 2H).

Example 1.4a (HCl Salt)

N-(1-(2,2-difluoro-2-(5-methylpyridin-2-yl)ethyl)piperidin-4-yl)-7H-pyrrolo[2,3-d]pyrimidin-4-amine hydrochloride (C-4.HCl)

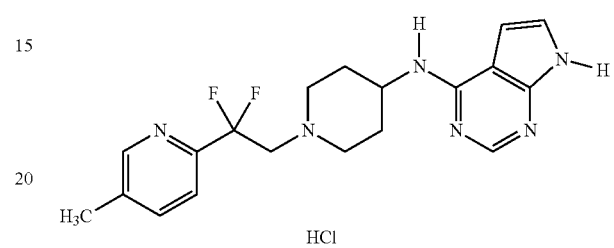

To a stirred solution of N-(1-(2,2-difluoro-2-(5-methylpyridin-2-yl)ethyl)piperidin-4-yl)-7H-pyrrolo[2,3-d]pyrimidin-4-amine (100 mg, 0.26 mmol) in MeOH (1.3 mL) was added HCl/Et$_2$O (2M, 0.13 mL, 0.26 mmol) at rt. After stirring for 15 min, the mixture was concentrated to afford the title compound as an off-white powder (109 mg, 98%). MS (ESI) calcd for $C_{19}H_{22}F_2N_6$: 372.2. found: 373.3 [M+H]. $^1$H NMR (400 MHz, CD$_3$OD) δ 8.52 (s, 1H), 8.22 (s, 1H), 7.84 (d, J=8.0 Hz, 1H), 7.68 (d, J=8.0 Hz, 1H), 7.29 (d, J=3.5 Hz, 1H), 6.85 (d, J=3.5 Hz, 1H), 4.02 (s, 1H), 3.60-3.53 (m, 2H), 3.26 (m, 2H), 2.83 (m, 2H), 2.45 (s, 3H), 2.08-2.05 (m, 2H), 1.90-1.73 (m, 2H).

Example 1.5

N-(1-(2,2-difluoro-2-(5-(trifluoromethyl)pyridin-2-yl)ethyl)piperidin-4-yl)-7H-pyrrolo[2,3-d]pyrimidin-4-amine (C-5)

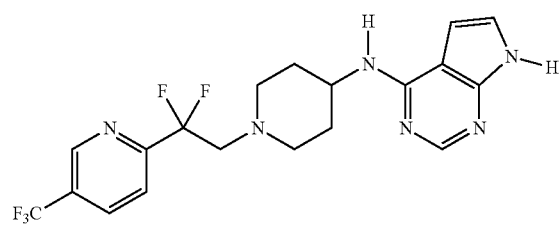

Step 1: ethyl 2,2-difluoro-2-(5-(trifluoromethyl)pyridin-2-yl)acetate

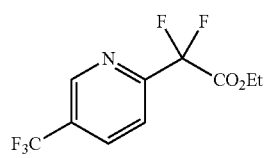

To a solution of ethyl 2,2-difluoro-2-iodoacetate (5.5 g, 22 mmol) and 2-bromo-5-trifluoromethyl-pyridine (5.0 g, 22 mmol) in DMSO (110 mL) was added Cu powder (2.8 g, 44 mmol). The mixture was heated at 80° C. for 20 hours. The reaction mixture was filtered through celite and the solid cake was extracted with ethyl acetate. The combined filtrates were extracted with ethyl acetate. The ethyl acetate layers were combined, dried over sodium sulfate, filtered, and concentrated. The concentrate was purified by column chromatography over silica gel (hexane/ethyl acetate=100:1) to afford the title compound as a colorless oil (2.5 g, 42%). $^1$H NMR (400 MHz, CDCl$_3$) δ 8.93 (s, 1H), 8.13 (d, J=7.9 Hz, 1H), 7.90 (d, J=8.1 Hz, 1H), 4.39 (q, J=7.1 Hz, 2H), 1.34 (t, J=7.1 Hz, 3H).

Step 2: 2,2-difluoro-2-(5-(trifluoromethyl)pyridin-2-yl)ethanol

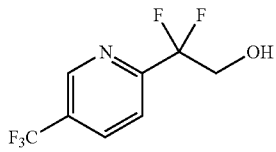

To a solution of ethyl 2,2-difluoro-2-(5-(trifluoromethyl)pyridin-2-yl)acetate (1.0 g, 3.7 mmol) in ethanol (19 mL) was added NaBH$_4$ (200 mg, 5.3 mmol) slowly. The mixture was stirred for 30 min at rt. The stirred reaction mixture was cooled, quenched with 1N HCl, concentrated and extracted with ethyl acetate. The ethyl acetate layer was washed with water and brine, dried over sodium sulfate and concentrated to afford the title compound as a white solid (850 mg) which was used in the next step without further purification. $^1$H NMR (400 MHz, CDCl$_3$) δ 8.92 (s, 1H), 8.13 (d, J=8.0 Hz, 1H), 7.88 (d, J=8.0 Hz, 1H), 4.28 (t, J=12 Hz, 2H), 2.42 (s, 1H).

Step 3: 2,2-difluoro-2-(5-(trifluoromethyl)pyridin-2-yl)ethyl trifluoromethanesulfonate

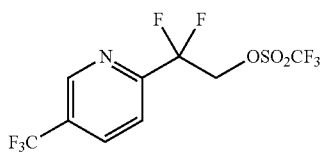

To a solution of 2,2-difluoro-2-(5-(trifluoromethyl)pyridin-2-yl)ethanol (750 mg, 3.3 mmol) and DIPEA (2.0 ml, 9.9 mmol) in anhydrous ether (33 mL) was added Tf$_2$O (1.1 ml, 6.6 mmol) at 0° C. After stirring for 1 hr at rt, the white suspension was filtered through celite. The solid mass was extracted with ether. The filtrate was concentrated and purified by column chromatography over silica gel (hexane) to afford the title compound as a colorless liquid (760 mg, 75%). $^1$H NMR (400 MHz, CDCl$_3$) δ 8.95 (s, 1H), 8.16 (d, J=8.2, 1H), 7.91 (d, J=8.2 Hz, 1H), 5.14 (t, J=11.8 Hz, 2H).

Step 4: tert-butyl-1-(2,2-difluoro-2-(5-(trifluoromethyl)pyridin-2-yl)ethyl)piperidin-4-ylcarbamate

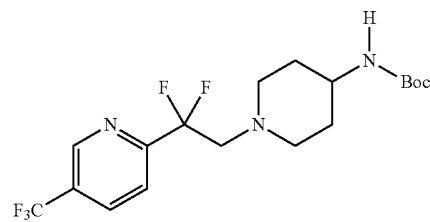

A mixture of 2,2-difluoro-2-(5-(trifluoromethyl)pyridin-2-yl)ethyl trifluoromethanesulfonate (1.04 g, 2.9 mmol), tert-butyl piperidin-4-ylcarbamate (1.16 g, 5.8 mmol) and DIPEA (1.5 mL, 8.7 mmol) in DCM (20 mL) was heated to 40° C. After stirring overnight at 40° C., the mixture was concentrated and extracted with EtOAc. The organic layer was washed with water and brine, dried and concentrated. The concentrate was purified by column chromatography over silica gel (hexane/EtOAc=5:1) to afford the title compound as a white solid (1.05 g, 92%). MS (ESI) calcd for C$_{18}$H$_{24}$F$_5$N$_3$O$_2$: 409.2. found: 410.2 [M+H]. $^1$H NMR (400 MHz, CDCl$_3$) δ 8.91 (s, 1H), 8.05 (d, J=8.2 Hz, 1H), 7.78 (d, J=8.2 Hz, 1H), 4.34 (brs, 1H), 3.39 (m, 1H), 3.22 (t, J=14.2 Hz, 2H), 2.83-2.78 (m, 2H), 2.41-2.35 (m, 2H), 1.81-1.77 (m, 2H), 1.42 (s, 9H), 1.20-1.30 (m, 2H), Step 5: 1-(2,2-difluoro-2-(5-(trifluoromethyl)pyridin-2-yl)ethyl)piperidin-4-amine

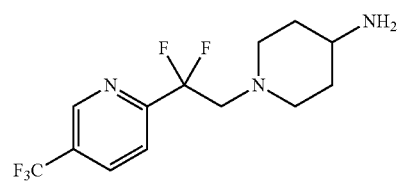

To a solution of tert-butyl 1-(2,2-difluoro-2-(5-(trifluoromethyl)pyridin-2-yl)ethyl)-piperidin-4-ylcarbamate (300 mg, 0.73 mmol) in DCM (8 mL) was added TFA (4.4 mL) at ice-water bath temperature. After stirring for 15 min at r.t., the mixture was concentrated. The concentrate was basified with 1N NaOH, and extracted with EtOAc. The organic phase was washed with brine, dried over Na$_2$SO$_4$, and concentrated to afford the title compound as a pale yellow oil (226 mg) which was used directly in the next step. MS (ESI) calcd for C$_{13}$H$_{16}$F$_5$N$_3$: 309.1. found: 310.3 [M+H]. $^1$H NMR (400 MHz, CDCl$_3$) δ 8.92 (s, 1H), 8.04 (d, J=8.2 Hz, 1H), 7.79 (d, J=8.2 Hz, 1H), 3.22 (t, J=14.1 Hz, 2H), 2.82-2.79 (m, 2H), 2.64-2.54 (m, 1H), 2.35-2.29 (m, 2H), 1.68-1.65 (m, 2H), 1.29-1.23 (m, 2H), 1.21-1.18 (m, 2H).

Step 6: N-(1-(2,2-difluoro-2-(5-(trifluoromethyl)pyridin-2-yl)ethyl)piperidin-4-yl)-7H-pyrrolo[2,3-d]pyrimidin-4-amine

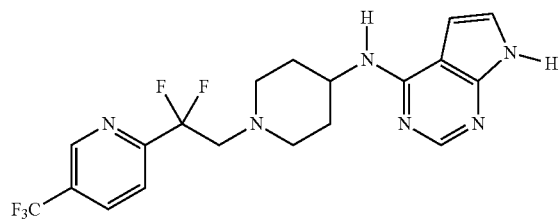

A mixture of 1-(2,2-difluoro-2-(5-(trifluoromethyl)pyridin-2-yl)ethyl) piperidin-4-amine (600 mg, 1.9 mmol), 4-chloro-7H-pyrrolo[2,3-d]pyrimidine (245 mg, 1.6 mmol) and DIPEA (0.6 mL, 3.2 mmol) in butyl alcohol (10 mL) was heated to 130° C. After stirring overnight at 130° C., the orange solution was concentrated. The concentrate was purified by column chromatography over silica gel (hexane/ethyl acetate=1:3) to afford the title compound as a gray powder (270 mg, 34%). MS (ESI) calcd for $C_{19}H_{19}F_5N_6$: 426.2. found: 427.2 [M+H]. $^1$H NMR (400 MHz, CDCl$_3$) δ 10.24 (s, 1H), 8.93 (s, 1H), 8.32 (s, 1H), 8.07 (dd, J=8.2 and 1.9 Hz, 1H), 7.82 (d, J=8.2 Hz, 1H), 7.06 (d, J=3.5 Hz, 1H), 6.32 (d, J=3.5 Hz, 1H), 4.92 (brs, 1H), 4.18-4.03 (m, 1H), 3.29 (t, J=14.2 Hz, 2H), 2.93-2.90 (m, 2H), 2.56-2.50 (m, 2H), 2.08-1.96 (m, 2H), 1.50-1.40 (m, 2H).

Example 1.5a (HCl Salt)

N-(1-(2,2-difluoro-2-(5-(trifluoromethyl)pyridin-2-yl)ethyl)piperidin-4-yl)-7H-pyrrolo[2,3-d]pyrimidin-4-amine hydrochloride (C-5.HCl)

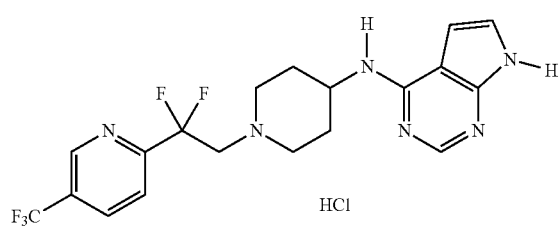

To the solution of N-(1-(2,2-difluoro-2-(5-(trifluoromethyl)pyridin-2-yl)ethyl)piperidin-4-yl)-7H-pyrrolo[2,3-d]pyrimidin-4-amine (237 mg, 0.56 mmol) in MeOH (3.0 mL) was added HCl/Et$_2$O (2M, 0.28 mL, 0.56 mmol) at rt. After stirring for 15 min, the mixture was concentrated to afford the title compound as an off-white powder (260 mg, 98%). MS (ESI) calcd for $C_{19}H_{19}F_5N_6$: 426.2. found: 427.2 [M+H]. $^1$H NMR (400 MHz, CD$_3$OD) δ 9.03 (s, 1H), 8.35 (dd, J=8.3, 1.9 Hz, 1H), 8.22 (s, 1H), 7.99 (d, J=8.3 Hz, 1H), 7.32 (d, J=3.5 Hz, 1H), 6.87 (d, J=3.5 Hz, 1H), 3.94 (m, 1H), 3.45 (m, 2H), 3.10 (m, 2H), 2.69 (m, 2H), 1.95 (m, 2H), 1.65 (m, 2H), 1.30 (m, 2H).

Example 1.6

N-(1-(2-(5-(difluoromethyl)pyridin-2-yl)-2,2-difluoroethyl)piperidin-4-yl)-7H-pyrrolo[2,3-d]pyrimidin-4-amine (C-6)

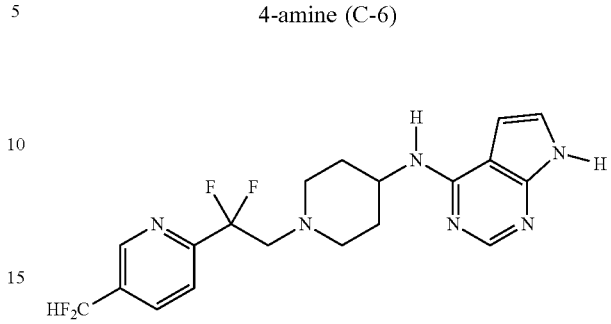

Step 1. 2-bromo-5-(difluoromethyl)pyridine

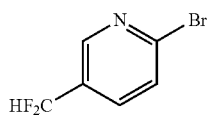

To a stirred solution of 6-bromonicotinaldehyde (10 g, 54 mmol) in DCM (300 mL) was added DAST (11 mL, 164 mmol) dropwise under ice bath cooling. The mixture was stirred at room temperature for 13 hours, quenched with ice-water under ice-water bath cooling, and neutralized with aqueous NaHCO$_3$. The aqueous phase was extracted with DCM. The combined organic phases were washed with brine, dried over anhydrous Na$_2$SO$_4$ and concentrated. The residue was purified by column chromatography over silica gel (EtOAc/Hex=1/10) to afford the title compound as a colorless oil (8.1 g, 72%). $^1$H NMR (400 MHz, CDCl$_3$) δ 8.52 (s, 1H), 7.72-7.69 (m, 1H), 7.61 (d, J=8.4 Hz, 1H), 6.70 (t, J=55.6 Hz, 1H).

Step 2. ethyl 2-(5-(difluoromethyl)pyridin-2-yl)-2,2-difluoroacetate

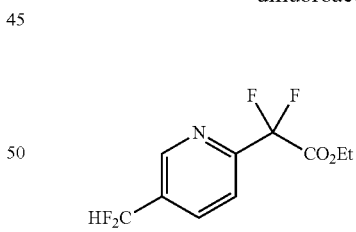

To a solution of ethyl 2-bromo-2,2-difluoroacetate (800 mg, 3.94 mmol) and 2-bromo-5-(difluoromethyl)pyridine (823 mg, 3.94 mmol) in DMSO (16 mL) was added Cu powder (500 mg, 7.88 mmol). The mixture was heated to 80° C. under N$_2$ with stirring for 20 hours. The mixture was cooled to room temperature and water was added. The mixture was stirred at ambient temperature for additional 30 min. The resulting suspension was filtered through a pad of celite and washed with ethyl acetate. The filtrate was extracted with ethyl acetate. The combined organic phases were washed with water, brine, dried over sodium sulfate, and concentrated. The concentrate was purified by column chromatography over silica gel (hexane/ethyl acetate=100:

1) to afford the title compound as a colorless liquid (597 mg, 60%). ¹H NMR (400 MHz, CDCl₃) δ 8.79 (s, 1H), 8.03 (d, J=8.4 Hz, 1H), 7.86 (d, J=8.4 Hz, 1H), 6.77 (t, J=55.6 Hz, 1H), 4.41-4.36 (m, 2H), 1.34 (t, J=7.2 Hz, 3H).

Step 3. 2-(5-(difluoromethyl)pyridin-2-yl)-2,2-difluoroethanol

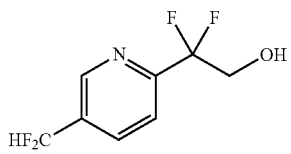

To a stirred solution of ethyl 2-(5-(difluoromethyl)pyridin-2-yl)-2,2-difluoroacetate (597 mg, 2.37 mmol) in ethanol (15 mL) was added NaBH₄ (135 mg, 3.57 mmol) portionwise slowly under ice bath cooling. The mixture was stirred for 30 min at 0° C. After the ester was consumed, the reaction mixture was quenched with 1N HCl. The mixture was concentrated and extracted with ethyl acetate. The ethyl acetate layer was washed with water, brine, dried and concentrated to afford the title compound as a white solid (455 mg, 92%). MS (ESI) calcd for C₈H₇F₄NO: 209.1. found: 210.2 [M+H]. ¹H NMR (400 MHz, CDCl₃) δ 8.77 (s, 1H), 8.03 (d, J=8.0 Hz, 1H), 7.84 (d, J=8.0 Hz, 1H), 6.77 (t, J=55.6 Hz, 1H), 4.30-4.22 m, 2H), 3.08 (t, J=6.8 Hz, 1H).

Step 4. 2-(5-(difluoromethyl)pyridin-2-yl)-2,2-difluoroethyl trifluoromethanesulfonate

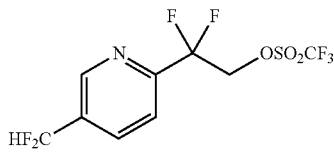

To a stirred solution of 2-(5-(difluoromethyl)pyridin-2-yl)-2,2-difluoroethanol (455 mg, 2.77 mmol) and DIPEA (0.76 mL, 4.34 mmol) in anhydrous ether (10 mL) was added Tf₂O (0.4 mL, 2.83 mmol) at 0° C. After stirring for 1 h, the white suspension was filtered through celite, and the filter mass was extracted with ether. The combined organic phases were concentrated and purified by column chromatography over silica gel (hexane) to afford the title compound as a colorless liquid (550 mg, 74%). ¹H NMR (400 MHz, CDCl₃) δ 8.81 (s, 1H), 8.06 (d, J=8.0 Hz, 1H), 7.87 (d, J=8.0 Hz, 1H), 6.79 (t, J=55.6 Hz, 1H), 5.13 (t, J=11.6 Hz, 2H).

Step 5: N-(1-(2-(5-(difluoromethyl)pyridin-2-yl)-2,2-difluoroethyl)piperidin-4-yl)-7-tosyl-7H-pyrrolo[2,3-d]pyrimidin-4-amine

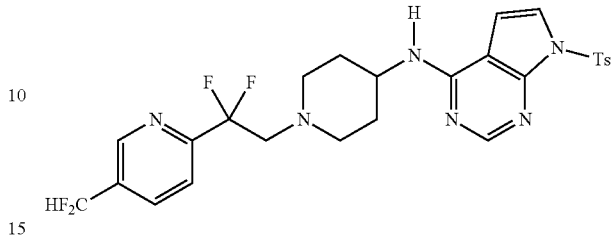

A stirred mixture of 2-(5-(difluoromethyl)pyridin-2-yl)-2,2-difluoroethyl trifluoromethanesulfonate (1.1 g, 3.3 mmol), N-(piperidin-4-yl)-7-tosyl-7H-pyrrolo[2,3-d]-pyrimidin-4-amine (Intermediate 1, 1.2 g, 3.3 mmol) and DIPEA (1.2 ml, 6.6 mmol) in DCM/DMF solvent mixture (10 mL/6 mL) was heated to 40° C. After stirring overnight at 40° C., the mixture was concentrated to dryness. The concentrate was purified by column chromatography over silica gel (hexane/EtOAc=1/1) to afford the title compound as a white powder (720 mg, 70%). ¹H NMR (400 MHz, CDCl₃) δ 8.79 (s, 1H), 8.40 (s, 1H), 8.05 (d, J=8.4 Hz, 2H), 7.96 (d, J=8.0 Hz, 1H), 7.76 (d, J=8.0 Hz, 1H), 7.44 (d, J=4.0 Hz, 1H), 7.28 (d, J=8.4 Hz, 2H), 6.77 (t, J=55.6 Hz, 1H), 6.37 (d, J=4.0 Hz, 1H), 4.78-4.76 (m, 1H), 4.07-3.96 (m, 1H), 3.26 (t, J=14.4 Hz, 2H), 2.90-2.87 (m, 2H), 2.52-2.46 (m, 2H), 2.38 (s, 3H), 1.95-1.93 (m, 2H), 1.44-1.35 (m, 2H).

Step 6: N-(1-(2-(5-(difluoromethyl)pyridin-2-yl)-2,2-difluoroethyl)piperidin-4-yl)-7H-pyrrolo[2,3-d]pyrimidin-4-amine

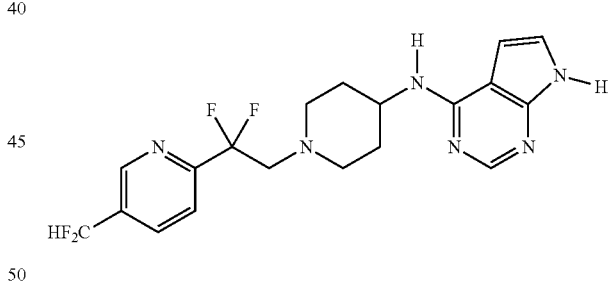

To a stirred solution of N-(1-(2-(5-(difluoromethyl)pyridin-2-yl)-2,2-difluoroethyl)-piperidin-4-yl)-7-tosyl-7H-pyrrolo[2,3-d]pyrimidin-4-amine (720 mg, 1.28 mmol) in THF (6 mL) was added 50% NaOH (6 ml) at room temperature. The mixture was stirred for 4 hours at 60° C. and then partitioned into DCM and water. The organic phase was washed with water and brine, dried over Na₂SO₄ and concentrated. The concentrate was purified by column chromatography over silica gel (DCM/MeOH=40:1) to afford the title compound as a white powder (360 mg, 69%). MS (ESI) calcd for C₁₉H₂₀F₄N₆: 408.2. found: 409.2 [M+H]. ¹H NMR (400 MHz, CD₃OD) δ 8.84 (s, 1H), 8.16 (d, J=8.0 Hz, 1H), 8.07 (s, 1H), 7.89 (d, J=8.0 Hz, 1H), 7.05 (d, J=3.6 Hz, 1H), 7.00 (t, J=55.2 Hz, 1H), 6.58 (d, J=3.6 Hz, 1H), 4.04-3.96 (m, 1H), 3.32-3.27 (m, 2H), 2.97-2.94 (m, 2H), 2.52-2.46 (m, 2H), 1.93-1.90 (m, 2H), 1.58-1.48 (m, 2H).

Example 1.6a (HCl Salt)

N-(1-(2-(5-(difluoromethyl)pyridin-2-yl)-2,2-difluoroethyl)piperidin-4-yl)-7H-pyrrolo[2,3-d]pyrimidin-4-amine hydrochloride (C-6.HCl)

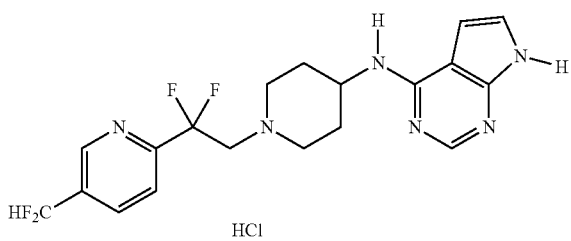

To a stirred solution of N-(1-(2-(5-(difluoromethyl)pyridin-2-yl)-2,2-difluoroethyl)-piperidin-4-yl)-7H-pyrrolo[2,3-d]pyrimidin-4-amine (345 mg, 0.84 mmol) in MeOH (4 mL) was added 2M MeOH/HCl (0.42 ml, 0.84 mmol). The mixture was stirred for 30 min. The solution was concentrated to afford the title compound as an off-white powder (370 mg, 99%). MS (ESI) calcd for $C_{19}H_{20}F_4N_6$: 408.2. found: 409.2 [M+H]. $^1$H NMR (400 MHz, CD$_3$OD) δ 8.87 (s, 1H), 8.24 (s, 1H), 8.20 (d, J=8.0 Hz, 1H), 7.93 (d, J=8.0 Hz, 1H), 7.32 (d, J=3.2 Hz, 1H), 7.02 (t, J=53.2 Hz, 1H), 6.88 (d, J=3.2 Hz, 1H), 4.02-3.97 (m, 1H), 3.63-3.56 (m, 2H), 3.25-3.22 (m, 2H), 2.81-2.76 (m, 2H), 2.08-2.05 (m, 2H), 1.82-1.73 (m, 2H).

Example 1.7

N-(1-(2,2-difluoro-2-(5-(fluoromethyl)pyridin-2-yl)ethyl)piperidin-4-yl)-7H-pyrrolo[2,3-d]pyrimidin-4-amine (C-7)

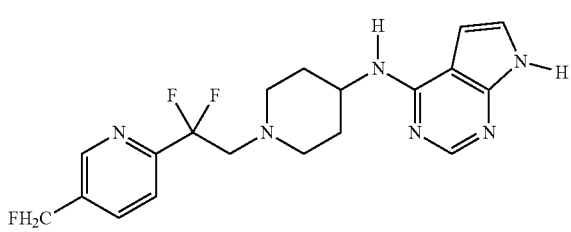

Step 1. Ethyl 2,2-difluoro-2-(5-(hydroxymethyl)pyridin-2-yl)acetate

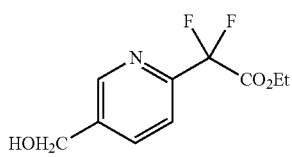

A mixture of (6-bromopyridin-3-yl)methanol (15.0 g, 79.8 mmol), ethyl 2-bromo-2,2-difluoroacetate (19.4 g, 95.7 mmol) and copper powder (10.2 g, 160 mmol) in DMSO (100 mL) was stirred at 80° C. overnight. After the mixture was cooled to rt, it was poured into water (300 mL). After stirring for 30 minutes, the solid was removed by filtration. The filter cake was extracted with ethyl acetate. The combined organic phases were washed with water, brine, dried over NaSO$_4$ and concentrated. The residue was purified by column chromatography over silica gel (eluent: Hexane:EtOAc=4:1) to afford the title compound as a yellow oil (3.66 g, 20%). $^1$H NMR (400 MHz, CDCl$_3$) δ 8.62 (s, 1H), 7.89 (dd, J=2.0 and 8.0 Hz, 1H), 7.73 (d, J=8.0 Hz, 1H), 4.81 (s, 2H), 4.37 (q, J=7.2 Hz, 2H), 1.32 (t, J=7.2 Hz, 3H).

Step 2. Ethyl 2,2-difluoro-2-(5-(fluoromethyl)pyridin-2-yl)acetate

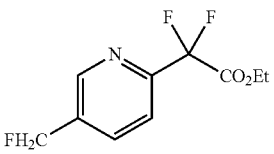

To a stirred solution of ethyl 2,2-difluoro-2-(5-(fluoromethyl)pyridin-2-yl)acetate (3.66 g, 15.8 mmol) in DCM (50 mL) was slowly added DAST at 0° C. The resulting mixture was warmed to rt. and stirred overnight. The reaction mixture was quenched by water under ice-water bath cooling, followed by addition of saturated aqueous Na$_2$CO$_3$ to adjust to pH=8-9. The aqueous layer was extracted with DCM. The combined organic layers were dried over Na$_2$SO$_4$ and concentrated under reduced pressure. The crude product was purified by column chromatography over silica gel (eluent: Hexane:EtOAc=10:1) to afford the title compound as a yellow oil (1.51 g, 41%). $^1$H NMR (400 MHz, CDCl$_3$) δ 8.64 (s, 1H), 7.89 (d, J=8.4 Hz, 1H), 7.78 (d, J=8.4 Hz, 1H), 5.48 (d, J=47.2 Hz, 2H), 4.37 (q, J=7.2 Hz, 2H), 1.32 (t, J=7.2 Hz, 3H).

Step 3. 2,2-difluoro-2-(5-(fluoromethyl)pyridin-2-yl)ethanol

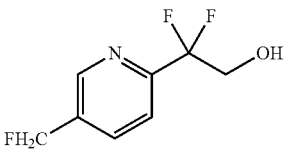

To a stirred solution of ethyl 2,2-difluoro-2-(5-(fluoromethyl)pyridin-2-yl)acetate (1.51 g, 6.48 mmol)) in ethanol was slowly added NaBH$_4$ (370 mg, 9.72 mmol) at 0° C. The resulting suspension was stirred for 1 hour. The reaction mixture was quenched by addition of 1M HCl under ice-water bath cooling. The mixture was concentrated and the residue was adjusted to pH=10. The aqueous phase was extracted with EtOAc. The organic layers were combined and dried over Na$_2$SO$_4$. The solvent was removed, and the crude product was purified by column chromatography over silica gel (eluent: Hexane:EtOAc=30:1-15:1) to afford the title compound as a yellow oil (1.1 g, 96%). $^1$H NMR (400 MHz, CDCl$_3$) δ 8.62 (s, 1H), 7.89 (d, J=8.0 Hz, 1H), 7.77 (d, J=8.0 Hz, 1H), 5.48 (d, J=47.2 Hz, 2H), 4.28-4.22 (m, 2H), 3.28-3.28 (m, 1H).

Step 4. 2,2-difluoro-2-(5-(fluoromethyl)pyridin-2-yl)ethyl trifluoromethanesulfonate

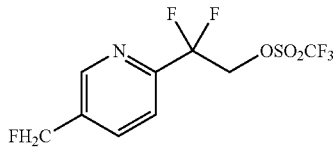

To a stirred solution of 2,2-difluoro-2-(5-(fluoromethyl)pyridin-2-yl)ethanol (800 mg, 4.18 mmol) in anhydrous diethyl ether (10 mL) was slowly added DIPEA and Tf$_2$O successively under N$_2$ atmosphere at 0° C. After stirring at 0° C. for 10 min, the resulting suspension was warmed to rt. and stirred for additional 1 hour. The suspension was filtered through a pad of celite and the filter cake was extracted with ether. The combined filtrates were concentrated under reduced pressure. The residue was purified by column chromatography over silica gel (eluent: Hexane:EtOAc=50:1) to afford the title compound as a colorless oil (750 mg, 56%). $^1$H NMR (400 MHz, CDCl$_3$) δ 8.66 (s, 1H), 7.91 (d, J=8.0 Hz, 1H), 7.79 (d, J=8.0 Hz, 1H), 5.50 (d, J=47.2 Hz, 2H), 5.12 (t, J=12.0 Hz, 2H).

Step 5. N-(1-(2,2-difluoro-2-(5-(fluoromethyl)pyridin-2-yl)ethyl)piperidin-4-yl)-7-tosyl-7H-pyrrolo[2,3-d]pyrimidin-4-amine

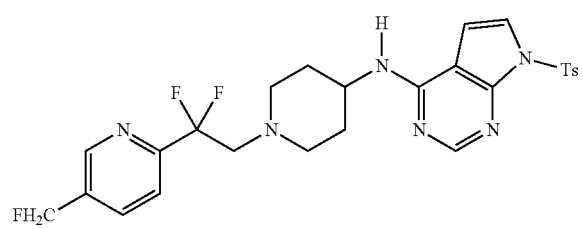

A mixture of 2,2-difluoro-2-(5-(fluoromethyl)pyridin-2-yl)ethyl trifluoromethanesulfonate (300 mg, 0.93 mmol), N-(piperidin-4-yl)-7-tosyl-7H-pyrrolo[2,3-d]pyrimidin-4-amine (380 mg, 1.02 mmol) and DIPEA (0.24 mL, 1.39 mmol) in DCM/DMF (V:V=3 mL:1 mL) was warmed to 60° C. and stirred overnight. The mixture was concentrated and the residue t was purified by column chromatography over silica gel (eluent: Hexane:EtOAc=1:1) to afford the title compound as a white powder (370 mg, 73%). $^1$H NMR (400 MHz, CDCl$_3$) δ 8.65 (s, 1H), 8.40 (s, 1H), 8.05 (d, J=8.4 Hz, 2H), 7.83 (d, J=8.0 Hz, 1H), 7.69 (d, J=8.0 Hz, 1H), 7.45 (d, J=4.0 Hz, 1H), 7.28 (d, J=8.0 Hz, 2H), 6.36 (d, J=4.0 Hz, 1H), 5.47 (d, J=47.2 Hz, 2H), 4.78-4.68 (m, 1H), 4.08-3.98 (m, 1H), 3.25 (d, J=14.4 Hz, 2H), 2.90-2.87 (m, 2H), 2.52-2.45 (m, 2H), 2.38 (s, 3H), 1.99-1.89 (m, 2H), 1.46-1.36 (m, 2H).

Step 6. N-(1-(2,2-difluoro-2-(5-(fluoromethyl)pyridin-2-yl)ethyl)piperidin-4-yl)-7H-pyrrolo[2,3-d]pyrimidin-4-amine

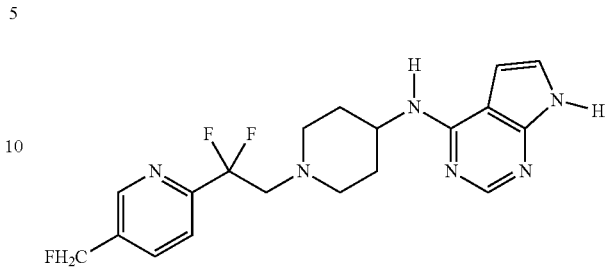

A mixture of N-(1-(2,2-difluoro-2-(5-(fluoromethyl)pyridin-2-yl)ethyl)piperidin-4-yl)-7-tosyl-7H-pyrrolo[2,3-d]pyrimidin-4-amine (360 mg, 0.66 mmol) and NaOH (50%, 3 mL) in THF was stirred at 60° C. for 1.5 hours. The green suspension was concentrated. The residue was adjusted to pH=10 with dilute aqueous HCl under ice-water bath cooling. The aqueous layer was extracted with DCM. The organic layers were combined, dried over Na$_2$SO$_4$, and concentrated. The crude product was purified by column chromatography over silica gel (eluent: DCM:MeOH=30:1) to afford the title compound as a yellow powder (207 mg, 80%). MS (ESI) calcd for C$_{19}$H$_{21}$F$_3$N$_6$: 390.2. found: 391.3 [M+H]. $^1$H NMR (400 MHz, CDCl$_3$) δ 10.47 (s, 1H), 8.67 (s, 1H), 8.32 (s, 1H), 7.84 (d, J=8.0 Hz, 1H), 7.72 (d, J=8.0 Hz, 1H), 7.07-7.05 (m, 1H), 6.34-6.30 (m, 1H), 5.48 (d, J=47.2 Hz, 2H), 4.86-4.85 (m, 1H), 4.17-4.04 (m, 1H), 3.27 (d, J=14.4 Hz, 2H), 2.96-2.87 (m, 2H), 2.55-2.50 (m, 2H), 2.03-2.00 (m, 2H), 1.52-1.42 (m, 2H).

Example 1.7a (HCl Salt)

N-(1-(2,2-difluoro-2-(5-(fluoromethyl)pyridin-2-yl)ethyl)piperidin-4-yl)-7H-pyrrolo[2,3-d]pyrimidin-4-amine hydrochloride (C-7.HCl)

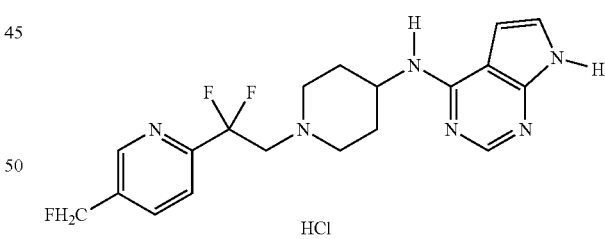

To a solution of N-(1-(2,2-difluoro-2-(5-(fluoromethyl)pyridin-2-yl)ethyl)piperidin-4-yl)-7H-pyrrolo[2,3-d]pyrimidin-4-amine (207 mg, 0.53 mmol) in MeOH (3 mL) was added HCl solution in MeOH (0.27 mL, 2M, 0.53 mmol). The mixture was stirred at rt. for 30 min. The solution was concentrated to afford the title compound as a white powder (226 mg, 100%). MS (ESI) calcd for C$_{19}$H$_{21}$N$_6$F$_3$: 390.2. found: 391.3 [M+H]. $^1$H NMR (400 MHz, CD$_3$OD) δ 8.72 (s, 1H), 8.25 (s, 1H), 8.06 (d, J=8.4 Hz, 1H), 7.85 (d, J=8.4 Hz, 1H), 7.32 (d, J=3.6 Hz, 1H), 6.89 (d, J=3.6 Hz, 1H), 5.55 (d, J=47.2 Hz, 2H), 4.11-4.07 (m, 1H), 3.79-3.76 (m, 2H), 3.43-3.40 (m, 2H), 3.00-2.98 (m, 2H), 2.17-2.13 (m, 2H), 1.95-1.86 (m, 2H).

Example 1.11

N-(1-(2,2-difluoro-2-(5-(trifluoromethoxy)pyridin-2-yl)ethyl)piperidin-4-yl)-7H-pyrrolo[2,3-d]pyrimidin-4-amine (C-11)

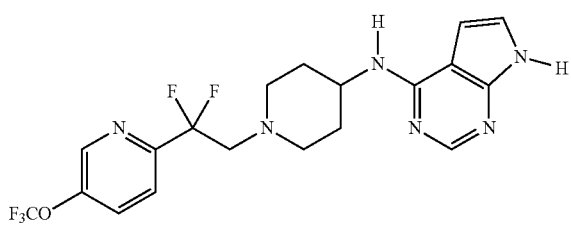 [SMILES: FC(F)(F)Oc1ccc(C(F)(F)CN2CCC(Nc3ncnc4[nH]ccc34)CC2)nc1]

Step 1: ethyl 2,2-difluoro-2-(5-(trifluoromethoxy)pyridin-2-yl)acetate

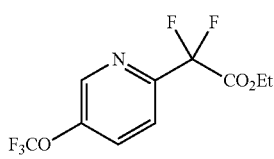

To a stirred solution of 2-bromo-5-(trifluoromethoxy)pyridine (2.0 g, 8.3 mmol) and ethyl 2-bromo-2,2-difluoroacetate (1.1 mL, 8.7 mmol) in DMSO (4 mL) was added copper powder (1.1 g, 17 mmol). The mixture was heated to 80° C. overnight, cooled to rt and poured into water. The suspension was filtered through a pad of celite and the filter mass was extracted with EtOAc. The combined organic phases were washed with water, brine, dried over $Na_2SO_4$ and concentrated under vacuum. The residue was purified by column chromatography over silica gel to afford the title compound as a colorless oil (1.48 g, 62%). $^1$H NMR (400 MHz, CDCl$_3$) δ 8.57 (d, J=2.0 Hz, 1H), 7.83 (d, J=8.8 Hz, 1H), 7.72 (dd, J=8.8 and 2.0 Hz, 1H), 4.39 (q, J=7.2 Hz, 2H), 1.34 (t, J=7.2 Hz, 3H).

Step 2: 2,2-difluoro-2-(5-(trifluoromethoxy)pyridin-2-yl)ethanol

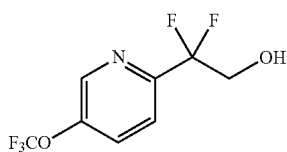 [SMILES: OCC(F)(F)c1ccc(OC(F)(F)F)cn1]

To a stirred solution of ethyl 2,2-difluoro-2-(5-(trifluoromethoxy)pyridin-2-yl)acetate (1.47 g, 5.18 mmol) in ethanol (25 mL) was added NaBH$_4$ (290 mg, 7.77 mmol) at room temperature. The reaction was exothermic, and gradually a clear solution was obtained. After stirring for 30 min, the ester was consumed. The reaction was quenched with ice water at 0° C., followed by concentration. The residue was extracted with EtOAc. The combined organic phases were washed with brine, dried over $Na_2SO_4$ and concentrated. The residue was purified by column chromatography over silica gel (hexane/EtOAc=10/1) to give the title compound as a colorless oil (820 mg, 65%). $^1$H NMR (400 MHz, CDCl$_3$) δ 8.56 (d, J=2.0 Hz, 1H), 7.81 (d, J=8.8 Hz, 1H), 7.73 (dd, J=8.8 and 2.0 Hz, 1H), 4.31-4.20 (m, 2H), 2.84 (t, J=7.2 Hz, 1H).

Step 3: 2,2-difluoro-2-(5-(trifluoromethoxy)pyridin-2-yl)ethyltrifluoromethanesulfonate

Tf$_2$O (0.75 mL, 4.38 mmol) was added dropwise to a stirred solution of 2,2-difluoro-2-(5-(trifluoromethoxy)pyridin-2-yl)ethanol (820 mg, 3.37 mmol) and DIPEA (1.7 mL, 10 mmol) in dry ether (15 mL) at 0° C. under N$_2$ atmosphere. The mixture was stirred for 1 h at room temperature, filtered through a pad of celite, and the filter mass was extracted with ether. The combined organic phases were concentrated and the residue was purified by column chromatography over silica gel (hexane/EtOAc=40/1) to yield the title compound as a colorless oil (1.17 g, 92%). $^1$H NMR (400 MHz, CDCl$_3$) δ 8.59 (d, J=1.9 Hz, 1H), 7.84 (d, J=8.6 Hz, 1H), 7.76 (dd, J=8.6 and 1.9 Hz, 1H), 5.11 (t, J=12.0 Hz, 2H).

Step 4: N-(1-(2,2-difluoro-2-(5-(trifluoromethoxy)pyridin-2-yl)ethyl)piperidin-4-yl)-7-tosyl-7H-pyrrolo[2,3-d]pyrimidin-4-amine

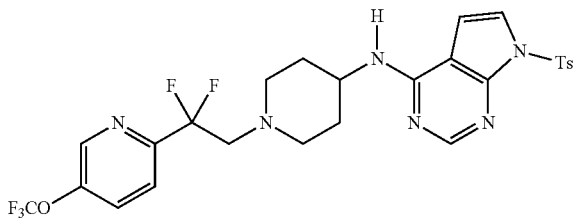 [SMILES: Cc1ccc(S(=O)(=O)n2ccc3c(NC4CCN(CC(F)(F)c5ccc(OC(F)(F)F)cn5)CC4)ncnc32)cc1]

A mixture of 2,2-difluoro-2-(5-(trifluoromethoxy)pyridin-2-yl)ethyltrifluoromethanesulfonate (620 mg, 1.65 mmol), N-(piperidin-4-yl)-7-tosyl-7H-pyrrolo[2,3-d]pyrimidin-4-amine (Intermediate 1, 740 mg, 1.98 mmol) and DIPEA (0.4 mL, 2.47 mmol) in mixed DMF/DCM solvent (v/v=5 mL/10 mL) was warmed to 60° C. After stirring overnight, the solution was cooled down to rt and concentrated. The residue was purified by column chromatography over silica gel (hexane/EtOAc=2/1) to afford the title compound as a white powder (750 mg, 76%). MS (ESI) calcd for $C_{26}H_{25}F_5N_6O_3S$: 596.2. found: 597.2 [M+H]. $^1$H NMR (400 MHz, CDCl$_3$) δ 8.57 (d, J=2.0 Hz, 1H), 8.40 (s, 1H), 8.06 (d, J=8.4 Hz, 2H), 7.72 (d, J=8.0 Hz, 1H), 7.67-7.65 (m, 1H), 7.44 (d, J=4.0 Hz, 1H), 7.28 (d, J=8.4 Hz, 2H), 6.37 (d, J=4.0 Hz, 1H), 4.85-4.76 (m, 1H), 4.08-3.97 (m, 1H), 3.24 (t, J=14.4 Hz, 2H), 2.92-2.89 (m, 2H), 2.53-2.44 (m, 2H), 2.38 (s, 3H), 1.97-1.94 (m, 2H), 1.46-1.34 (m, 2H).

Step 5: N-(1-(2,2-difluoro-2-(5-(trifluoromethoxy)
pyridin-2-yl)ethyl)piperidin-4-yl)-7H-pyrrolo[2,3-d]
pyrimidin-4-amine

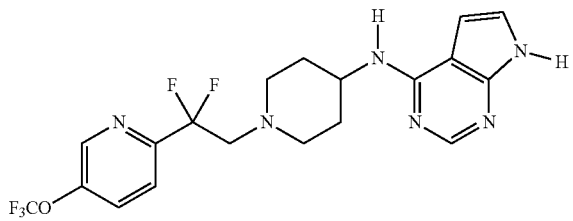

N-(1-(2,2-difluoro-2-(5-(trifluoromethoxy)pyridin-2-yl)
ethyl)piperidin-4-yl)-7-tosyl-7H-pyrrolo[2,3-d]pyrimidin-
4-amine (750 mg, 1.25 mmol) was dissolved in THF (6 mL),
followed by addition of 50% aqueous NaOH (3 mL). The
mixture thus obtained was heated to 60° C. After stirring for
3 hours, the mixture was allowed to cool to room temperature
and was concentrated. The residual aqueous phase was
acidified to pH=10, and extracted with EtOAc. The combined
organic phases were washed with brine, dried over
$Na_2SO_4$ and concentrated. The residue was purified by
column chromatography over silica gel (DCM/MeOH=30/1)
to yield the title compound as an off-white powder (460 mg,
82%). MS (ESI) calcd for $C_{19}H_{19}F_5N_6O$: 442.2. found:
443.2 [M+H]. $^1$H NMR (400 MHz, $CD_3OD$) δ 8.64 (d, J=2.0
Hz, 1H), 8.05 (s, 1H), 7.93 (dd, J=8.0, 2.0 Hz, 1H), 7.86 (d,
J=8.0 Hz, 1H), 7.02 (d, J=4.0 Hz, 1H), 6.56 (d, J=4.0 Hz,
1H), 4.03-3.93 (m, 1H), 3.25 (t, J=14.3 Hz, 2H), 2.99-2.90
(m, 2H), 2.52-2.41 (m, 2H), 1.93-1.86 (m, 2H), 1.58-1.45
(m, 2H).

Example 1.11a (HCl Salt)

N-(1-(2,2-difluoro-2-(5-(trifluoromethoxy)pyridin-2-
yl)ethyl)piperidin-4-yl)-7H-pyrrolo[2,3-d]pyrimidin-
4-amine hydrochloride (C-11.HCl)

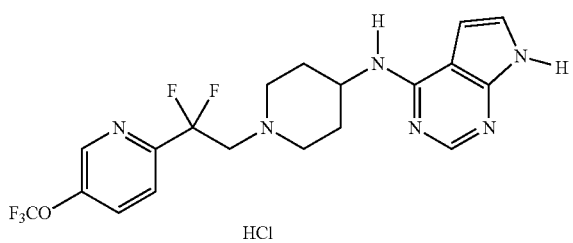 [SMILES: FC(F)(F)Oc1ccc(C(F)(F)CN2CCC(Nc3ncnc4[nH]ccc34)CC2)nc1 ; Cl]

To a solution of N-(1-(2,2-difluoro-2-(5-(trifluoromethoxy)pyridin-2-yl)ethyl)piperidin-4-yl)-7H-pyrrolo[2,3-d]pyrimidin-4-amine (450 mg, 1.0 mmol) in methanol (5 mL) was added methanolic HCl (2.0 M, 0.51 mL, 1.0 mmol) at room temperature. After stirring for 30 min, the solution was concentrated to afford the title compound as an off-white powder (460 mg, 94%). MS (ESI) calcd for $C_{19}H_{19}F_5N_6O$: 442.2. found: 443.3 [M+H]. $^1$H NMR (400 MHz, $CD_3OD$) δ 8.68 (d, J=2.0 Hz, 1H), 8.23 (s, 1H), 7.98 (d, J=8.8 and 2.0 Hz, 1H), 7.91 (d, J=8.7 Hz, 1H), 7.30 (d, J=3.6 Hz, 1H), 6.88 (d, J=3.6 Hz, 1H), 4.07-3.93 (m, 1H), 3.60 (t, J=14.0 Hz, 2H), 3.29-3.19 (m, 2H), 2.88-2.74 (m, 2H), 2.11-2.03 (m, 2H), 1.85-1.71 (m, 2H).

Example 1.12

N-(1-(2-(5-(difluoromethoxy)pyridin-2-yl)-2,2-difluoroethyl)piperidin-4-yl)-7H-pyrrolo[2,3-d]pyrimidin-4-amine (C-12)

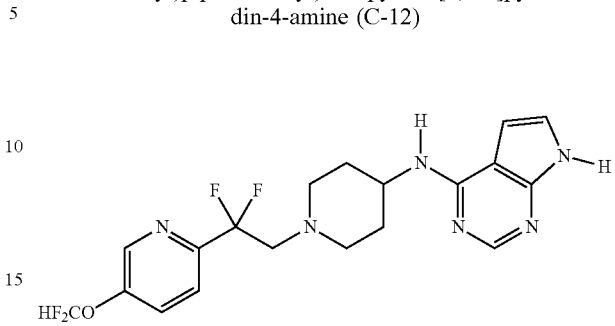

Step 1. Ethyl-2-(5-(difluoromethoxy)pyridin-2-yl)-2,
2-difluoroacetate

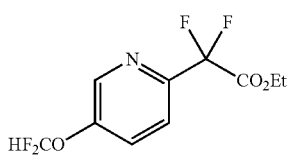

To a stirred solution of 2-bromo-5-(difluoromethoxy)
pyridine (12.0 g, 54 mmol) and ethyl 2-bromo-2,2-difluoroacetate (7.6 mL, 59 mmol) in DMSO (130 mL) was added copper powder (6.90 g, 107 mmol). The resulting mixture was stirred at 50° C. overnight. The mixture was then poured into water, and stirred for 30 min. The suspension was filtered through a pad of celite, and the filter mass was extracted with ethyl acetate. The combined organic phases were washed with brine, dried over $Na_2SO_4$ and concentrated in vacuo. The residue was purified by column chromatography over silica gel to afford the title compound as a colorless oil (12.0 g, 84%).

Step 2. 2-(5-(difluoromethoxy)pyridin-2-yl)-2,2-
difluoroethanol

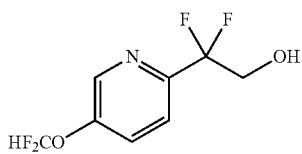

To a stirred solution of ethyl 2-(5-(difluoromethoxy)
pyridin-2-yl)-2,2-difluoroacetate (1.4 g, 5.7 mmol) in ethanol (20 mL) was added $NaBH_4$ (300 mg, 7.9 mmol) slowly under ice-water bath cooling. The mixture was stirred for 30 min and quenched with 1N HCl under ice-water bath cooling. The mixture was concentrated and extracted with ethyl acetate. The ethyl acetate layer was washed with water, brine, dried over $Na_2SO_4$ and concentrated to afford the title compound as a white solid (1.06 g, 91%). $^1$H NMR (400 MHz, $CDCl_3$) δ 8.48 (d, J=2.8 Hz, 1H), 7.76 (d, J=8.4 Hz, 1H), 7.65 (dd, J=8.4, 2.8 Hz, 1H), 6.61 (t, J=72.0 Hz, 1H), 4.28-4.20 (m, 2H), 3.02 (t, J=7.2 Hz, 1H).

Step 3. 2-(5-(difluoromethoxy)pyridin-2-yl)-2,2-difluoroethyltrifluoromethanesulfonate

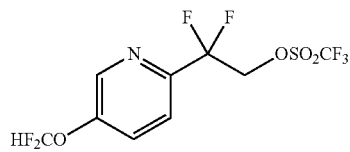

To a stirred solution of 2-(5-(difluoromethoxy)pyridin-2-yl)-2,2-difluoroethanol (1.0 g, 4.4 mmol) and DIPEA (1.2 mL, 6.7 mmol) in dry ether (20 mL) was added $Tf_2O$ (0.9 mL, 5.3 mmol) at 0° C. After stirring for 1 h, the white suspension was filtered through a pad of celite, and the filter mass was extracted with ether. The combined organic phases were concentrated and the residue was purified by column chromatography over silica gel (hexane) to afford the title compound as a colorless oil (1.35 g, 84%). $^1$H NMR (400 MHz, $CDCl_3$) δ 8.51 (d, J=2.4 Hz, 1H), 7.78 (d, J=8.4 Hz, 1H), 7.66 (dd, J=8.4, 2.4 Hz, 1H), 6.61 (t, J=72.0 Hz, 1H), 5.10 (t, J=12.0 Hz, 2H).

Step 4. N-(1-(2-(5-(difluoromethoxy)pyridin-2-yl)-2,2-difluoroethyl)piperidin-4-yl)-7-tosyl-7H-pyrrolo[2,3-d]pyrimidin-4-amine

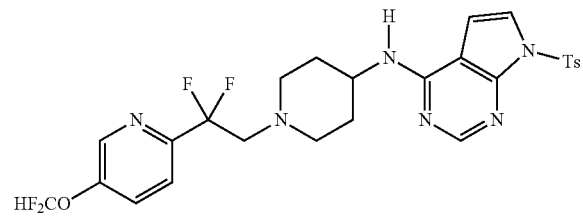

A mixture of 2-(5-(difluoromethoxy)pyridin-2-yl)-2,2-difluoroethyltrifluoromethanesulfonate (500 mg, 1.4 mmol), N-(piperidin-4-yl)-7-tosyl-7H-pyrrolo[2,3-d]pyrimidin-4-amine (Intermediate 1, 623 mg, 1.68 mmol) and DIPEA (0.36 mL, 2.1 mmol) in a DCM/DMF solvent mixture (6 mL/3 mL) was heated to 60° C. After stirring overnight at 60° C., the mixture was concentrated. The concentrate was purified by column chromatography over silica gel to afford the title compound as a white powder (580 mg, 76%). $^1$H NMR (400 MHz, $CDCl_3$) δ 8.50 (d, J=2.4 Hz, 1H), 8.40 (s, 1H), 8.05 (d, J=8.4 Hz, 2H), 7.68 (d, J=8.8 Hz, 1H), 7.57 (dd, J=8.8 and 2.4 Hz, 1H), 7.45 (d, J=4.0 Hz, 2H), 7.28 (d, J=8.4 Hz, 2H), 6.60 (t, J=72.0 Hz, 1H), 6.37 (d, J=4.0 Hz, 1H), 4.79-4.72 (m, 1H), 4.08-3.99 (m, 1H), 3.23 (t, J=14.8 Hz, 2H), 2.93-2.85 (m, 2H), 2.53-2.46 (m, 2H), 2.38 (s, 3H), 1.99-1.93 (m, 2H), 1.47-1.37 (m, 2H).

Step 5. N-(1-(2-(5-(difluoromethoxy)pyridin-2-yl)-2,2-difluoroethyl)piperidin-4-yl)-7H-pyrrolo[2,3-d]pyrimidin-4-amine

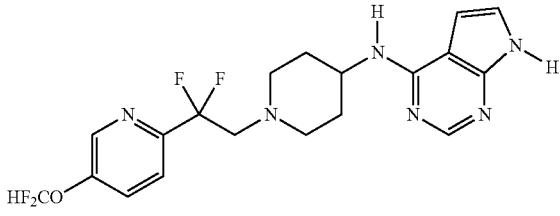

To a stirred solution of N-(1-(2-(5-(difluoromethoxy)pyridin-2-yl)-2,2-difluoroethyl)-piperidin-4-yl)-7-tosyl-7H-pyrrolo[2,3-d]pyrimidin-4-amine (580 mg, 1.03 mmol) in THF (5 mL) was added the 50% NaOH (5 mL) at room temperature. The mixture was stirred at 60° C. for 4 hours, cooled to room temperature and then partitioned into DCM and water. The organic phase was washed with water, brine, dried over $Na_2SO_4$ and concentrated. The concentrate was purified by column chromatography over silica gel (DCM/MeOH=80:1) to afford the title compound as a white powder (360 mg, 78%). MS (ESI) calcd for $C_{19}H_{20}F_4N_6O$: 424.2. found: 425.2 [M+H]. $^1$H NMR (400 MHz, $CD_3OD$) δ 8.52 (d, J=2.4 Hz, 1H), 8.07 (s, 1H), 7.85-7.75 (m, 2H), 7.06 (t, J=70 Hz, 1H), 7.05 (s, 1H), 6.58 (d, J=3.6 Hz, 1H), 4.05-3.95 (m, 2H), 3.30 (t, J=14.4 Hz, 2H), 2.98-2.92 (m, 2H), 2.52-2.46 (m, 2H), 1.94-1.90 (m, 2H), 1.60-1.50 (m, 2H).

Example 1.12a (HCl Salt)

N-(1-(2-(5-(difluoromethoxy)pyridin-2-yl)-2,2-difluoroethyl)piperidin-4-yl)-7H-pyrrolo[2,3-d]pyrimidin-4-amine hydrochloride (C-12.HCl)

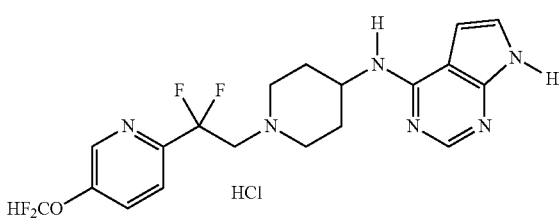

To a stirred solution of N-(1-(2-(5-(difluoromethoxy)pyridin-2-yl)-2,2-difluoroethyl)-piperidin-4-yl)-7H-pyrrolo[2,3-d]pyrimidin-4-amine (360 mg, 0.84 mmol) in MeOH (5 mL) was added 2M HCl (0.42 mL, 0.84 mmol). The mixture was stirred for 30 min. The solution was concentrated to afford the title compound as an off-white powder (345 mg, 96%). MS (ESI) calcd for $C_{19}H_{20}F_4N_6O$: 424.2. found: 425.2 [M+H]. $^1$H NMR (400 MHz, $CD_3OD$) δ 8.55 (s, 1H), 8.22 (s, 1H), 7.86-7.79 (m, 2H), 7.30 (d, J=3.6 Hz, 1H), 7.06 (t, J=72.0 Hz, 1H), 7.30 (d, J=3.6 Hz, 1H), 4.05-3.97 (m, 2H), 3.60-3.50 (m, 2H), 3.29-3.18 (m, 2H), 2.85-2.71 (m, 2H), 2.08-2.05 (m, 2H), 1.82-1.73 (m, 2H).

Example 1.16

N-(1-(2-(5-chloro-3-fluoropyridin-2-yl)-2,2-difluoroethyl)piperidin-4-yl)-7H-pyrrolo[2,3-d]pyrimidin-4-amine (C-16)

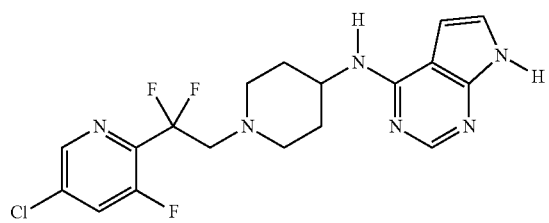 [SMILES: Fc1cc(Cl)cnc1C(F)(F)CN1CCC(Nc2ncnc3[nH]ccc23)CC1]

Step 1: 2-bromo-5-chloro-3-fluoropyridine

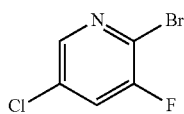

5-chloro-3-fluoropyridin-2-amine (5.0 g, 34 mmol) was slowly added to 48% HBr solution (20 mL) with stirring at 0° C. To the resulting mixture $Br_2$ (5.24 mL, 102.3 mmol) was then added over 20 minutes at 0° C. The reaction mixture was cooled to −10° C. A solution of $NaNO_2$ (5.88 g, 85.3 mmol) in water (20 mL) was added over 1.5 hours, and the mixture stirred for additional 30 minutes. A solution of NaOH (12 g, 306 mmol) in water (20 mL) was added over 30 minutes and the mixture was allowed to warm to room temperature. The mixture was extracted with ether (3×100 mL). The combined organic phases were washed with brine, dried over sodium sulfate, filtered, and concentrated to afford the title compound as a pale yellow solid (6.43 g, 90%). $^1$H NMR (400 MHz, $CDCl_3$) δ 8.23 (d, J=2.1 Hz, 1H), 7.48 (dd, J=7.1, 2.1 Hz, 1H).

Step 2: ethyl 2-(5-chloro-3-fluoropyridin-2-yl)-2,2-difluoroacetate

To the solution of 2-bromo-5-chloro-3-fluoropyridine (2.0 g, 9.5 mmol) and ethyl 2-bromo-2,2-difluoroacetate (1.93 g, 9.5 mmol) in DMSO (40 mL) was added Cu powder (1.21 g, 19 mmol). The mixture was heated to 80° C. for 20 hours and poured into a solution of dibasic potassium hydrogen phosphate trihydrate (21 g, 95 mmol) in water (200 mL) with vigorous stirring. The reaction mixture was filtered through celite and the solid cake was extracted with ethyl acetate. The filtrate was extracted with ethyl acetate. The ethyl acetate layers were combined, dried over sodium sulfate, filtered, and concentrated. The concentrate was purified by column chromatography over silica gel (hexane/ethyl acetate=50:1) to afford the title compound as a colorless oil (2.08 g, 86%). MS (ESI) calcd for $C_9H_7ClF_3NO_2$: 253.0. found: 254.2 [M+H]. $^1$H NMR (400 MHz, $CDCl_3$) δ 8.42 (d, J=1.8 Hz, 1H), 7.61 (dd, J=9.4, 1.8 Hz, 1H), 4.46-4.39 (q, J=7.1 Hz, 2H), 1.37 (t, J=7.1 Hz, 3H).

Step 3: 2-(5-chloro-3-fluoropyridin-2-yl)-2,2-difluoroethanol

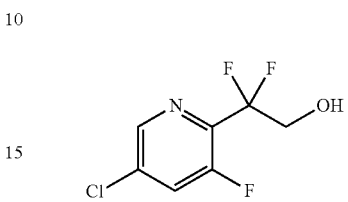

To a solution of ethyl 2-(5-chloro-3-fluoropyridin-2-yl)-2,2-difluoroacetate (2.1 g, 8.2 mmol) in ethanol (40 mL) was added $NaBH_4$ (341 mg, 9.02 mmol) slowly at 0° C. The mixture was stirred for 1 hour at room temperature. The stirred reaction mixture was cooled, quenched with 1N HCl, concentrated and extracted with ethyl acetate. The ethyl acetate layer was washed with water and brine, dried over sodium sulfate and concentrated to afford the title compound as a white solid (1.72 g, 99%). MS (ESI) calcd for $C_7H_5ClF_3NO$: 211.0. found: 212.2 [M+H]. $^1$H NMR (400 MHz, $CDCl_3$) δ 8.40 (d, J=1.3 Hz, 1H), 7.63 (dd, J=9.5, 1.3 Hz, 1H), 4.26 (m, 2H).

Step 4: 2-(5-chloro-3-fluoropyridin-2-yl)-2,2-difluoroethyl trifluoromethanesulfonate

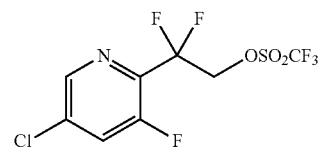

To the solution of 2-(5-chloro-3-fluoropyridin-2-yl)-2,2-difluoroethanol (1.0 g, 4.7 mmol) and DIPEA (2.5 mL, 14 mmol) in anhydrous ether (45 mL) was added $Tf_2O$ (1.6 mL, 9.5 mmol) slowly at 0° C. The reaction mixture was allowed to warm to rt and stirred for 1 h. The orange suspension was filtered through celite, and the solid was washed with ether. The filtrate was concentrated to afford the crude title compound as a pale yellow oil (1.65 g, 100%). The compound was used directly in the next step without further purification.

Step 5: tert-butyl 1-(2-(5-chloro-3-fluoropyridin-2-yl)-2,2-difluoroethyl)piperidin-4-ylcarbamate

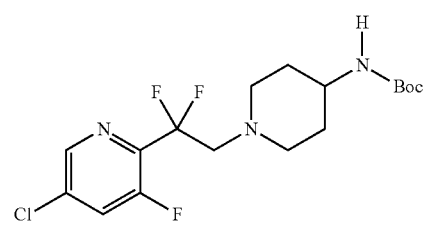 [SMILES: CC(C)(C)OC(=O)NC1CCN(CC(F)(F)c2ncc(Cl)cc2F)CC1]

A mixture of 2-(5-chloro-3-fluoropyridin-2-yl)-2,2-difluoroethyl trifluoromethanesulfonate (1.65 g, 4.7 mmol), tert-butyl piperidin-4-ylcarbamate (1.92 g, 9.6 mmol) and DIPEA (2.5 mL, 14 mmol) in DCM (25 mL) was heated to 40° C. After stirring overnight at 40° C., the mixture was concentrated and extracted with EtOAc. The organic layer was washed with water and brine, dried and concentrated. The concentrate was purified by column chromatography over silica gel (hexane/EtOAc=10:1) to afford the title compound as a pale yellow solid (1.64 g, 87%). MS (ESI) calcd for $C_{17}H_{23}ClF_3N_3O_2$: 393.1. found: 394.2 [M+H]. $^1$H NMR (400 MHz, CDCl$_3$) δ 8.43 (s, 1H), 7.54 (dd, J=9.8, 1.8 Hz, 1H), 4.34 (s, 1H), 3.38 (s, 1H), 3.18 (t, 2H), 2.91-2.80 (m, 2H), 2.42-2.35 (m, 2H), 1.85-1.75 (m, 2H), 1.31-1.22 (m, 2H).

Step 6: 1-(2-(5-chloro-3-fluoropyridin-2-yl)-2,2-difluoroethyl)piperidin-4-amine

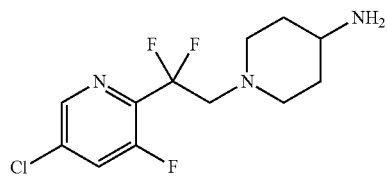 [SMILES: NC1CCN(CC(F)(F)c2ncc(Cl)cc2F)CC1]

To a solution of tert-butyl 1-(2-(5-chloro-3-fluoropyridin-2-yl)-2,2-difluoroethyl)-piperidin-4-ylcarbamate (1.64 g, 4.16 mmol) in DCM (20 mL) was added TFA (10 mL) at 0° C. After stirring for 15 min at r.t., the mixture was concentrated. The concentrate was basified with 1N NaOH, and extracted with EtOAc. The organic phase was washed with brine, dried over Na$_2$SO$_4$, and concentrated to afford the crude title compound as a pale yellow oil (1.43 g, 100%) which was used directly in the next step without further purification. MS (ESI) calcd for $C_{12}H_{15}ClF_3N_3$: 293.1. found: 294.2 [M+H]. $^1$H NMR (400 MHz, CDCl$_3$) δ 8.43 (s, 1H), 7.54 (dd, J=9.8, 1.7 Hz, 1H), 3.18 (t, J=14.4 Hz, 2H), 2.88-2.84 (m, 2H), 2.66-2.54 (m, 1H), 2.36-2.28 (m, 2H), 1.70-1.64 (m, 2H), 1.29-1.15 (m, 2H).

Step 7. N-(1-(2-(5-chloro-3-fluoropyridin-2-yl)-2,2-difluoroethyl)piperidin-4-yl)-7H-pyrrolo[2,3-d]pyrimidin-4-amine

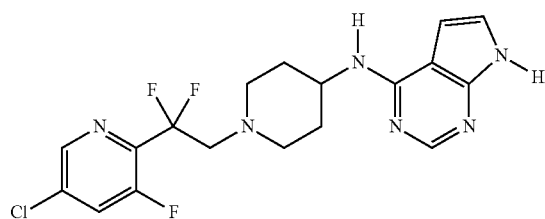 [SMILES: Fc1cc(Cl)cnc1C(F)(F)CN1CCC(Nc2ncnc3[nH]ccc23)CC1]

The mixture of 1-(2-(5-chloro-3-fluoropyridin-2-yl)-2,2-difluoroethyl)piperidin-4-amine (200 mg, 0.68 mmol), 4-chloro-7H-pyrrolo[2,3-d]pyrimidine (87.2 mg, 0.567 mmol) and DIPEA (0.2 mL, 1.13 mmol) in n-butyl alcohol (3 mL) was heated to 130° C. After stirring overnight at 130° C., the reaction solution was concentrated and extracted with EtOAc. The organic layers were washed with water and brine, dried and concentrated. The concentrate was purified by column chromatography over silica gel (hexane/EtOAc=1/3) to afford the title compound as a white solid (35 mg, 13%). MS (ESI) calcd for $C_{18}H_{18}ClF_3N_6$: 410.1. found: 411.2 [M+H]. $^1$H NMR (400 MHz, CD$_3$OD) δ 8.52 (s, 1H), 8.08 (s, 1H), 7.99-7.93 (m, 1H), 7.05 (d, J=3.5 Hz, 1H), 6.58 (d, J=3.5 Hz, 1H), 4.01 (m, 1H), 3.27 (m, 2H), 3.01 (m, 2H), 2.50 (m, 2H), 1.93 (m, 2H), 1.53 (m, 2H).

Example 1.16a (HCl Salt)

N-(1-(2-(5-chloro-3-fluoropyridin-2-yl)-2,2-difluoroethyl)piperidin-4-yl)-7H-pyrrolo[2,3-d]pyrimidin-4-amine hydrochloride (C-16.HCl)

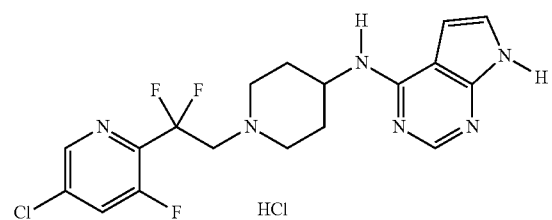 [SMILES: Fc1cc(Cl)cnc1C(F)(F)CN1CCC(Nc2ncnc3[nH]ccc23)CC1 ; Cl]

To a stirred solution of N-(1-(2-(5-chloro-3-fluoropyridin-2-yl)-2,2-difluoroethyl)-piperidin-4-yl)-7H-pyrrolo[2,3-d]pyrimidin-4-amine (24.5 mg, 0.060 mmol) in MeOH (1 mL) was added HCl/MeOH (2M, 0.03 mL, 0.060 mmol) at rt. After stirring for 10 min, the mixture was concentrated to afford the title compound as a pale yellow solid (26 mg, 100%). MS (ESI) calcd for $C_{18}H_{18}ClF_3N_6$: 410.1. found: 411.2 [M+H]. $^1$H NMR (400 MHz, CD$_3$OD) δ 8.43 (s, 1H), 8.13 (s, 1H), 7.91 (dd, J=10.3, 1.7 Hz, 1H), 7.22 (d, J=3.5 Hz, 1H), 6.78 (d, J=3.5 Hz, 1H), 3.89 (s, 1H), 3.50 (s, 2H), 3.16 (s, 2H), 2.69 (s, 2H), 2.02-1.92 (m, 2H), 1.67 (m, 2H).

Example 1.17

N-(1-(2,2-difluoro-2-(3-fluoro-5-methylpyridin-2-yl)ethyl)piperidin-4-yl)-7H-pyrrolo[2,3-d]pyrimidin-4-amine (C-17)

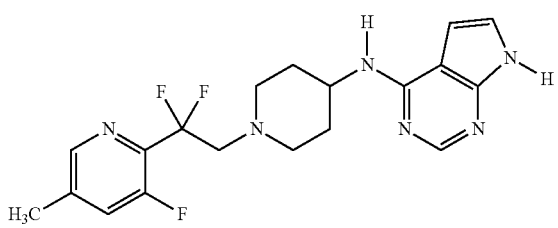 [SMILES: Cc1cnc(C(F)(F)CN2CCC(Nc3ncnc4[nH]ccc34)CC2)c(F)c1]

Step 1: ethyl 2,2-difluoro-2-(3-fluoro-5-methylpyridin-2-yl)acetate

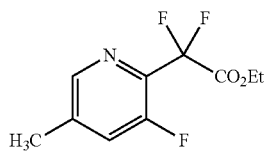

To a solution of 2-bromo-3-fluoro-5-methylpyridine (1.8 g, 9.5 mmol) and ethyl 2-bromo-2,2-difluoroacetate (1.8 mL, 14.2 mmol) in DMSO (30 mL) was added copper powder (1.2 g, 19 mmol). After stirring overnight at 50° C., the mixture was diluted with EtOAc. The mixture was poured into water, and stirred for 30 min. The suspension was filtered through a pad of celite. The organic phase was washed with water and brine, dried over Na$_2$SO$_4$ and concentrated. The concentrate was purified by column chromatography over silica gel (hexane) to afford the title compound as a white solid (1.6 g, 70%). $^1$H NMR (400 MHz, CDCl$_3$) δ 8.26 (s, 1H), 7.36 (d, J=10.6 Hz, 1H), 4.42 (q, J=7.1 Hz, 2H), 2.42 (s, 3H), 1.36 (t, J=7.1 Hz, 3H).

Step 2: 2,2-difluoro-2-(3-fluoro-5-methylpyridin-2-yl)ethanol

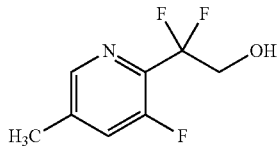

To a solution of ethyl 2,2-difluoro-2-(3-fluoro-5-methylpyridin-2-yl)acetate (1.68 g, 7.22 mmol) in ethanol (30 mL) was added the NaBH$_4$ (410 mg, 10.8 mmol) at room temperature. After stirring for 30 min, the reaction mixture was quenched with aqueous 1N HCl at 0° C. The mixture was extracted with EtOAc. The combined organic phases were washed with brine, dried over Na$_2$SO$_4$ and concentrated to afford the product as a white powder (1.3 g, 100%). $^1$H NMR (400 MHz, CDCl$_3$) δ 8.22 (s, 1H), 7.39 (d, J=10.8 Hz, 1H), 4.32-4.20 (m, 2H), 3.45-3.35 (m, 1H), 2.43 (s, 3H).

Step 3: 2,2-difluoro-2-(3-fluoro-5-methylpyridin-2-yl)ethyl trifluoromethanesulfonate

To a solution of 2,2-difluoro-2-(3-fluoro-5-methylpyridin-2-yl)ethanol (120 mg, 0.63 mmol) and DIPEA (0.15 mL, 0.95 mmol) in dry ether (5 mL) was added dropwise Tf$_2$O (0.15 mL, 0.76 mmol) at 0° C. under N$_2$ atmosphere. After stirring for 1 h, the suspension was filtered, and the filtrate was concentrated to afford the crude title compound (200 mg) which was used directly without further purification in the next step.

Step 4. N-(1-(2,2-difluoro-2-(3-5-methylpyridin-2-yl)ethyl)piperidin-4-yl)-1-tosyl-1H-pyrazolo[3,4-d]pyrimidin-4-amine

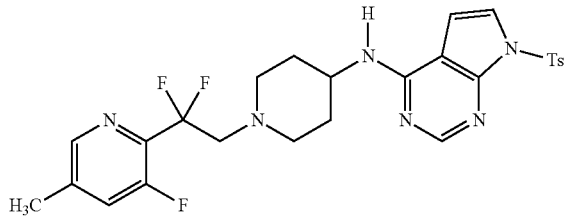

A mixture of 2,2-difluoro-2-(3-fluoro-5-methylpyridin-2-yl)ethyl trifluoromethanesulfonate (1.33 g, 3.9 mmol), N-(piperidin-4-yl)-7-tosyl-7H-pyrrolo[2,3-d]pyrimidin-4-amine (1.16 mg, 3.14 mmol) and DIPEA (1.0 mL, 5.9 mmol) in DCM (65 mL) was heated to 50° C. After stirring overnight at 50° C., the mixture was concentrated to dryness. The concentrate was purified by column chromatography over silica gel (ethyl acetate, 100%) to afford the title compound as a white powder (500 mg, 62%). MS (ESI) calcd for C$_{26}$H$_{27}$F$_3$N$_6$O$_2$S: 544.2. found: 545.2 [M+H]. $^1$H NMR (400 MHz, CDCl$_3$) δ 8.41 (s, 1H), 8.27 (s, 1H), 8.05 (d, J=8.4 Hz, 2H), 7.45 (d, J=4.0 Hz, 1H), 7.37-7.21 (m, 3H), 6.37 (d, J=4.0 Hz, 1H), 4.76-4.74 (m, 1H), 4.07-3.97 (m, 1H), 3.23 (t, J=14.4 Hz, 2H), 2.97-2.93 (m, 2H), 2.53-2.47 (m, 2H), 2.41 (s, 3H), 2.38 (s, 3H), 1.97-1.94 (m, 2H), 1.48-1.38 (m, 2H).

Step 5: N-(1-(2,2-difluoro-2-(3-fluoro-5-methylpyridin-2-yl)ethyl)piperidin-4-yl)-7H-pyrrolo[2,3-d]pyrimidin-4-amine

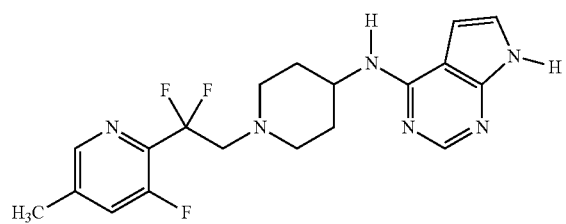

To a stirred solution of N-(1-(2,2-difluoro-2-(3-fluoro-5-methylpyridin-2-yl)ethyl)piperidin-4-yl)-1-tosyl-1H-pyrazolo[3,4-d]pyrimidin-4-amine (410 mg, 0.75 mmol) in THF (4 mL) was added 50% NaOH (4 mL) at room temperature, and the mixture was warmed to 60° C. After stirring for 4 hours at 60° C., the mixture was partitioned between DCM and water. The organic phase was washed with water, brine, dried over Na$_2$SO$_4$ and concentrated. The concentrate was purified by column chromatography over silica gel (DCM/MeOH=80:1) to afford the title compound as a white powder (246 mg, 84%). MS (ESI) calcd for C$_{19}$H$_{21}$F$_3$N$_6$: 390.2. found: 391.3 [M+H]. $^1$H NMR (400 MHz, CD$_3$OD) δ 8.31 (s, 1H), 8.07 (s, 1H), 7.60 (d, J=11.6 Hz, 1H), 7.05 (d, J=3.6 Hz, 1H), 6.58 (d, J=3.6 Hz, 1H), 4.04-3.97 (m, 1H), 3.27 (t, J=14.4 Hz, 2H), 3.02-2.99 (m, 2H), 2.52-2.48 (m, 2H), 2.45 (s, 3H), 1.94-1.91 (m, 2H), 1.60-1.50 (m, 2H).

Example 1.17a (HCl Salt)

N-(1-(2,2-difluoro-2-(3-fluoro-5-methylpyridin-2-yl)ethyl)piperidin-4-yl)-1H-pyrazolo[3,4-d]pyrimidin-4-amine hydrochloride (C-17.HCl)

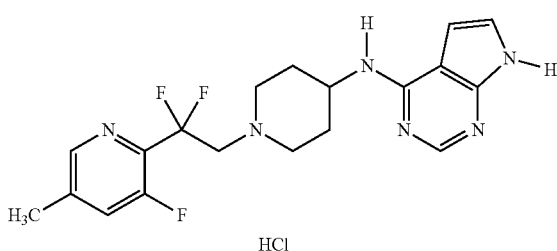

To a stirred solution of N-(1-(2,2-difluoro-2-(3-fluoro-5-methylpyridin-2-yl)ethyl)-piperidin-4-yl)-7H-pyrrolo[2,3-d]pyrimidin-4-amine (246 mg, 0.63 mmol) in MeOH (3 mL) was added 2M methanesulfonic acid in methanol (0.35 mL, 0.63 mmol). The mixture was stirred for 30 min. The solution was concentrated to afford the product as an off-white powder (265 mg, 98%). MS (ESI) calcd for $C_{19}H_{21}F_3N_6$: 390.2. found: 391.3 [M+H]. $^1$H NMR (400 MHz, CD$_3$OD) δ 8.34 (s, 1H), 8.21 (s, 1H), 7.64 (d, J=11.6 Hz, 1H), 7.29 (d, J=3.6 Hz, 1H), 6.85 (d, J=3.6 Hz, 1H), 4.04-3.97 (m, 1H), 3.63-3.50 (m, 2H), 3.28 (m, 2H), 2.81-2.75 (m, 2H), 2.46 (s, 3H), 2.07 (m, 2H), 1.82-1.73 (m, 2H).

Example 1.18

N-(1-(2,2-difluoro-2-(3-fluoro-5-(trifluoromethyl)pyridin-2-yl)-ethyl)piperidin-4-yl)-7H-pyrrolo[2,3-d]pyrimidin-4-amine (C-18)

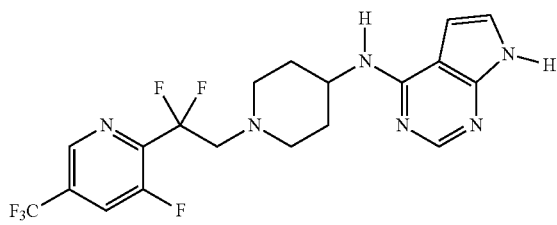

Step 1: ethyl 2,2-difluoro-2-(3-fluoro-5-(trifluoromethyl)pyridin-2-yl)acetate

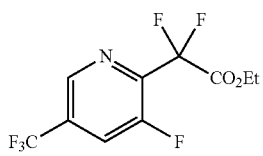

To the solution of ethyl 2-bromo-2,2-difluoroacetate (1.0 g, 4.8 mmol) and 2-bromo-3-fluoro-5-(trifluoromethyl)pyridine (1.1 g, 4.4 mmol) in DMSO (20 mL) was added Cu powder (568 mg, 8.8 mmol). The mixture was heated at 80° C. for 20 hours. The reaction mixture was filtered through celite and the filter pad was extracted with ethyl acetate. The combined organic phases were washed with brine, dried over sodium sulfate, filtered, and concentrated. The concentrate was purified by column chromatography over silica gel (hexane/ethyl acetate=100:1) to afford the title compound as a colorless oil (980 mg, 83%). $^1$H NMR (400 MHz, CDCl$_3$) δ 8.73 (s, 1H), 7.81 (d, J=9.6 Hz, 1H), 4.45 (q, J=7.2 Hz, 2H), 1.38 (t, J=7.2 Hz, 3H).

Step 2: 2,2-difluoro-2-(3-fluoro-5-(trifluoromethyl)pyridin-2-yl)ethanol

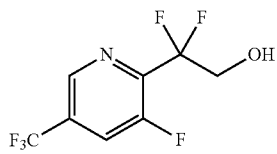

To the solution of 2,2-difluoro-2-(3-fluoro-5-(trifluoromethyl)pyridin-2-yl)acetate (980 mg, 3.41 mmol) in ethanol (20 mL) was added NaBH$_4$ (194 mg, 5.12 mmol) slowly at ice bath temperature and the mixture stirred for 30 min. The reaction mixture was quenched with 1N HCl, concentrated and extracted with ethyl acetate. The ethyl acetate layer was washed with water and brine, then dried and concentrated to afford the title compound as a white solid (780 mg, 93%). $^1$H NMR (400 MHz, CDCl$_3$) δ 8.72 (s, 1H), 7.84 (d, J=9.2 Hz, 1H), 4.30 (t, J=12.4 Hz, 2H), 2.86 (brs, 1H).

Step 3: 2,2-difluoro-2-(3-fluoro-5-(trifluoromethyl)pyridin-2-yl)ethyl trifluoromethanesulfonate

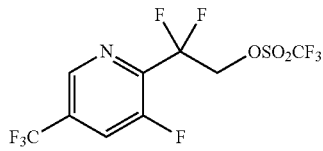

To the solution of 2,2-difluoro-2-(3-fluoro-5-(trifluoromethyl)pyridin-2-yl)ethanol (780 mg, 3.18 mmol) and DIPEA (1.6 mL, 9.6 mmol) in dry ether (15 ml) was added Tf$_2$O (0.9 mL, 6.36 mmol) at 0° C. After stirring for 1 hr at rt, the white suspension was filtered through celite, and the filter mass was extracted with ether. The filtrate was concentrated and purified by column chromatography over silica gel (hexane) to afford the title compound as a colorless oil (870 mg) which was used for the next step directly.

Step 4. N-(1-(2,2-difluoro-2-(3-fluoro-5-(trifluoromethyl)pyridin-2-yl)ethyl)piperidin-4-yl)-7-tosyl-7H-pyrrolo[2,3-d]pyrimidin-4-amine

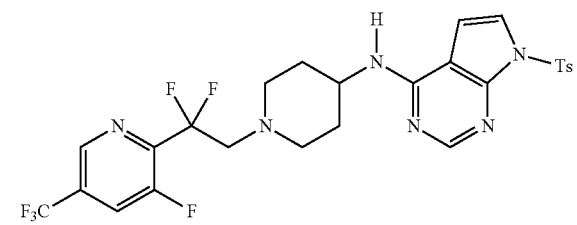 [SMILES: Cc1ccc(S(=O)(=O)n2ccc3c(NC4CCN(CC(F)(F)c5ncc(C(F)(F)F)cc5F)CC4)ncnc32)cc1]

A mixture of 2,2-difluoro-2-(3-fluoro-5-(trifluoromethyl)pyridin-2-yl)ethyltrifluoromethanesulfonate (760 mg, 2.02 mmol), N-(piperidin-4-yl)-7-tosyl-7H-pyrrolo[2,3-d]pyrimidin-4-amine (Intermediate 1, 824 mg, 2.22 mmol) and DIPEA (0.53 mL, 3.02 mmol) in DMF/DCM (V/V=1:3, 10 mL) was warmed to 40° C. and stirred overnight. The mixture was concentrated and the crude product was purified by column chromatography over silica gel (eluent: Hexane:EtOAc=3:1) to afford the title compound as a pale yellow powder (950 mg, 79%). MS (ESI) calcd for $C_{26}H_{24}F_6N_6O_2S$: 598.2. found: 599.2 [M+H]. $^1$H NMR (400 MHz, CDCl$_3$) δ 8.73 (s, 1H), 8.40 (s, 1H), 8.06-8.01 (m, 3H), 7.77-7.34 (m, 1H), 7.45 (d, J=4.0 Hz, 1H), 7.28 (d, J=8.4 Hz, 2H), 6.36 (d, J=4.0 Hz, 1H), 4.76-4.74 (m, 1H), 4.10-3.97 (m, 1H), 3.26 (t, J=14.0 Hz, 2H), 2.97-2.90 (m, 3H), 2.88 (s, 1H), 2.53-2.46 (m, 2H), 2.38 (s, 3H), 1.97-1.94 (m, 2H), 1.42-1.35 (m, 2H).

Step 5. N-(1-(2,2-difluoro-2-(3-fluoro-5-(trifluoromethyl)pyridin-2-yl)ethyl)piperidin-4-yl)-7H-pyrrolo[2,3-d]pyrimidin-4-amine

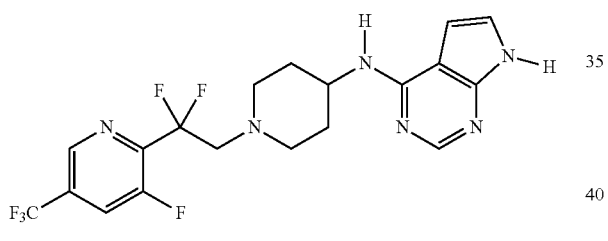

A mixture of N-(1-(2,2-difluoro-2-(3-fluoro-5-(trifluoromethyl)pyridin-2-yl)ethyl)-piperidin-4-yl)-7-tosyl-7H-pyrrolo[2,3-d]pyrimidin-4-amine (950 mg, 1.60 mmol) and 50% aqueous NaOH (5 mL) in THF was stirred at 60° C. for 1.5 hours. The mixture was concentrated and the residue was adjusted to pH=10 with dilute aqueous HCl. The aqueous layer was extracted with DCM. The combined organic layers were dried over Na$_2$SO$_4$ and concentrated. The crude product was purified by column chromatography over silica gel (eluent: DCM:MeOH=80:1~20:1) to afford the title compound as a yellow powder (380 mg, 54%). MS (ESI) calcd for $C_{19}H_{18}N_6F_6$: 444.2. found: 445.3 [M+H]. $^1$H NMR (400 MHz, CDCl$_3$) δ 9.57 (s, 1H), 8.75 (s, 1H), 8.31 (s, 1H), 7.77 (d, J=10.0 Hz, 1H), 7.05-7.03 (m, 1H), 6.32-6.31 (m, 1H), 4.87-4.81 (m, 1H), 4.15-4.07 (m, 1H), 3.29 (t, J=14.4 Hz, 2H), 2.98-2.95 (m, 2H), 2.57-2.51 (m, 2H), 2.05-2.01 (m, 2H), 1.48-1.39 (m, 2H).

Example 1.18a (HCl Salt)

N-(1-(2,2-difluoro-2-(3-fluoro-5-(trifluoromethyl)pyridin-2-yl)ethyl)piperidin-4-yl)-7H-pyrrolo[2,3-d]pyrimidin-4-amine hydrochloride (C-18.HCl)

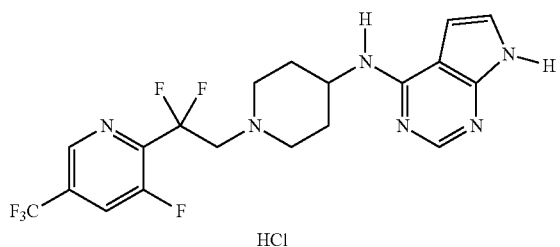 [SMILES: Fc1cc(C(F)(F)F)cnc1C(F)(F)CN1CCC(Nc2ncnc3[nH]ccc23)CC1 ; Cl]

To a stirred solution of N-(1-(2,2-difluoro-2-(3-fluoro-5-(trifluoromethyl)pyridin-2-yl)ethyl)-piperidin-4-yl)-7H-pyrrolo[2,3-d]pyrimidin-4-amine (380 mg, 0.86 mmol) in MeOH (5 mL) was added the 2.0M hydrochloric acid (0.43 mL, 0.86 mmol). The resulting solution was stirred at r.t. for 30 min. The solution was concentrated to afford the title compound as a yellow powder (410 mg, 100%). MS (ESI) calcd for $C_{19}H_{19}ClN_6F_6$: 444.2. found: 445.3 [M+H]. $^1$H NMR (400 MHz, CDCl$_3$) δ 12.12-11.88 (m, 1H), 9.09 (s, 1H), 8.74 (s, 1H), 8.43 (s, 1H), 7.79 (d, J=9.2 Hz, 1H), 7.32 (s, 1H), 6.60 (s, 1H), 4.07-3.83 (m, 1H), 3.37-3.31 (m, 2H), 3.09-3.07 (m, 2H), 2.63-2.61 (m, 2H), 2.10-2.03 (m, 2H), 1.80-1.73 (m, 2H).

Example 1.47

N-(1-(2,2-difluoro-2-(5-methylpyridin-2-yl)ethyl)piperidin-4-yl)-N-methyl-7H-pyrrolo[2,3-d]pyrimidin-4-amine (C-47)

Step 1: N-(1-(2,2-difluoro-2-(5-methylpyridin-2-yl)ethyl)piperidin-4-yl-7-tosyl-7H-pyrrolo[2,3-d]pyrimidin-4-amine

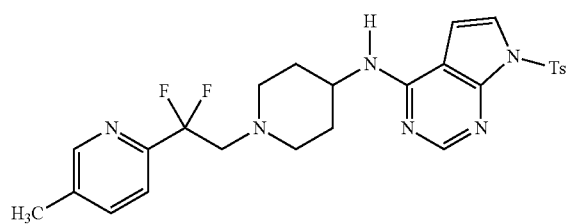

A mixture of 2,2-difluoro-2-(5-methylpyridin-2-yl)ethyl trifluoromethanesulfonate (1.33 g, 3.9 mmol), N-(piperidin-4-yl)-7-tosyl-7H-pyrrolo[2,3-d]pyrimidin-4-amine (1.16 g, 3.2 mmol) and DIPEA (1 mL, 6 mmol) in DCM (65 mL) was heated to 50° C. After stirring overnight at 50° C., the mixture was concentrated to dryness. The concentrate was purified by column chromatography over silica gel (ethyl acetate, 100%) to afford the title compound as a white powder (500 mg, 62%). MS (ESI) calcd for $C_{26}H_{27}F_3N_6O_2S$: 544.2. found: 545.2 [M+H]. $^1$H NMR (400 MHz, $CDCl_3$) δ 8.41 (s, 1H), 8.27 (s, 1H), 8.05 (d, J=8.4 Hz, 2H), 7.45 (d, J=4.0 Hz, 1H), 7.37-7.21 (m, 3H), 6.37 (d, J=4.0 Hz, 1H), 4.76-4.74 (m, 1H), 4.07-3.97 (m, 1H), 3.23 (t, J=14.4 Hz, 2H), 2.97-2.93 (m, 2H), 2.53-2.47 (m, 2H), 2.41 (s, 3H), 2.38 (s, 3H), 1.97-1.94 (m, 2H), 1.48-1.38 (m, 2H).

Step 2: N-(1-(2,2-difluoro-2-(5-methylpyridin-2-yl)ethyl)piperidin-4-yl)-N-methyl-7-tosyl-7H-pyrrolo[2,3-d]pyrimidin-4-amine

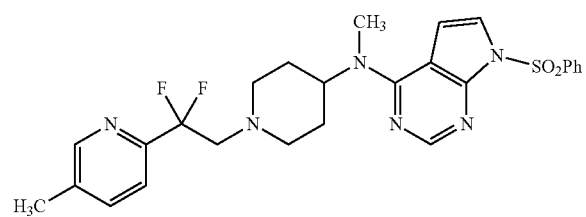

To a stirred solution of N-(1-(2,2-difluoro-2-(5-methylpyridin-2-yl)ethyl)piperidin-4-yl)-7-tosyl-7H-pyrrolo[2,3-d]pyrimidin-4-amine (100 mg, 0.189 mmol) in dry DMF (3 mL) was added 60% NaH in mineral oil (20 mg, 0.5 mmol) at 0° C. under nitrogen atmosphere. After stirring for 15 min, MeI (24 μL, 0.38 mmol) was added. After the starting material was consumed, the reaction was quenched with water at 0° C. The mixture thus obtained was partitioned into EtOAc and water. The organic phase was washed with brine, dried over $Na_2SO_4$ and concentrated under vacuum. The residue was purified by column chromatography over silica gel (50% EtOAc in hexane) to afford the title compound as a pale yellow powder (30 mg, 30%). MS (ESI) calcd for $C_{27}H_{30}F_2N_6O_2S$: 540.2. found: 541.3 [M+H]. $^1$H NMR (400 MHz, $CDCl_3$) δ 8.47 (s, 1H), 8.36 (s, 1H), 8.05-8.03 (m, 2H), 7.62-7.59 (m, 1H), 7.55 (d, J=8.0 Hz, 1H), 7.43 (d, J=4.0 Hz, 1H), 7.27 (d, J=8.0 Hz, 2H), 6.59 (d, J=4.0 Hz, 1H), 4.72-4.52 (m, 1H), 3.24 (t, J=14.8 Hz, 2H), 3.11 (s, 3H), 3.03-3.00 (m, 2H), 2.52-2.46 (m, 2H), 2.39 (s, 3H), 2.37 (s, 3H), 1.82-1.72 (m, 2H), 1.61-1.58 (m, 2H).

Step 3: N-(1-(2,2-difluoro-2-(5-methylpyridin-2-yl)ethyl)piperidin-4-yl)-N-methyl-7H-pyrrolo[2,3-d]pyrimidin-4-amine

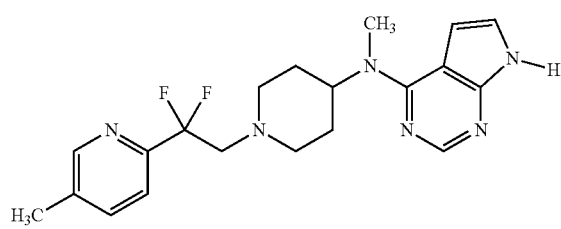

To a stirred solution of N-(1-(2,2-difluoro-2-(5-methylpyridin-2-yl)ethyl)piperidin-4-yl)-N-methyl-7-tosyl-7H-pyrrolo[2,3-d]pyrimidin-4-amine (30 mg, 0.06 mmol) in THF (1 mL) was added 50% aqueous NaOH (1 mL). The mixture was heated to 60° C. After the starting material was consumed, the mixture was cooled down to rt and concentrated. The residue was partitioned into EtOAc and water. The organic phase was washed with brine, dried over $Na_2SO_4$ and concentrated. The residue was purified by column chromatography over silica gel (EtOAc/MeOH=20/1) to afford the title compound as a pale yellow powder (15 mg, 68%). MS (ESI) calcd for $C_{20}H_{24}F_2N_6$: 386.2. found: 387.2 [M+H]. $^1$H NMR (400 MHz, $CD_3OD$) δ 8.48 (s, 1H), 8.08 (s, 1H), 7.81-7.79 (m, 1H), 7.64 (d, J=8.0 Hz, 1H), 7.08 (d, J=4.0 Hz, 1H), 6.61 (d, J=4.0 Hz, 1H), 4.73-4.67 (m, 1H), 3.25 (t, J=14.4 Hz, 2H), 3.20 (s, 3H), 3.02-2.99 (m, 2H), 2.53-2.47 (m, 2H), 2.42 (s, 3H), 1.90-1.80 (m, 2H), 1.65-1.62 (m, 2H).

Example 1.47a (HCl Salt)

N-(1-(2,2-difluoro-2-(5-methylpyridin-2-yl)ethyl)piperidin-4-yl)-N-methyl-7H-pyrrolo[2,3-d]pyrimidin-4-amine hydrochloride (C-47.HCl)

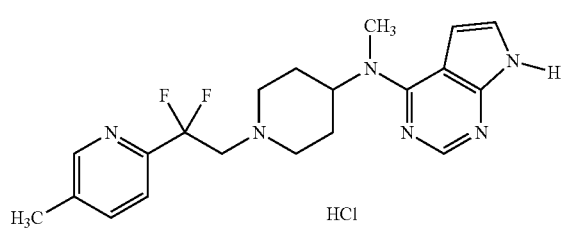 [SMILES: Cc1ccc(C(F)(F)CN2CCC(N(C)c3ncnc4[nH]ccc34)CC2)nc1 ; Cl]

To a stirred solution of N-(1-(2,2-difluoro-2-(5-methylpyridin-2-yl)ethyl)piperidin-4-yl)-N-methyl-7H-pyrrolo[2,3-d]pyrimidin-4-amine (23 mg, 0.06 mmol) in methanol (1 mL) was added the methanolic solution of HCl (2.0M, 30 μL) at ambient temperature. After stirring for 30 min, the clear solution was concentrated to afford the title compound as a pale yellow powder (25 mg, 100%). MS (ESI) calcd for $C_{20}H_{24}F_2N_6$: 386.2. found: 387.2 [M+H]. $^1$H NMR (400 MHz, $CD_3OD$) δ 8.56 (s, 1H), 8.33 (s, 1H), 7.87 (d, J=8.0 Hz, 1H), 7.74 (d, J=8.0 Hz, 1H), 7.36 (d, J=4.0 Hz, 1H), 6.94 (d, J=4.0 Hz, 1H), 5.08-4.94 (m, 1H), 4.13-4.06 (m, 2H), 3.76-3.73 (m, 2H), 3.43 (s, 3H), 3.42-3.32 (m, 2H), 3.45 (s, 3H), 2.39-2.30 (m, 2H), 2.09-2.06 (m, 2H).

Example 1.127

N-(1-(2,2-difluoro-2-(6-(trifluoromethyl)pyridin-3-yl)ethyl)piperidin-4-yl)-1H-pyrazolo[3,4-d]pyrimidin-4-amine (C-127)

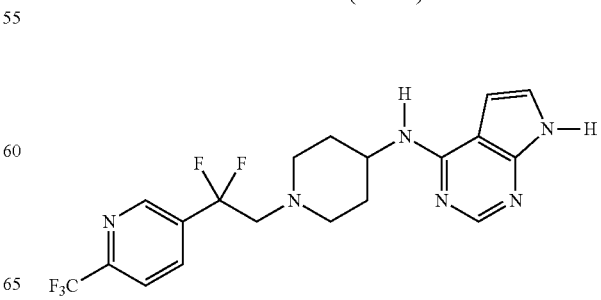

Step 1: 5-iodo-2-(trifluoromethyl)pyridine

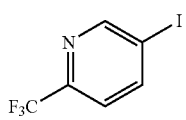

A solution of 6-(trifluoromethyl)pyridin-3-amine (9.96 g, 0.062 mol) in 5N HCl (70 mL) was cooled to −5° C. and sodium nitrite (6.39 g, 0.093 mol) in 30 mL of water was added dropwise while maintaining the internal temperature below 5° C. After 10 min, KI (22.5 g, 0.136 mol) in 30 mL of water was added dropwise at −5° C. while maintaining the internal temperature below 10° C. over the course of the addition. The reaction mixture was warmed to rt and 250 mL of EtOAc was added. The pH of the aqueous layer was adjusted to 11 by the addition of 50 mL of 6N NaOH. The organic layer was separated and washed with 120 mL of 0.3M $Na_2S_2O_3$. The EtOAc layer was concentrated and the concentrate was purified by column chromatography over silica gel (hexane/EtOAc=25/1) to afford the title compound as a white solid (14.6 g, 87%). MS (ESI) calcd for $C_6H_3F_3IN$: 273.0. found: 274.0 [M+H]. $^1$H NMR (400 MHz, $CDCl_3$) δ 8.96 (s, 1H), 8.22 (d, J=8.2 Hz, 1H), 7.47 (d, J=8.2 Hz, 1H).

Step 2: ethyl 2,2-difluoro-2-(6-(trifluoromethyl)pyridin-3-yl)acetate

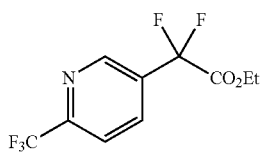

To a solution of 5-iodo-2-(trifluoromethyl)pyridine (14.5 g, 53.2 mmol) and ethyl 2-bromo-2,2-difluoroacetate (10.8 g, 53.2 mmol) in DMF (250 mL) was added Cu powder (6.76 g, 106 mmol). The mixture was heated at 80° C. for 20 hours and the reaction mixture was poured into a solution of dibasic potassium hydrogen phosphate, trihydrate (121 g, 532 mmol) in water (1500 mL) with vigorous stirring. The suspension was filtered and the solid was extracted with ether. The filtrate was added to brine and extracted with ether (2×). The combined organic phases were washed with brine, dried over sodium sulfate, filtered, and concentrated. The concentrate was purified by column chromatography over silica gel (hexane/EtOAc=50:1) to afford the title compound as a colorless liquid (8.96 g, 63%). MS (ESI) calcd for $C_{10}H_8F_5NO_2$: 269.2. found: 270.3 [M+H]. $^1$H NMR (400 MHz, $CDCl_3$) δ 8.98 (s, 1H), 8.14 (d, J=8.2 Hz, 1H), 7.81 (d, J=8.2 Hz, 1H), 4.35 (q, J=7.1 Hz, 2H), 1.34 (t, J=7.1 Hz, 3H).

Step 3: 2,2-difluoro-2-(6-(trifluoromethyl)pyridin-3-yl)ethanol

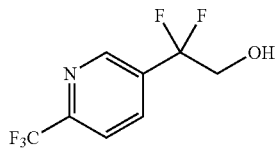

To the solution of ethyl 2,2-difluoro-2-(6-(trifluoromethyl)pyridin-3-yl)acetate (8.86 g, 32.9 mmol) in ethanol (165 mL) was added $NaBH_4$ (1.79 g, 47.4 mmol) slowly at rt. The mixture was stirred for 30 min at rt. After 30 min, the reaction mixture was quenched with 1N HCl at ice-water bath temperature. The mixture was concentrated and extracted with EtOAc. The EtOAc layer was washed with water and brine, then dried and concentrated to afford the title compound as a white solid (6.13 g, 82%). MS (ESI) calcd for $C_8H_6F_5NO$: 227.0. found: 228.2 [M+H]. $^1$H NMR (400 MHz, $CDCl_3$) δ 8.91 (s, 1H), 8.06 (d, J=8.2 Hz, 1H), 7.79 (d, J=8.2 Hz, 1H), 4.06 (td, J=12.4 and 7.0 Hz, 2H), 2.16 (t, J=7.0 Hz, 1H).

Step 4: 2,2-difluoro-2-(6-(trifluoromethyl)pyridin-3-yl)ethyl trifluoromethanesulfonate

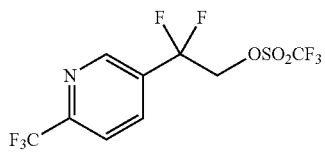

To the solution of 2,2-difluoro-2-(6-(trifluoromethyl)pyridin-3-yl)ethanol (1.0 g, 4.4 mmol) and DIPEA (2.39 mL, 13.2 mmol) in dry ether (44 mL) was added $Tf_2O$ (1.48 mL, 8.8 mmol) at 0° C. After stirring for 1 hr at rt, the orange suspension was filtered through celite, and the filter mass was extracted with ether. The combined organic phases were concentrated, and purified by column chromatography to afford the title compound as a pale yellow solid (1.47 g, 93%). $^1$H NMR (400 MHz, $CDCl_3$) δ 8.92 (s, 1H), 8.07 (d, J=8.2 Hz, 1H), 7.86 (d, J=8.2 Hz, 1H), 4.78 (t, J=11.2 Hz, 2H).

Step 5: tert-butyl 1-(2,2-difluoro-2-(6-(trifluoromethyl)pyridin-3-yl)ethyl)piperidin-4-yl-carbamate

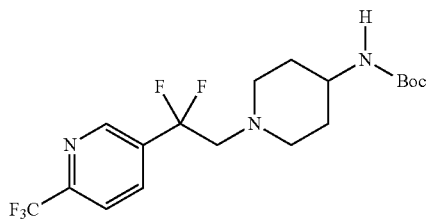

A mixture of 2,2-difluoro-2-(6-(trifluoromethyl)pyridin-3-yl)ethyl trifluoromethanesulfonate (1.46 g, 4.07 mmol), tert-butyl piperidin-4-ylcarbamate (1.63 g, 8.13 mmol) and DIPEA (2.2 ml, 12.2 mmol) in DCM (20 ml) was heated to 40° C. After stirring overnight at 40° C., the mixture was concentrated to dryness. The concentrate was purified by column chromatography over silica gel (hexane/EtOAc=10/1) to afford the title compound as a white solid (1.37 g, 83%). MS (ESI) calcd for $C_{18}H_{24}F_5N_3O_2$: 409.2. found: 410.4 [M+H]. $^1$H NMR (400 MHz, CDCl$_3$) δ 8.89 (s, 1H), 8.01 (d, J=8.2 Hz, 1H), 7.75 (d, J=8.2 Hz, 1H), 4.37 (brs, 1H), 3.40 (brs, 1H), 2.97 (t, J=13.2 Hz, 2H), 2.74-2.69 (m, 2H), 2.42-2.36 (m, 2H), 1.87-1.81 (m, 2H), 1.43 (s, 9H), 1.36-1.23 (m, 2H).

Step 6: 1-(2,2-difluoro-2-(6-(trifluoromethyl)pyridin-3-yl)ethyl)piperidin-4-amine

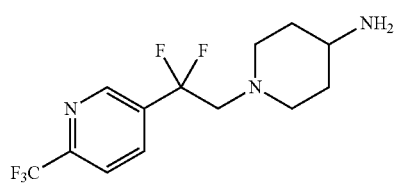

To a stirred solution of tert-butyl 1-(2,2-difluoro-2-(6-(trifluoromethyl)pyridin-3-yl)-ethyl)piperidin-4-ylcarbamate (1.36 g, 3.32 mmol) in DCM (16 mL) was added TFA (8 mL) under ice-water bath cooling. After stirring for 30 mins at rt, the starting material was consumed, and the mixture was concentrated. The concentrate was basified with 1M NaOH, and extracted with EtOAc. The organic phase was washed with brine, dried Na$_2$SO$_4$, and concentrated to afford the title compound as a white solid (1.0 g, 100%). MS (ESI) calcd for $C_{13}H_{16}F_5N_3$: 309.1. found: 310.3 [M+H]. $^1$H NMR (400 MHz, CD$_3$OD) δ 8.92 (s, 1H), 8.24 (d, J=8.2 Hz, 1H), 7.95 (d, J=8.2 Hz, 1H), 3.16 (t, J=13.5 Hz, 2H), 3.06-2.94 (m, 1H), 2.91-2.84 (m, 2H), 2.47-2.38 (m, 2H), 1.92-1.86 (m, 2H), 1.56-1.45 (m, 2H), 1.36-1.30 (m, 2H).

Step 7. N-(1-(2,2-difluoro-2-(6-(trifluoromethyl)pyridin-3-yl)ethyl)piperidin-4-yl)-7H-pyrrolo[2,3-d]pyrimidin-4-amine

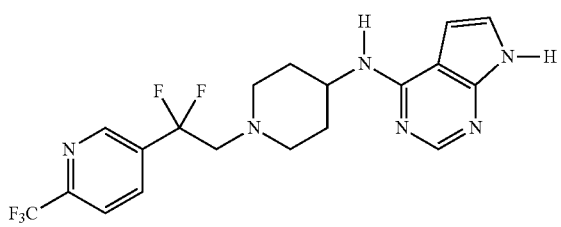 [SMILES: FC(F)(F)c1ccc(C(F)(F)CN2CCC(Nc3ncnc4[nH]ccc34)CC2)cn1]

The mixture of 1-(2,2-difluoro-2-(6-(trifluoromethyl)pyridin-3-yl)ethyl)piperidin-4-amine (625 mg, 2.02 mmol) and DIPEA (0.62 mL, 3.37 mmol) in n-butyl alcohol (10 mL) was heated to 130° C. After stirring overnight at 130° C., the reaction mixture was concentrated. The concentrate was purified by column chromatography over silica gel (hexane/EtOAc=1/1-1/3) to afford the product as a white solid (230 mg, 27%). MS (ESI) calcd for $C_{19}H_{19}F_5N_6$: 426.2. found: 427.4 [M+H]. $^1$H NMR (400 MHz, CDCl$_3$) δ 8.94 (s, 1H), 8.30 (s, 1H), 8.05 (d, J=8.2 Hz, 1H), 7.77 (d, J=8.2 Hz, 1H), 7.08 (d, J=3.5 Hz, 1H), 6.37 (s, 1H), 4.18-4.10 (m, 1H), 3.04 (t, J=13.1 Hz, 2H), 2.86-2.80 (m, 2H), 2.58-2.51 (m, 2H), 2.09-2.00 (m, 2H), 1.61-1.45 (m, 2H).

Example 1.127a (HCl Salt)

N-(1-(2,2-difluoro-2-(6-(trifluoromethyl)pyridin-3-yl)ethyl)piperidin-4-yl)-7H-pyrrolo[2,3-d]pyrimidin-4-amine hydrochloride (C-127.HCl)

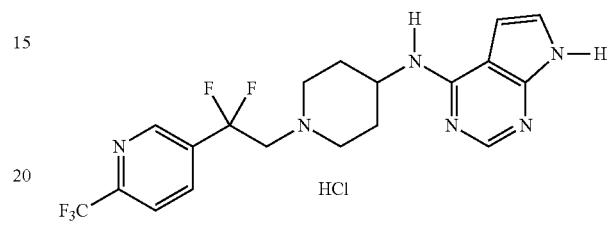

To a stirred solution of N-(1-(2,2-difluoro-2-(6-(trifluoromethyl)pyridin-3-yl)-ethyl)piperidin-4-yl)-7H-pyrrolo[2,3-d]pyrimidin-4-amine (181 mg, 0.424 mmol) in MeOH (2 mL) was added HCl/Et$_2$O (2M, 0.21 mL, 0.424 mmol) at rt. After stirring for 15 min, the mixture was concentrated to afford the product as an off-white powder (197 mg, 100%). MS (ESI) calcd for $C_{19}H_{19}F_5N_6$: 426.2. found: 427.5 [M+H]. $^1$H NMR (400 MHz, CDCl$_3$) δ 11.90 (brs, 1H), 8.91 (s, 1H), 8.43 (s, 1H), 8.06 (d, J=8.0 Hz, 1H), 7.79 (d, J=8.1 Hz, 1H), 7.32 (s, 1H), 6.60 (s, 1H), 4.07 (brs, 1H), 3.08 (t, J=13.1 Hz, 2H), 2.96-2.88 (m, 2H), 2.59 (t, J=9.6 Hz, 2H), 2.09-2.02 (m, 2H), 1.82-1.78 (m, 2H).

Example 1.128

N-(1-(2,2-difluoro-2-(6-methylpyridin-3-yl)ethyl)piperidin-4-yl)-7H-pyrrolo-[2,3-d]pyrimidin-4-amine (C-128)

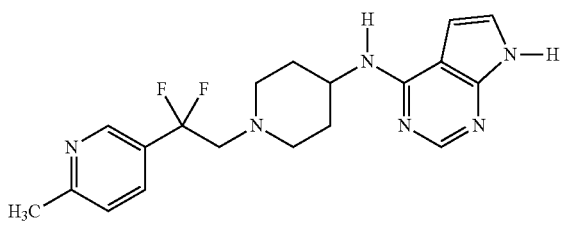 [SMILES: FC(F)(F)c1ccc(C(F)(F)CN2CCC(Nc3ncnc4[nH]ccc34)CC2)cn1]

Step 1. ethyl 2,2-difluoro-2-(6-methylpyridin-3-yl)acetate

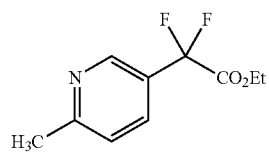

To a stirred solution of ethyl 2-bromo-2,2-difluoroacetate (1.94 g, 9.56 mmol) and 5-iodo-2-methylpyridine (2.00 g, 9.56 mmol) in DMSO (45 mL) was added Cu powder (1.20 g, 18.8 mmol). The reaction mixture was heated at 80° C. for 20 hours. The mixture was allowed to cool to room temperature, filtered through celite and extracted with ethyl acetate. The combined organic phases were washed with brine, dried over sodium sulfate, filtered, and concentrated. The concentrate was purified by column chromatography over silica gel (hexane/ethyl acetate=5:1) to afford the title compound as a colorless oil (1.16 g, 59%). $^1$H NMR (400 MHz, CDCl$_3$) δ 8.75 (s, 1H), 7.81 (dd, J=2.0 and 8.0 Hz, 1H), 7.26 (d, J=8.0 Hz, 1H), 4.32 (q, J=7.2 Hz, 2H), 2.62 (s, 3H), 1.33 (t, J=7.2 Hz, 3H).

Step 2. 2,2-difluoro-2-(6-methylpyridin-3-yl)acetic acid hydrochloride

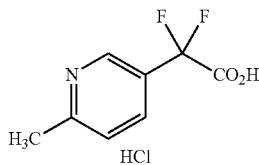

To the solution of ethyl 2,2-difluoro-2-(6-methylpyridin-3-yl)acetate (1.16 g, 5.39 mmol) in methanol (30 mL) was added 50% aqueous KOH (30 mL) at room temperature. After 2 hours, the reaction mixture was acidified with 3N HCl to pH=2. The mixture was concentrated, dissolved in ethyl acetate (30 mL), stirred for 30 min, filtered, and concentrated to give the title compound (550 mg, 46%). MS (ESI) calcd for C$_8$H$_7$F$_2$NO$_2$: 187.1. found: 188.2 [M+H].

Step 3. tert-butyl 1-(2,2-difluoro-2-(6-methylpyridin-3-yl)acetyl)piperidin-4-ylcarbamate

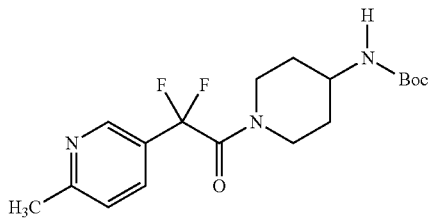 [SMILES: Cc1ccc(C(F)(F)C(=O)N2CCC(NC(=O)OC(C)(C)C)CC2)cn1]

A mixture of 2,2-difluoro-2-(6-methylpyridin-3-yl)acetic acid hydrochloride (400 mg, 2.14 mmol), oxalyl chloride (0.22 mL, 2.56 mmol) and a drop of DMF in DCM (8 mL) was stirred at room temperature for 1 hr. DIPEA (1.62 mL, 9.35 mmol) was added followed by tert-butyl piperidin-4-ylcarbamate (480 mg, 0.22 mmol). After 14 hours the reaction mixture was poured into 1M citric acid and extracted with ethylacetate. The combined organic layers were washed with saturated sodium bicarbonate, water, brine, dried over sodium sulfate and concentrated. The concentrate was purified by column chromatography over silica gel (hexane/ethyl acetate=1:1) to afford the title compound as a white solid (520 mg, 68%). $^1$H NMR (400 MHz, CDCl$_3$) δ 8.66 (d, J=1.2 Hz, 1H), 7.73 (dd, J=1.2 and 8.0 Hz, 1H), 7.25 (d, J=8.0 Hz, 1H), 4.52-4.39 (m, 2H), 4.05-4.00 (m, 1H), 3.72-3.62 (m, 1H), 3.12-3.05 (m, 1H), 2.95-2.85 (m, 1H), 2.62 (s, 3H), 2.04-1.90 (m, 2H), 1.45 (s, 9H), 1.38-1.29 (m, 1H).

Step 4. 1-(4-aminopiperidin-1-yl)-2,2-difluoro-2-(6-methylpyridin-3-yl)ethanone hydrochloride

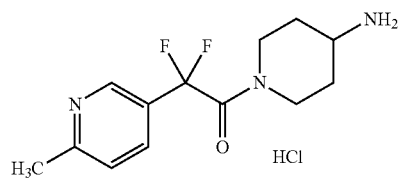 [SMILES: Cc1ccc(C(F)(F)C(=O)N2CCC(N)CC2)cn1 ; Cl]

To a solution of tert-butyl 1-(2,2-difluoro-2-(6-methylpyridin-3-yl)acetyl)piperidin-4-ylcarbamate (100 mg, 0.27 mmol) in DCM (1 mL) was added trifluoroacetic acid (1 mL) and the resulting solution was stirred at room temperature. After one hour, the reaction mixture was concentrated, treated with a saturated solution of HCl in ether and concentrated to afford the title compound as a yellow solid (73 mg, 88%) which was used in the next step without further purification.

Step 5. 1-(2,2-difluoro-2-(6-methylpyridin-3-yl)ethyl)piperidin-4-amine

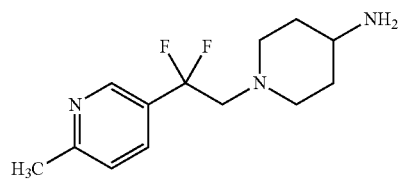

To a stirred solution of 1-(4-aminopiperidin-1-yl)-2,2-difluoro-2-(6-methylpyridin-3-yl)ethanone hydrochloride (306 mg, 1.14 mmol) in THF (45 mL) was added 1M borane in THF (14 mL, 14 mmol)) under nitrogen at room temperature. The reaction mixture was heated at 70° C. for 2 hours. The reaction mixture was cooled to room temperature, quenched with 6N HCl (43 mL) and heated to 70° C. After 1 hour, the reaction mixture was basified to pH>13 with 5M NaOH and extracted with ethyl acetate. The ethyl acetate layer was dried over sodium sulfate, filtered, and concentrated to give the title compound as an off-white powder (100 mg, 39%). MS (ESI) calcd for C$_{13}$H$_{19}$F$_2$N$_3$: 255.1. found: 256.3 [M+H]. $^1$H NMR (400 MHz, CDCl$_3$) δ 8.64 (d, J=1.6 Hz, 1H), 7.72 (dd, J=2.0 and 8.0 Hz, 1H), 7.20 (d, J=8.0 Hz, 1H), 2.94 (t, J=13.6 Hz, 2H), 2.80-2.71 (m, 2H), 2.69-2.61 (m, 1H), 2.60 (s, 3H), 2.36-2.27 (m, 2H), 1.76-1.68 (m, 2H), 1.36-1.29 (m, 2H).

Step 6. N-(1-(2,2-difluoro-2-(6-methylpyridin-3-yl)ethyl)piperidin-4-yl)-7H-pyrrolo-[2,3-d]pyrimidin-4-amine

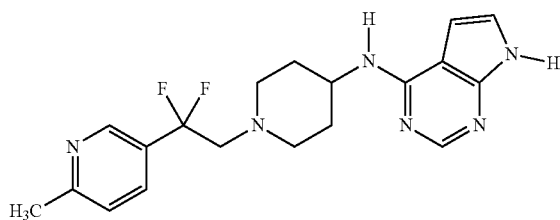

A mixture of 1-(2,2-difluoro-2-(6-methylpyridin-3-yl)ethyl)piperidin-4-amine (64 mg, 0.25 mmol), 4-chloro-7H-pyrrolo[2,3-d]pyrimidine (40 mg, 0.25 mmol) and DIPEA (0.09 mL, 0.5 mmol) in butyl alcohol (1.5 mL) was heated to 130° C. with stirring overnight. The mixture was allowed to cool to room temperature and the orange solution was concentrated. The concentrate was purified by column chromatography over silica gel (hexane/ethyl acetate=3:1) to afford the title compound as a gray powder (20 mg, 28%). MS (ESI) calcd for $C_{19}H_{22}F_2N_6$: 372.2. found: 373.3 [M+H]. $^1$H NMR (400 MHz, $CD_3OD$) δ 8.62 (d, 1H), 8.08 (s, 1H), 7.93 (d, J=8.0 Hz, 1H), 7.43 (d, J=8.0 Hz, 1H), 7.05 (d, J=3.6 Hz, 1H), 6.61 (d, J=3.6 Hz, 1H), 4.05-3.95 (m, 1H), 3.10 (t, J=14.4 Hz, 2H), 2.94-2.86 (m, 2H), 2.60 (s, 3H), 2.55-2.45 (m, 2H), 1.96-1.87 (m, 2H), 1.62-1.55 (m, 2H).

Example 1.175

N-(1-(2,2-difluoro-2-(4-fluorophenyl)ethyl)piperidin-4-yl)-7H-pyrrolo[2,3-d]-pyrimidin-4-amine (C-175)

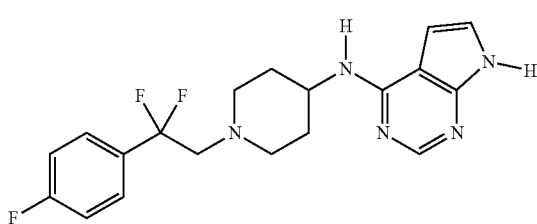

Step 1. ethyl 2,2-difluoro-2-(4-fluorophenyl)acetate

A mixture of 1-fluoro-4-iodobenzene (15.0 g, 67.6 mmol), ethyl 2-bromo-2,2-difluoroacetate (14.5 g, 71 mmol) and copper powder (10.8 g, 35.6 mmol) in DMSO (50 mL) was heated to 90° C. After stirring overnight at 90° C., the mixture was cooled down to rt, and diluted with EtOAc. A solution of $K_2HPO_4 \cdot 3H_2O$ (10 g) in water (100 mL) was added into the above mentioned mixture. The mixture was stirred for 30 min and filtered through a pad of celite. The filter mass was extracted with EtOAc. The combined organic phases were washed with water and brine, dried over $Na_2SO_4$ and concentrated. The concentrate was purified by column chromatography over silica gel (eluent: 100% hexane) to afford the title compound as a colorless oil (8.18 g, 55%). MS (ESI) calcd for $C_{10}H_9F_3O_2$: 218.20. found: [M+H]. $^1$H NMR (400 MHz, $CDCl_3$) δ 7.61 (dd, J=8.4, 5.2 Hz, 2H), 7.14 (t, J=8.6 Hz, 2H), 4.30 (q, J=7.6 Hz, 2H), 1.31 (t, J=7.6 Hz, 3H).

Step 2. 2,2-difluoro-2-(4-fluorophenyl)ethanol

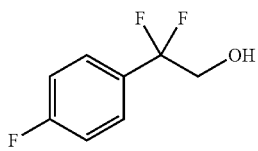

To a stirred solution of ethyl 2,2-difluoro-2-(4-fluorophenyl)acetate (7.6 g, 35 mmol) in ethanol (150 mL) was slowly added $NaBH_4$ (1.98 g, 52.3 mmol) at room temperature. After stirring for 30 min, the suspension was gradually transformed into the clear solution, and the ester was consumed. The reaction mixture was quenched with aqueous 1.0M HCl under ice-water bath cooling. The mixture was concentrated, and the concentrate was extracted with EtOAc. The combined organic phases were washed with brine, dried over $Na_2SO_4$ and concentrated to afford the title compound as a colorless oil (5.8 g, 90%). MS (ESI) calcd for $C_8H_7F_3O$: 176.20. found: [M+H]. $^1$H NMR (400 MHz, $CDCl_3$) δ 7.52 (dd, J=8.4, 5.2 Hz, 2H), 7.14 (t, J=8.6 Hz, 2H), 4.00 (t, J=13.2 Hz, 2H).

Step 3. 2,2-difluoro-2-(4-fluorophenyl)ethyl trifluoromethanesulfonate

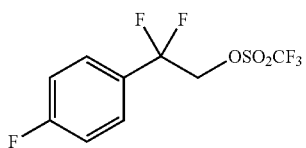

To a stirred solution of 2,2-difluoro-2-(4-fluorophenyl)ethanol (2.0 g, 11 mmol) and DIPEA (3 mL, 17 mmol) in dry ether (100 mL) was added $Tf_2O$ (2.5 mL, 15 mmol) at 0° C. under $N_2$ atmosphere. After stirring for 1 h at 0° C., the white suspension was stirred for another 1 h. The suspension was filtered. The filtrate was concentrated and purified by column chromatography over silica gel (eluent: hexane/EtOAc=100% to 10%) to afford the title compound as a colorless oil (1.77 g, 77%). MS (ESI) calcd for $C_9H_6F_6O_3S$: 307.20. found: [M+H].

Step 4. tert-butyl 1-(2,2-difluoro-2-(4-fluorophenyl)ethyl)piperidin-4-ylcarbamate

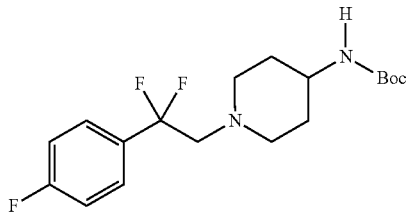

A solution of 2,2-difluoro-2-(4-fluorophenyl)ethyl trifluoromethanesulfonate (1.77 g, 5.74 mmol), tert-butyl piperidin-4-ylcarbamate (2.3 g, 11 mmol) and DIPEA (2.2 mL, 13 mmol) in DCM (30 mL) was heated to 40° C. After stirring overnight at 40° C., the reaction mixture was concentrated, and purified by column chromatography over silica gel (eluent: hexane/EtOAc=10/1) to afford the title compound as a white powder (1.39 g, 70%). MS (ESI) calcd for $C_{18}H_{25}F_3N_2O_2$: 358.20. found: 359.4 [M+H]. $^1$H NMR (400 MHz, CDCl$_3$) δ 7.48 (dd, J=8.6, 5.4 Hz, 2H), 7.08 (t, J=8.6 Hz, 2H), 4.37 (s, 1H), 3.40 (s, 1H), 2.91 (t, J=14.0 Hz, 2H), 2.76-2.72 (m, 2H), 2.37-2.31 (m, 2H), 1.82 (d, J=11.6 Hz, 2H), 1.43 (s, 9H), 1.38-1.29 (m, 2H).

Step 5. 1-(2,2-difluoro-2-(4-fluorophenyl)ethyl)piperidin-4-amine

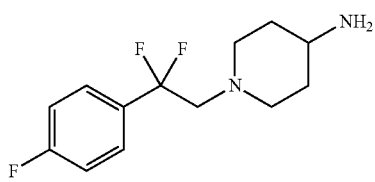 [SMILES: NC1CCN(CC(F)(F)c2ccc(F)cc2)CC1]

To a stirred solution of tert-butyl 1-(2,2-difluoro-2-(4-fluorophenyl)ethyl)piperidin-4-ylcarbamate (1.39 g, 3.87 mmol) in DCM (20 mL) was added TFA (10 mL) under ice-water bath cooling. After stirring for 1 h at room temperature, the starting material was consumed, and the reaction mixture was concentrated. The concentrate was basified with 1N aqueous NaOH and mixture was extracted with DCM. The combined organic phases were washed with brine, dried over Na$_2$SO$_4$ and concentrated to afford the title compound as an off-white powder (1.0 g, 100%). MS (ESI) calcd for $C_{13}H_{17}F_3N_2$: 258.20. found: 259.3 [M+H]. $^1$H NMR (400 MHz, CDCl$_3$) δ 7.50 (dd, J=8.6, 5.4 Hz, 2H), 7.08 (t, J=8.6 Hz, 2H), 2.91 (t, J=13.8 Hz, 2H), 2.76-2.73 (m, 2H), 2.65-2.58 (m, 1H), 2.32-2.26 (m, 2H), 1.71-1.68 (m, 2H), 1.35-1.28 (m, 2H).

Step 6. N-(1-(2,2-difluoro-2-(4-fluorophenyl)ethyl)piperidin-4-yl)-7H-pyrrolo[2,3-d]-pyrimidin-4-amine

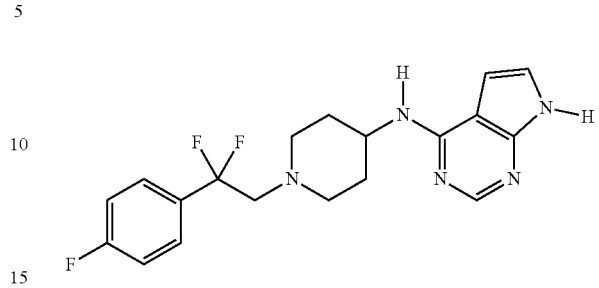

A mixture of 4-chloro-7H-pyrrolo[2,3-d]pyrimidine (200 mg, 1.30 mmol), 1-(2,2-difluoro-2-(4-fluorophenyl)ethyl)piperidin-4-amine (440 mg, 1.69 mmol) and DIPEA (0.45 mL, 2.60 mmol) in n-BuOH (6 mL) was heated to 130° C. in a sealed tube. After stirring overnight, the brown solution was concentrated. The concentrate was purified by column chromatography over silica gel (eluent: DCM/MeOH=50/1) to afford the title compound as a powder (350 mg, 70%). MS (ESI) calcd for $C_{19}H_{20}F_3N_5$: 375.20. found: 376.4 [M+H]. $^1$H NMR (400 MHz, CDCl$_3$) δ 10.43 (m, 1H), 8.30 (s, 1H), 7.52 (dd, J=8.6, 5.4 Hz, 2H), 7.10 (t, J=8.6 Hz, 2H), 7.06 (d, J=3.6 Hz, 1H), 6.34 (d, J=3.6 Hz, 1H), 4.98 (s, 1H), 4.15-4.07 (m, 1H), 2.97 (t, J=14.0 Hz, 2H), 2.86-2.3 (m, 2H), 2.53-2.47 (m, 2H), 2.06-2.03 (m, 2H), 1.59-1.49 (m, 2H)

Example 1.175a (HCl Salt)

N-(1-(2,2-difluoro-2-(4-fluorophenyl)ethyl)piperidin-4-yl)-7H-pyrrolo[2,3-d]-pyrimidin-4-amine hydrochloride (C-175.HCl)

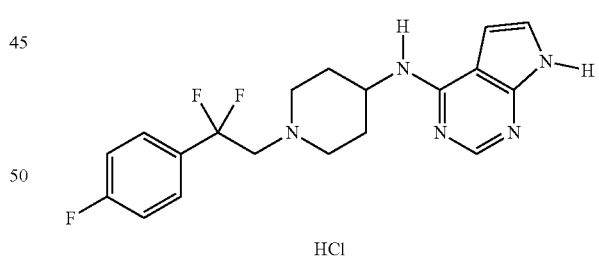

To a stirred solution of N-(1-(2,2-difluoro-2-(4-fluorophenyl)ethyl)piperidin-4-yl)-7H-pyrrolo-[2,3-d]pyrimidin-4-amine (350 mg, 0.93 mmol) in MeOH (5 mL) was added 2M HCl in methanol (0.47 mL, 0.93 mmol) at room temperature. After stirring for 30 min, the clear solution was concentrated to afford the title compound as an off-white powder (370 mg, 98%). MS (ESI) calcd for $C_{19}H_{20}F_3N_5$: 375.20. found: 376.4 [M+H]. $^1$H NMR (400 MHz, CDCl$_3$) δ 8.39 (s, 1H), 7.52-7.49 (m, 2H), 7.28 (s, 1H), 7.11 (t, J=8.6 Hz, 2H), 6.57 (d, J=3.2 Hz, 1H), 4.04 (s, 1H), 3.49 (s, 1H), 3.01 (t, J=13.6 Hz, 2H), 2.94-2.91 (m, 2H), 2.57 (t, J=9.6 Hz, 2H), 2.08-2.05 (m, 2H), 1.83-1.76 (m, 2H).

Example 1.176

N-(1-(2-(4-chlorophenyl)-2,2-difluoroethyl)piperidin-4-yl)-7H-pyrrolo[2,3-d]pyrimidin-4-amine (C-176)

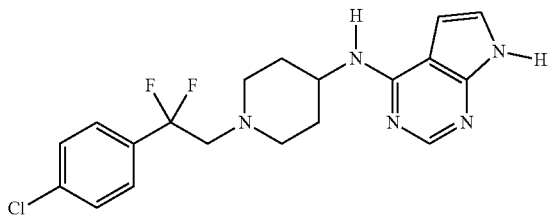 [SMILES: FC(F)(CN1CCC(Nc2ncnc3[nH]ccc23)CC1)c1ccc(Cl)cc1]

Step 1. ethyl 2-(4-chlorophenyl)-2,2-difluoroacetate

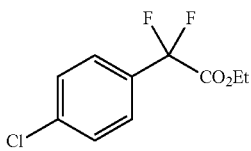 [SMILES: CCOC(=O)C(F)(F)c1ccc(Cl)cc1]

To a stirred solution of 1-chloro-4-iodobenzene (15.0 g, 63 mmol) and ethyl 2-bromo-2,2-difluoroacetate (12.8 g, 63 mmol) in DMSO (300 mL) was added Cu powder (8.0 g, 126 mmol). The mixture was heated to 80° C., and stirred for 20 hrs. The mixture was cooled to rt, and poured into an aqueous solution of $K_2HPO_4 \cdot 3H_2O$ (110 g) in water (1.5 L) under stirring. After stirring for 30 min at rt, the mixture was filtered through a pad of celite. The filter cake was extracted with ether. The combined organic phases were washed with water and brine, dried over $Na_2SO_4$ and concentrated. The concentrate was purified column chromatography over silica gel (eluent: hexane) to afford the title compound as a colorless oil (6.8 g, 46%). $^1$H NMR (400 MHz, $CDCl_3$) δ 7.55 (d, J=8.4 Hz, 2H), 7.44 (d, J=8.4 Hz, 2H), 4.30 (q, J=7.1 Hz, 2H), 1.31 (t, J=7.1 Hz, 3H).

Step 2. 2-(4-chlorophenyl)-2,2-difluoroethanol

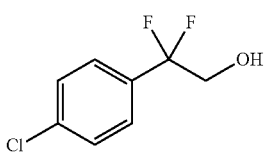 [SMILES: OCC(F)(F)c1ccc(Cl)cc1]

To a stirred solution of ethyl 2-(4-chlorophenyl)-2,2-difluoroacetate (6.7 g, 29 mmol) in EtOH (130 mL) was added $NaBH_4$ (1.56 g, 41 mmol) at room temperature. The suspension was slowly transformed to a clear solution. After stirring for 30 min at rt, the ester was consumed. The reaction mixture was quenched with aqueous 1N HCl under ice-water bath cooling. The mixture was extracted with EtOAc. The organic phases were washed with brine, dried over $Na_2SO_4$ and concentrated to afford the title compound as a colorless liquid (5.39 g, 95%). $^1$H NMR (400 MHz, $CDCl_3$) δ 7.46 (d, J=8.8 Hz, 2H), 7.42 (d, J=8.8 Hz, 2H), 3.95 (t, J=13.1 Hz, 2H).

Step 3. 2-(4-chlorophenyl)-2,2-difluoroethyl trifluoromethanesulfonate

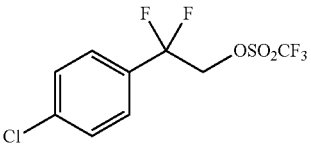

To a stirred solution of 2-(4-chlorophenyl)-2,2-difluoroethanol (1.5 g, 7.8 mmol) and DIPEA (4.2 mL, 23 mmol) in dry ether (78 mL) was added the $Tf_2O$ (2.7 mL, 16 mmol) at 0° C. After stirring for 2 hrs at rt, the white suspension was filtered through celite, and the filter mass was washed with ether. The filtrate was concentrated and purified by column chromatography over silica gel to afford the title compound as a colorless oil (1.28 g, 51%) which was used in the next step without further purification.

Step 4. tert-butyl-1-(2-(4-chlorophenyl)-2,2-difluoroethyl)piperidin-4-yl-carbamate

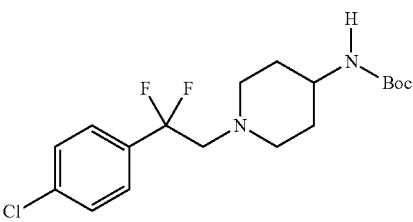 [SMILES: CC(C)(C)OC(=O)NC1CCN(CC(F)(F)c2ccc(Cl)cc2)CC1]

The mixture of 2,2-difluoro-2-p-tolylethyl trifluoromethanesulfonate (1.28 g, 3.9 mmol), tert-butyl piperidin-4-ylcarbamate (1.20 g, 5.9 mmol) and DIPEA (2.1 mL, 12 mmol) in DCM (20 mL) was heated to 40° C. After stirring overnight at 40° C., the mixture was concentrated to dryness. The concentrate was purified by column chromatography over silica gel (hexane/EtOAc=50/1) to afford the title compound as a white solid (850 mg, 65%). MS (ESI) calcd for $C_{18}H_{25}F_2N_2O_2$: 374.1. found: 375.4 [M+H]. $^1$H NMR (400 MHz, $CDCl_3$) δ 7.43 (d, J=8.6 Hz, 2H), 7.38 (d, J=8.6 Hz, 2H), 4.40 (s, 1H), 3.40 (s, 1H), 2.91 (t, J=13.9 Hz, 2H), 2.74 (m, 2H), 2.33 (m, 2H), 1.82 (m, 2H), 1.43 (s, 9H), 1.33 (m, 2H).

Step 5. 1-(2-(4-chlorophenyl)-2,2-difluoroethyl)piperidin-4-amine

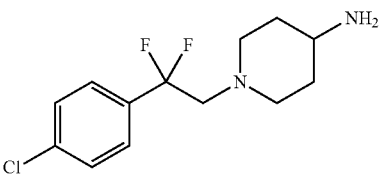 [SMILES: NC1CCN(CC(F)(F)c2ccc(Cl)cc2)CC1]

To a stirred solution of tert-butyl 1-(2,2-difluoro-2-p-tolylethyl) piperidin-4-ylcarbamate (850 mg, 2.27 mmol) in DCM (12 mL) was added TFA (11 mL) under ice-water bath cooling. After stirring for 30 min at rt, the starting material was consumed, and the mixture was concentrated. The concentrate was basified with aqueous 1M NaOH, and extracted with EtOAc. The organic phase was washed with brine, dried over $Na_2SO_4$, and concentrated to afford the title compound as an off-white powder (620 mg, 100%). MS (ESI) calcd for $C_{13}H_{17}ClF_2N_2$: 274.1. found: 275.4 [M+H]. $^1$H NMR (400 MHz, $CD_3OD$) δ 7.54 (d, J=8.6 Hz, 2H), 7.48 (d, J=8.6 Hz, 2H), 3.10-3.01 (m, 3H), 2.88-2.85 (M, 2H), 2.41-2.35 (m, 2H), 1.88-1.85 (m, 2H), 1.58-1.48 (m, 2H).

Step 6. N-(1-(2-(4-chlorophenyl)-2,2-difluoroethyl) piperidin-4-yl)-7H-pyrrolo[2,3-d]-pyrimidin-4-amine

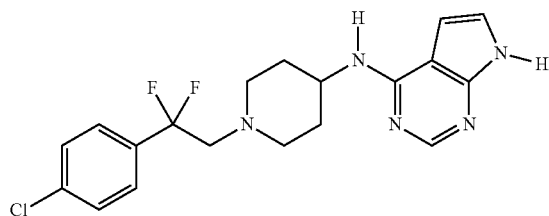 [SMILES: FC(F)(CN1CCC(Nc2ncnc3[nH]ccc23)CC1)c1ccc(Cl)cc1]

The mixture of 1-(2-(4-chlorophenyl)-2,2-difluoroethyl) piperidin-4-amine (322 mg, 1.17 mmol), 4-chloro-7H-pyrrolo[2,3-d]pyrimidine (150 mg, 0.98 mmol) and DIPEA (0.4 mL, 1.95 mmol) in isopropanol (6 mL) was heated to 85° C. After stirring overnight at 85° C., the resulting orange solution was concentrated. The concentrate was purified by column chromatography over silica gel (DCM/MeOH=50/1~30/1) to afford the title compound as a gray powder (240 mg, 56%). MS (ESI) calcd for $C_{19}H_{20}F_3N_5$: 391.1. found: 392.4 [M+H]. $^1$H NMR (400 MHz, $CDCl_3$) δ 10.44 (s, 1H), 8.32 (s, 1H), 7.47 (d, J=8.5 Hz, 2H), 7.40 (d, J=8.5 Hz, 2H), 7.08 (d, J=3.4 Hz, 1H), 6.36 (d, J=3.4 Hz, 1H), 4.11 (s, 1H), 3.00-2.94 (m, 2H), 2.85-2.82 (m, 2H), 2.53-2.48 (m, 2H), 2.06-2.03 (dm, 3H), 1.61-1.48 (m, 2H).

Example 1.176a (HCl Salt)

N-(1-(2-(4-chlorophenyl)-2,2-difluoroethyl)piperidin-4-yl)-7H-pyrrolo[2,3-d]pyrimidin-4-amine hydrochloride (C-176.HCl)

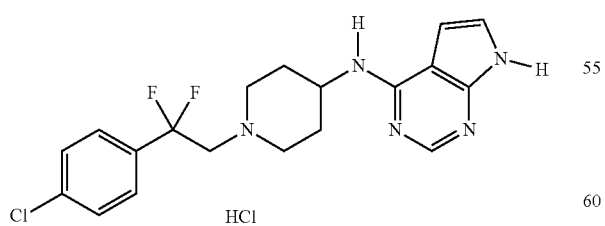

To a stirred solution of N-(1-(2,2-difluoro-2-p-tolylethyl) piperidin-4-yl)-7H-pyrrolo[2,3-d]-pyrimidin-4-amine (210 mg, 0.54 mmol) in MeOH (3.0 mL) was added HCl/$Et_2O$ (2M, 0.30 mL, 0.60 mmol) at rt. After stirring for 15 min, the mixture was concentrated to afford the title compound as an off-white powder (210 mg, 92%). MS (ESI) calcd for $C_{19}H_{20}ClF_2N_5$: 391.1. found: 392.4 [M+H]. $^1$H NMR (400 MHz, $CD_3OD$) δ 8.27 (s, 1H), 7.62-7.54 (m, 7.9 Hz, 4H), 7.35 (s, 1H), 6.93 (s, 1H), 4.08 (s, 1H), 3.50 (s, 2H), 2.92 (s, 2H), 2.14 (s, 2H), 1.93 (s, 2H), 1.31 (s, 1H).

Example 1.177

N-(1-(2,2-difluoro-2-p-tolylethyl)piperidin-4-yl)-7H-pyrrolo[2,3-d]-pyrimidin-4-amine (C-177)

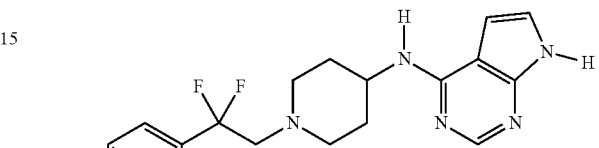

Step 1. ethyl 2,2-difluoro-2-(p-tolyl)acetate

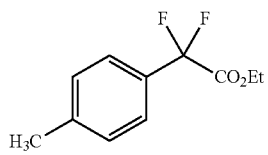

To a stirred solution of 1-iodo-4-methylbenzene (20.0 g, 91.7 mmol) and ethyl 2-bromo-2,2-difluoroacetate (19.7 g, 97.2 mmol) in DMSO (125 mL) was added Cu powder (13.4 g, 211 mmol). The mixture was heated to 50° C. for 14 hours. Isopropyl acetate (100 mL) was added to the mixture, and the reaction was quenched with an aqueous solution of $K_2HPO_4 \cdot 3H_2O$ (23 g) in water (250 mL). The mixture was stirred for 30 min at rt and filtered. The filter cake was washed with isopropyl acetate. The combined organic phases were washed with water and brine, dried over $Na_2SO_4$ and concentrated. The concentrate was purified by column chromatography over silica gel (100% hexane) to afford the title compound as colorless oil (14.7 g, 77%). $^1$H NMR (400 MHz, CDCl3) δ 7.49 (d, J=8.0 Hz, 2H), 7.25 (d, J=7.4 Hz, 2H), 4.29 (q, J=7.1 Hz, 2H), 2.39 (s, 3H), 1.30 (t, J=7.1 Hz, 3H).

Step 2. 2,2-difluoro-2-(p-tolyl)ethanol

To a stirred solution of ethyl 2,2-difluoro-2-(p-tolyl)acetate (14.5 g, 68 mmol) in the ethanol (120 mL) was added $NaBH_4$ (3.7 g, 98 mmol) at ambient temperature. The suspension was slowly transformed into clear solution, and the reaction was exothermic. After stirring for 15 min at room temperature, the ester was consumed. The reaction was carefully quenched with 1N HCl under ice-water bath. The mixture was extracted with EtOAc. The combined organic phases were washed with sat. NaHCO$_3$ and brine, dried over Na$_2$SO$_4$ and concentrated to afford the title compound as a white solid (11.5 g, 99%). $^1$H NMR (400 MHz, CDCl$_3$) δ 7.40 (d, J=8.0 Hz, 2H), 7.24 (d, J=7.8 Hz, 2H), 3.97-3.89 (m, 2H), 2.38 (s, 3H), 2.13 (t, J=6.1 Hz, 1H).

Step 3. 2,2-difluoro-2-(p-tolylethyl)trifluoromethanesulfonate

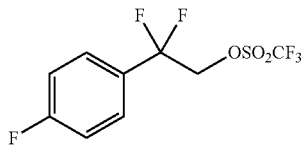

To a stirred solution of 2,2-difluoro-2-(p-tolyl)ethanol (600 mg, 3.5 mmol) and DIPEA (1.9 mL, 111 mmol) in dried ether (35 mL) was added the Tf$_2$O (1.2 mL, 7.0 mmol) at 0° C. After stirring for 2 hrs at rt, the white suspension was filtered through celite, and the filter mass was washed with ether. The filtrate was concentrated and purified by column chromatography over silica gel to afford the title compound as a colorless oil (860 mg, 86%). $^1$H NMR (400 MHz, CDCl$_3$) δ 7.40 (d, J=7.8 Hz, 2H), 7.24 (d, J=7.7 Hz, 2H), 4.67 (t, J=12.0 Hz, 2H), 2.41 (s, 3H).

Step 4. tert-butyl 1-(2,2-difluoro-2-(p-tolyl)ethyl)piperidin-4-ylcarbamate

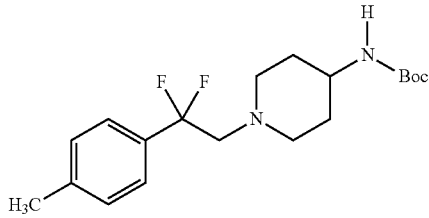 [SMILES: Cc1ccc(C(F)(F)CN2CCC(NC(=O)OC(C)(C)C)CC2)cc1]

A mixture of 2,2-difluoro-2-p-tolylethyl trifluoromethanesulfonate (860 mg, 2.8 mmol), tert-butyl piperidin-4-ylcarbamate (1.1 g, 5.6 mmol) and DIPEA (1.5 mL, 8.4 mmol) in DCM (14 mL) was heated to 40° C. After stirring overnight at 40° C., the mixture was concentrated to dryness. The concentrate was purified by column chromatography over silica gel (hexane/EtOAc=50/1) to afford the title compound as a white solid (650 mg, 70%). MS (ESI) calcd for C$_{18}$H$_{28}$F$_2$N$_2$O$_2$: 354.21. found: 355.5 [M+H]. $^1$H NMR (400 MHz, CDCl$_3$) δ 7.37 (d, J=8.0 Hz, 2H), 7.20 (d, J=8.0 Hz, 2H), 4.40 (brs, 1H), 3.40 (brs, 1H), 2.92 (t, J=14.4 Hz, 2H), 2.80-2.77 (m, 2H), 2.38 (s, 3H), 2.34-2.31 (m, 2H), 1.84-1.81 (m, 2H), 1.58 (s, 2H), 1.43 (s, 9H), 1.41-1.34 (m, 2H).

Step 5. 1-(2,2-difluoro-2-p-tolylethyl)piperidin-4-amine

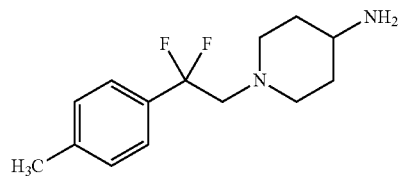

To a stirred solution of tert-butyl 1-(2,2-difluoro-2-p-tolylethyl)piperidin-4-ylcarbamate (650 mg, 1.83 mmol) in DCM (9 mL) was added TFA (9 mL) under ice-water bath cooling. After stirring for 30 min at rt, the starting material was consumed, and the mixture was concentrated. The concentrate was basified with aq.NaCO$_3$, and extracted with EtOAc. The organic phase was washed with brine, dried over Na$_2$SO$_4$, and concentrated to afford the title compound as an off-white powder (460 mg, 100%). MS (ESI) calcd for C$_{14}$H$_{20}$F$_2$N$_2$: 254.16. found: 255.4 [M+H]. $^1$H NMR (400 MHz, CDCl$_3$) δ 7.35 (d, J=8.0 Hz, 2H), 7.20 (d, J=8.0 Hz, 2H), 3.05-2.95 (m, 1H), 2.93 (t, J=14.0 Hz, 2H), 2.88-2.84 (m, 2H), 2.37 (s, 3H), 2.33 (s, 2H), 1.89-1.86 (m, 2H), 1.66-1.56 (m, 2H).

Step 6. N-(1-(2,2-difluoro-2-(p-tolyl)ethyl)piperidin-4-yl)-7H-pyrrolo[2,3-d]-pyrimidin-4-amine

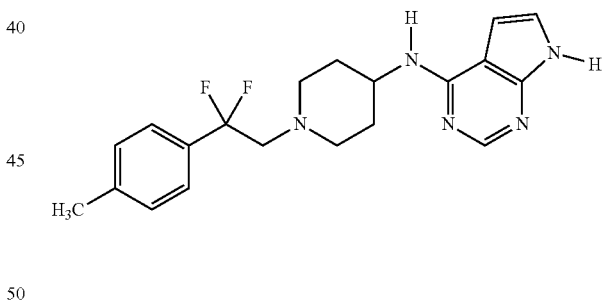

A mixture of 1-(2,2-difluoro-2-p-tolylethyl) piperidin-4-amine (397 mg, 1.56 mmol), 4-chloro-7H-pyrrolo[2,3-d]pyrimidine (200 mg, 1.30 mmol) and DIPEA (0.45 mL, 2.60 mmol) in isopropanol (6 mL) was heated to 85° C. After stirring overnight at 85° C., the orange solution was concentrated. The concentrate was purified by column chromatography over silica gel (DCM/MeOH=50/1~30/1) to afford the title compound as a gray powder (270 mg, 56%). MS (ESI) calcd for C$_{20}$H$_{23}$F$_2$N$_5$: 371.19. found: 372.4 [M+H]. $^1$H NMR (400 MHz, CDCl$_3$) δ 10.38 (s, 1H), 8.32 (s, 1H), 7.40 (d, J=8.0 Hz, 2H), 7.22 (d, J=8.0 Hz, 2H), 7.08 (d, J=3.3 Hz, 1H), 6.35 (d, J=3.3 Hz, 1H), 4.11 (s, 1H), 2.97 (t, J=14.4 Hz, 2H), 2.92-2.85 (m, 2H), 2.53-2.48 (m, 2H), 2.39 (s, 3H), 2.06-2.04 (m, 2H), 1.62-1.53 (m, 2H).

Example 1.177a (HCl Salt)

N-(1-(2,2-difluoro-2-(p-tolyl)ethyl)piperidin-4-yl)-7H-pyrrolo[2,3-d]pyrimidin-4-amine hydrochloride (C-177.HCl)

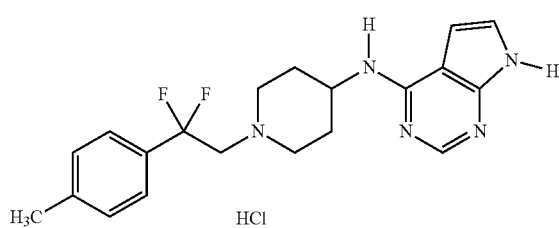 [SMILES: Cc1ccc(C(F)(F)CN2CCC(Nc3ncnc4[nH]ccc34)CC2)cc1 ; Cl]

To a stirred solution of N-(1-(2,2-difluoro-2-(p-tolyl)ethyl)piperidin-4-yl)-7H-pyrrolo[2,3-d]pyrimidin-4-amine (240 mg, 0.64 mmol) in MeOH (3.5 mL) was added HCl/Et$_2$O (2M, 0.35 mL, 0.70 mmol) at rt. After stirring for 15 min, the mixture was concentrated to afford the title compound as an off-white powder (235 mg, 96%). MS (ESI) calcd for C$_{19}$H$_{24}$ClF$_2$N$_5$: 407.17. found: 372.5 [M+H]. $^1$H NMR (400 MHz, CD3OD) δ 8.19 (s, 1H), 7.45 (d, J=8.0 Hz, 2H), 7.30 (d, J=8.0 Hz, 2H), 7.25 (d, J=3.5 Hz, 1H), 6.82 (d, J=3.5 Hz, 1H), 4.0 (brs, 1H), 3.45-3.35 (m, 1H), 3.25-3.15 (m, 2H), 2.85-2.70 (m, 2H), 2.40 (s, 3H), 2.09-2.06 (m, 2H), 1.88-1.79 (m, 2H).

Example 1.178

N-(1-(2,2-difluoro-2-(4-(trifluoromethyl)phenyl)ethyl)piperidin-4-yl)-7H-pyrrolo-[2,3-d]pyrimidin-4-amine (C-178)

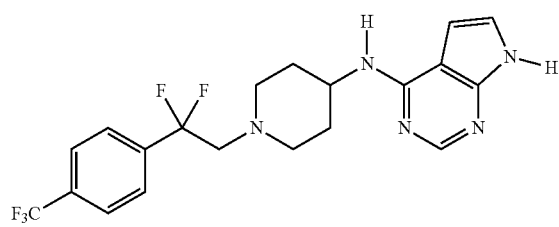

Step 1. ethyl 2,2-difluoro-2-(4-(trifluoromethyl)phenyl)acetate

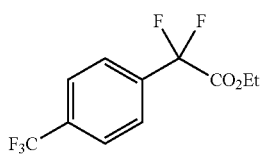

A mixture of 1-iodo-4-(trifluoromethyl)benzene (10 g, 36 mmol), ethyl 2-bromo-2,2-difluoroacetate (7.5 g, 36 mmol) and copper powder (4.60 g, 72 mmol) in DMSO (120 mL) was heated to 80° C. After stirring for 20 hrs at 80° C., the mixture was cooled down to rt and diluted with EtOAc. The mixture thus obtained was poured into the water and stirred for 0.5 h. The suspension was filtered through a pad of celite, and the filter mass was extracted with EtOAc. The combined organic phases were washed with water and brine, dried over Na$_2$SO$_4$ and concentrated. The concentrate was purified by column chromatography over silica gel (100% hexane) to afford the title compound as a pale brown oil (6.35 g, 64%). $^1$H NMR (400 MHz, CDCl$_3$) δ 7.78-7.70 (m, 4H), 4.31 (q, J=7.1 Hz, 2H), 1.31 (t, J=7.1 Hz, 3H).

Step 2. 2,2-difluoro-2-(4-(trifluoromethyl)phenyl)ethanol

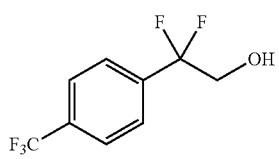 [SMILES: OCC(F)(F)c1ccc(C(F)(F)F)cc1]

To a suspension of LiBH$_4$ (3.25 g, 15 mmol) in dry THF (35 mL) was added a solution of ethyl 2,2-difluoro-2-(4-(trifluoromethyl)phenyl)acetate (2.0 g, 7.5 mmol) in THF, dropwise at 0° C. The mixture thus obtained was stirred for 30 min at room temperature. After the ester was consumed, the reaction was quenched with 1M aqueous HCl at 0° C., and the mixture was extracted with EtOAc. The combined organic phases were washed with brine, dried over Na$_2$SO$_4$ and concentrated to afford the title compound as a brown liquid (1.68 g, 100%). $^1$H NMR (400 MHz, CDCl$_3$) δ 7.75-7.64 (m, 4H), 4.00 (t, J=13.0 Hz, 2H).

Step 3. 2,2-difluoro-2-(4-(trifluoromethyl)phenyl)ethyltrifluoromethanesulfonate

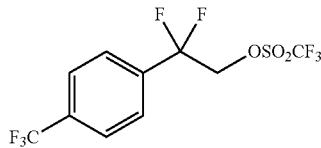

To a stirred solution of 2,2-difluoro-2-(4-(trifluoromethyl)phenyl)ethanol (140 mg, 0.67 mmol) and DIPEA (0.3 mL, 1.7 mmol) in dry ether (5 mL) was added Tf$_2$O (0.3 mL, 1.5 mmol) dropwise at 0° C. under N$_2$ atmosphere. After stirring for 30 min at 0° C., the suspension was stirred an additional 1 h at ambient temperature. After the alcohol was consumed, the suspension was filtered through a pad of Celite. The filtrate was concentrated and purified by column chromatography over silica gel (100% hexane) to afford the title compound as a colorless oil (220 mg, 52%). $^1$H NMR (400 MHz, CDCl$_3$) δ 7.78 (d, J=8.2 Hz, 2H), 7.67 (d, J=8.2 Hz, 2H), 4.72 (t, J=11.6 Hz, 2H).

Step 4. tert-butyl 1-(2,2-difluoro-2-(4-(trifluoromethyl)phenyl)ethyl)piperidin-4-ylcarbamate

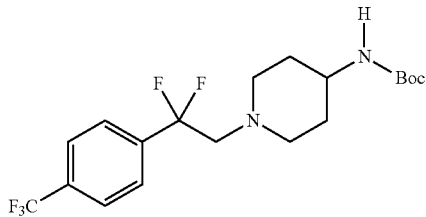 [SMILES: CC(C)(C)OC(=O)NC1CCN(CC(F)(F)c2ccc(C(F)(F)F)cc2)CC1]

A solution of 2,2-difluoro-2-(4-(trifluoromethyl)phenyl) ethyl trifluoromethanesulfonate (220 mg, 0.61 mmol), tert-butyl piperidin-4-ylcarbamate (360 mg, 1.82 mmol) and DIPEA (0.15 mL, 0.91 mmol) in DCM (5 mL) was heated to 40° C. After stirring overnight at 40° C., the solution was concentrated and purified by column chromatography over silica gel (eluent: 10% of EtOAc in hexane) to afford the title compound as an off-white powder (200 mg, 80%). $^1$H NMR (400 MHz, CDCl$_3$) δ 7.67 (d, J=8.4 Hz, 2H), 7.62 (d, J=8.4 Hz, 2H), 4.43-4.33 (m, 1H), 3.47-3.31 (m, 1H), 2.94 (t, J=13.8 Hz, 2H), 2.77-2.69 (m, 2H), 2.40-2.31 (m, 2H), 1.87-1.78 (m, 2H), 1.59 (s, 1H), 1.43 (s, 9H), 1.38-1.26 (m, 2H).

Step 5. 1-(2,2-difluoro-2-(4-(trifluoromethyl)phenyl)ethyl)piperidin-4-amine

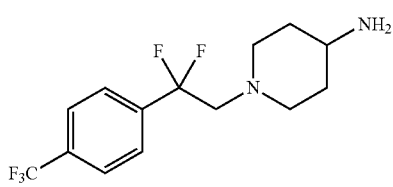 [SMILES: NC1CCN(CC(F)(F)c2ccc(C(F)(F)F)cc2)CC1]

To a stirred solution of tert-butyl 1-(2,2-difluoro-2-(4-(trifluoromethyl)phenyl)ethyl)-piperidin-4-ylcarbamate (200 mg, 0.49 mmol) in DCM (5 mL) was added TFA (5 mL). After stirring for 30 min, the mixture was concentrated, and the residue was dissolved in ice-water. The aqueous solution was basified with 1M aqueous NaOH. The aqueous phase was extracted with EtOAc. The combined organic phases were washed with brine, dried over Na$_2$SO$_4$ and concentrated to afford the title compound as an off-white powder (140 mg, 93%). MS (ESI) calcd for C$_{14}$H$_{17}$F$_5$N$_2$: 308.2. found: 309.2 [M+H]. $^1$H NMR (400 MHz, CDCl$_3$) δ 7.70-7.60 (m, 4H), 2.94 (t, J=13.8 Hz, 2H), 2.79-2.70 (m, 2H), 2.66-2.57 (m, 1H), 2.35-2.24 (m, 2H), 1.73-1.66 (m, 2H), 1.62 (s, 2H), 1.35-1.23 (m, 2H).

Step 6. N-(1-(2,2-difluoro-2-(4-(trifluoromethyl)phenyl)ethyl)piperidin-4-yl)-7H-pyrrolo-[2,3-d]pyrimidin-4-amine

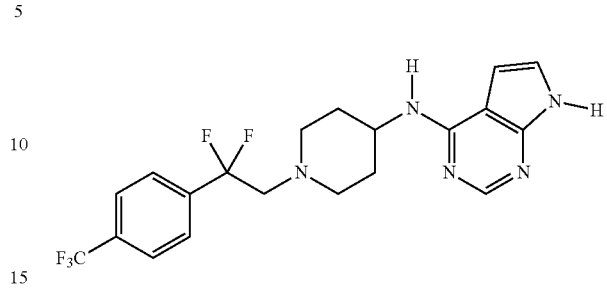

A mixture of 1-(2,2-difluoro-2-(4-(trifluoromethyl)phenyl)ethyl)piperidin-4-amine (1.0 g, 6.5 mmol) and 4-chloro-7H-pyrrolo[2,3-d]pyrimidine (6.0 g, 19.5 mmol) in n-BuOH (32 mL) was heated to 130° C. After stirring overnight at 130° C., the reaction solution was concentrated and extracted with EtOAc. The organic layers were washed with water and brine, dried and concentrated. The concentrate was purified by column chromatography over silica gel (hexane/EtOAc=1/3) to afford the title compound as a white solid (1.62 g, 58%). MS (ESI) calcd for C$_{20}$H$_{20}$F$_5$N$_5$: 425.2. found: 426.4 [M+H]. $^1$H NMR (400 MHz, DMSO-d6) δ 11.43 (s, 1H), 8.06 (s, 1H), 7.88 (d, J=8.3 Hz, 2H), 7.80 (d, J=8.2 Hz, 2H), 7.09 (d, J=7.8 Hz, 1H), 7.06-7.00 (m, 1H), 6.54 (m, 1H), 4.06-3.93 (m, 1H), 3.14 (t, J=14 Hz, 2H), 2.82-2.76 (m, 2H), 2.36 (t, J=11.6 Hz, 2H), 1.82-1.76 (m, 2H), 1.48-1.38 (m, 2H).

Example 1.178a (Mesylate Salt)

N-(1-(2,2-difluoro-2-(4-(trifluoromethyl)phenyl)ethyl)-piperidin-4-yl)-7H-pyrrolo-[2,3-d]pyrimidin-4-amine methanesulfonate (C-178.CH$_3$SO$_3$H)

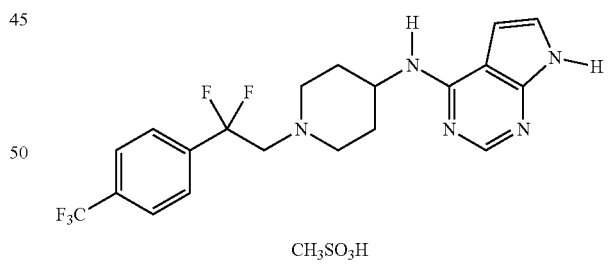

To a solution of N-(1-(2,2-difluoro-2-(4-(trifluoromethyl)phenyl)ethyl)piperidin-4-yl)-7H-pyrrolo[2,3-d]pyrimidin-4-amine (800 mg, 1.88 mmol) in MeOH (9 mL) was added methanesulfonic acid (0.18 g, 1.88 mmol) at rt. After stirring for 10 min, the mixture was concentrated to afford the title compound as a white solid (943 mg, 96%). MS (ESI) calcd for C$_{20}$H$_{20}$F$_5$N$_5$: 425.16. found: 426.4 [M+H]. $^1$H NMR (400 MHz, CD$_3$OD) δ 8.26 (s, 1H), 7.87-7.79 (m, 4H), 7.35 (d, J=3.5 Hz, 1H), 6.91 (d, J=3.5 Hz, 1H), 4.02 (brs, 1H), 3.52-3.42 (m, 2H), 3.28-3.21 (m, 2H), 2.90-2.80 (m, 2H), 2.74 (s, 3H), 2.16-2.08 (m, 2H), 1.91-1.82 (m, 2H).

Example 1.179

N-(1-(2-(4-(difluoromethyl)phenyl)-2,2-difluoro-ethyl)piperidin-4-yl)-7H-pyrrolo[2,3-d]pyrimidin-4-amine (C-179)

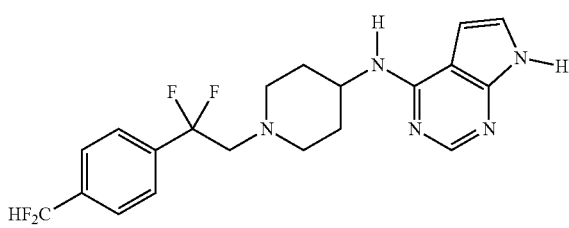

Step 1. 1-(difluoromethyl)-4-iodobenzene

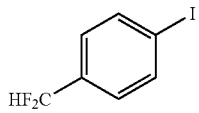

Diethylamino sulfur trifluoride (15.8 mL, 129 mmol) was added slowly to a solution of 4-iodobenzaldehyde (10 g, 43 mmol) in DCM (215 mL) at 0° C. The mixture was stirred for 1 hour before allowing to warm to rt. The reaction mixture was carefully quenched with sat. NaHCO$_3$ (50 mL) and extracted with DCM. The combined organic phases were dried and concentrated. The concentrate was purified by column chromatography over silica gel (hexane/EtOAc=100:1) to afford the title compound as a white solid (8.52 g, 78%), $^1$H NMR (400 MHz, CDCl$_3$) δ 7.81 (d, J=8.2 Hz, 2H), 7.23 (d, J=8.2 Hz, 2H), 6.60 (t, J=56 Hz, 1H).

Step 2. ethyl 2-(4-(difluoromethyl)phenyl)-2,2-difluoroacetate

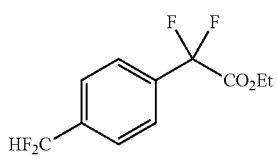

To a stirred solution of 1-(difluoromethyl)-4-iodobenzene (8.52 g, 33.6 mmol) and ethyl 2-bromo-2,2-difluoroacetate (6.82 g, 33.6 mmol) in DMSO (168 mL) was added Cu powder (4.27 g, 67.2 mmol). The mixture was heated at 80° C. for 20 hours. After 20 hours, the reaction mixture was poured into a solution of dibasic potassium hydrogen phosphate, trihydrate (76.7 g, 336 mmol) in water (950 mL) with vigorous stirring. The suspension was filtered and the solid was rinsed with ether. The filtrate was added to brine and extracted with ether (2×). The combined organic phases were washed with brine, dried over sodium sulfate, filtered, and concentrated. The concentrate was purified by column chromatography over silica gel (hexane/EtOAc=70:1) to afford the title compound as a colorless oil (6.78 g, 81%).

Step 3. 2-(4-(difluoromethyl)phenyl)-2,2-difluoroethanol

To a stirred solution of ethyl 2-(4-(difluoromethyl)phenyl)-2,2-difluoroacetate (6.78 g, 27.1 mmol) in ethanol (140 mL) was added NaBH$_4$ (1.48 g, 39.1 mmol) slowly at rt. The mixture was stirred for 30 min at rt. After 30 min, the reaction mixture was quenched with 1N HCl under ice-water bath cooling. The mixture was concentrated and extracted with EtOAc. The EtOAc layer was washed with water and brine, then dried and concentrated to afford the title compound as a white solid (5.29 g, 94%). $^1$H NMR (400 MHz, CDCl$_3$) δ 7.58-7.65 (m, 4H), 6.68 (t, J=56 Hz, 1H), 3.98 (t, J=13.2 Hz, 2H), 2.06 (brs, 1H).

Step 4. 2-(4-(difluoromethyl)phenyl)-2,2-difluoroethyl trifluoromethanesulfonate

To a stirred solution of 2-(4-(difluoromethyl)phenyl)-2,2-difluoroethanol (2.0 g, 9.6 mmol) and DIPEA (5.27 mL, 28.8 mmol) in dry ether (96 mL) was added Tf$_2$O (3.23 mL, 19.2 mmol) at 0° C. After stirring for 1 hr at rt, the orange suspension was filtered through celite and the filter mass was extracted with ether. The combined organic phases were concentrated, and purified by column chromatography over silica gel (hexane/EtOAc=50:1) to afford the title compound as a pale yellow solid (2.86 g, 88%). $^1$H NMR (400 MHz, CDCl$_3$) δ 7.66 (d, J=8.7 Hz, 2H), 7.63 (d, J=8.7 Hz, 2H), 6.70 (t, J=56 Hz, 1H), 4.71 (t, J=14 Hz, 2H).

Step 5. tert-butyl 1-(2-(4-(difluoromethyl)phenyl)-2,2-difluoroethyl)piperidin-4-ylcarbamate

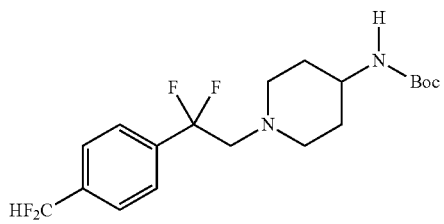

A mixture of 2-(4-(difluoromethyl)phenyl)-2,2-difluoroethyl trifluoromethanesulfonate (2.86 g, 8.41 mmol), tert-butyl piperidin-4-ylcarbamate (3.37 g, 16.8 mmol) and DIPEA (4.41 mL, 25.2 mmol) in DCM (40 mL) was heated to 40° C. After stirring overnight at 40° C., the mixture was concentrated to dryness. The concentrate was purified by column chromatography over silica gel (hexane/EtOAc=8/1) to afford the title compound as a white solid (2.67 g, 82%). MS (ESI) calcd for $C_{19}H_{26}F_4N_2O_2$: 390.2. found: 391.2 [M+H]. $^1$H NMR (400 MHz, CDCl$_3$) δ 7.60 (d, J=8.3 Hz, 2H), 7.55 (d, J=8.3 Hz, 2H), 6.68 (t, J=56 Hz, 1H), 4.38 (brs, 1H), 3.39 (brs, 1H), 2.94 (t, J=14 Hz, 2H), 2.72-2.76 (m, 2H), 2.34-2.38 (m, 2H), 1.80-1.85 (m, 2H), 1.43 (s, 9H), 1.30-1.40 (m, 2H).

Step 6. 1-(2-(4-(difluoromethyl)phenyl)-2,2-difluoroethyl)piperidin-4-amine

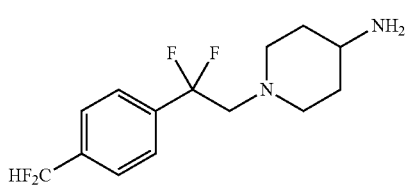

To a stirred solution of tert-butyl 1-(2-(4-(difluoromethyl)phenyl)-2,2-difluoroethyl)-piperidin-4-ylcarbamate (2.67 g, 6.84 mmol) in DCM (25 mL) was added TFA (13 mL) under ice-water bath cooling. After stirring for 30 min at rt, the starting material was consumed, and the mixture was concentrated. The concentrate was basified with 1M NaOH, and extracted with EtOAc. The organic phase was washed with brine, dried Na$_2$SO$_4$, and concentrated to afford the title compound as a white solid (1.79 g, 90%). MS (ESI) calcd for $C_{14}H_{18}F_4N_2$: 290.1. found: 291.4 [M+H]. $^1$H NMR (400 MHz, CDCl$_3$) δ 7.61 (d, J=8.2 Hz, 2H), 7.55 (d, J=8.2 Hz, 2H), 6.68 (t, J=56 Hz, 1H), 2.94 (t, J=13.6 Hz, 2H), 2.75 (m, 2H), 2.65-2.56 (m, 1H), 2.30 (m, 2H), 1.69 (m, 2H), 1.29 (m, 2H).

Step 7. N-(1-(2-(4-(difluoromethyl)phenyl)-2,2-difluoroethyl)piperidin-4-yl)-7H-pyrrolo[2,3-d]pyrimidin-4-amine

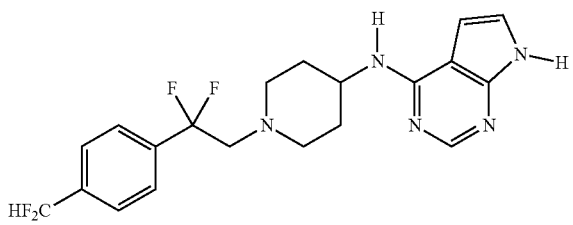

A mixture of 1-(2-(4-(difluoromethyl)phenyl)-2,2-difluoroethyl)piperidin-4-amine (218 mg, 0.75 mmol), 4-chloro-7H-pyrrolo[2,3-d]pyrimidine (96 mg, 0.63 mmol) and DIPEA (0.22 mL, 1.26 mmol) in n-butyl alcohol (3.5 mL) was heated to 130° C. After stirring overnight at 130° C., the reaction solution was concentrated. The concentrate was purified by column chromatography over silica gel (100% EtOAc) to afford the title compound as a white solid (201 mg, 79%). MS (ESI) calcd for $C_{20}H_{21}F_4N_5$: 407.2. found: 408.5 [M+H]. $^1$H NMR (400 MHz, CDCl$_3$) δ 10.42 (brs, 1H), 8.34 (s, 1H), 7.65 (d, J=8.2 Hz, 2H), 7.60 (d, J=8.2 Hz, 2H), 7.10 (d, J=3.4 Hz, 1H), 6.71 (t, J=56 Hz, 1H), 6.38 (d, J=3.3 Hz, 1H), 5.08 (brs, 1H), 4.13 (brs, 1H), 3.03 (t, J=14 Hz, 2H), 2.80-2.90 (m, 2H), 2.46-2.53 (m, 2H), 2.01-2.10 (m, 2H), 1.50-1.60 (m, 2H).

Example 1.179a (HCl Salt)

N-(1-(2-(4-(difluoromethyl)phenyl)-2,2-difluoroethyl)piperidin-4-yl)-7H-pyrrolo[2,3-d]pyrimidin-4-amine hydrochloride (C-179.HCl)

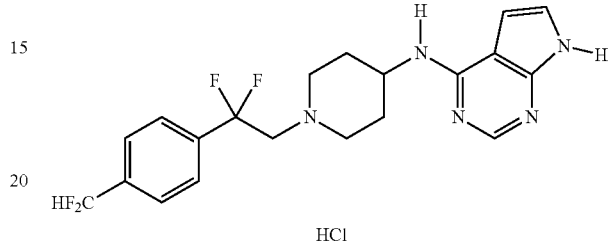

To the solution of N-(1-(2-(4-(difluoromethyl)phenyl)-2,2-difluoroethyl)piperidin-4-yl)-7H-pyrrolo[2,3-d]pyrimidin-4-amine (198 mg, 0.486 mmol) in MeOH (2.5 mL) was added HCl/Et$_2$O (2 M, 0.24 mL, 0.49 mmol) at rt. After stirring for 15 min, the mixture was concentrated to afford the title compound as a pale yellow solid (214 mg, 99%). MS (ESI) calcd for $C_{20}H_{21}F_4N_5$: 407.2. found: 408.5 [M+H]. $^1$H NMR (400 MHz, CDCl$_3$) δ 8.42 (s, 1H), 7.64 (d, J=8.4 Hz, 2H), 7.60 (d, J=8.4 Hz, 2H), 7.29 (brs, 1H), 6.70 (t, J=54 Hz, 1H), 6.55 (brs, 1H), 4.05 (brs, 1H), 3.05 (t, J=14 Hz, 2H), 2.85-2.93 (m, 2H), 2.50-2.60 (m, 2H), 2.02-2.10 (m, 2H), 1.70-1.80 (m, 2H).

Example 1.230

N-(1-(2,2-difluoro-2-(5-methylpyrazin-2-yl)ethyl)piperidin-4-yl)-7H-pyrrolo[2,3-d]pyrimidin-4-amine (C-230)

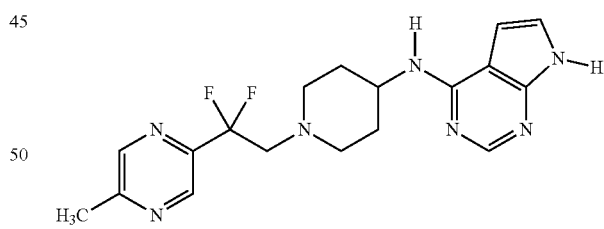

Step 1. ethyl 2,2-difluoro-2-(5-methylpyrazin-2-yl)acetate

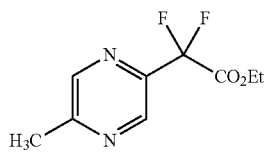

To a stirred solution of ethyl 2-iodo-5-methylpyrazine (2.3 g, 10 mmol) and 2-bromo-5-(trifluoromethyl)pyridine (2.1 g, 10 mmol) in DMSO (25 mL) was added Cu powder (1.3 g, 21 mmol). The mixture was heated at 80° C. for 20 hours. The reaction mixture was allowed to cool to room temperature, filtered through celite and the filter pad was extracted with ethyl acetate. The combined organic phases were washed with brine, dried over sodium sulfate, filtered, and concentrated. The concentrate was purified by column chromatography over silica gel (hexane/ethyl acetate=10:1) to afford the title compound as a colorless oil (800 mg, 40%) which was used directly in the next step.

Step 2. 2,2-difluoro-2-(5-methylpyrazin-2-yl)ethanol

To a stirred solution of ethyl 2,2-difluoro-2-(5-methylpyrazin-2-yl)acetate (600 mg, 2.78 mmol) in ethanol (14 mL) was added NaBH₄ (150 mg, 4.0 mmol) slowly under ice-water bath cooling. The mixture was allowed to warm to room temperature and stirred for 30 min. The reaction mixture was then quenched with 1N HCl under ice-water bath cooling. The mixture was concentrated and extracted with ethyl acetate. The ethyl acetate layer was washed with water and brine, then dried and concentrated to afford the title compound as a white solid (480 mg, 100%) which was used in the next step without further purification.

Step 3. 2,2-difluoro-2-(5-methylpyrazin-2-yl)ethyl-trifluoromethanesulfonate

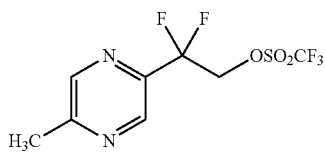

To a stirred solution of 2,2-difluoro-2-(5-methylpyrazin-2-yl)ethanol (480 mg, 2.7 mmol) and DIPEA (1.8 mL, 8.1 mmol) in dry ether (30 mL) was added the Tf₂O (0.9 mL, 2.7 mmol) at 0° C. After stirring for 1 h at rt, the white suspension was filtered through celite, and the filter mass was washed with ether. The filtrate was concentrated to afford the title compound as a colorless oil (800 mg, 100%) which was used in the next step without further purification.

Step 4. tert-butyl-1-(2,2-difluoro-2-(5-methyl-pyrazin-2-yl)ethyl)piperidin-4-ylcarbamate

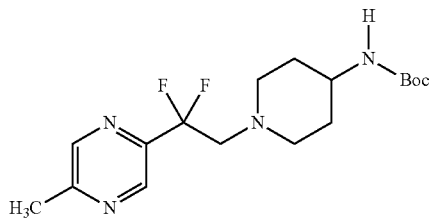 [SMILES: Cc1cnc(C(F)(F)CN2CCC(NC(=O)OC(C)(C)C)CC2)cn1]

A mixture of 2,2-difluoro-2-(5-methylpyrazin-2-yl)ethyl-trifluoromethanesulfonate (800 mg, 2.6 mmol), tert-butyl piperidin-4-ylmethylcarbamate (1.0 g, 5.2 mmol) and DIPEA (3.3 mL, 7.8 mmol) in DCM (13 ml) was heated to 40° C. After stirring overnight at 40° C., the mixture was concentrated to dryness. The concentrate was purified by column chromatography over silica gel (hexane/ethyl acetate=4/1) to afford the title compound as a white solid (125 mg, 14%). MS (ESI) calcd for $C_{17}H_{26}F_2N_4O_2$: 356.2. found: 357.3 [M+H]. $^1$H NMR (400 MHz, CDCl₃) δ 8.77 (s, 1H), 8.48 (s, 1H), 4.30 (brs, 1H), 3.40 (brs, 1H), 3.16 (t, J=14.1 Hz, 2H), 2.72-2.82 (m, 2H), 2.63 (s, 3H), 2.35-2.42 (m, 2H), 1.75-1.82 (m, 2H), 1.51-1.58 (m, 2H), 1.42 (s, 9H).

Step 5. 1-(2,2-difluoro-2-(5-methylpyrazin-2-yl)ethyl)piperidin-4-amine

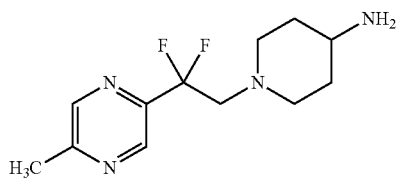 [SMILES: Cc1cnc(C(F)(F)CN2CCC(N)CC2)cn1]

To a stirred solution of tert-butyl 1-(2,2-difluoro-2-(5-methylpyrazin-2-yl)ethyl)-piperidin-4-ylcarbamate (125 mg, 0.35 mmol) in DCM (2 ml) was added TFA (1 ml) under ice-water bath cooling. After stirring for 30 min at rt, the starting material was consumed, and the mixture was concentrated. The concentrate was basified with 1 N NaOH, and extracted with ethyl acetate. The organic phase was washed with brine, dried over Na₂SO₄, and concentrated to afford the title compound as an off-white powder (90 mg, 100%) which was used in the next step without further purification. MS (ESI) calcd for $C_{12}H_{18}F_2N_4$: 256.2. found: 257.3 [M+H]. $^1$H NMR (400 MHz, CDCl₃) δ 8.79 (s, 1H), 8.50 (s, 1H), 3.19 (t, J=14.0 Hz, 2H), 2.80-2.88 (m, 2H), 2.66 (s, 3H), 2.60-2.65 (m, 1H), 2.30-2.38 (m, 2H), 1.65-1.72 (m, 2H), 1.20-1.29 (m, 2H).

Step 6. N-(1-(2,2-difluoro-2-(5-methylpyrazin-2-yl)ethyl)piperidin-4-yl)-7H-pyrrolo[2,3-d]pyrimidin-4-amine

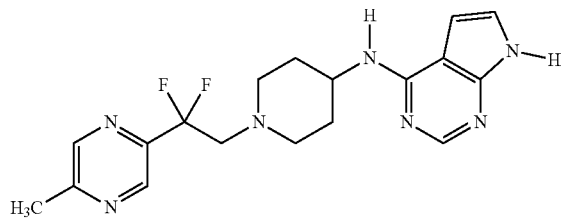

A mixture of 1-(2,2-difluoro-2-(5-methylpyrazin-2-yl)ethyl)piperidin-4-amine (90 mg, 0.35 mmol), 4-chloro-7H-pyrrolo[2,3-d]pyrimidine (153 mg, 0.3 mmol) and DIPEA (0.25 mL, 0.6 mmol) in butyl alcohol (2 mL) was heated to 130° C. After stirring overnight at 130° C., the orange solution was concentrated. The concentrate was purified by column chromatography over silica gel (DCM/MeOH=20:1) to afford the title compound as a gray powder (58 mg, 41%). MS (ESI) calcd for $C_{18}H_{21}F_2N_7$: 373.2. found: 374.3 [M+H]. $^1$H NMR (400 MHz, $CD_3OD$) δ 8.80 (d, J=1.2 Hz, 1H), 8.63 (s, 1H), 8.07 (s, 1H), 7.05 (d, J=3.5 Hz, 1H), 6.58 (d, J=3.5 Hz, 1H), 4.06-3.95 (m, 1H), 3.27 (t, J=14.2 Hz, 2H), 2.94 (d, J=12.0 Hz, 2H), 2.65 (s, 3H), 2.46-2.52 (m, 2H), 1.88-1.94 (m, 2H), 1.48-1.56 (m, 2H).

Example 1.230a (HCl Salt)

N-(1-(2,2-difluoro-2-(5-methylpyrazin-2-yl)ethyl)piperidin-4-yl)-7H-pyrrolo-[2,3-d]pyrimidin-4-amine hydrochloride (C-230.HCl)

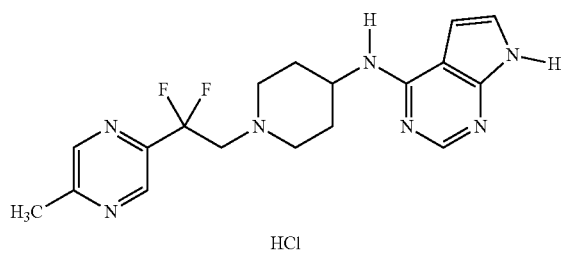 [SMILES: Cc1cnc(C(F)(F)CN2CCC(Nc3ncnc4[nH]ccc34)CC2)cn1 ; Cl]

HCl

To a stirred solution of N-(1-(2,2-difluoro-2-(5-methylpyrazin-2-yl)ethyl)piperidin-4-yl)-7H-pyrrolo[2,3-d]pyrimidin-4-amine (54 mg, 0.144 mmol) in MeOH (0.72 mL) was added HCl/MeOH (2M, 0.072 mL, 0.144 mmol) at room temperature. After stirring for 15 min, the mixture was concentrated to afford the title compound as a yellow powder (58 mg, 99%). MS (ESI) calcd for $C_{18}H_{21}F_2N_7$: 373.2. found: 374.3 [M+H]. $^1$H NMR (400 MHz, $CD_3OD$) δ 8.83 (d, J=0.9 Hz, 1H), 8.65 (s, 1H), 8.23 (s, 1H), 7.33 (d, J=3.5 Hz, 1H), 6.89 (d, J=3.5 Hz, 1H), 3.96 (brs, 1H), 3.50 (brs, 2H), 3.10-3.20 (m, 2H), 2.68-2.73 (m, 2H), 2.66 (s, 3H), 2.02-2.10 (m, 2H), 1.70-1.80 (m, 2H).

Example 2

Assays

Example 2.1

NR2B Antagonist Activity

HEK293 cell lines stably expressing cloned human NR1/NR2B and NR1/NR2A, respectively, were established according to standard previously described methods (Hansen et al., *Comb. Chem High Throughput Screen.* 11:304, 2008). Activation of the NR2A or NR2B subtype of NMDA receptor with glutamate as an agonist and glycine co-agonist on these cells results in calcium influx, which can be monitored with fluorescent indicator Fluo-4. A cell based assay has been implemented to evaluate the effect of a compound on NR2A and NR2B receptors by measuring the fluorescent changes (Hansen et al., *Comb. Chem High Throughput Screen.* 11:304, 2008).

HEK293 cells stably expressing NR2A or NR2B receptors were cultured at 37° C. in a humidified $CO_2$ incubator in DMEM supplemented with 10% fetal bovine serum (FBS) (Hyclone), 10 μM MK801 (Sigma-Aldrich) and 50 μM AP-5 (Tocris). For experiments, the cells were seeded onto poly-D-lysine-coated 96-well black plates with clear bottom (Corning) at a density of 50,000 cells/well. After overnight culture, the growth medium was removed from the wells and the cells were incubated at 37° C. for 60 min in Hanks buffer containing 4 μM fluo-4-AM (Invitrogen) and 0.1% bovine serum albumin (BSA). After dye-loading, the cells were washed three times with Hanks buffer and incubated for 10 min at room temperature with various concentrations of test compounds prepared in Hanks buffer with 0.1% BSA. The cell plates were placed onto FDSS μCell fluorescence reader (Hamamatsu). After 20 sec reading of background fluorescence, agonist glutamate at final 100 μM and co-agonist glycine at final 50 μM were added to the cells to activate the receptor, and the resulting fluorescence changes were recorded and quantified. Based on the changes in fluorescence intensity, the pharmacological effect of test compounds were analyzed and the $IC_{50}$ values derived from a non-linear least squares fitting of the concentration-dependent response to a standard logistic equation using Prism (Graphpad, Inc):

Amplitude=Max Amplitude/(1+($IC_{50}$/[antagonist])$^n$).

Results are shown in the table below.

| Compound | Free Base Structure | NR2B $IC_{50}$ | NR2A $IC_{50}$ |
|---|---|---|---|
| C-2 | | 124 nM | >10 μM |

-continued

| Compound | Free Base Structure | NR2B IC$_{50}$ | NR2A IC$_{50}$ |
|---|---|---|---|
| C-3 | | 22 nM | >10 μM |
| C-4 | | 35 nM | >10 μM |
| C-5 | | 30 nM | >10 μM |
| C-16 | | 47 nM | >10 μM |
| C-18 | | 84 nM | >10 μM |
| C-17 | | 44 nM | >10 μM |

-continued

| Compound | Free Base Structure | NR2B IC$_{50}$ | NR2A IC$_{50}$ |
|---|---|---|---|
| C-47 | | 140 nM | >10 μM |
| C-230 | | 88 nM | >10 μM |
| C-1 | | 159 nM | >10 μM |
| C-127 | | 45 nM | >10 μM |
| C-128 | | 89 nM | >10 μM |
| C-6 | | 31 nM | >10 μM |

-continued

| Compound | Free Base Structure | NR2B IC$_{50}$ | NR2A IC$_{50}$ |
|---|---|---|---|
| C-7 | | 14 nM | >10 μM |
| C-11 | | 43 nM | >10 μM |
| C-12 | | 24 nM | >10 μM |
| C-178 | | 64 nM | >10 μM |
| C-179 | | 23 nM | >10 μM |
| C-175 | | 22 nM | >10 μM |
| C-176 | | 26 nM | >10 μM |

| Compound | Free Base Structure | NR2B IC$_{50}$ | NR2A IC$_{50}$ |
|---|---|---|---|
| C-177 | | 27 nM | >10 μM |

Example 2.2 hERG Channel Inhibition

The assay was performed on hERG channel stably expressed in HEK293 cells. The cells were cultured at 37° C. in a humidified CO$_2$ incubator in the growth medium consisting of DMEM, 10% fetal bovine serum and antibiotics. Prior to the assay, the cells were seeded onto a 12 mm PDL-coated glass coverslip and cultured in a 35 mm Petri dish. After 16 to 40 hr culture, the cover slip was transferred into the chamber of OctaFlow perfusion system (ALA Instrument) and under a constant flow of extracellular solution (140 mM NaCl, 4 mM KCl, 1 mM MgCl$_2$, 2 mM CaCl$_2$, 10 mM HEPES, 10 mM D-glucose, pH 7.35, osmolarity 290). Whole cell patch clamping was performed with a glass micropipette filled with intracellular solution (120 mM KCl, 1.75 mM MgCl$_2$, 5.4 mM CaCl$_2$, 10 mM HEPES, 10 mM EGTA, and 4 mM ATP-K$_2$, PH 7.2, osmolarity 310). Gigaseal was maintained during the test. The voltage control and current measurement were carried out using Axon amplifier 700B, Digidata 1440A and CLAMPEX10 software (Molecular Devices). Whole-cell hERG currents were recorded following the Petroski protocol: the cell was held at −80 mV, and the voltage step jumped from −80 to 30 mV and stay for 2 sec with a 20 ms prepulse at −40 mV. After depolarization, the voltage was decreased to −40 mV and stay for 2 sec, and returned back to −80 mV. Test compound was applied by quartz capillary tubes tip (200 μm inner diameter), and the flow rate was controlled at 2-3 mL/min with OctaFlow perfusion system. Different concentrations of the compound were applied to the cells for 5 min and the hERG current was measured three times before, during and after compound treatment. The data were analyzed using Clampfit 10 software (Molecular Devices) to generate IC$_{50}$ values. Results are shown in the table below.

| Compound | Structure | hERG IC$_{50}$ | hNR2B IC$_{50}$ |
|---|---|---|---|
| LX-1 | 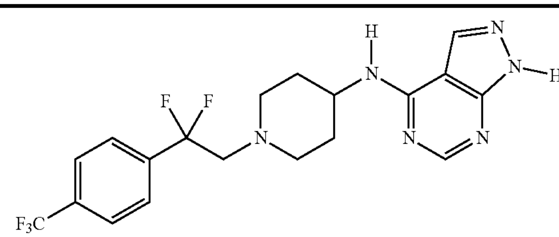 | 4.5 μM | 24 nM |
| C-3 | 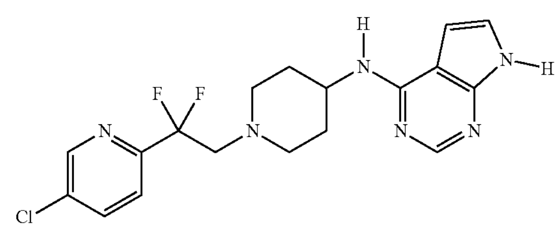 [SMILES: FC(F)(CN1CCC(Nc2ncnc3[nH]ccc23)CC1)c1ccc(Cl)cn1] | 7.0 μM | 22 nM |
| C-4 | 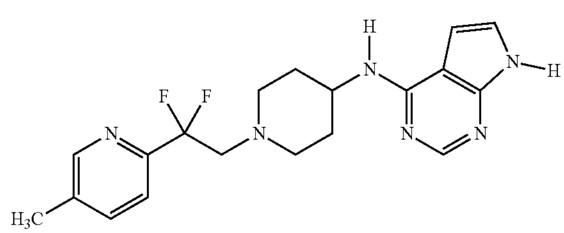 [SMILES: Cc1ccc(C(F)(F)CN2CCC(Nc3ncnc4[nH]ccc34)CC2)nc1] | 11.4 μM | 35 nM |

-continued

| Compound | Structure | hERG IC$_{50}$ | hNR2B IC$_{50}$ |
|---|---|---|---|
| C-5 | 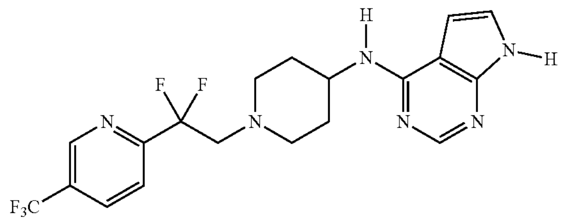 [SMILES: FC(F)(F)c1ccc(C(F)(F)CN2CCC(Nc3ncnc4[nH]ccc34)CC2)nc1] | 9.5 μM | 30 nM |
| C-230 | 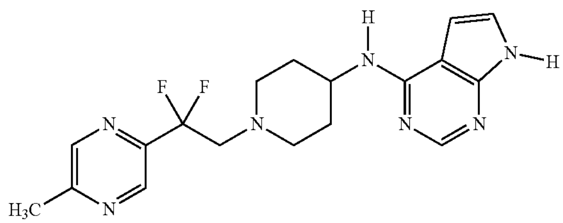 [SMILES: Cc1cnc(C(F)(F)CN2CCC(Nc3ncnc4[nH]ccc34)CC2)cn1] | 13.8 μM | 88 nM |
| C-127 | 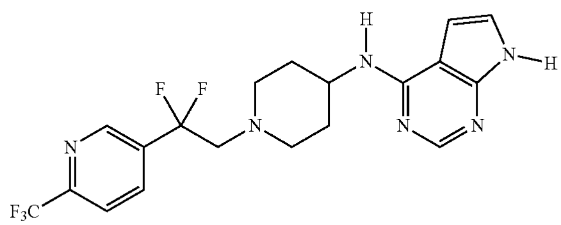 [SMILES: FC(F)(F)c1ccc(C(F)(F)CN2CCC(Nc3ncnc4[nH]ccc34)CC2)cn1] | 6 μM | 45 nM |
| C-128 | 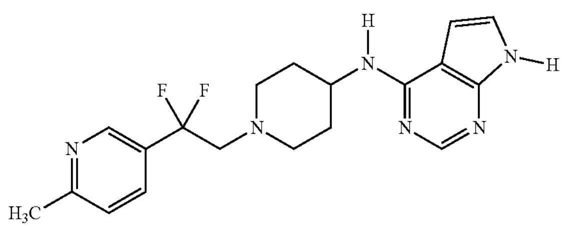 | 28 μM | 89 nM |
| C-175 | 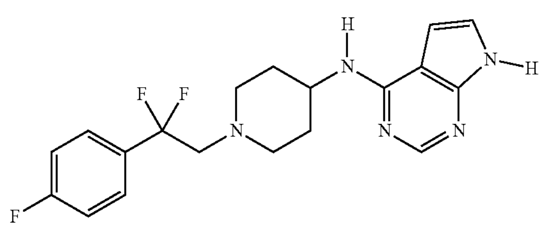 [SMILES: Fc1ccc(C(F)(F)CN2CCC(Nc3ncnc4[nH]ccc34)CC2)cc1] | 4.5 μM | 22 nM |

Example 2.3

CYP P450 Enzyme Inhibition

Inhibitory activities of test compounds on 5 major isoforms of CYP P450 were evaluated by using pooled human liver microsome (HLM, purchased from BD Gentest) and selective substrates for those isoforms. Those CYP isoforms and their corresponding probe substrates are as follows: CYP1A2 (phenacetin, 30 μM), CYP2C9 (tolutamide, 100 μM), CYP2C19 (S-mephenytoin, 40 μM), CYP2D6 (dextromethorphan, 5 μM) and CYP3A4 (midazolam, 1 μM). All probe substrates were used at concentrations near or below their K$_{ms}$. For experiment, a reaction mixture of test compound at 10 μM or in serial dilution, CYP probe substrate described above and 0.2 mg/mL pooled HLM in phosphate buffer, pH 7.4 in a final volume of 200 μL was pre-incubated at 37° C. for 10 minutes in triplicate. The reaction was initiated by addition of NADPH at final concentration of 1 mM. The reaction was terminated after 10 minutes (CYP1A2, CYP2D6 and CYP3A4) or 30 minutes (CYP2C9 and CYP2C19) by addition of 100 μL ice-cold acetonitrile with internal standard (IS). The samples were then centrifuged at 13,000 rpm and the supernatants were injected to LC-MS/MS (Agilent Technologies) to quantify the concentration of the specific metabolites of the probe substrates formed by individual CYP450 isoforms. The inhibition ratio is calculated as:

$$(M_t - M_0)/M_{water} \times 100\%$$

in which $M_t$ and $M_0$ represent the concentrations of the specific probe substrate metabolite, which was formed by individual CYP450 isoform, at the beginning and end of the reaction in the presence of test compound; while $M_{water}$ represents the concentration of the specific metabolite at the end of the reaction in the absence of test compound. Test compound concentration-dependent response data experiments performed in triplicate. Mean CYP2D6 IC$_{50}$ values were derived from non-linear, least-squares fitting of dose-dependent response data to a standard logistic equation (Prism, GraphPad Software, Inc) to generate the CYP2D6 IC$_{50}$ results shown in the table below.

| Compound | Free Base Structure | CYP2D6 IC$_{50}$ | NR2B IC$_{50}$ |
|---|---|---|---|
| LX-1 | | 1.0 μM | 24 nM |
| C-3 | | 12 μM | 22 nM |
| C-5 | | 33 μM | 30 nM |
| C-127 | | 11 μM | 45 nM |
| C-178 | | 6.7 μM | 64 nM |
| C-179 | | 4.9 μM | 23 nM |

| Compound | Free Base Structure | CYP2D6 IC$_{50}$ | NR2B IC$_{50}$ |
|---|---|---|---|
| C-175 | [structure] | 2.3 µM | 22 nM |

Example 2.4

Forced Swim Test

The forced swim test was used to evaluate antidepressant activity (Porsolt et al., 1977 *Arch. Int. Pharmacodyn.* 229: 327-336). Mice that are forced to swim in a situation from which they cannot escape, rapidly become immobile. Drugs with antidepressant activity, such as imipramine, reduce the amount of time spent in the immobile state. Therefore, the amount of immobility time during a test conducted after drug administration represents a useful indicator of antidepressant activity (Lucki et al., 2001, *Psychopharmacology* 155:315-322).

Male mice (strain NLMN) weighing 25-35 g were used for testing. All animals were housed in a temperature (22-24° C.) and humidity (50-60%) controlled environment with free access to food and water on a 12-hour light-dark cycle. Test compounds were dissolved in 0.5% dimethylsulfoxide, 4% hydroxypropyl-b-cyclodextrin water to generate the appropriate dosing solution. Drugs were administered by intraperitoneal injection at a dose volume of 10 mL/kg. Testing was initiated 20-60 minutes after dosing. Testing for antidepressant activity was conducted as described by Darci et al. (Darci et al., 2004, *Eur. J. Pharmacol.* 499.135-146). Mice were placed in a white plastic cylinder 20 cm high with a diameter of 21 cm containing 10 cm of water at 25±2° C. The mice were videotaped for 6 minutes, and the last 4 minutes of video were analyzed by a blinded observer off-line. The observer judged the animal to be immobile when it ceased all activity (struggling, swimming, jumping etc.) and floated passively atop the water. The amount of time each animal spent in the immobile state was recorded and used for statistical analysis of compound effect. Group differences were evaluated by student's t-test or one-way ANOVA followed by post-hoc Dunnett's test.

Figure 2:
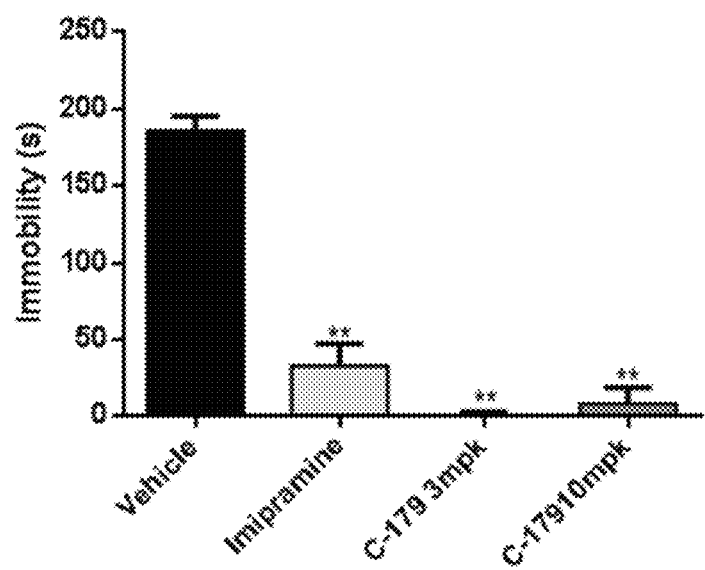
FIG. 2 shows the results of compound C-179 in the forced swim test as described in Example 2.4.2.

In both Examples 2.4.1 and 2.4.2, the positive control compound, imipramine (32 mg/kg, IP) showed the expected antidepressant activity (see FIGS. 1 and 2). These results indicate that provided compounds exhibit antidepressant activity when tested in a standard model for human depression.

Example 2.4.1

Compound C-178

Results are shown in FIG. 1: Bars represent the mean±SEM immobility time for each dose group (n=10, */: different from vehicle group, p<0.001/0.01 respectively, One-way ANOVA, Dunnett's post-test). Doses are given as milligram per kilogram (mpk). The dose of imipramine was 32 mpk.

Example 2.4.2

Compound C-179

Results are shown in FIG. 2: Bars represent the mean±SEM immobility time for each study group (n=10, */: different from vehicle group, p<0.001/0.01 respectively, One-way ANOVA, Dunnett's post-test). Doses are given as milligram per kilogram (mpk). The dose of imipramine was 32 mpk.

Example 2.5

Haloperidol-Induced Catalepsy (HIC) Model

The Haloperidol-induced Catalepsy (HIC) model detects antipsychotic activity and the action of NR2B selective antagonists (Steece-Collier et al. *Exp. Neurol.* 163: 239, 2000). The test was based on methods described by Chermat and Simon (*J. Pharmacol.*, 6, 493-496, 1975). The capacity to induce catalepsy serves as an index of the liability of a test substance to induce extrapyramidal side-effects, in particular Parkinsonism. Antagonism of antipsychotic-induced catalepsy can thus serve to detect anti-Parkinson potential.

Rats were injected with haloperidol (1 mg/kg i.p.) and were examined for catalepsy at 30 minute intervals up to 360 minutes. Presence (+) or absence (−) of catalepsy was assessed by three procedures: 1) imposed crossing of the ipsilateral fore- and hind-limbs; 2) placing the animal in the Buddha position; 3) the tilting board, an automatic device that, 5 seconds after positioning the rat, displaces the rat from a horizontal to vertical position and back while it clings to a wire grid with its front paws Akinesia and catalepsy are assessed depending on whether or not the animal moves before (akinesia) or during operation of the board (catalepsy).

The 4 scores were cumulated over time to give a global catalepsy score per animal. Six rats were studied per group. The test was performed blind (test substances versus vehicle). Test substances were evaluated at 1 or more doses, administered p.o. 15 minutes before haloperidol (i.e. 45 minutes before the first measurement), and compared with a vehicle control group. Amphetamine (8 mg/kg p.o.), administered 60 minutes before the test (i.e. 90 minutes before the first measurement), was used as reference substance. The experiment therefore included 8 groups. Data with the test substances were analysed by comparing treated groups (7 groups except for the reference substance) with vehicle control using Kruskal-Wallis Test followed by Mann-Whitney U tests at each time and for cumulated score. Data with the reference substance were analysed using Mann-Whitney U tests.

Figure 3:
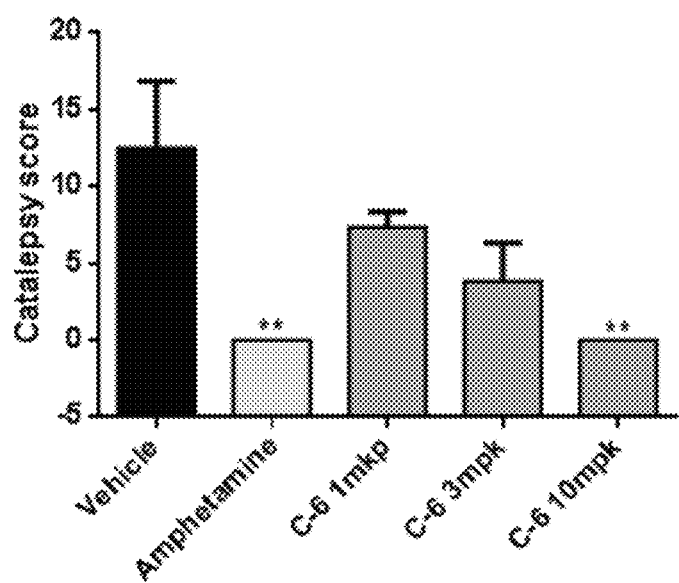
FIG. 3 shows the results of compound C-6 in the haloperidol-induced catalepsy model as described in Example 2.5.1.
Figure 4:
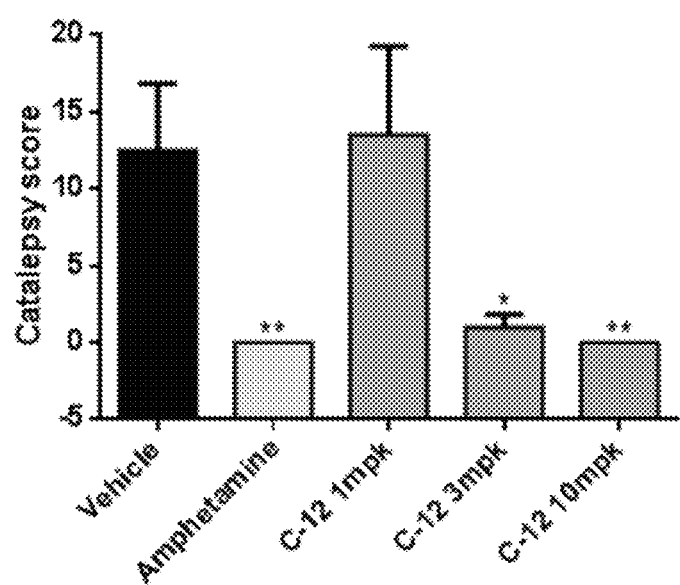
FIG. 4 shows the results of compound C-12 in the haloperidol-induced catalepsy model as described in Example 2.5.2.
Figure 5:
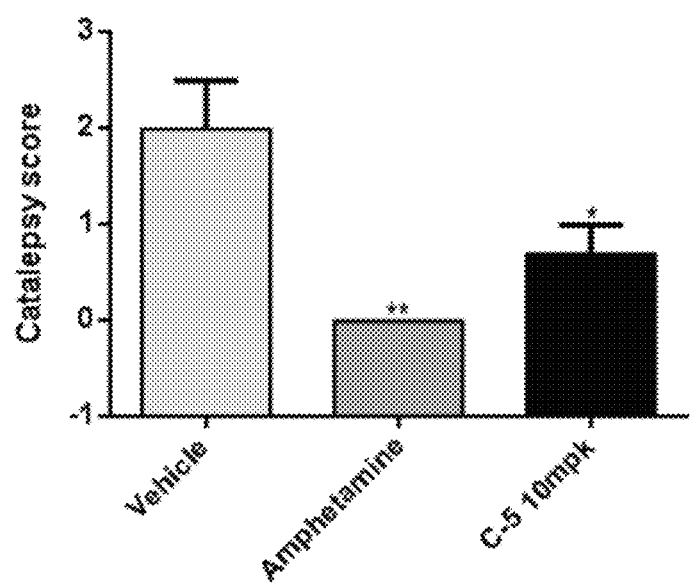
FIG. 5 shows the results of compound C-5 in the haloperidol-induced catalepsy model as described in Example 2.5.3.

In examples 2.5.1, 2.5.2 and 2.5.3, the positive control compound amphetamine (8 mg/kg IP) showed the expected robust anticataleptic activity (FIGS. 3, 4 and 5). These results indicate that provided compounds effectively block NR2B receptors in this rat model.

Example 2.5.1

Compound C-6

Results are shown in FIG. 3: Bars represent the mean±SEM global catalepsy score measured over the entire course of the 4 hour test period (n=6, **: different from vehicle group, p<0.01, one-way ANOVA, Dunnetts post test). Doses are given as milligram per kilogram (mpk). The dose of amphetamine was 8 mpk.

Example 2.5.2

Compound C-12

Results are shown in FIG. 4: Bars represent the mean±SEM global catalepsy score measured over the entire course of the 4 hour test period (n=6, */**: different from vehicle group, p<0.05/0.01 respectively one-way ANOVA, Dunnetts post test). Doses are given as milligram per kilogram (mpk). The dose of amphetamine was 8 mpk.

Example 2.5.3

Compound C-5

Results are shown in FIG. 5: Bars represent the mean±SEM catalepsy score measured at the 3.5 hour test time point (n=6, */**: different from vehicle group, p<0.05/0.01 respectively, Students t-test). Doses are given as milligram per kilogram (mpk). The dose of amphetamine was 8 mpk.

Example 2.6

Electroconvulsive Threshold (ECT) Test

The ECT method, which detects proconvulsant or anticonvulsant activity, follows that described by Swinyard et al (*J. Pharmacol. Exp. Ther.*, 106, 319-330, 1952). The electronconvulsive threshold (ECT) test is commonly used in the screening of anti-epileptic drugs in rodent models. Use of electrically-induced convulsions is recommended to assess proconvulsant and anticonvulsant activity. The effect of NR2B antagonism on pro- and anticonvulsant activity can, therefore, be measured with the ECT test. (N. O. Dalby et al., *Epilepsy Res.* 28: 63-72, 1997; E. Esneault et al., *J. Pharm. Toxicol. Methods*, 72: 59-66, 2015).

Rats were administered ECS (rectangular current: 0.6 ms pulse width, 1.5 s duration, 200 Hz) via earclip electrodes connected to a constant current shock generator (Ugo Basile: type 7801). Treatment groups of 20 rats were exposed to ECS as follows: Animal #1 was exposed to 30 mA of ECS. If animal #1 did not show convulsions (tonic convulsions) within 5 seconds maximum, animal #2 was exposed to 35 mA, etc. (increases of 5 mA) until the first tonic convulsion was observed. Once the first tonic convulsion was observed, the intensity of ECS was decreased by 2 mA for the next animal and then decreased or increased by 2 mA from animal to animal depending on whether the previous animal convulsed or not. If the first animal did convulse (tonic convulsions) within 5 seconds, animal #2 was exposed to 25 mA, etc. (decreases of 5 mA) until the absence of tonic convulsions was observed. At this point, the intensity of ECS was increased by 2 mA for the next animal and then decreased or increased by 2 mA from animal to animal depending on whether the previous animal convulsed or not. The minimum current intensity applied is 5 mA and the maximum 95 mA. The first 5 animals serve to approach threshold current and were not included in the analysis. The results are presented as the mean current intensity administered to the final 15 animals of a group. The test was performed blind to treatment. A positive percent change indicates an anticonvulsant effect. A negative percent change indicates a proconvulsant effect. The test substance was evaluated at 3 doses, administered p.o. 60 minutes before ECS, and compared with a vehicle control group. All statistical analyses were conducted using Microsoft Excel.

Theophylline (128 mg/kg p.o.) and diazepam (16 mg/kg p.o.), administered under the same experimental conditions, were used as reference substances. Test compounds, C-11, C-127 and C-179 were administered orally 1 hour before the beginning of the test.

Figure 6:
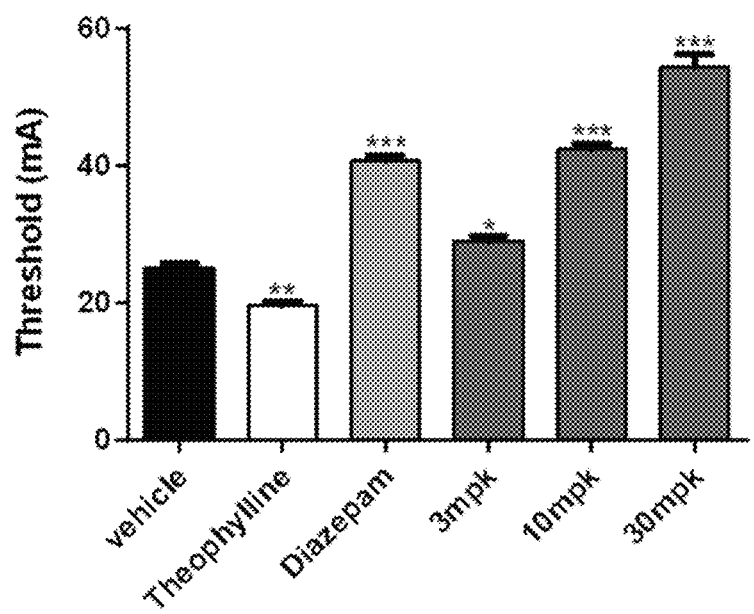
FIG. 6 shows the results of compound C-11 in the electroconvulsive threshold test as described in Example 2.6.1.
Figure 7:
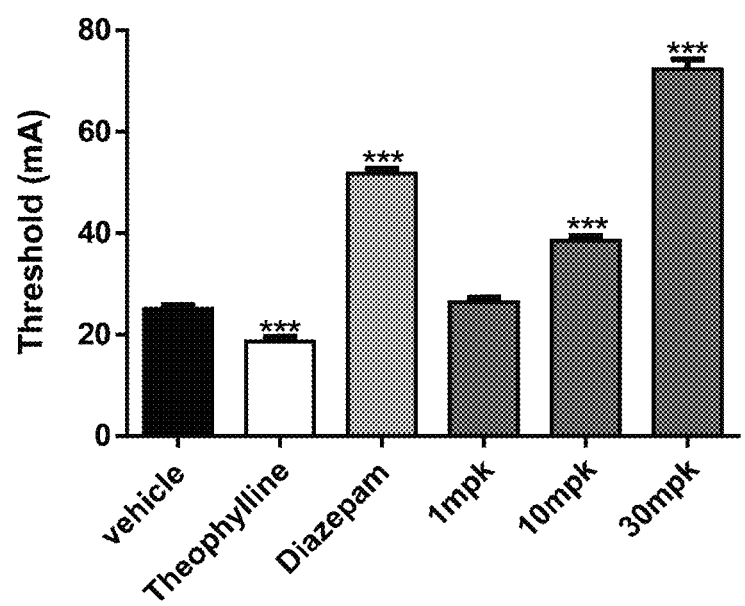
FIG. 7 shows the results of compound C-127 in the electroconvulsive threshold test as described in Example 2.6.2.
Figure 8:
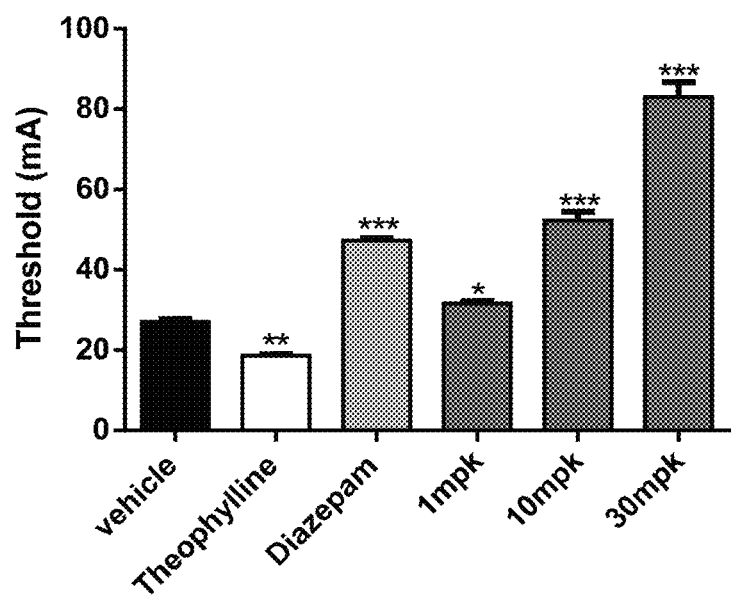
FIG. 8 shows the results of compound C-179 in the electroconvulsive threshold test as described in Example 2.6.3.

In each of Examples 2.6.1, 2.6.2 and 2.6.3 the positive control compounds, theophylline (128 mg/kg, p.o.) and diazepam (16 mg/kg p.o.) showed the expected pro- and anticonvulsant activities (see FIGS. 6, 7 & 8). These results indicate that provided compounds exhibit anticonvulsant activity when tested in a standard model for human convulsions.

Example 2.6.1

Compound C-11 in the ECT Test

Results are shown in FIG. 6. Bars represent the mean±SEM electroconvulsive threshold for each study group (n=15, *//*: different from vehicle group, p<0.05/0.01/0.001 respectively, One-way ANOVA, Dunnett's post-test). Doses are given as milligram per kilogram (mpk). The dose of theophylline was 128 mpk (p.o.) and the dose of diazepam was 16 mpk (p.o.).

Example 2.6.2

Compound C-127 in the ECT Test

Results are shown in FIG. 7. Bars represent the mean±SEM electroconvulsive threshold in mA for each dose group (n=15, ***: different from vehicle group, p<0.001, One-way ANOVA, Dunnett's post-test). Doses are given as milligram per kilogram (mpk). The dose of theophylline was 128 mpk (p.o.) and the dose of diazepam was 16 mpk (p.o.).

Example 2.6.3

Compound C-179 in the ECT Test

Results are shown in FIG. 8. Bars represent the mean±SEM electroconvulsive threshold for each study group (n=15, *//*: different from vehicle group, p<0.05/0.01/0.001 respectively, One-way ANOVA, Dunnett's post-test). Doses are given as milligram per kilogram (mpk). The dose of theophylline was 128 mpk (p.o.) and the dose of diazepam was 16 mpk (p.o.).

Example 2.7

6 Hz Seizure Test

The 6 Hz seizure test, which detects anticonvulsant activity of test compounds, was conducted according to methods described by Brown et al. (*J. Pharmacol. Exp. Ther.* 107, 273-283, 1953) and Barton et al. (*Epilepsy Res.* 47, 217-227, 2001). Mice, were administered a rectangular current (44 mA, rectangular pulse: 0.2 ms pulse width, 3 s duration, 6 Hz) via corneal electrodes connected to a constant current shock generator (Ugo Basile: type 7801). The results for the number of seizures as reflected by forelimb clonus and Straub-tail were recorded during the first minute following current administration. Forelimb clonus was scored as absent (0), mild (1) and strong (2) whereas Straub tail was rated as absent (0) or present (1). 15 mice were studied per group. The test was performed partially blind (test substance vs vehicle). Test substance (Compound C-179) was evaluated at 3 doses, administered p.o. 30 minutes before the test and compared with a vehicle control group. Diazepam (8 mg/kg p.o.), administered 60 minutes before the test, was used as reference substance. Quantitative data (scores) with the test substance was analyzed by comparing treated groups with vehicle control using Kruskall-Wallis test followed by Mann-Whitney U tests.

Example 2.7.1

Compound C-139 in the 6 Hz Seizure Test

Figure 9:
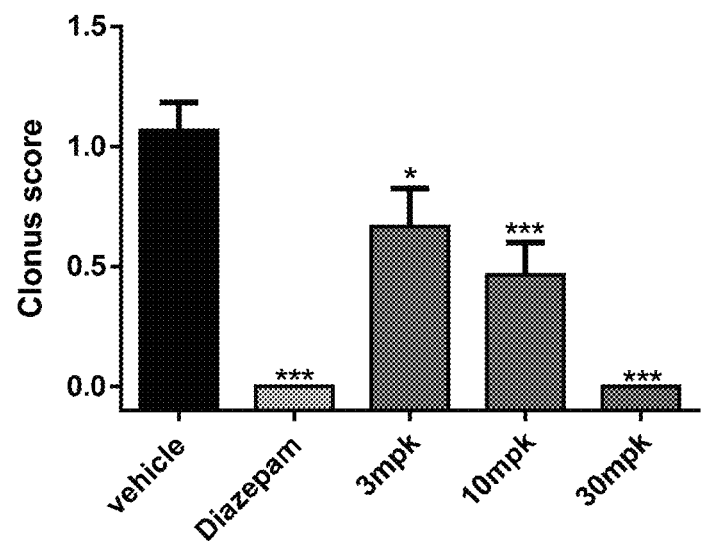
FIG. 9 shows the results of compound C-179 in the 6 Hz seizure test as described in Example 2.7.1.

Results are shown in FIG. 9. Bars represent the mean±SEM forelimb clonus score (arbitrary units) for each dose group (n=15, */***: different from vehicle group, p<0.05/0.001, One-way ANOVA, Dunnett's post-test). Doses are given as milligram per kilogram (mpk). The dose of diazepam was 8 mpk (p.o.).

What is claimed is:

1. A chemical entity, which is a compound of formula I:

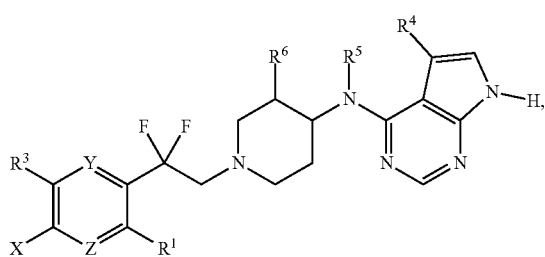

I or a pharmaceutically acceptable salt thereof, wherein:
Y and Z are independently N or C($R^2$);
X is —H; halo; $C_1$-$C_6$ alkyl optionally substituted with 1 to 6 fluoro; $C_3$-$C_6$ cycloalkyl;
$C_1$-$C_4$ alkoxy optionally substituted with 1 to 6 fluoro; —CN; —NO$_2$; —N($R^7$)($R^8$); —SR$^7$; —S(O)$_2$R$^9$; or —C(O)OR$^7$;
$R^1$ is —H; halo; $C_1$-$C_4$ alkyl optionally substituted with 1 to 3 fluoro; $C_3$-$C_6$ cycloalkyl; $C_1$-$C_4$ alkoxy optionally substituted with 1 to 3 fluoro; —CN; —NO$_2$; —N($R^7$)($R^8$); —C(O)OR$^7$; or —C(O)N($R^7$)($R^8$);

$R^2$ is —H; halo; $C_1$-$C_4$ alkyl optionally substituted with 1 to 3 fluoro; cyclopropyl; or $C_1$-$C_4$ alkoxy optionally substituted with 1 to 3 fluoro;
$R^3$ is —H, —F, —Cl, —CH$_3$, —CF$_3$ or —OCH$_3$;
$R^4$ is —H; —F; —Cl; $C_1$-$C_3$ alkyl optionally substituted with 1 to 3 fluoro; or cyclopropyl;
$R^5$ is —H or —CH$_3$;
$R^6$ is —H, —F or —CH$_3$;
each instance of $R^7$ independently is $C_1$-$C_4$ alkyl;
each instance of $R^8$ independently is —H or $C_1$-$C_4$ alkyl; and
$R^9$ is $C_1$-$C_4$ alkyl optionally substituted with 1 to 3 fluoro.

2. The chemical entity of claim 1, wherein:
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH$_2$CF$_2$CF$_3$, —CH(CF$_3$)$_2$, cyclopropyl, —OCH$_3$, —OCF$_3$, —OCHF$_2$, —OCFH$_2$, —CN, —NO$_2$, —NH(CH$_3$), —N(CH$_3$)$_2$, —N(CH$_3$)(CH$_2$CH$_3$), —SCH$_3$, —SCH$_2$CH$_3$, —SO$_2$CH$_3$, —SO$_2$CH$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or —C(O)N(CH$_3$)(CH$_2$CH$_3$);
$R^2$ is —H, —F, —Cl, —CH$_3$, —CH$_2$CH$_3$, —CH(CH$_3$)$_2$, —CF$_3$, cyclopropyl, —OCH$_3$, —OCHF$_2$ or —OCFH$_2$;
$R^3$ is —H, —F, —Cl, —CH$_3$, —CF$_3$ or —OCH$_3$;
$R^4$ is —H, —F, —Cl, —CH$_3$ or cyclopropyl;
$R^5$ is —H or —CH$_3$; and
$R^6$ is —H, —F or —CH$_3$.

3. The chemical entity of claim 1, wherein:
X is —H, —F, —Cl, —CH$_3$, —CH$_2$CH$_3$, —CH(CH$_3$)$_2$, —CF$_3$, —CHF$_2$, cyclopropyl, —OCH$_3$, —OCHF$_2$, —CN or —SCH$_3$;
$R^1$ is —H, —F, —Cl, —CH$_3$ or —CF$_3$;
$R^2$ is —H, —F, —Cl, —CH$_3$ or —CF$_3$;
$R^3$ is —H, —F, —Cl, —CH$_3$ or —CF$_3$;
$R^4$ is —H, —Cl or —CH$_3$;
$R^5$ is —H or —CH$_3$; and
$R^6$ is —H, —F or —CH$_3$.

4. The chemical entity of claim 1, which is a chemical entity of formula (Ia):

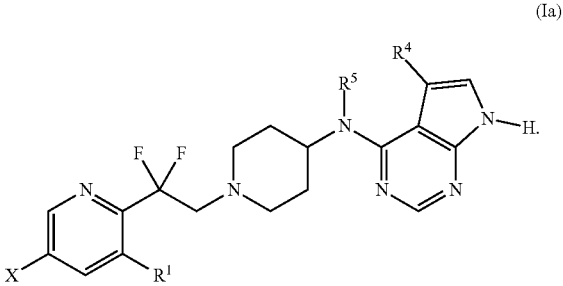

(Ia)

5. The chemical entity of claim 1, which is a chemical entity of formula (II):

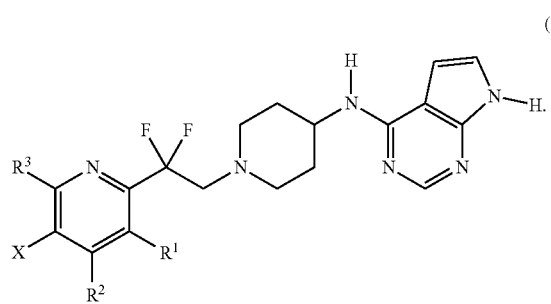

(II)

6. The chemical entity of claim 1, which is a chemical entity of formula (IIa):

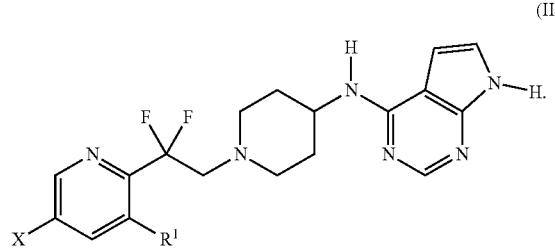

(IIa)

7. The chemical entity of claim 1, which is a chemical entity of formula (III):

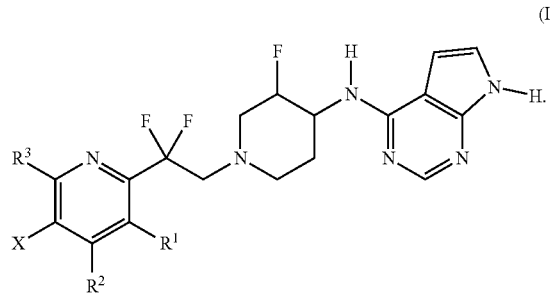

(III)

8. The chemical entity of claim 1, which is a chemical entity of formula (IV):

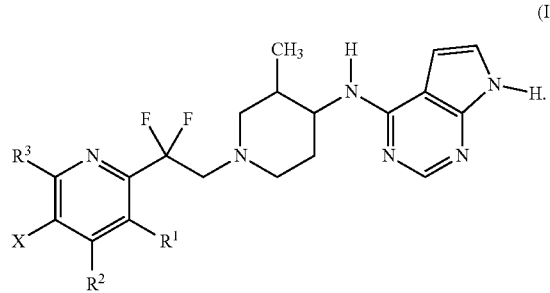

(IV)

9. The chemical entity of claim 1, which is a chemical entity of formula (V):

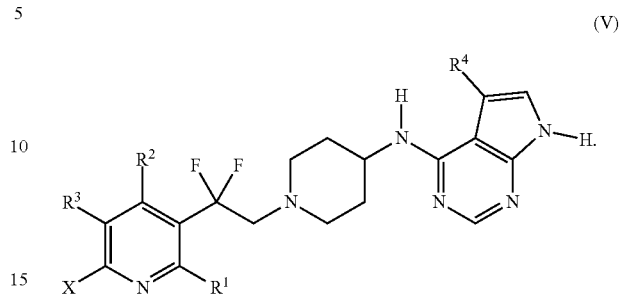

(V)

10. The chemical entity of claim 1, which is a chemical entity of formula (Va):

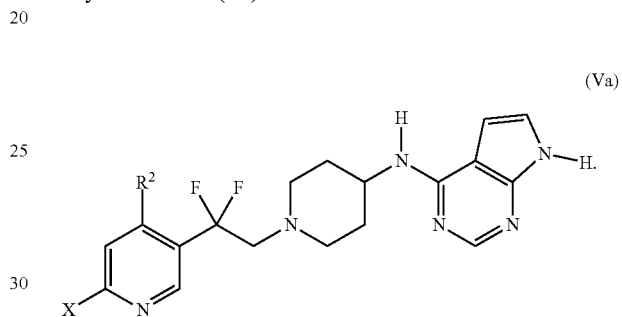

(Va)

11. The chemical entity of claim 1, which is a chemical entity of formula (VI):

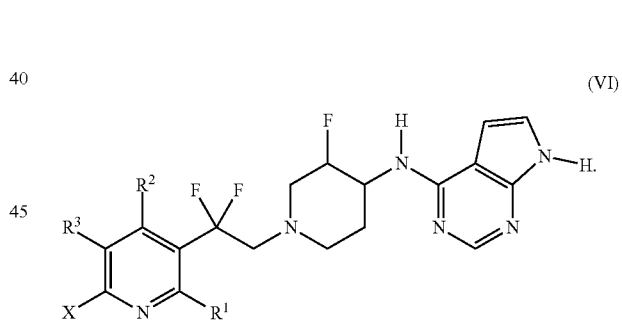

(VI)

12. The chemical entity of claim 1, which is a chemical entity of formula (VII):

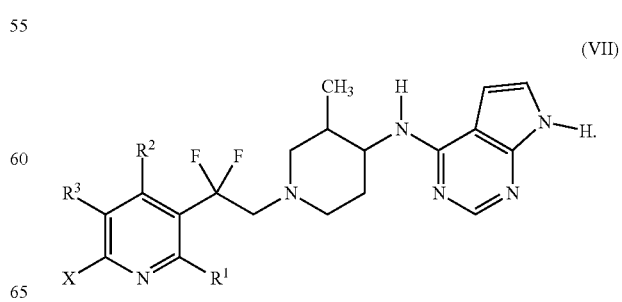

(VII)

13. The chemical entity of claim 1, which is a chemical entity of formula (VIII):

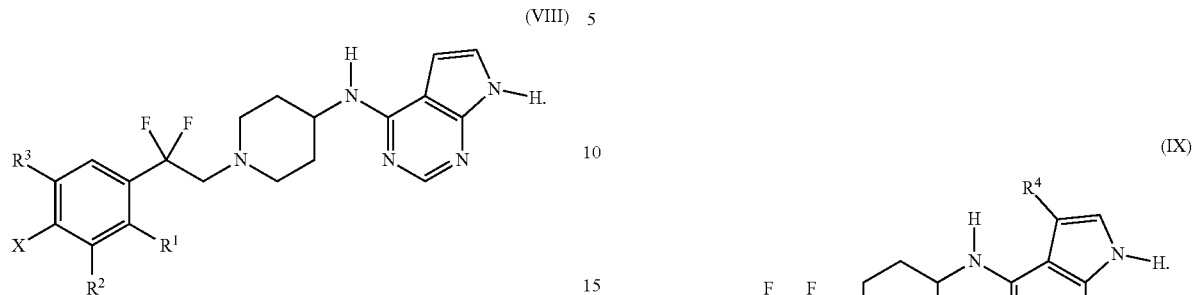

(VIII)

14. The chemical entity of claim 1, which is a chemical entity of formula (VIIIa):

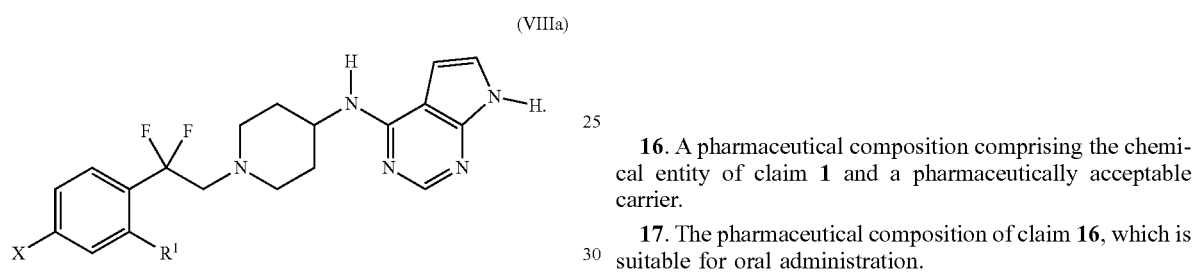

(VIIIa)

15. The chemical entity of claim 1, which is a chemical entity of formula (IX):

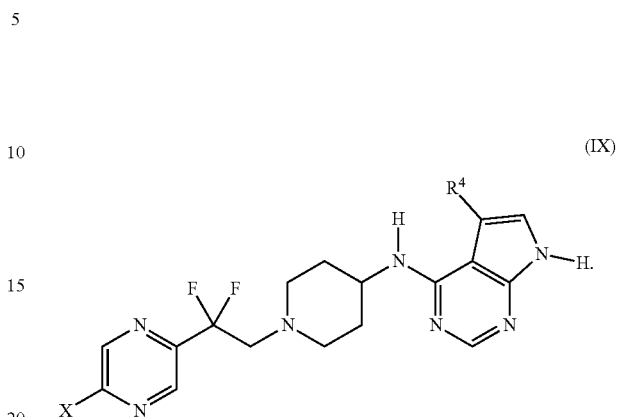

(IX)

16. A pharmaceutical composition comprising the chemical entity of claim 1 and a pharmaceutically acceptable carrier.

17. The pharmaceutical composition of claim 16, which is suitable for oral administration.

* * * * *

UNITED STATES PATENT AND TRADEMARK OFFICE
CERTIFICATE OF CORRECTION

PATENT NO. : 9,567,341 B2
APPLICATION NO. : 14/855010
DATED : February 14, 2017
INVENTOR(S) : Gideon Shapiro It is certified that error appears in the above-identified patent and that said Letters Patent is hereby corrected as shown below:

In the Claims

Column 142, Line 26 (Claim 2): Please replace the text "-$CF_3$, cyclopropyl, -$OCH_3$, -$OCHF_2$, -$OCFH_2$" with -- -$CF_3$, cyclopropyl, -$OCH_3$, -$OCF_3$, -$OCHF_2$, -$OCFH_2$ --.

Column 142, Line 31 (Claim 2): Please replace the text "-$CF_3$, cyclopropyl, -$OCH_3$, -$OCHF_2$ or -$OCFH_2$" with -- -$CF_3$, cyclopropyl, -$OCH_3$, -$OCF_3$, -$OCHF_2$ or -$OCFH_2$ --.

Column 142, Line 41 (Claim 3): Please replace the text "-$CF_3$, -$CHF_2$, cyclopropyl, -$OCH_3$, -$OCHF_2$" with -- -$CF_3$, -$CHF_2$, $CH_2F$, cyclopropyl, -$OCH_3$, -$OCF_3$, -$OCHF_2$ --.

Signed and Sealed this
Thirtieth Day of May, 2017

Michelle K. Lee
*Director of the United States Patent and Trademark Office*